(12) United States Patent
Boye et al.

(10) Patent No.: US 12,359,221 B2
(45) Date of Patent: Jul. 15, 2025

(54) COMPOSITIONS AND METHODS FOR EXPRESSING OTOFERLIN

(71) Applicants: University of Florida Research Foundation, Incorporated, Gainesville, FL (US); The Regents of the University of California, Oakland, CA (US)

(72) Inventors: Sanford L. Boye, Gainesville, FL (US); Frank M. Dyka, Gainesville, FL (US); William W. Hauswirth, Gainesville, FL (US); Omar Akil, San Francisco, CA (US)

(73) Assignees: The Regents of the University of California, Oakland, CA (US); University of Florida Research Foundation, Incorporated, Gainesville, FL (US)

( * ) Notice: Subject to any disclaimer, the term of this patent is extended or adjusted under 35 U.S.C. 154(b) by 1347 days.

(21) Appl. No.: 16/611,049

(22) PCT Filed: May 4, 2018

(86) PCT No.: PCT/US2018/031009
§ 371 (c)(1),
(2) Date: Nov. 5, 2019

(87) PCT Pub. No.: WO2018/204734
PCT Pub. Date: Nov. 8, 2018

(65) Prior Publication Data
US 2020/0157573 A1 May 21, 2020

Related U.S. Application Data

(60) Provisional application No. 62/502,462, filed on May 5, 2017.

(51) Int. Cl.
*C12N 15/90* (2006.01)
*C07K 14/47* (2006.01)
*C12N 15/86* (2006.01)

(52) U.S. Cl.
CPC ............ *C12N 15/902* (2013.01); *C07K 14/47* (2013.01); *C12N 15/86* (2013.01); *C12N 2750/14143* (2013.01)

(58) Field of Classification Search
CPC ....... C12N 15/902; C12N 15/86; C07K 14/47
See application file for complete search history.

(56) References Cited

U.S. PATENT DOCUMENTS

| 8,298,818 | B2 | 10/2012 | Boye et al. |
|---|---|---|---|
| 10,214,572 | B2 | 2/2019 | Boye et al. |
| 11,325,956 | B2 | 5/2022 | Boye et al. |
| 11,525,139 | B2 | 12/2022 | Simons et al. |
| 11,781,145 | B2 | 10/2023 | Simons et al. |
| 11,807,867 | B2 | 11/2023 | Simons et al. |
| 12,188,041 | B2 | 1/2025 | Dyka et al. |
| 2007/0161110 | A1 | 7/2007 | Iida et al. |
| 2010/0003218 | A1* | 1/2010 | Duan ............... C07K 14/4707 435/320.1 |
| 2010/0266551 | A1 | 10/2010 | Richard et al. |
| 2012/0003190 | A1* | 1/2012 | Yamoah ............... A61P 25/00 435/7.1 |
| 2012/0087862 | A1 | 4/2012 | Hood et al. |
| 2013/0210895 | A1* | 8/2013 | Boye .................. A61K 48/005 435/320.1 |
| 2014/0249208 | A1 | 9/2014 | Bancel et al. |
| 2014/0256802 | A1 | 9/2014 | Boye et al. |
| 2016/0022836 | A1 | 1/2016 | Banfi et al. |
| 2016/0076054 | A1* | 3/2016 | Auricchio ............. C12N 15/86 435/320.1 |
| 2018/0015172 | A1 | 1/2018 | Muzyczka et al. |
| 2019/0002916 | A1 | 1/2019 | Kalatzis et al. |
| 2019/0153050 | A1 | 5/2019 | Boye et al. |
| 2019/0309326 | A1 | 10/2019 | Maclaren et al. |
| 2021/0130421 | A1 | 5/2021 | Boye et al. |
| 2021/0395778 | A1 | 12/2021 | Dyka et al. |
| 2023/0149565 | A1 | 5/2023 | Boye et al. |
| 2024/0011039 | A1 | 1/2024 | Simons et al. |

FOREIGN PATENT DOCUMENTS

| CA | 3034527 | A1 | 3/2018 |
|---|---|---|---|
| CN | 110225975 | A | 9/2019 |
| JP | 2016-516424 | A | 6/2016 |
| JP | 7240675 | B2 | 3/2023 |
| KR | 10-2007-0004636 | A | 1/2007 |
| WO | WO 2001/070972 | A2 | 9/2001 |
| WO | WO 2008/088895 | A2 | 7/2008 |

(Continued)

OTHER PUBLICATIONS

Geleoc et al. "Sound strategies for hearing restoration", Science. May 9, 2014;344(6184):1241062 (Year: 2014).*
Trapani et al. "Effective delivery of large genes to the retina by dual AAV vectors", EMBO Mol Med. Feb. 2014;6(2):194-211. (Year: 2014).*
GenPept Accession NP_001274418.1, dated Apr. 23, 2017, retrieved from https://www.ncbi.nlm.nih.gov/protein/566559996?sat=46 &satkey=73202094 (Year: 2017).*
International Preliminary Report on Patentability mailed Nov. 14, 2019 for Application No. PCT/US2018/031009.
International Search Report and Written Opinion mailed Jul. 30, 2018 for Application No. PCT/US2018/031009.

(Continued)

*Primary Examiner* — Amy E Juedes
*Assistant Examiner* — Peter Johansen
(74) *Attorney, Agent, or Firm* — Wolf, Greenfield & Sacks, P.C.

(57) ABSTRACT

Provided herein are methods and compositions for expressing Otoferlin, e.g., utilizing adeno-associated viral (AAV) particles. Such methods and compositions may be useful for treatment of diseases such as Deafness, Autosomal Recessive 9 (DFNB9).

9 Claims, 30 Drawing Sheets
Specification includes a Sequence Listing.

(56) References Cited

FOREIGN PATENT DOCUMENTS

| WO | WO 2013/075008 A1 | 5/2013 | |
|---|---|---|---|
| WO | WO 2014/140051 A1 | 9/2014 | |
| WO | WO 2014/170480 A1 | 10/2014 | |
| WO | WO 2014/193716 A2 | 12/2014 | |
| WO | WO-2016131981 A1 * | 8/2016 | ........... A61K 35/761 |
| WO | WO 2016/139321 A1 | 9/2016 | |
| WO | WO 2017/049252 A1 | 3/2017 | |
| WO | WO 2017/100791 A1 | 6/2017 | |
| WO | WO 2017/216560 A1 | 12/2017 | |
| WO | WO 2018/039375 A1 | 3/2018 | |
| WO | WO 2018/162748 A1 | 9/2018 | |
| WO | WO 2018/204734 A1 | 11/2018 | |
| WO | WO 2019/165292 A1 | 8/2019 | |
| WO | WO 2019/183641 A1 | 9/2019 | |
| WO | WO 2020/148458 A1 | 7/2020 | |
| WO | WO 2021/087296 A1 | 5/2021 | |

OTHER PUBLICATIONS

International Search Report and Written Opinion mailed Feb. 20, 2020 for Application No. PCT/US2019/059549.
Akil et al., Dual AAV-mediated gene therapy restores hearing in a DFNB9 mouse model. Proc Natl Acad Sci U S A. Mar. 5, 2019;116(10):4496-4501. doi: 10.1073/pnas.1817537116. Epub Feb. 19, 2019.
PCT/US2018/031009, Jul. 30, 2018, International Search Report and Written Opinion.
PCT/US2018/031009, Nov. 14, 2019, International Preliminary Report on Patentability.
PCT/US2019/059549 Feb. 20, 2020, International Search Report and Written Opinion.
International Preliminary Report on Patentability for Application No. PCT/US2019/059549, mailed May 14, 2021.
International Search Report and Written Opinion for International Application No. PCT/US2012/065645 mailed Mar. 29, 2013.
International Preliminary Report on Patentability for International Application No. PCT/US2012/065645 mailed May 30, 2014.
Invitation to Pay Additional Fees for International Application No. PCT/US2021/025281 mailed Jun. 29, 2021.
International Search Report and Written Opinion for International Application No. PCT/US2021/025281 mailed Sep. 10, 2021.
International Preliminary Report on Patentability for International Application No. PCT/US2021/025281 mailed Oct. 13, 2022.
[No Author Listed], NCBI Accession No. NM_001632.5. *Homo sapiens* alkaline phosphatase, placental (ALPP), mRNA. Dec. 7, 2018. 4 pages.
[No Author Listed], NCBI Accession No. NP_000251. unconventional myosin-VIIa isoform 1 [*Homo sapiens*]. Aug. 14, 2022. 5 pages.
[No Author Listed], NCBI Accession No. U39226.1. Human myosin Viia (USH1B) mRNA, complete cds. Jul. 11, 1996. 5 pages.
Akil et al., Restoration of hearing in the VGLUT3 knockout mouse using virally mediated gene therapy. Neuron. Jul. 26, 2012;75(2):283-93. doi: 10.1016/j.neuron.2012.05.019.
Al-Hussaini et al., Mature retinal pigment epithelium cells are retained in the cell cycle and proliferate in vivo. Mol Vis. 2008;14:1784-91. Epub Oct. 6, 2008.
Allocca et al., Serotype-dependent packaging of large genes in adeno-associated viral vectors results in effective gene delivery in mice. J Clin Invest. May 1, 2008; 118(5): 1955-1964. Published online Apr. 15, 2008. doi: 10.1172/JCI34316.
Chen et al., Molecular cloning and domain structure of human myosin-VIIa, the gene product defective in Usher syndrome 1B. Genomics. Sep. 15, 1996;36(3):440-8. doi: 10.1006/geno.1996.0489.
Daya et al., Gene therapy using adeno-associated virus vectors. Clin Microbiol Rev. Oct. 2008;21(4):583-93. doi: 10.1128/CMR.00008-08.

Dong et al., Characterization of genome integrity for oversized recombinant AAV vector. Mol Ther. Jan. 2010;18(1):87-92. doi: 10.1038/mt.2009.258. Epub Nov. 10, 2009.
Duan et al., Circular intermediates of recombinant adeno-associated virus have defined structural characteristics responsible for long-term episomal persistence in muscle tissue. J Virol. Nov. 1998;72(11):8568-77.
Duan et al., Expanding AAV packaging capacity with trans-splicing or overlapping vectors: a quantitative comparison. Mol Ther. Oct. 2001;4(4):383-91.
Ghosh et al., A hybrid vector system expands adeno-associated viral vector packaging capacity in a transgene-independent manner. Mol Ther. Jan. 2008;16(1):124-30. doi: 10.1038/sj.mt.6300322. Epub Nov. 6, 2007.
Hashimoto et al., Lentiviral gene replacement therapy of retinas in a mouse model for Usher syndrome type 1B. Gene Therapy. 2007:14;584-594.
Jacobson et al., Usher syndromes due to MYO7A, PCDH15, USH2A or GPR98 mutations share retinal disease mechanism. Hum Mol Genet. Aug. 1, 2008;17(15):2405-15. doi: 10.1093/hmg/ddn140. Epub May 7, 2008.
Lai et al., Evidence for the Failure of Adeno-associated Virus Serotype 5 to Package a Viral Genome ≥8.2 kb. Mol Ther. 2010; 18 1, 75-79. doi:10.1038/mt.2009.256.
Li et al., High-efficiency transduction of fibroblasts and mesenchymal stem cells by tyrosine-mutant AAV2 vectors for their potential use in cellular therapy. Hum Gene Ther. Nov. 2010;21(11):1527-43. doi: 10.1089/hum.2010.005. Epub Oct. 6, 2010.
Lopes et al., Retinal gene therapy with a large MYO7A cDNA using adeno-associated virus. Gene Ther. Aug. 2013;20(8):824-33. doi: 10.1038/gt.2013.3. Epub Jan. 24, 2013. Author Manuscript, 21 pages.
Petrs-Silva et al., Novel properties of tyrosine-mutant AAV2 vectors in the mouse retina. Mol Ther. Feb. 2011;19(2):293-301. doi: 10.1038/mt.2010.234. Epub Nov. 2, 2010.
Trapani et al., Effective delivery of large genes to the retina by dual AAV vectors. EMBO Mol Med. Feb. 2014;6(2):194-211. doi: 10.1002/emmm.201302948. Epub Dec. 15, 2013.
Weil et al., Human myosin VIIA responsible for the Usher 1B syndrome: a predicted membrane-associated motor protein expressed in developing sensory epithelia. Proc Natl Acad Sci U S A. Apr. 16, 1996;93(8):3232-7. doi: 10.1073/pnas.93.8.3232.
Wu et al., Effect of genome size on AAV vector packaging. Mol Ther. Jan. 2010;18(1):80-6. doi: 10.1038/mt.2009.255. Epub Nov. 10, 2009.
Yan et al., Inverted terminal repeat sequences are important for intermolecular recombination and circularization of adeno-associated virus genomes. J Virol. Jan. 2005;79(1):364-79.
Yan et al., Recombinant AAV-mediated gene delivery using dual vector heterodimerization. Methods Enzymol. 2002;346:334-57. doi: 10.1016/s0076-6879(02)46065-x.
Extended European Search Report for European Application No. EP 18793935.0 mailed on Feb. 22, 2021.
Alemi et al., Progress Report: AOS Research Grant: Restoration of Hearing in the Otoferlin Knockout Mouse using Viral Gene Therapy. 145th Annual Meeting. American Otological Society, Inc. Apr. 21-22, 2012; p. 68. Available online at: https://www.americanotologicalsociety.org/assets/2012.pdf.
Al-Moyed et al., A dual-AAV approach restores fast exocytosis and partially rescues auditory function in deaf otoferlin knock-out mice. EMBO Mol Med. Jan. 2019;11(1):e9396. doi: 10.15252/emmm.201809396.
Dyka et al., Dual adeno-associated virus vectors result in efficient in vitro and in vivo expression of an oversized gene, MYO7A. Hum Gene Ther Methods. Apr. 2014;25(2):166-77. doi: 10.1089/hgtb.2013.212.
Ghosh et al., Efficient transgene reconstitution with hybrid dual AAV vectors carrying the minimized bridging sequences. Hum Gene Ther. Jan. 2011;22(1):77-83. doi: 10.1089/hum.2010.122. Epub Dec. 12, 2010.
U.S. Appl. No. 17/290,082, filed Apr. 29, 2021, Dyka et al.
U.S. Appl. No. 16/952,016, filed Nov. 18, 2020, Boye et al.
U.S. Appl. No. 17/916,308, filed Sep. 30, 2022, Boye et al.

(56) References Cited

OTHER PUBLICATIONS

PCT/US2019/059549, May 14, 2021, International Preliminary Report on Patentability for Application.
PCT/US2012/065645, Mar. 29, 2013, International Search Report and Written Opinion.
PCT/US2012/065645, May 30, 2014, International Preliminary Report on Patentability.
PCT/US2021/025281, Jun. 29, 2021, Invitation to Pay Additional Fees.
PCT/US2021/025281, Sep. 10, 2021, International Search Report and Written Opinion.
PCT/US2021/025281, Oct. 13, 2022, International Preliminary Report on Patentability for Application.
[No Author Listed], NCBI Accession No. NP_001274418. OTOF otoferlin [ *Homo sapiens* (human) ]. Nov. 17, 2023. 3 pages.
Avraham, What's hot about otoferlin. EMBO J. Dec. 1, 2016;35(23):2502-2504. doi: 10.15252/embj.201695881. Epub Nov. 7, 2016.
Gao et al., The Dystrophin Complex: Structure, Function, and Implications for Therapy. Compr Physiol. Jul. 1, 2015;5(3):1223-39. doi: 10.1002/cphy.c140048. Author Manuscript, 33 pages.
Hirsch et al., Delivering Transgenic DNA Exceeding the Carrying Capacity of AAV Vectors. Methods Mol Biol. 2016;1382:21-39. doi: 10.1007/978-1-4939-3271-9_2. Author Manuscript, 20 pages.
Lostal et al., Full-length dystrophin reconstitution with adeno-associated viral vectors. Hum Gene Ther. Jun. 2014;25(6):552-62. doi: 10.1089/hum.2013.210. Epub Mar. 31, 2014.
Majewski et al., GT repeats are associated with recombination on human chromosome 22. Genome Res. Aug. 2000;10(8):1108-14. doi: 10.1101/gr.10.8.1108.
Pryadkina et al., A comparison of AAV strategies distinguishes overlapping vectors for efficient systemic delivery of the 6.2 kb Dysferlin coding sequence. Mol Ther Methods Clin Dev. Mar. 25, 2015;2:15009. doi: 10.1038/mtm.2015.9.
Yasunaga et al., OTOF encodes multiple long and short isoforms: genetic evidence that the long ones underlie recessive deafness DFNB9. Am J Hum Genet. Sep. 2000;67(3):591-600. doi: 10.1086/303049. Epub Jul. 19, 2000.
Extended European Search Report for European Application No. EP 21781660.2 mailed on Apr. 9, 2024.
[No Author Listed] Basics of Sound, the Ear, and Hearing, Hearing Loss: Determining Eligibility for Social Security Benefits. Dobie RA, Van Hemel S, editors. Washington (DC): National Academies Press (US); 2004, p. 42-68.
[No Author Listed] Children's Hospital of Philadelphia Performs First Gene Therapy Procedure to Treat Genetic Hearing Loss in United States, American Academy of Audiology, Accessed online: <https://www.audiology.org/childrens-hospital-of-philadelphia-performs-first-gene-therapy-procedure-to-treat-genetic-hearing-loss-in-united-states/>, dated Jan. 26, 2024 (2 pages).
[No Author Listed] Genetic Hearing Loss With No Associated Abnormalities, Hereditary Hearing Loss and Its Syndromes, Third Edition. Helga V. Toriello and Shelley D. Smith (Eds.), 2013, p. 164-165 (4 pages).
[No Author Listed] OTOF sequence comparison of Yasunaga SEQ ID No. 70 with present SEQ ID No. 5 (dated Apr. 12, 2024), from U.S. Appl. No. 17/290,082 Office Action, Apr. 18, 2024, 5 pages.
Ahmed et al., Emerging Gene Therapies for Genetic Hearing Loss. J Assoc Res Otolaryngol. Oct. 2017;18(5):649-670. doi: 10.1007/s10162-017-0634-8. Epub Aug. 16, 2017.
Akil et al., AAV-Mediated Gene Delivery to the Inner Ear. Methods Mol Biol. 2019;1950:271-282. doi: 10.1007/978-1-4939-9139-6_16.
Akil et al., Surgical method for virally mediated gene delivery to the mouse inner ear through the round window membrane. J Vis Exp. Mar. 16, 2015;(97):52187. doi: 10.3791/52187.
Calabro, Exploring MYO&A function in novel mouse models and improving AAV-Dual Vector gene therapy for Usher Syndrome 1B. PHD dissertation. University of Florida. pp. 1-138 (Year: 2019).

Hamosh et al., OTOFERLIN; OTOF, OMIM. (Apr. 2015) Retrieved via The Wayback Machine on Jul. 29, 2015, URL: <https://web.archive.org/web/20150729163826/http://omim.org/entry/603681>, 8 pages.
Holt et al., Split otoferlins reunited. EMBO Mol Med. Jan. 2019;11(1):e9995. doi: 10.15252/emmm.201809995.
Kilpatrick et al., Adeno-associated virus-mediated gene delivery into the scala media of the normal and deafened adult mouse ear. Gene Ther. Jun. 2011;18(6):569-78. doi: 10.1038/gt.2010.175. Epub Jan. 6, 2011.
Langouet-Astrie et al., Characterization of intravitreally delivered capsid mutant AAV2-Cre vector to induce tissue-specific mutations in murine retinal ganglion cells. Exp Eye Res. Oct. 2016;151:61-7. doi: 10.1016/j.exer.2016.07.019. Epub Jul. 30, 2016.
Li et al., A novel bispecific molecule delivered by recombinant AAV2 suppresses ocular inflammation and choroidal neovascularization. J Cell Mol Med. Aug. 2017;21(8):1555-1571. doi: 10.1111/jcmm.13086. Epub Mar. 22, 2017.
Liu et al., Specific and efficient transduction of Cochlear inner hair cells with recombinant adeno-associated virus type 3 vector. Mol Ther. Oct. 2005;12(4):725-33. doi: 10.1016/j.ymthe.2005.03.021.
Lopes-Pacheco et al., Self-complementary and tyrosine-mutant rAAV vectors enhance transduction in cystic fibrosis bronchial epithelial cells. Exp Cell Res. Nov. 15, 2018;372(2):99-107. doi: 10.1016/j.yexcr.2018.09.015. Epub Sep. 20, 2018.
McClements et al., A fragmented adeno-associated viral dual vector strategy for treatment of diseases caused by mutations in large genes leads to expression of hybrid transcripts. J Genet Syndr Gene Ther. Nov. 14, 2016;7(5):311. doi: 10.4172/2157-7412.1000311. Author Manuscript, 16 pages.
Pangrsic et al., Otoferlin: a multi-C2 domain protein essential for hearing. Trends Neurosci. Nov. 2012;35(11):671-80. doi: 10.1016/j.tins.2012.08.002. Epub Sep. 7, 2012.
Petrs-Silva et al., High-efficiency transduction of the mouse retina by tyrosine-mutant AAV serotype vectors. Mol Ther. Mar. 2009;17(3):463-71. doi: 10.1038/mt.2008.269. Epub Dec. 16, 2008.
Roux et al., Otoferlin, defective in a human deafness form, is essential for exocytosis at the auditory ribbon synapse. Cell. Oct. 20, 2006;127(2):277-89. doi: 10.1016/j.cell.2006.08.040.
Suzuki et al., Cochlear gene therapy with ancestral AAV in adult mice: complete transduction of inner hair cells without cochlear dysfunction. Sci Rep. Apr. 3, 2017;7:45524. doi: 10.1038/srep45524.
Tao et al., Delivery of Adeno-Associated Virus Vectors in Adult Mammalian Inner-Ear Cell Subtypes Without Auditory Dysfunction. Hum Gene Ther. Apr. 2018;29(4):492-506. doi: 10.1089/hum.2017.120. Epub Jan. 22, 2018.
Tertrais et al., Viral Transfer of Mini-Otoferlins Partially Restores the Fast Component of Exocytosis and Uncovers Ultrafast Endocytosis in Auditory Hair Cells of Otoferlin Knock-Out Mice. J Neurosci. May 1, 2019;39(18):3394-3411. doi: 10.1523/JNEUROSCI.1550-18.2018. Epub Mar. 4, 2019.
Yoshimura et al., Enhanced viral-mediated cochlear gene delivery in adult mice by combining canal fenestration with round window membrane inoculation. Sci Rep. Feb. 14, 2018;8(1):2980. doi: 10.1038/s41598-018-21233-z. Supplemental Information, 4 pages.
Yoshimura et al., Targeted Allele Suppression Prevents Progressive Hearing Loss in the Mature Murine Model of Human TMC1 Deafness. Mol Ther. Mar. 6, 2019;27(3):681-690. doi: 10.1016/j.ymthe.2018.12.014. Epub Jan. 7, 2019. Supplemental Information, 7 pages.
Zhang et al., Cochlear Gene Therapy for Sensorineural Hearing Loss: Current Status and Major Remaining Hurdles for Translational Success. Front Mol Neurosci. Jun. 26, 2018;11:221. doi: 10.3389/fnmol.2018.00221.
Zhang et al., Temperature sensitive auditory neuropathy. Hear Res. May 2016;335:53-63. doi: 10.1016/j.heares.2016.01.008. Epub Jan. 15, 2016.
[No Author Listed] Types of CFTR Mutations, Cystic Fibrosis Foundation. Printout from https://www.cff.org/research-clinical-trials/types-cftr-mutations#:-:text=. Printed 2024. pp. 1-9.

(56) References Cited

OTHER PUBLICATIONS

Barnes et al., Remarkable Rigidity of the Single α-Helical Domain of Myosin-VI as Revealed by NMR Spectroscopy. J Am Chem Soc. Jun. 5, 2019;141(22):9004-9017. doi: 10.1021/jacs.9b03116. Epub May 23, 2019.

Laine et al., Cell cycle regulation in the inner ear sensory epithelia: role of cyclin D1 and cyclin-dependent kinase inhibitors. Dev Biol. Jan. 1, 2010;337(1):134-46. doi: 10.1016/j.ydbio.2009.10.027. Epub Oct. 23, 2009.

Orthwein et al., A mechanism for the suppression of homologous recombination in G1 cells. Nature. Dec. 17, 2015;528(7582):422-6. doi: 10.1038/nature16142. Epub Dec. 9, 2015. Retraction in: Nature. Jan. 27, 2025. doi: 10.1038/s41586-025-08644-5.

Regalado et al., Some deaf children in China can hear after gene therapy treatment. MIT Technology Review. Oct. 27, 2023. Accessed online: https://www.technologyreview.com/2023/10/27/1082551/gene-treatment-deaf-children-hearing-china/.

Zhang et al., Single amino acid change alters specificity of the multi-allelic wheat stem rust resistance locus SR9. Nat Commun. Nov. 14, 2023;14(1):7354. doi: 10.1038/s41467-023-42747-9.

\* cited by examiner pTR22-smCBA-otoferlinNT-APSD-APhead

| Nucleotide positions | Abbreviation | Description |
|---|---|---|
| 20-162 | TR: | inverted terminal repeat sequence of AAV2 |
| 186-440 | CBA promoter: | -CMVie enhancer |
| 441-835 | | -chicken b-actin promoter |
| 836-1130 | | -Exon1 and chimeric intron |
| 1153-3600 | Otoferlin NT: | Otoferlin coding sequence 5' part |
| 3601-3684 | APSD: | Splice Donor |
| 3691-3977 | APhead: | homologous sequence for recombination |
| 4017-4159 | TR: | inverted terminal repeat sequence of AAV2 |
| | ColE2: | replication origin for E. coli |
| | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTTAATT
ATTTTGTGCAGCGATGGGGGCGGGGGGGGGGGGGGCGCGCGCCAGGCGGGGCG
GGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTCCTACAGCTCCTGGGCAAC
GTGCTGGTTATTGTGCTGTCTCATCATTTTGGCAAAGAATTCTAGCGGCCGCCACCATG
GCCCTGATTGTTCACCTCAAGACTGTCTCAGAGCTCCGAGGCAAAGGTGACCGGATTG
CCAAAGTCACTTTCCGAGGGCAGTCTTTCTACTCCCGGGTCCTGGAGAACTGCGAGGG
TGTGGCTGACTTTGATGAGACGTTCCGGTGGCCAGTGGCCAGCAGCATCGACCGGAAT
GAAGTGTTGGAGATTCAGATTTTCAACTACAGCAAAGTCTTCAGCAACAAGCTGATAGG
GACCTTCTGCATGGTGCTGCAGAAAGTGGTGGAGGAGAATCGGGTAGAGGTGACCGA
CACGCTGATGGATGACAGCAATGCTATCATCAAGACCAGCCTGAGCATGGAGGTCCGG
TATCAGGCCACAGATGGCACTGTGGGCCCCTGGGATGATGGAGACTTCCTGGGAGAT
GAATCCCTCCAGGAGGAGAAGGACAGCCAGGAGACAGATGGGCTGCTACCTGGTTCC
CGACCCAGCACCCGGATATCTGGCGAGAAGAGCTTTCGCAGCAAAGGCAGAGAGAAG
ACCAAGGGAGGCAGAGATGGCGAGCACAAAGCGGGAAGGAGTGTGTTCTCGGCCATG
AAACTCGGCAAAACTCGGTCCCACAAAGAGGAGCCCCAAAGACAAGATGAGCCAGCAG
TGCTGGAGATGGAGGACCTGGACCACCTAGCCATTCAGCTGGGGGATGGGCTGGATC
CTGACTCCGTGTCTCTAGCCTCGGTCACCGCTCTCACCAGCAATGTCTCCAACAAACG
GTCTAAGCCAGATATTAAGATGGAGCCCAGTGCTGGAAGGCCCATGGATTACCAGGTC
AGCATCACAGTGATTGAGGCTCGGCAGCTGGTGGGCTTGAACATGGACCCTGTGGTGT
```

FIG. 3A

```
GTGTGGAGGTGGGTGATGACAAGAAATACACGTCAATGAAGGAGTCCACAAACTGCCC
TTACTACAACGAGTACTTTGTCTTCGACTTCCATGTCTCTCCTGATGTCATGTTTGACAA
GATCATCAAGATCTCGGTTATCCATTCTAAGAACCTGCTTCGGAGCGGCACCCTGGTG
GGTTCCTTCAAAATGGATGTGGGGACTGTGTATTCCCAGCCTGAACACCAGTTCCATCA
CAAATGGGCCATCCTGTCAGACCCCGATGACATCTCTGCTGGGTTGAAGGGTTATGTA
AAGTGTGATGTCGCTGTGGTGGGCAAGGGAGACAACATCAAGACACCCACAAGGCCA
ACGAGACGGATGAGGACGACATTGAAGGGAACTTGCTGCTCCCGAGGGCGTGCCCC
CCGAACGGCAGTGGGCACGGTTCTATGTGAAAATTTACCGAGCAGAGGGACTGCCCC
GGATGAACACAAGCCTCATGGCCAACGTGAAGAAGGCGTTCATCGGTGAGAACAAGGA
CCTCGTCGACCCCTATGTGCAAGTCTTCTTTGCTGGACAAAAGGGCAAAACATCAGTGC
AGAAGAGCAGCTATGAGCCGCTATGGAATGAGCAGGTCGTCTTCACAGACTTGTTCCC
CCCACTCTGCAAACGCATGAAGGTGCAGATCCGGGACTCTGACAAGGTCAATGATGTG
GCCATCGGCACCCACTTCATCGACCTGCGCAAGATTTCCAACGATGGAGACAAAGGCT
TCCTGCCTACCCTCGGTCCAGCCTGGGTGAACATGTACGGCTCCACGCGCAACTACAC
ACTGCTGGACGAGCACCAGGACTTGAATGAAGGCCTGGGGAGGGTGTGTCCTTCCG
GGCCCGCCTCATGTTGGGACTAGCTGTGGAGATCCTGGACACCTCCAACCCAGAGCTC
ACCAGCTCCACGGAGGTGCAGGTGGAGCAGGCCACGCCTGTCTCGGAGAGCTGCACA
GGGAGAATGGAAGAATTTTTTCTATTTGGAGCCTTCTTGGAAGCCTCAATGATTGACCG
GAAAAATGGGGACAAGCCAATTACCTTTGAGGTGACCATAGGAAACTACGGCAATGAA
GTCGATGGTATGTCCCGGCCCCTGAGGCCTCGGCCCCGGAAAGAGCCTGGGGATGAA
GAAGAGGTAGACCTGATTCAGAACTCCAGTGACGATGAAGGTGACGAAGCCGGGGAC
CTGGCCTCGGTGTCCTCCACCCCACCTATGCGGCCCCAGATCACGGACAGGAACTATT
TCCACCTGCCCTACCTGGAGCGCAAGCCCTGCATCTATATCAAGAGCTGGTGGCCTGA
CCAGAGGCGGCGCCTCTACAATGCCAACATCATGGATCACATTGCTGACAAGCTGGAA
GAAGGCCTGAATGATGTACAGGAGATGATCAAAACGGAGAAGTCCTACCCGGAGCGCC
GCCTGCGGGGTGTGCTAGAGGAACTCAGCTGTGGCTGCCACCGCTTCCTCTCCCTCTC
GGACAAGGACCAGGGCCGCTCGTCCCGCACCAGGCTGGATCGAGAGCGTCTTAAGTC
CTGTATGAGGGAGTTGGTAAGTATCAAGGTTACAAGACAGGTTTAAGGAGACCAATAGA
AACTGGGCTTGTCGAGACAGAGAAGACTCTTGCGTTTCTGAGCTAGCCCCCGGGTGCG
CGGCGTCGGTGGTGCCGGCGGGGGCGCCAGGTCGCAGGCGGTGTAGGGCTCCAG
GCAGGCGGCGAAGGCCATGACGTGCGCTATGAAGGTCTGCTCCTGCACGCCGTGAAC
CAGGTGCGCCTGCGGGCCGCGCGCAACACCGCCACGTCCTCGCCTGCGTGGGTCT
CTTCGTCCAGGGGCACTGCTGACTGCTGCCGATACTCGGGGCTCCCGCTCTCGCTCTC
GGTAACATCCGGCCGGGCGCCGTCCTTGAGCACATAGCCTGGACCGTTTCGTCGACT
GTTAATTAAGCATGCTGGGGAGAGATCTAGGAACCCCTAGTGATGGAGTTGGCCACTC
CCTCTCTGCGCGCTCGCTCGCTCACTGAGGCCGCCCGGGCAAAGCCCGGGCGTCGG
GCGACCTTTGGTCGCCCGGCCTCAGTGAGCGAGCGAGCGCGCAGAGAGGGAGTGGC
CAACCCCCCCCCCCCCCCCTGCAGCCCTGCATTAATGAATCGGCCAACGCGCGGG
GAGAGGCGGTTTGCGTATTGGGCGCTCTTCCGCTTCCTCGCTCACTGACTCGCTGCGC
TCGGTCGTTCGGCTGCGGCGAGCGGTATCAGCTCACTCAAAGGCGGTAATACGGTTAT
CCACAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGAC
GAGCATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCAATGCT
CACGCTGTAGGTATCTCAGTTCGGTGTAGGTCGTTCGCTCCAAGCTGGGCTGTGTGCA
CGAACCCCCCGTTCAGCCCGACCGCTGCGCCTTATCCGGTAACTATCGTCTTGAGTCC
AACCCGGTAAGACACGACTTATCGCCACTGGCAGCAGCCACTGGTAACAGGATTAGCA
GAGCGAGGTATGTAGGCGGTGCTACAGAGTTCTTGAAGTGGTGGCCTAACTACGGCTA
CACTAGAAGGACAGTATTTGGTATCTGCGCTCTGCTGAAGCCAGTTACCTTCGGAAAAA
GAGTTGGTAGCTCTTGATCCGGCAAACAAACCACCGCTGGTAGCGGTGGTTTTTTTGTT
TGCAAGCAGCAGATTACGCGCAGAAAAAAGGATCTCAAGAAGATCCTTTGATCTTTTC
TACGGGGTCTGACGCTCAGTGGAACGAAAACTCACGTTAAGGGATTTTGGTCATGAGA
```

FIG. 3A (continued)

TTATCAAAAAGGATCTTCACCTAGATCCTTTTAAATTAAAAATGAAGTTTTAAATCAATCT
AAAGTATATATGAGTAAACTTGGTCTGACAGTTACCAATGCTTAATCAGTGAGGCACCTA
TCTCAGCGATCTGTCTATTTCGTTCATCCATAGTTGCCTGACTCCCCGTCGTGTAGATAA
CTACGATACGGGAGGGCTTACCATCTGGCCCCAGTGCTGCAATGATACCGCGAGACCC
ACGCTCACCGGCTCCAGATTTATCAGCAATAAACCAGCCAGCCGGAAGGGCCGAGCG
CAGAAGTGGTCCTGCAACTTTATCCGCCTCCATCCAGTCTATTAATTGTTGCCGGGAAG
CTAGAGTAAGTAGTTCGCCAGTTAATAGTTTGCGCAACGTTGTTGCCATTGCTACAGGC
ATCGTGGTGTCACGCTCGTCGTTTGGTATGGCTTCATTCAGCTCCGGTTCCCAACGATC
AAGGCGAGTTACATGATCCCCATGTTGTGCAAAAAGCGGTTAGCTCCTTCGGTCCTC
CGATCGTTGTCAGAAGTAAGTTGGCCGCAGTGTTATCACTCATGGTTATGGCAGCACTG
CATAATTCTCTTACTGTCATGCCATCCGTAAGATGCTTTTCTGTGACTGGTGAGTACTCA
ACCAAGTCATTCTGAGAATAGTGTATGCGGCGACCGAGTTGCTCTTGCCCGGCGTCAA
TACGGGATAATACCGCGCCACATAGCAGAACTTTAAAAGTGCTCATCATTGGAAAACGT
TCTTCGGGGCGAAAACTCTCAAGGATCTTACCGCTGTTGAGATCCAGTTCGATGTAACC
CACTCGTGCACCCAACTGATCTTCAGCATCTTTTACTTTCACCAGCGTTTCTGGGTGAG
CAAAAACAGGAAGGCAAAATGCCGCAAAAAGGGAATAAGGGCGACACGGAAATGTTG
AATACTCATACTCTTCCTTTTTCAATATTATTGAAGCATTTATCAGGGTTATTGTCTCATG
AGCGGATACATATTTGAATGTATTTAGAAAAATAAACAAATAGGGGTTCCGCGCACATTT
CCCCGAAAAGTGCCACCTGACGTCTAAGAAACCATTATTATCATGACATTAACCTATAAA
AATAGGCGTATCACGAGGCCCTTTCGTCTCGCGCGTTTCGGTGATGACGGTGAAAACC
TCTGACACATGCAGCTCCCGGAGACGGTCACAGCTTGTCTGTAAGCGGATGCCGGGA
GCAGACAAGCCCGTCAGGGCGCGTCAGCGGGTGTTGGCGGGTGTCGGGGCTGGCTT
AACTATGCGGCATCAGAGCAGATTGTACTGAGAGTGCACCATATGCGGTGTGAAATAC
CGCACAGATGCGTAAGGAGAAAATACCGCATCAGGAAATTGTAAACGTTAATATTTTGT
TAAAATTCGCGTTAAATTTTTGTTAAATCAGCTCATTTTTTAACCAATAGGCCGAAATCGG
CAAAATCCCTTATAAATCAAAAGAATAGACCGAGATAGGGTTGAGTGTTGTTCCAGTTTG
GAACAAGAGTCCACTATTAAAGAACGTGGACTCCAACGTCAAAGGGCGAAAAACCGTC
TATCAGGGCGATGGCCCACTACGTGAACCATCACCCTAATCAAGTTTTTTGGGGTCGAG
GTGCCGTAAAGCACTAAATCGGAACCCTAAAGGGAGCCCCCGATTTAGAGCTTGACGG
GGAAAGCCGGCGAACGTGGCGAGAAAGGAAGGGAAGAAAGCGAAAGGAGCGGGCGC
TAGGGCGCTGGCAAGTGTAGCGGTCACGCTGCGCGTAACCACCACACCCGCCGCGCT
TAATGCGCCGCTACAGGGCGCGTCGCGCCATTCGCCATTCAGGCTACGCAACTGTTGG
GAAGGGCGATCGGTGCGGGCCTCTTCGCTATTACGCCAGGCTGC
(SEQ ID NO: 1)

FIG. 3A (continued)

pTR22-APhead-APSA-otoferlinCT

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4095 | Otoferlin CT: | Otoferlin coding sequence 3' part |
| 4133-4354 | bGH PolyA: | bovine growth hormone polyadenylation signal |
| 4421-4563 | TR: | inverted terminal repeat sequence of AAV2 |
|  | ColE2: | replication origin for E. coli |
|  | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAGAGC
ATGGGACAGCAGGCCAAGAGCCTGAGGGCTCAGGTGAAGCGGCACACTGTTCGGGAC
AAGCTGAGGTCATGCCAGAACTTTCTGCAGAAGCTACGCTTCCTGGCGGATGAGCCCC
AGCACAGCATTCCTGATGTGTTCATTTGGATGATGAGCAACAACAAACGTATCGCCTAT
GCCCGCGTGCCTTCCAAAGACCTGCTCTTCTCCATCGTGGAGGAGGAACTGGGCAAG
GACTGCGCCAAAGTCAAGACCCTCTTCCTGAAGCTGCCAGGGAAGAGGGGCTTCGGC
TCGGCAGGCTGGACAGTACAGGCCAAGCTGGAGCTCTACCTGTGGCTGGGCCTCAGC
AAGCAGCGAAAGGACTTCCTGTGTGGTCTGCCCTGTGGCTTCGAGGAGGTCAAGGCA
GCCCAAGGCCTGGGCCTGCATTCCTTTCCGCCCATCAGCCTAGTCTACACCAAGAAGC
AAGCCTTCCAGCTCCGAGCACACATGTATCAGGCCCGAAGCCTCTTTGCTGCTGACAG
CAGTGGGCTCTCTGATCCCTTTGCCCGTGTCTTCTTCATCAACCAGAGCCAATGCACTG
AGGTTCTAAACGAGACACTGTGTCCCACCTGGGACCAGATGCTGGTATTTGACAACCT
GGAGCTGTACGGTGAAGCTCACGAGTTACGAGATGATCCCCCCATCATTGTCATTGAAA
TCTACGACCAGGACAGCATGGGCAAAGCCGACTTCATGGGCCGGACCTTCGCCAAGC
CCCTGGTGAAGATGGCAGATGAAGCATACTGCCCACCTCGCTTCCCGCCGCAGCTTGA
GTACTACCAGATCTACCGAGGCAGTGCCACTGCCGGAGACCTACTGGCTGCCTTCGAG
CTGCTGCAGATTGGGCCATCAGGGAAGGCTGACCTGCCACCCATCAATGGCCCAGTG
GACATGGACAGAGGGCCCATCATGCCTGTGCCCGTGGGAATCCGGCCAGTGCTCAGC
AAGTACCGAGTGGAGGTGCTGTTCTGGGGCCTGAGGGACCTAAAGAGGGTGAACCTG
GCCCAGGTGGACCGACCACGGGTGGACATCGAGTGTGCAGGAAAGGGGGTACAATCC
TCCCTGATTCACAATTATAAGAAGAACCCCAACTTCAACACGCTGGTCAAGTGGTTTGA
AGTGGACCTCCCGGAGAATGAGCTCCTGCACCCACCCTTGAACATCCGAGTGGTAGAT
TGCCGGGCCTTTGGACGATACACCCTGGTGGGTTCCCACGCAGTCAGCTCACTGAGG
CGCTTCATCTACCGACCTCCAGACCGCTCAGCCCCCAACTGGAACACCACAGGGGAG
GTTGTAGTAAGCATGGAGCCTGAGGAGCCAGTTAAGAAGCTGGAGACCATGGTGAAAC
TGGATGCGACTTCTGATGCTGTGGTCAAGGTGGATGTGGCTGAAGATGAGAAGGAAAG
GAAGAAGAAGAAAAAGAAAGGCCCGTCAGAGGAGCCAGAGGAGGAAGAGCCCGATGA
GAGCATGCTGGATTGGTGGTCCAAGTACTTCGCCTCCATCGACACAATGAAGGAGCAA
CTTCGACAACATGAGACCTCTGGAACTGACTTGGAAGAGAAGGAAGAGATGGAAAGCG
CTGAGGGCCTGAAGGGACCAATGAAGAGCAAGGAGAAGTCCAGAGCTGCAAAGGAGG
```

FIG. 3B

```
AGAAAAAGAAGAAAAACCAGAGCCCTGGCCCTGGCCAGGGATCGGAGGCTCCTGAGA
AGAAGAAAGCCAAGATCGATGAGCTTAAGGTGTACCCCAAGGAGCTGGAATCGGAGTT
TGACAGCTTTGAGGACTGGCTGCACACCTTCAACCTGTTGAGGGGCAAGACGGGAGAT
GATGAGGATGGCTCCACAGAGGAGGAGCGCATAGTAGGCCGATTCAAGGGCTCCCTC
TGTGTGTACAAAGTGCCACTCCCAGAAGATGTATCTCGAGAAGCTGGCTATGATCCAC
CTATGGAATGTTCCAGGGCATCCCAAGCAATGACCCCATCAATGTGCTGGTCCGAATCT
ATGTGGTCCGGGCCACAGACCTGCACCCGGCCGACATCAATGGCAAAGCTGACCCCT
ATATTGCCATCAAGTTAGGCAAGACCGACATCCGAGACAAGGAGAACTACATCTCCAAG
CAGCTCAACCCTGTGTTTGGGAAGTCCTTTGACATTGAGGCCTCCTTCCCCATGGAGTC
CATGTTGACAGTGGCCGTGTACGACTGGGATCTGGTGGGCACTGATGACCTCATCGGA
GAAACCAAGATTGACCTGGAAACCGCTTCTACAGCAAGCATCGCGCCACCTGCGGCA
TCGCACAGACCTATTCCATACATGGCTACAATATCTGGAGGGACCCCATGAAGCCCAG
CCAGATCCTGACACGCCTCTGTAAAGAGGGCAAAGTGGACGGCCCCCACTTTGGTCCC
CATGGGAGAGTGAGGGTTGCCAACCGTGTCTTCACGGGGCCTTCAGAAATAGAGGATG
AGAATGGTCAGAGGAAGCCCACAGATGAGCACGTGGCACTGTCTGCTCTGAGACACTG
GGAGGACATCCCCCGGGTGGGCTGCCGCCTTGTGCCGGAACACGTGGAGACCAGGC
CGCTGCTCAACCCTGACAAGCCAGGCATTGAGCAGGGCCGCCTGGAGCTGTGGGTGG
ACATGTTCCCCATGGACATGCCAGCCCTGGGACACCTCTGGATATATCCCCCAGGAA
ACCCAAGAAGTACGAGCTGCGGGTCATCGTGTGGAACACAGACGAGGTGGTCCTGGA
AGACGATGATTTCTTCACGGGAGAGAAGTCCAGTGACATTTTTGTGAGGGGGTGGCTG
AAGGGCCAGCAGGAGGACAAACAGGACACAGATGTCCACTATCACTCCCTCACGGGG
GAGGGCAACTTCAACTGGAGATACCTCTTCCCCTTCGACTACCTAGCGGCCGAAGAGA
AGATCGTTATGTCCAAAAAGGAGTCTATGTTCTCCTGGGATGAGACGGAGTACAAGATC
CCTGCGCGGCTCACCCTGCAGATCTGGGACGCTGACCACTTCTCGGCTGACGACTTCC
TGGGGGCTATCGAGCTGGACCTGAACCGGTTCCCGAGGGGCGCTAAGACAGCCAAGC
AGTGCACCATGGAGATGGCCACCGGGGAGGTGGACGTACCCCTGGTTTCCATCTTTAA
ACAGAAACGTGTCAAAGGCTGGTGGCCCCTCCTGGCCCGCAATGAGAATGATGAGTTT
GAGCTCACAGGCAAAGTGGAGGCGGAGCTACACCTACTCACGGCAGAGGAGGCAGAG
AAGAACCCTGTGGGCCTGGCTCGCAATGAACCTGATCCCCTAGAAAAACCCAACCGGC
CTGACACGGCATTCGTCTGGTTCCTGAACCCACTCAAATCTATCAAGTACCTCATCTGC
ACCCGGTACAAGTGGCTGATCATCAAGATCGTGCTGGCGCTGCTGGGGCTGCTCATGC
TGGCCCTCTTCCTTTACAGCCTCCCAGGCTACATGGTCAAGAAGCTCCTAGGGGCCTG
AGCGGCCGCGGTACCAAGGGCGAATTCTGCAGTCGACTAGAGCTCGCTGATCAGCCT
CGACTGTGCCTTCTAGTTGCCAGCCATCTGTTGTTTGCCCCTCCCCCGTGCCTTCCTTG
ACCCTGGAAGGTGCCACTCCCACTGTCCTTTCCTAATAAAATGAGGAAATTGCATCGCA
TTGTCTGAGTAGGTGTCATTCTATTCTGGGGGGTGGGGTGGGGCAGGACAGCAAGGG
GGAGGATTGGGAAGACAATAGCAGGCATGCTGGGGAGAGATCTGAGGACTAGTCCGT
CGACTGTTAATTAAGCATGCTGGGGAGAGATCTAGGAACCCCTAGTGATGGAGTTGGC
CACTCCCTCTCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAG
TGGCCAACCCCCCCCCCCCCCCCCTGCAGCCCTGCATTAATGAATCGGCCAACGCG
CGGGGAGAGGCGGTTTGCGTATTGGGCGCTCTTCCGCTTCCTCGCTCACTGACTCGCT
GCGCTCGGTCGTTCGGCTGCGGCGAGCGGTATCAGCTCACTCAAAGGCGGTAATACG
GTTATCCACAGAATCAGGGGATAACGCAGGAAAGAACATGTGAGCAAAAGGCCAGCAA
AAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACT
ATAAAGATACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGCGCTTTCTC
AATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTT
GAGTCCAACCCGGTAAGACACGACTTATCGCCACTGGCAGCAGCCACTGGTAACAGGA
TTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCG
```

FIG. 3B (continued)

```
GAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAAAT
CAATCTAAAGTATATATGAGTAAACTTGGTCTGACAGTTACCAATGCTTAATCAGTGAGG
CACCTATCTCAGCGATCTGTCTATTTCGTTCATCCATAGTTGCCTGACTCCCCGTCGTG
TAGATAACTACGATACGGGAGGGCTTACCATCTGGCCCCAGTGCTGCAATGATACCGC
GAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCC
GGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCC
AACGATCAAGGCGAGTTACATGATCCCCATGTTGTGCAAAAAAGCGGTTAGCTCCTTC
GGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGA
GTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTG
TCTCATGAGCGGATACATATTTGAATGTATTTAGAAAAATAAACAAATAGGGGTTCCGCG
CACATTTCCCCGAAAAGTGCCACCTGACGTCTAAGAAACCATTATTATCATGACATTAAC
CTATAAAAATAGGCGTATCACGAGGCCCTTTCGTCTCGCGCGTTTCGGTGATGACGGT
GAAAACCTCTGACACATGCAGCTCCCGGAGACGGTCACAGCTTGTCTGTAAGCGGATG
CCGGGAGCAGACAAGCCCGTCAGGGCGCGTCAGCGGGTGTTGGCGGGTGTCGGGGC
TGGCTTAACTATGCGGCATCAGAGCAGATTGTACTGAGAGTGCACCATATGCGGTGTG
AAATACCGCACAGATGCGTAAGGAGAAAATACCGCATCAGGAAATTGTAAACGTTAATA
TTTTGTTAAAATTCGCGTTAAATTTTGTTAAATCAGCTCATTTTTTAACCAATAGGCCGA
AATCGGCAAAATCCCTTATAAATCAAAAGAATAGACCGAGATAGGGTTGAGTGTTGTTC
CAGTTTGGAACAAGAGTCCACTATTAAAGAACGTGGACTCCAACGTCAAAGGGCGAAAA
ACCGTCTATCAGGGCGATGGCCCACTACGTGAACCATCACCCTAATCAAGTTTTTTGGG
GTCGAGGTGCCGTAAAGCACTAAATCGGAACCCTAAAGGGAGCCCCCGATTTAGAGCT
TGACGGGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCACACCCGC
CGCGCTTAATGCGCCGCTACAGGGCGCGTCGCGCCATTCGCCATTCAGGCTACGCAA
CTGTTGGGAAGGGCGATCGGTGCGGGCCTCTTCGCTATTACGCCAGGCTGC
(SEQ ID NO: 2)
```

FIG. 3B (continued)

pTR22-smCBA-otoferlinNT Hs var 1+5-APSD-APhead

| Nucleotide positions | Abbreviation | Description |
|---|---|---|
| 20-162 | TR: | inverted terminal repeat sequence of AAV2 |
| 186-440 | CBA promoter: | -CMVie enhancer |
| 441-835 | | -chicken b-actin promoter |
| 836-1130 | | -Exon1 and chimeric intron |
| 1153-3558 | Otoferlin NT: | Otoferlin coding sequence 5' part |
| 3559-3642 | APSD: | Splice Donor |
| 3649-3935 | APhead: | homologous sequence for recombination |
| 3975-4117 | TR: | inverted terminal repeat sequence of AAV2 |
| | ColE2: | replication origin for E. coli |
| | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTCGGTACCCTAGTTATTAATAGTAATCAATTACGGGGTCATTAGT
TCATAGCCCATATATGGAGTTCCGCGTTACATAACTTACGGTAAATGGCCCGCCTGGCT
GACCGCCCAACGACCCCCGCCCATTGACGTCAATAATGACGTATGTTCCCATAGTAAC
GCCAATAGGGACTTTCCATTGACGTCAATGGGTGGACTATTTACGGTAAACTGCCCACT
TGGCAGTACATCAAGTGTATCATATGCCAAGTACGCCCCCTATTGACGTCAATGACGGT
AAATGGCCCGCCTGGCATTATGCCCAGTACATGACCTTATGGGACTTTCCTACTTGGCA
GTACATCTACGTATTAGTCATCGCTATTACCATGGTCGAGGTGAGCCCCACGTTCTGCT
TCACTCTCCCCATCTCCCCCCCCTCCCCACCCCCAATTTTGTATTTATTTATTTTTAATT
ATTTTGTGCAGCGATGGGGGCGGGGGGGGGGGGGGCGCGCGCCAGGCGGGGCG
GGGCGGGGCGAGGGGCGGGGCGGGGCGAGGCGGAGAGGTGCGGCGGCAGCCAATC
AGAGCGGCGCGCTCCGAAAGTTTCCTTTTATGGCGAGGCGGCGGCGGCGGCGGCCCT
ATAAAAAGCGAAGCGCGCGGCGGGCGGGAGTCGCTGCGACGCTGCCTTCGCCCCGT
GCCCCGCTCCGCCGCCGCCTCGCGCCGCCCGCCCCGGCTCTGACTGACCGCGTTACT
CCCACAGGTGAGCGGGCGGGACGGCCCTTCTCCTCCGGGCTGTAATTAGCGCTTGGT
TTAATGACGGCTTGTTTCTTTTCTGTGGCTGCGTGAAAGCCTTGAGGGGCTCCGGGAG
CTAGAGCCTCTGCTAACCATGTTCATGCCTTCTTCTTTTTCCTACAGCTCCTGGGCAAC
GTGCTGGTTATTGTGCTGTCTCATCATTTTGGCAAAGAATTCTAGCGGCCGCCACCATG
GCCTTGCTCATCCACCTCAAGACAGTCTCGGAGCTGCGGGGCAGGGCGACCGGATC
GCCAAAGTGACTTTCCGAGGGCAATCCTTCTACTCTCGGGTCCTGGAGAACTGTGAGG
ATGTGGCTGACTTTGATGAGACATTTCGGTGGCCGGTGGCCAGCAGCATCGACAGAAA
TGAGATGCTGGAGATTCAGGTTTTCAACTACAGCAAAGTCTTCAGCAACAAGCTCATCG
GGACCTTCCGCATGGTGCTGCAGAAGGTGGTAGAGGAGAGCCATGTGGAGGTGACTG
ACACGCTGATTGATGACAACAATGCTATCATCAAGACCAGCCTGTGCGTGGAGGTCCG
GTATCAGGCCACTGACGGCACAGTGGGCTCCTGGGACGATGGGGACTTCCTGGGAGA
TGAGTCTCTTCAAGAGGAAGAGAAGGACAGCCAAGAGACGGATGGACTGCTCCCAGG
CTCCCGGCCCAGCTCCCGGCCCCCAGGAGAGAAGAGCTTCCGGAGAGCCGGGAGGA
GCGTGTTCTCCGCCATGAAGCTCGGCAAAAACCGGTCTCACAAGGAGGAGCCCCAAAG
ACCAGATGAACCGGCGGTGCTGGAGATGGAAGACCTTGACCATCTGGCCATTCGGCTA
GGAGATGGACTGGATCCCGACTCGGTGTCTCTAGCCTCAGTCACAGCTCTCACCACTA
ATGTCTCCAACAAGCGATCTAAGCCAGACATTAAGATGGAGCCAAGTGCTGGGCGGCC
CATGGATTACCAGGTCAGCATCACGGTGATCGAGGCCCGGCAGCTGGTGGGCTTGAA
CATGGACCCTGTGGTGTGCGTGGAGGTGGGTGACGACAAGAAGTACACATCCATGAAG
GAGTCCACTAACTGCCCCTATTACAACGAGTACTTCGTCTTCGACTTCCATGTCTCTCC
GGATGTCATGTTTGACAAGATCATCAAGATTTCGGTGATTCACTCCAAGAACCTGCTGC
GCAGTGGCACCCTGGTGGGCTCCTTCAAAATGGACGTGGGAACCGTGTACTCGCAGC
CAGAGCACCAGTTCCATCACAAGTGGGCCATCCTGTCTGACCCCGATGACATCTCCTC
```

```
GGGGCTGAAGGGCTACGTGAAGTGTGACGTTGCCGTGGTGGGCAAAGGGGACAACAT
CAAGACGCCCCACAAGGCCAATGAGACCGACGAAGATGACATTGAGGGGAACTTGCTG
CTCCCCGAGGGGGTGCCCCCCGAACGCCAGTGGGCCCGGTTCTATGTGAAAATTTAC
CGAGCAGAGGGGCTGCCCCGTATGAACACAAGCCTCATGGCCAATGTAAAGAAGGCTT
TCATCGGTGAAAACAAGGACCTCGTGGACCCCTACGTGCAAGTCTTCTTTGCTGGCCA
GAAGGGCAAGACTTCAGTGCAGAAGAGCAGCTATGAGCCCCTGTGGAATGAGCAGGT
CGTCTTTACAGACCTCTTCCCCCACTCTGCAAACGCATGAAGGTGCAGATCCGAGACT
CGGACAAGGTCAACGACGTGGCCATCGGCACCCACTTCATTGACCTGCGCAAGATTTC
TAATGACGGAGACAAAGGCTTCCTGCCCACACTGGGCCCAGCCTGGGTGAACATGTAC
GGCTCCACACGTAACTACACGCTGCTGGATGAGCATCAGGACCTGAACGAGGGCCTG
GGGGAGGGTGTGTCCTTCCGGGCCCGGCTCCTGCTGGGCCTGGCTGTGGAGATCGTA
GACACCTCCAACCCTGAGCTCACCAGCTCCACAGAGGTGCAGGTGGAGCAGGCCACG
CCCATCTCGGAGAGCTGTGCAGGTAAAATGGAAGAATTCTTTCTCTTTGGAGCCTTCCT
GGAGGCCTCAATGATCGACCGGAGAAACGGAGACAAGCCCATCACCTTTGAGGTCACC
ATAGGCAACTATGGGAACGAAGTTGATGGCCTGTCCCGGCCCCAGCGGCCTCGGCCC
CGGAAGGAGCCGGGGGATGAGGAAGAAGTAGACCTGATTCAGAACGCAAGTGATGAC
GAGGCCGGTGATGCCGGGGACCTGGCCTCAGTCTCCTCCACTCCACCAATGCGGCCC
CAGGTCACCGACAGGAACTACTTCCATCTGCCCTACCTGGAGCGAAAGCCCTGCATCT
ACATCAAGAGCTGGTGGCCGGACCAGCGCCGCCGCCTCTACAATGCCAACATCATGGA
CCACATTGCCGACAAGCTGGAAGAAGGCCTGAACGACATACAGGAGATGATCAAAACG
GAGAAGTCCTACCCTGAGCGTCGCCTGCGGGGCGTCCTGGAGGAGCTGAGCTGTGGC
TGCTGCCGCTTCCTCTCCCTCGCTGACAAGGACCAGGGCCACTCATCCCGCACCAGGC
TTGACCGGGAGCGCCTCAAGTCCTGCATGAGGGAGCTGGTAAGTATCAAGGTTACAAG
ACAGGTTTAAGGAGACCAATAGAAACTGGGCTTGTCGAGACAGAGAAGACTCTTGCGT
TTCTGAGCTAGCCCCCGGGTGCGCGGCGTCGGTGGTGCCGGCGGGGGCGCCAGGT
CGCAGGCGGTGTAGGGCTCCAGGCAGGCGGCGAAGGCCATGACGTGCGCTATGAAG
GTCTGCTCCTGCACGCCGTGAACCAGGTGCGCCTGCGGGCCGCGCGCGAACACCGC
CACGTCCTCGCCTGCGTGGGTCTCTTCGTCCAGGGGCACTGCTGACTGCTGCCGATAC
TCGGGGCTCCCGCTCTCGCTCTCGGTAACATCCGGCCGGGCGCCGTCCTTGAGCACA
TAGCCTGGACCGTTTCGTCGACTGTTAATTAAGCATGCTGGGGAGAGATCTAGGAACC
CCTAGTGATGGAGTTGGCCACTCCCTCTCTGCGCGCTCGCTCGCTCACTGAGGCCGCC
CGGGCAAAGCCCGGGCGTCGGGCGACCTTTGGTCGCCCGGCCTCAGTGAGCGAGCG
AGCGCGCAGAGAGGGAGTGGCCAACCCCCCCCCCCCCCCCCTGCAGCCCTGCATTA
ATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTT
TCCATAGGCTCCGCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTT
CGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAG
CAGCCACTGGTAACAGGATTAGCAGAGCGAGGTATGTAGGCGGTGCTACAGAGTTCTT
GAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCAC
CGCTGGTAGCGGTGGTTTTTTGTTTGCAAGCAGCAGATTACGCGCAGAAAAAAGGAT
CTCAAGAAGATCCTTTGATCTTTTCTACGGGGTCTGACGCTCAGTGGAACGAAAACTCA
CGTTAAGGGATTTTGGTCATGAGATTATCAAAAAGGATCTTCACCTAGATCCTTTTAAAT
TAAAAATGAAGTTTTAAATCAATCTAAAGTATATATGAGTAAACTTGGTCTGACAGTTACC
AATGCTTAATCAGTGAGGCACCTATCTCAGCGATCTGTCTATTTCGTTCATCCATAGTTG
CCTGACTCCCCGTCGTGTAGATAACTACGATACGGGAGGGCTTACCATCTGGCCCCAG
TGCTGCAATGATACCGCGAGACCCACGCTCACCGGCTCCAGATTTATCAGCAATAAAC
```

FIG. 13 (continued)

```
CAGCCAGCCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAATAGTTTGCG
CAACGTTGTTGCCATTGCTACAGGCATCGTGGTGTCACGCTCGTCGTTTGGTATGGCTT
CATTCAGCTCCGGTTCCCAACGATCAAGGCGAGTTACATGATCCCCATGTTGTGCAAA
AAAGCGGTTAGCTCCTTCGGTCCTCCGATCGTTGTCAGAAGTAAGTTGGCCGCAGTGT
TATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGA
CCGAGTTGCTCTTGCCCGGCGTCAATACGGGATAATACCGCGCCACATAGCAGAACTT
TAAAAGTGCTCATCATTGGAAAACGTTCTTCGGGGCGAAAACTCTCAAGGATCTTACCG
CTGTTGAGATCCAGTTCGATGTAACCCACTCGTGCACCCAACTGATCTTCAGCATCTTT
TACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTATTGA
AGCATTTATCAGGGTTATTGTCTCATGAGCGGATACATATTTGAATGTATTTAGAAAAAT
AAACAAATAGGGGTTCCGCGCACATTTCCCCGAAAAGTGCCACCTGACGTCTAAGAAA
CCATTATTATCATGACATTAACCTATAAAAATAGGCGTATCACGAGGCCCTTTCGTCTCG
CGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGG
TGTTGGCGGGTGTCGGGGCTGGCTTAACTATGCGGCATCAGAGCAGATTGTACTGAGA
GTGCACCATATGCGGTGTGAAATACCGCACAGATGCGTAAGGAGAAAATACCGCATCA
GGAAATTGTAAACGTTAATATTTTGTTAAAATTCGCGTTAAATTTTTGTTAAATCAGCTCA
TTTTTTAACCAATAGGCCGAAATCGGCAAAATCCCTTATAAATCAAAAGAATAGACCGAG
ATAGGGTTGAGTGTTGTTCCAGTTTGGAACAAGAGTCCACTATTAAAGAACGTGGACTC
CAACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGC
GCGTAACCACCACACCCGCCGCGCTTAATGCGCCGCTACAGGGCGCGTCGCGCCATT
CGCCATTCAGGCTACGCAACTGTTGGGAAGGGCGATCGGTGCGGGCCTCTTCGCTATT
ACGCCAGGCTGC
(SEQ ID NO: 14)
```

FIG. 13 (continued)

pTR22-APhead-APSA-otoferlinCT Hs var 1

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | Otoferlin CT: | Otoferlin coding sequence 3' part |
| 4190-4411 | bGH PolyA: | bovine growth hormone polyadenylation signal |
| 4478-4620 | TR: | inverted terminal repeat sequence of AAV2 |
| | ColE2: | replication origin for E. coli |
| | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAC
ATGGGGCAGCAGGCCAGGATGCTGCGGGCCCAGGTGAAGCGGCACACGGTGCGGGA
CAAGCTGAGGCTGTGCCAGAACTTCCTGCAGAAGCTGCGCTTCCTGGCGGACGAGCC
CCAGCACAGCATTCCCGACATCTTCATCTGGATGATGAGCAACAACAAGCGTGTCGCC
TATGCCCGTGTGCCCTCCAAGGACCTGCTCTTCTCCATCGTGGAGGAGGAGACTGGCA
AGGACTGCGCCAAGGTCAAGACGCTCTTCCTTAAGCTGCCAGGGAAGCGGGGCTTCG
GCTCGGCAGGCTGGACAGTGCAGGCCAAGGTGGAGCTGTACCTGTGGCTGGGCCTCA
GCAAACAGCGCAAGGAGTTCCTGTGCGGCCTGCCCTGTGGCTTCCAGGAGGTCAAGG
CAGCCCAGGGCCTGGGCCTGCATGCCTTCCCACCCGTCAGCCTGGTCTACACCAAGA
AGCAGGCGTTCCAGCTCCGAGCGCACATGTACCAGGCCCGCAGCCTCTTTGCCGCCG
ACAGCAGCGGACTCTCAGACCCCTTTGCCCGCGTCTTCTTCACAATCAGAGTCAGTGC
ACAGAGGTGCTGAATGAGACCCTGTGTCCCACCTGGGACCAGATGCTGGTGTTCGACA
ACCTGGAGCTCTATGGTGAAGCTCATGAGCTGAGGGACGATCCGCCCATCATTGTCAT
TGAAATCTATGACCAGGATTCCATGGGCAAAGCTGACTTCATGGGCCGTGACCTTCGC
CAAACCCCTGGTGAAGATGGCAGACGAGGCGTACTGCCCACCCCGCTTCCCACCTCA
GCTCGAGTACTACCAGATCTACCGTGGCAACGCCACAGCTGGAGACCTGCTGGCGGC
CTTCGAGCTGCTGCAGATTGGACCAGCAGGGAAGGCTGACCTGCCCCCATCAATGG
CCCGGTGGACGTGGACCGAGGTCCCATCATGCCCGTGCCCATGGGCATCCGGCCCGT
GCTCAGCAAGTACCGAGTGGAGGTGCTGTTCTGGGGCCTACGGGACCTAAAGCGGGT
GAACCTGGCCCAGGTGGACCGGCCACGGGTGGACATCGAGTGTGCAGGGAAGGGGG
TGCAGTCGTCCCTGATCCACAATTATAAGAAGAACCCCAACTTCAACACCCTCGTCAAG
TGGTTTGAAGTGGACCTCCCAGAGAACGAGCTGCTGCACCCGCCCTTGAACATCCGTG
TGGTGGACTGCCGGGCCTTCGGTCGCTACACACTGGTGGGCTCCATGCCGTCAGCT
CCCTGCGACGCTTCATCTACCGGCCCCAGACCGCTCGGCCCCAGCTGGAACACCA
CGGTCAGGCTTCTCCGGCGCTGCCGTGTGCTGTGCAATGGGGGCTCCTCCTCTCACTC
CACAGGGGAGGTTGTGGTGACTATGGAGCCAGAGGTACCCATCAAGAAACTGGAGAC
CATGGTGAAGCTGGACGCGACTTCTGAAGCTGTTGTCAAGGTGGATGTGGCTGAGGAG
GAGAAGGAGAAGAAGAAGAAGAAGGGCACTGCGGAGGAGCCAGAGGAGGAGGA
GCCAGACGAGAGCATGCTGGACTGGTGGTCCAAGTACTTTGCCTCCATTGACACCATG
AAGGAGCAACTTCGACAACAAGAGCCCTCTGGAATTGACTTGGAGGAGAAGGAGGAAG
TGGACAATACCGAGGGCCTGAAGGGGTCAATGAAGGGCAAGGAGAAGGCAAGGGCTG
CCAAAGAGGAGAAGAAGAAGAAAACTCAGAGCTCTGGCTCTGGCCAGGGGTCCGAGG
```

FIG. 14

```
CCCCCGAGAAGAAGAAACCCAAGATTGATGAGCTTAAGGTATACCCCAAAGAGCTGGA
GTCCGAGTTTGATAACTTTGAGGACTGGCTGCACACTTTCAACTTGCTTCGGGGCAAGA
CCGGGGATGATGAGGATGGCTCCACCGAGGAGGAGCGCATTGTGGGACGCTTCAAGG
GCTCCCTCTGCGTGTACAAAGTGCCACTCCCAGAGGACGTGTCCCGGGAAGCCGGCT
ACGACTCCACCTACGGCATGTTCCAGGGCATCCCGAGCAATGACCCCATCAATGTGCT
GGTCCGAGTCTATGTGGTCCGGGCCACGGACCTGCACCCTGCTGACATCAACGGCAA
AGCTGACCCCTACATCGCCATCCGGCTAGGCAAGACTGACATCCGCGACAAGGAGAAC
TACATCTCCAAGCAGCTCAACCCTGTCTTTGGGAAGTCCTTTGACATCGAGGCCTCCTT
CCCCATGGAATCCATGCTGACGGTGGCTGTGTATGACTGGGACCTGGTGGGCACTGAT
GACCTCATTGGGGAAACCAAGATCGACCTGGAGAACCGCTTCTACAGCAAGCACCGCG
CCACCTGCGGCATCGCCCAGACCTACTCCACACATGGCTACAATATCTGGCGGGACCC
CATGAAGCCCAGCCAGATCCTGACCCGCCTCTGCAAAGACGGCAAAGTGGACGGCCC
CCACTTTGGGCCCCTGGGAGAGTGAAGGTGGCCAACCGCGTCTTCACTGGGCCCTC
TGAGATTGAGGACGAGAACGGTCAGAGGAAGCCCACAGACGAGCATGTGGCGCTGTT
GGCCCTGAGGCACTGGGAGGACATCCCCGCGCAGGCTGCCGCCTGGTGCCAGAGC
ATGTGGAGACGAGGCCGCTGCTCAACCCCGACAAGCCGGGCATCGAGCAGGGCCGC
CTGGAGCTGTGGGTGGACATGTTCCCCATGGACATGCCAGCCCCTGGGACGCCTCTG
GACATCTCACCTCGGAAGCCCAAGAAGTACGAGCTGCGGGTCATCATCTGGAACACAG
ATGAGGTGGTCTTGGAGGACGACGACTTCTTCACAGGGGAGAAGTCCAGTGACATCTT
CGTGAGGGGGTGGCTGAAGGGCCAGCAGGAGGACAAGCAGGACACAGACGTCCACTA
CCACTCCCTCACTGGCGAGGGCAACTTCAACTGGCGCTACCTGTTCCCCTTCGACTAC
CTGGCGGCGGAGGAGAAGATCGTCATCTCCAAGAAGGAGTCCATGTTCTCCTGGGAC
GAGACCGAGTACAAGATCCCCGCGCGGCTCACCCTGCAGATCTGGGATGCGGACCAC
TTCTCCGCTGACGACTTCCTGGGGGCCATCGAGCTGGACCTGAACCGGTTCCCGCGG
GGCGCAAAGACAGCCAAGCAGTGCACCATGGAGATGGCCACCGGGGAGGTGGACGT
GCCCCTCGTGTCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAGCTGCATTTAC
TGACAGCAGAGGAGGCAGAGAAGAACCCAGTGGGCCTGGCCCGCAATGAACCTGACC
CCCTAGAGAAACCCAACCGGCCCGACACGAGCTTCATCTGGTTCCTGAACCCTCTCAA
GTCGGCTCGCTACTTCTTGTGGCACACGTATCGCTGGCTGCTCCTCAAACTGTTGCTG
CTCCTGCTGCTGCTCCTCCTCCTCGCCCTGTTCCTCTACTCTGTGCCTGGCTACCTGGT
CAAGAAAATCCTCGGGGCCTGAGCGGCCGCGGTACCAAGGGCGAATTCTGCAGTCGA
CTAGAGCTCGCTGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCTGGGGA
GAGATCTGAGGACTAGTCCGTCGACTGTTAATTAAGCATGCTGGGGAGAGATCTAGGA
ACCCCTAGTGATGGAGTTGGCCACTCCCTCTCTGCGCGCTCGCTCGCTCACTGAGGCC
GCCCGGGCAAAGCCCGGGCGTCGGGCGACCTTTGGTCGCCCGGCCTCAGTGAGCGA
GCGAGCGCGCAGAGAGGGAGTGGCCAACCCCCCCCCCCCCCCCCTGCAGCCCTGC
ATTAATGAATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCTGGC
GTTTTTCCATAGGCTCCGCCCCCTGACGAGCATCACAAAAATCGACGCTCAAGTCAGA
GGTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTT
CGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTT
CTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACC
```

FIG. 14 (continued)

ACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTCTAAGA
AACCATTATTATCATGACATTAACCTATAAAAATAGGCGTATCACGAGGCCCTTTCGTCT
CGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGATTGTACTGA
GAGTGCACCATATGCGGTGTGAAATACCGCACAGATGCGTAAGGAGAAAATACCGCAT
CAGGAAATTGTAAACGTTAATATTTTGTTAAAATTCGCGTTAAATTTTGTTAAATCAGCT
CATTTTTTAACCAATAGGCCGAAATCGGCAAAATCCCTTATAAATCAAAAGAATAGACCG
AGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCAT
CACCCTAATCAAGTTTTTTGGGGTCGAGGTGCCGTAAAGCACTAAATCGGAACCCTAAA
GGGAGCCCCCGATTTAGAGCTTGACGGGGAAAGCCGGCGAACGTGGCGAGAAGGAA
GGGAAGAAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGTCGCGCCA
TTCGCCATTCAGGCTACGCAACTGTTGGGAAGGGCGATCGGTGCGGGCCTCTTCGCTA
TTACGCCAGGCTGC
(SEQ ID NO: 15)

FIG. 14 (continued)

pTR22-APhead-APSA-otoferlinCT Hs var 5

| Nucleotide positions | Abbreviation | Description |
|---|---|---|
| 20-162 | TR: | inverted terminal repeat sequence of AAV2 |
| 207-493 | APhead: | homologous sequence for recombination |
| 516-564 | APSA: | Splice Acceptor |
| 565-4152 | Otoferlin CT: | Otoferlin coding sequence 3' part |
| 4190-4411 | bGH PolyA: | bovine growth hormone polyadenylation signal |
| 4478-4620 | TR: | inverted terminal repeat sequence of AAV2 |
|  | ColE2: | replication origin for E. coli |
|  | Amp r: | beta-lactamase gene = Ampicillin resistance |

```
AGGGGGGGGGGGGGGGGGGTTGGCCACTCCCTCTCTGCGCGCTCGCTCGCTCACTG
AGGCCGGGCGACCAAAGGTCGCCCGACGCCCGGGCTTTGCCCGGGCGGCCTCAGTG
AGCGAGCGAGCGCGCAGAGAGGGAGTGGCCAACTCCATCACTAGGGGTTCCTCAGAT
CTGGCGCGCCCAATTGGCTTCGAATTCTAGCGGCCGCCCCGGGTGCGCGGCGTCGG
TGGTGCCGGCGGGGGGCGCCAGGTCGCAGGCGGTGTAGGGCTCCAGGCAGGCGGC
GAAGGCCATGACGTGCGCTATGAAGGTCTGCTCCTGCACGCCGTGAACCAGGTGCGC
CTGCGGGCCGCGCGCGAACACCGCCACGTCCTCGCCTGCGTGGGTCTCTTCGTCCAG
GGGCACTGCTGACTGCTGCCGATACTCGGGGCTCCCGCTCTCGCTCTCGGTAACATCC
GGCCGGGCGCCGTCCTTGAGCACATAGCCTGGACCGTTTCCTTAAGCGACGCATGCTC
GCGATAGGCACCTATTGGTCTTACTGACATCCACTTTGCCTTTCTCTCCACAGGAAAAC
ATGGGGCAGCAGGCCAGGATGCTGCGGGCCCAGGTGAAGCGGCACACGGTGCGGGA
CAAGCTGAGGCTGTGCCAGAACTTCCTGCAGAAGCTGCGCTTCCTGGCGGACGAGCC
CCAGCACAGCATTCCCGACATCTTCATCTGGATGATGAGCAACAACAAGCGTGTCGCC
TATGCCCGTGTGCCCTCCAAGGACCTGCTCTTCTCCATCGTGGAGGAGGAGACTGGCA
AGGACTGCGCCAAGGTCAAGACGCTCTTCCTTAAGCTGCCAGGGAAGCGGGGCTTCG
GCTCGGCAGGCTGGACAGTGCAGGCCAAGGTGGAGCTGTACCTGTGGCTGGGCCTCA
GCAAACAGCGCAAGGAGTTCCTGTGCGGCCTGCCCTGTGGCTTCCAGGAGGTCAAGG
CAGCCCAGGGCCTGGGCCTGCATGCCTTCCCACCCGTCAGCCTGGTCTACACCAAGA
AGCAGGCGTTCCAGCTCCGAGCGCACATGTACCAGGCCCGCAGCCTCTTTGCCGCCG
ACAGCAGCGGACTCTCAGACCCCTTTGCCCGCGTCTTCTTCATCAATCAGAGTCAGTG
CACAGAGGTGCTGAATGAGACCCTGTGTCCCACCTGGGACCAGATGCTGGTGTTCGAC
AACCTGGAGCTCTATGGTGAAGCTCATGAGCTGAGGGACGATCCGCCCATCATTGTCA
TTGAAATCTATGACCAGGATTCCATGGGCAAAGCTGACTTCATGGGCCGGACCTTCGC
CAAACCCCTGGTGAAGATGGCAGACGAGGCGTACTGCCCACCCCGCTTCCCACCTCA
GCTCGAGTACTACCAGATCTACCGTGGCAACGCCACAGCTGGAGACCTGCTGGCGGC
CTTCGAGCTGCTGCAGATTGGACCAGCAGGGAAGGCTGACCTGCCCCCCATCAATGG
CCCGGTGGACGTGGACCGAGGTCCCATCATGCCCGTGCCCATGGGCATCCGGCCCGT
GCTCAGCAAGTACCGAGTGGAGGTGCTGTTCTGGGGCCTACGGGACCTAAAGCGGGT
GAACCTGGCCCAGGTGGACCGGCCACGGGTGGACATCGAGTGTGCAGGGAAGGGGG
TGCAGTCGTCCCTGATCCACAATTATAAGAAGAACCCCAACTTCAACACCCTCGTCAAG
TGGTTTGAAGTGGACCTCCCAGAGAACGAGCTGCTGCACCCGCCCTTGAACATCCGTG
TGGTGGACTGCCGGGCCTTCGGTCGCTACACACTGGTGGGCTCCATGCCGTCAGCT
CCCTGCGACGCTTCATCTACCGGCCCCAGACCGCTCGGCCCCAGCTGGAACACCA
CGGTCAGGCTTCTCCGGCGCTGCCGTGTGCTGTGCAATGGGGCTCCTCCTCTCACTC
CACAGGGGAGGTTGTGGTGACTATGGAGCCAGAGGTACCCATCAAGAAACTGGAGAC
CATGGTGAAGCTGGACGCGACTTCTGAAGCTGTTGTCAAGGTGGATGTGGCTGAGGAG
GAGAAGGAGAAGAAGAAGAAGAAGGGCACTGCGGAGGAGCCAGAGGAGGAGGA
GCCAGACGAGAGCATGCTGGACTGGTGGTCCAAGTACTTTGCCTCCATTGACACCATG
AAGGAGCAACTTCGACAACAAGAGCCCTCTGGAATTGACTTGGAGGAGAAGGAGGAAG
TGGACAATACCGAGGGCCTGAAGGGGTCAATGAAGGGCAAGGAGAAGGCAAGGGCTG
CCAAAGAGGAGAAGAAGAAGAAAACTCAGAGCTCTGGCTCTGGCCAGGGGTCCGAGG
```

FIG. 15

```
CCCCCGAGAAGAAGAAACCCAAGATTGATGAGCTTAAGGTATACCCCAAAGAGCTGGA
GTCCGAGTTTGATAACTTTGAGGACTGGCTGCACACTTTCAACTTGCTTCGGGGCAAGA
CCGGGGATGATGAGGATGGCTCCACCGAGGAGGAGCGCATTGTGGGACGCTTCAAGG
GCTCCCTCTGCGTGTACAAAGTGCCACTCCCAGAGGACGTGTCCCGGGAAGCCGGCT
ACGACTCCACCTACGGCATGTTCCAGGGCATCCCGAGCAATGACCCCATCAATGTGCT
GGTCCGAGTCTATGTGGTCCGGGCCACGGACCTGCACCCTGCTGACATCAACGGCAA
AGCTGACCCCTACATCGCCATCCGGCTAGGCAAGACTGACATCCGCGACAAGGAGAAC
TACATCTCCAAGCAGCTCAACCCTGTCTTTGGGAAGTCCTTTGACATCGAGGCCTCCTT
CCCCATGGAATCCATGCTGACGGTGGCTGTGTATGACTGGGACCTGGTGGGCACTGAT
GACCTCATTGGGGAAACCAAGATCGACCTGGAGAACCGCTTCTACAGCAAGCACCGCG
CCACCTGCGGCATCGCCCAGACCTACTCCACACATGGCTACAATATCTGGCGGGACCC
CATGAAGCCCAGCCAGATCCTGACCCGCCTCTGCAAAGACGGCAAAGTGGACGGCCC
CCACTTTGGGCCCCTGGGAGAGTGAAGGTGGCCAACCGCGTCTTCACTGGGCCCTC
TGAGATTGAGGACGAGAACGGTCAGAGGAAGCCCACAGACGAGCATGTGGCGCTGTT
GGCCCTGAGGCACTGGGAGGACATCCCCGCGCAGGCTGCCGCCTGGTGCCAGAGC
ATGTGGAGACGAGGCCGCTGCTCAACCCCGACAAGCCGGGCATCGAGCAGGGCCGC
CTGGAGCTGTGGGTGGACATGTTCCCCATGGACATGCCAGCCCCTGGGACGCCTCTG
GACATCTCACCTCGGAAGCCCAAGAAGTACGAGCTGCGGGTCATCATCTGGAACACAG
ATGAGGTGGTCTTGGAGGACGACGACTTCTTCACAGGGGAGAAGTCCAGTGACATCTT
CGTGAGGGGGTGGCTGAAGGGCCAGCAGGAGGACAAGCAGGACACAGACGTCCACTA
CCACTCCCTCACTGGCGAGGGCAACTTCAACTGGCGCTACCTGTTCCCCTTCGACTAC
CTGGCGGCGGAGGAGAAGATCGTCATCTCCAAGAAGGAGTCCATGTTCTCCTGGGAC
GAGACCGAGTACAAGATCCCCGCGCGGCTCACCCTGCAGATCTGGGATGCGGACCAC
TTCTCCGCTGACGACTTCCTGGGGGCCATCGAGCTGGACCTGAACCGGTTCCCGCGG
GGCGCAAAGACAGCCAAGCAGTGCACCATGGAGATGGCCACCGGGGAGGTGGACGT
GCCCCTCGTGTCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAGCTGCATTTAC
TGACAGCAGAGGAGGCAGAGAAGAACCCAGTGGGCCTGGCCCGCAATGAACCTGACC
CCCTAGAGAAACCCAACCGGCCCGACACGGCCTTCGTCTGGTTCCTCAACCCTCTCAA
GTCCATCAAGTACCTCATCTGCACCCGGTACAAGTGGCTCATCATCAAGATCGTGCTGG
CGCTGTTGGGGCTGCTCATGTTGGGGCTCTTCCTCTACAGCCTCCCTGGCTACATGGT
CAAAAAGCTCCTTGGGGCATGAGCGGCCGCGGTACCAAGGGCGAATTCTGCAGTCGA
CTAGAGCTCGCTGATCAGCCTCGACTGTGCCTTCTAGTTGCCAGCCATCTGTTGTTTGC
CCCTCCCCCGTGCCTTCCTTGACCCTGGAAGGTGCCACTCCCACTGTCCTTTCCTAATA
AAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCTGGGGA
GAGATCTGAGGACTAGTCCGTCGACTGTTAATTAAGCATGCTGGGGAGAGATCTAGGA
ACCCCTAGTGATGGAGTTGGCCACTCCCTCTCTGCGCGCTCGCTCGCTCACTGAGGCC
GCCCGGGCAAAGCCCGGGCGTCGGGCGACCTTTGGTCGCCCGGCCTCAGTGAGCGA
GCGAGCGCGCAGAGAGGGAGTGGCCAACCCCCCCCCCCCCCCCCTGCAGCCCTGC
ATTAATGAATCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAGCGGTATCAG
CTCACTCAAAGGCGGTAATACGGTTATCCACAGAATCAGGGGATAACGCAGGAAAGAA
CATGTGAGCAAAAGGCCAGCAAAAGGCCAGGAACCGTAAAAAGGCCGCGTTGCTGGC
GTTTTTCCATAGGCTCCGCCCCCTGACGAGCATCACAAAAATCGACGCTCAAGTCAGA
GGTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTT
CGGGAAGCGTGGCGCTTTCTCAATGCTCACGCTGTAGGTATCTCAGTTCGGTGTAGGT
CGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTT
CTTGAAGTGGTGGCCTAACTACGGCTACACTAGAAGGACAGTATTTGGTATCTGCGCTC
TGCTGAAGCCAGTTACCTTCGGAAAAAGAGTTGGTAGCTCTTGATCCGGCAAACAAACC
```

FIG. 15 (continued)

```
ACCGCTGGTAGCGGTGGTTTTTTTGTTTGCAAGCAGCAGATTACGCGCAGAAAAAAAG
GATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTA
AATTAAAAATGAAGTTTTAAATCAATCTAAAGTATATATGAGTAAACTTGGTCTGACAGTT
ACCAATGCTTAATCAGTGAGGCACCTATCTCAGCGATCTGTCTATTTCGTTCATCCATAG
TTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAGTTT
GCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTG
CAAAAAAGCGGTTAGCTCCTTCGGTCCTCCGATCGTTGTCAGAAGTAAGTTGGCCGCA
GTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCG
GCGACCGAGTTGCTCTTGCCCGGCGTCAATACGGGATAATACCGCGCCACATAGCAGA
ACTTTAAAAGTGCTCATCATTGGAAAACGTTCTTCGGGGCGAAAACTCTCAAGGATCTT
ACCGCTGTTGAGATCCAGTTCGATGTAACCCACTCGTGCACCCAACTGATCTTCAGCAT
CTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTAT
TGAAGCATTTATCAGGGTTATTGTCTCATGAGCGGATACATATTTGAATGTATTTAGAAA
AATAAACAAATAGGGGTTCCGCGCACATTTCCCCGAAAAGTGCCACCTGACGTCTAAGA
AACCATTATTATCATGACATTAACCTATAAAAATAGGCGTATCACGAGGCCCTTTCGTCT
CGCGCGTTTCGGTGATGACGGTGAAAACCTCTGACACATGCAGCTCCCGGAGACGGTC
ACAGCTTGTCTGTAAGCGGATGCCGGGAGCAGACAAGCCCGTCAGGGCGCGTCAGCG
GGTGTTGGCGGGTGTCGGGGCTGGCTTAACTATGCGGCATCAGAGCAGATTGTACTGA
GAGTGCACCATATGCGGTGTGAAATACCGCACAGATGCGTAAGGAGAAAATACCGCAT
CAGGAAATTGTAAACGTTAATATTTTGTTAAAATTCGCGTTAAATTTTGTTAAATCAGCT
CATTTTTTAACCAATAGGCCGAAATCGGCAAAATCCCTTATAAATCAAAAGAATAGACCG
AGATAGGGTTGAGTGTTGTTCCAGTTTGGAACAAGAGTCCACTATTAAAGAACGTGGAC
TCCAACGTCAAAGGGCGAAAAACCGTCTATCAGGGCGATGGCCCACTACGTGAACCAT
CACCCTAATCAAGTTTTTTGGGGTCGAGGTGCCGTAAAGCACTAAATCGGAACCCTAAA
GGGAGCCCCCGATTTAGAGCTTGACGGGGAAAGCCGGCGAACGTGGCGAGAAAGGAA
GGGAAGAAAGCGAAAGGAGCGGGCGCTAGGGCGCTGGCAAGTGTAGCGGTCACGCT
GCGCGTAACCACCACACCCGCCGCGCTTAATGCGCCGCTACAGGGCGCGTCGCGCCA
TTCGCCATTCAGGCTACGCAACTGTTGGGAAGGGCGATCGGTGCGGGCCTCTTCGCTA
TTACGCCAGGCTGC
```
(SEQ ID NO: 16)

FIG. 15 (continued)

SEQUENCE LISTING

```
<160> NUMBER OF SEQ ID NOS: 16

<210> SEQ ID NO 1
<211> LENGTH: 7009
<212> TYPE: DNA
<213> ORGANISM: Artificial sequence
<220> FEATURE:
<223> OTHER INFORMATION: pTR22-smCBA-otoferlinNT-APSD-APhead

<400> SEQUENCE: 1 agggggggggg ggggggggggt tggccactcc ctctctgcgc gctcgctcgc tcactgaggc      60
cgggcgacca aaggtcgccc gacgcccggg ctttgcccgg gcggcctcag tgagcgagcg     120
agcgcgcaga gagggagtgg ccaactccat cactaggggt tcctcagatc tggcgcgccc     180
aattcggtac cctagttatt aatagtaatc aattacgggg tcattagttc atagcccata     240
tatggagttc cgcgttacat aacttacggt aaatggcccg cctggctgac cgcccaacga     300
cccccgccca ttgacgtcaa taatgacgta tgttcccata gtaacgccaa tagggacttt     360
ccattgacgt caatgggtgg actatttacg gtaaactgcc cacttggcag tacatcaagt     420
gtatcatatg ccaagtacgc cccctattga cgtcaatgac ggtaaatggc ccgcctggca     480
ttatgcccag tacatgacct tatgggactt tcctacttgg cagtacatct acgtattagt     540
catcgctatt accatggtcg aggtgagccc cacgttctgc ttcactctcc ccatctcccc     600
ccctccccca cccccaattt tgtatttatt tattttttaa ttattttgtg cagcgatggg     660
ggcggggggg gggggggggc gcgcgccagg cggggcgggg cggggcgagg ggcggggcgg     720
ggcgaggcgg agaggtgcgg cggcagccaa tcagagcggc gcgctccgaa agtttccttt     780
tatggcgagg cggcggcggc ggcggcccta taaaaagcga agcgcgcggc gggcgggagt     840
cgctgcgacg ctgccttcgc cccgtgcccc gctccgccgc cgcctcgcgc cgcccgcccc     900
```

```
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagcta gagcctctgc taaccatgtt catgccttct tcttttcct    1080
acagctcctg ggcaacgtgc tggttattgt gctgtctcat cattttggca aagaattcta   1140
gcggccgcca ccatggccct gattgttcac ctcaagactg tctcagagct ccgaggcaaa   1200
ggtgaccgga ttgccaaagt cacttccga gggcagtctt tctactcccg ggtcctggag    1260
aactgcgagg gtgtggctga cttgatgag acgttccggt ggccagtggc cagcagcatc    1320
gaccggaatg aagtgttgga gattcagatt ttcaactaca gcaaagtctt cagcaacaag   1380
ctgataggga ccttctgcat ggtgctgcag aaagtggtgg aggagaatcg ggtagaggtg   1440
accgacacgc tgatggatga cagcaatgct atcatcaaga ccagcctgag catggaggtc   1500
cggtatcagg ccacagatgg cactgtgggc cctgggatg atggagactt cctgggagat    1560
gaatccctcc aggaggagaa ggacagccag agacagatg ggctgctacc tggttcccga    1620
cccagcaccc ggatatctgg cgagaagagc tttcgcagca aaggcagaga gaagaccaag   1680
ggaggcagag atggcgagca caaagcggga aggagtgtgt tctcggccat gaaactcggc   1740
aaaactcggt cccacaaaga ggagcccaa agacaagatg agccagcagt gctggagatg    1800
gaggacctgg accacctagc cattcagctg ggggatgggc tggatcctga ctccgtgtct   1860
ctagcctcgg tcaccgctct caccagcaat gtctccaaca acggtctaa ccagatatt    1920
aagatggagc ccagtgctgg aaggcccatg gattaccagg tcagcatcac agtgattgag   1980
gctcggcagc tggtgggctt gaacatggac cctgtggtgt gtgtggaggt gggtgatgac   2040
aagaaataca cgtcaatgaa ggagtccaca aactgcccct actacaacga gtactttgtc   2100
ttcgacttcc atgtctctcc tgatgtcatg tttgacaaga tcatcaagat ctcggttatc   2160
cattctaaga acctgcttcg gagcggcacc ctggtgggtt ccttcaaaat ggatgtgggg   2220
actgtgtatt cccagcctga acaccagttc atcacaaat gggccatcct gtcagacccc    2280
gatgacatct ctgctgggtt gaagggttat gtaaagtgtg atgtcgctgt ggtgggcaag   2340
ggagacaaca tcaagacacc ccacaaggcc aacgagacgg atgaggacga cattgaaggg   2400
aacttgctgc tccccgaggg cgtgcccccc gaacggcagt gggcacggtt ctatgtgaaa   2460
atttaccgag cagagggact gccccggatg aacacaagcc tcatggccaa cgtgaagaag   2520
gcgttcatcg gtgagaacaa ggacctcgtc gaccccctatg tgcaagtctt ctttgctgga   2580
caaaagggca aacatcagt gcagaagagc agctatgagc cgctatggaa tgagcaggtc    2640
gtcttcacag acttgttccc cccactctgc aaacgcatga aggtgcagat ccgggactct   2700
gacaaggtca atgatgtggc catcggcacc cacttcatcg acctgcgcaa gatttccaac   2760
gatggagaca aaggcttcct gcctaccctc ggtccagcct gggtgaacat gtacggctcc   2820
acgcgcaact acacactgct ggacgagcac caggacttga atgaaggcct gggggagggt   2880
gtgtccttcc gggcccgcct catgttggga ctagctgtgg agatcctgga cacctccaac   2940
ccagagctca ccagctccac ggaggtgcag gtggagcagg ccacgcctgt ctcggagagc   3000
tgcacaggga gaatgaagga atttttttcta tttggagcct tcttggaagc tcaatgatt    3060
gaccggaaaa atggggacaa gccaattacc tttgaggtga ccataggaaa ctacggcaat   3120
gaagtcgatg gtatgtcccg gcccctgagg cctcggcccc ggaaagagcc tggggatgaa   3180
gaagaggtag acctgattca gaactccagt gacgatgaag gtgacgaagc cggggacctg   3240
gcctcggtgt cctccacccc acctatgcgg ccccagatca cggacaggaa ctatttccac   3300
```

```
ctgccctacc tggagcgcaa gccctgcatc tatatcaaga gctggtggcc tgaccagagg    3360
cggcgcctct acaatgccaa catcatggat cacattgctg acaagctgga agaaggcctg    3420
aatgatgtac aggagatgat caaaacggag aagtcctacc cggagcgccg cctgcggggt    3480
gtgctagagg aactcagctg tggctgccac cgcttcctct ccctctcgga caaggaccag    3540
ggccgctcgt cccgcaccag gctggatcga gagcgtctta agtcctgtat gagggagttg    3600
gtaagtatca aggttacaag acaggtttaa ggagaccaat agaaactggg cttgtcgaga    3660
cagagaagac tcttgcgttt ctgagctagc ccccgggtgc gcggcgtcgg tggtgccggc    3720 gggggcgcc aggtcgcagg cggtgtaggg ctccaggcag gcggcgaagg ccatgacgtg    3780
cgctatgaag gtctgctcct gcacgccgtg aaccaggtgc gcctgcgggc cgcgcgcgaa    3840
caccgccacg tcctcgcctg cgtgggtctc ttcgtccagg ggcactgctg actgctgccg    3900
atactcgggg ctcccgctct cgctctcggt aacatccggc cgggcgccgt ccttgagcac    3960
atagcctgga ccgtttcgtc gactgttaat taagcatgct ggggagagat ctaggaaccc    4020
ctagtgatgg agttggccac tccctctctg cgcgctcgct cgctcactga ggccgcccgg    4080
gcaaagcccg ggcgtcgggc gacctttggt cgccccggcct cagtgagcga gcgagcgcgc    4140
agagagggag tggccaaccc cccccccccc cccctgcag ccctgcatta atgaatcggc    4200
caacgcgcgg ggagaggcgg tttgcgtatt gggcgctctt ccgcttcctc gctcactgac    4260
tcgctgcgct cggtcgttcg gctgcggcga gcggtatcag ctcactcaaa ggcggtaata    4320
cggttatcca cagaatcagg ggataacgca ggaaagaaca tgtgagcaaa aggccagcaa    4380
aaggccagga accgtaaaaa ggccgcgttg ctggcgtttt tccataggct ccgcccccct    4440
gacgagcatc acaaaaatcg acgctcaagt cagaggtggc gaaacccgac aggactataa    4500
agataccagg cgtttccccc tggaagctcc ctcgtgcgct ctcctgttcc gaccctgccg    4560
cttaccggat acctgtccgc ctttctccct tcgggaagcg tggcgctttc tcaatgctca    4620
cgctgtaggt atctcagttc ggtgtaggtc gttcgctcca agctgggctg tgtgcacgaa    4680
ccccccgttc agcccgaccg ctgcgcctta tccggtaact atcgtcttga gtccaacccg    4740
gtaagacacg acttatcgcc actggcagca gccactggta acaggattag cagagcgagg    4800
tatgtaggcg gtgctacaga gttcttgaag tggtggccta actacggcta cactagaagg    4860
acagtatttg gtatctgcgc tctgctgaag ccagttacct tcggaaaaag agttggtagc    4920
tcttgatccg gcaaacaaac caccgctggt agcggtggtt ttttgtttg caagcagcag    4980 attacgcgca gaaaaaaagg atctcaagaa gatcctttga tcttttctac ggggtctgac    5040
gctcagtgga acgaaaactc acgttaaggg attttggtca tgagattatc aaaaaggatc    5100
ttcacctaga tccttttaaa ttaaaaatga agttttaaat caatctaaag tatatatgag    5160
taaacttggt ctgacagtta ccaatgctta atcagtgagg cacctatctc agcgatctgt    5220
ctatttcgtt catccatagt tgcctgactc ccgtcgtgt agataactac gatacgggag    5280
ggcttaccat ctggccccag tgctgcaatg ataccgcgag acccacgctc accggctcca    5340
gatttatcag caataaacca gccagccgga agggccgagc gcagaagtgg tcctgcaact    5400
ttatccgcct ccatccagtc tattaattgt tgccgggaag ctagagtaag tagttcgcca    5460
gttaatagtt tgcgcaacgt tgttgccatt gctacaggca tcgtggtgtc acgctcgtcg    5520
tttggtatgg cttcattcag ctccggttcc caacgatcaa ggcgagttac atgatccccc    5580
atgttgtgca aaaaagcggt tagctccttc ggtcctccga tcgttgtcag aagtaagttg    5640
```

```
gccgcagtgt tatcactcat ggttatggca gcactgcata attctcttac tgtcatgcca    5700
tccgtaagat gcttttctgt gactggtgag tactcaacca agtcattctg agaatagtgt    5760
atgcggcgac cgagttgctc ttgcccggcg tcaatacggg ataataccgc gccacatagc    5820
agaactttaa aagtgctcat cattggaaaa cgttcttcgg ggcgaaaact ctcaaggatc    5880
ttaccgctgt tgagatccag ttcgatgtaa cccactcgtg cacccaactg atcttcagca    5940
tcttttactt tcaccagcgt ttctgggtga gcaaaaacag gaaggcaaaa tgccgcaaaa    6000
aagggaataa gggcgacacg gaaatgttga atactcatac tcttcctttt tcaatattat    6060
tgaagcattt atcagggtta ttgtctcatg agcggataca tatttgaatg tatttagaaa    6120
aataaacaaa taggggttcc gcgcacattt ccccgaaaag tgccacctga cgtctaagaa    6180
accattatta tcatgacatt aacctataaa aataggcgta tcacgaggcc ctttcgtctc    6240
gcgcgtttcg gtgatgacgg tgaaaacctc tgacacatgc agctcccgga cggtcaca    6300
gcttgtctgt aagcggatgc cgggagcaga caagcccgtc agggcgcgtc agcgggtgtt    6360
ggcgggtgtc ggggctggct taactatgcg gcatcagagc agattgtact gagagtgcac    6420
catatgcggt gtgaaatacc gcacagatgc gtaaggagaa ataccgcat caggaaattg    6480
taaacgttaa tattttgtta aaattcgcgt taaattttg ttaaatcagc tcatttttta    6540
accaataggc cgaaatcggc aaaatcccctt ataaatcaaa agaatagacc gagatagggt    6600
tgagtgttgt tccagtttgg aacaagagtc cactattaaa gaacgtggac tccaacgtca    6660
aagggcgaaa aaccgtctat cagggcgatg gcccactacg tgaaccatca ccctaatcaa    6720
gttttttggg gtcgaggtgc cgtaaagcac taaatcggaa ccctaaaggg agcccccgat    6780
ttagagcttg acggggaaag ccggcgaacg tggcgagaaa ggaagggaag aaagcgaaag    6840
gagcgggcgc tagggcgctg gcaagtgtag cggtcacgct gcgcgtaacc accacacccg    6900
ccgcgcttaa tgcgccgcta cagggcgcgt cgcgccattc gccattcagg ctacgcaact    6960
gttgggaagg gcgatcggtg cgggcctctt cgctattacg ccaggctgc                7009
```

<210> SEQ ID NO 2  
<211> LENGTH: 7413  
<212> TYPE: DNA  
<213> ORGANISM: Artificial sequence  
<220> FEATURE:  
<223> OTHER INFORMATION: pTR22-APhead-APSA-otoferlinCT

<400> SEQUENCE: 2

```
agggggggg ggggggggt tggccactcc ctctctgcgc gctcgctcgc tcactgaggc      60
cgggcgacca aaggtcgccc gacgcccggg ctttgcccgg gcggcctcag tgagcgagcg    120
agcgcgcaga gagggagtgg ccaactccat cactaggggt tcctcagatc tggcgcgccc    180
aattggcttc gaattctagc ggccgccccc gggtgcgcgc gtcggtggt gccggcgggg    240
ggcgccaggt cgcaggcggt gtagggctcc aggcaggcgg cgaaggccat gacgtgcgct    300
atgaaggtct gctcctgcac gccgtgaacc aggtgcgcct gcgggccgcg cgcgaacacc    360
gccacgtcct cgcctgcgtg ggtctcttcg tccagggggca ctgctgactg ctgccgatac    420
tcggggctcc cgctctcgct ctcggtaaca tccggccggg cgccgtcctt gagcacatag    480
cctggaccgt ttccttaagc gacgcatgct cgcgataggc acctattggt cttactgaca    540
tccactttgc ctttctctcc acaggagagc atgggacagc aggccaagag cctgagggct    600
caggtgaagg ggcacactgt tcgggacaag ctgaggtcat gccagaactt ctgcagaag    660
ctacgcttcc tggcggatga gccccagcac agcattcctg atgtgttcat ttggatgatg    720
```

```
agcaacaaca aacgtatcgc ctatgcccgc gtgccttcca aagacctgct cttctccatc    780
gtggaggagg aactgggcaa ggactgcgcc aaagtcaaga ccctcttcct gaagctgcca    840
gggaagaggg gcttcggctc ggcaggctgg acagtacagg ccaagctgga gctctacctg    900
tggctgggcc tcagcaagca gcgaaaggac ttcctgtgtg gtctgccctg tggcttcgag    960
gaggtcaagg cagcccaagg cctgggcctg cattcctttc cgcccatcag cctagtctac   1020
accaagaagc aagccttcca gctccgagca cacatgtatc aggcccgaag cctctttgct   1080
gctgacagca gtgggctctc tgatcccttt gcccgtgtct tcttcatcaa ccagagccaa   1140
tgcactgagg ttctaaacga gacactgtgt cccacctggg accagatgct ggtatttgac   1200
aacctggagc tgtacggtga agctcacgag ttacgagatg atcccccat cattgtcatt    1260 gaaatctacg accaggacag catgggcaaa gccgacttca tgggccggac cttcgccaag   1320
cccctggtga agatggcaga tgaagcatac tgcccacctc gcttcccgcc gcagcttgag   1380
tactaccaga tctaccgagg cagtgccact gccgagacc tactggctgc cttcgagctg    1440
ctgcagattg ggccatcagg gaaggctgac ctgccaccca tcaatggccc agtggacatg   1500
gacagagggc ccatcatgcc tgtgcccgtg ggaatccggc cagtgctcag caagtaccga   1560
gtggaggtgc tgttctgggg cctgagggac ctaaagaggg tgaacctggc ccaggtggac   1620
cgaccacggg tggacatcga gtgtgcagga aaggggtac aatcctccct gattcacaat    1680
tataagaaga ccccaacttt caacacgctg gtcaagtggt ttgaagtgga cctcccggag   1740
aatgagctcc tgcacccacc cttgaacatc cgagtggtag attgccgggc ctttggacga   1800
tacaccctgg tgggttccca cgcagtcagc tcactgaggc gcttcatcta ccgacctcca   1860
gaccgctcag cccccaactg gaacaccaca ggggaggttg tagtaagcat ggagcctgag   1920
gagccagtta agaagctgga gaccatggtg aaactggatg cgacttctga tgctgtggtc   1980
aaggtggatg tggctgaaga tgagaaggaa aggaagaaga agaaaaagaa aggcccgtca   2040
gaggagccag aggaggaaga gcccgatgag agcatgctgg attggtggtc caagtacttc   2100
gcctccatcg acacaatgaa ggagcaactt cgacaacatg agacctctgg aactgacttg   2160
gaagagaagg aagagatgga aagcgctgag ggcctgaagg accaatgaa gagcaaggag    2220 aagtccagag ctgcaaagga ggagaaaaag aagaaaaacc agagccctgg ccctggccag   2280
ggatcggagg ctcctgagaa aagaaagcc aagatcgatg agcttaaggt gtaccccaag    2340
gagctggaat cggagtttga cagctttgag gactggctgc acaccttcaa cctgttgagg   2400
ggcaagacgg gagatgatga ggatggctcc acagaggagg agcgcatagt aggccgattc   2460
aagggctccc tctgtgtgta caaagtgcca ctcccagaag atgtatctcg agaagctggc   2520
tatgatccca cctatggaat gttccaggc atcccaagca tgacccat caatgtgctg      2580 gtccgaatct atgtggtccg ggccacagac ctgcacccgg ccgacatcaa tggcaaagct   2640
gacccctata ttgccatcaa gttaggcaag accgacatcc gagacaagga gaactacatc   2700
tccaagcagc tcaaccctgt gtttgggaag tcctttgaca ttgaggcctc cttccccatg   2760
gagtccatgt tgacagtggc cgtgtacgac tgggatctgg tgggcactga tgacctcatc   2820
ggagaaacca agattgacct ggaaaaccgc ttctacagca gcatcgcgc cacctgcggc   2880 atcgcacaga cctattccat acatggctac aatatctgga gggaccccat gaagcccagc   2940
cagatcctga cacgcctctg taagagggc aaagtggacg ccccactt tggtccccat     3000 gggagagtga gggttgccaa ccgtgtcttc acggggcctt cagaaataga ggatgagaat   3060
```

```
ggtcagagga agcccacaga tgagcacgtg gcactgtctg ctctgagaca ctgggaggac    3120
atcccccggg tgggctgccg ccttgtgccg gaacacgtgg agaccaggcc gctgctcaac    3180
cctgacaagc caggcattga gcagggccgc ctggagctgt gggtggacat gttccccatg    3240
gacatgccag cccctgggac acctctggat atatccccca ggaaacccaa gaagtacgag    3300
ctgcgggtca tcgtgtggaa cacagacgag gtggtcctgg aagacgatga tttcttcacg    3360
ggagagaagt ccagtgacat ttttgtgagg ggtggctga agggccagca ggaggacaaa    3420
caggacacag atgtccacta tcactccctc acggggagg gcaacttcaa ctggagatac    3480
ctcttcccct tcgactacct agcggccgaa gagaagatcg ttatgtccaa aaaggagtct    3540
atgttctcct gggatgagac ggagtacaag atccctgcgc ggctcaccct gcagatctgg    3600
gacgctgacc acttctcggc tgacgacttc ctggggcta tcgagctgga cctgaaccgg    3660
ttcccgaggg gcgctaagac agccaagcag tgcaccatgg agatggccac cggggaggtg    3720
gacgtacccc tggtttccat ctttaaacag aaacgtgtca aaggctggtg gcccctcctg    3780
gcccgcaatg agaatgatga gtttgagctc acaggcaaag tggaggcgga gctacaccta    3840
ctcacggcag aggaggcaga gaagaaccct gtgggcctgg ctcgcaatga acctgatccc    3900
ctagaaaaac ccaaccggcc tgacacggca ttcgtctggt tcctgaaccc actcaaatct    3960
atcaagtacc tcatctgcac ccggtacaag tggctgatca tcaagatcgt gctggcgctg    4020
ctggggctgc tcatgctggc cctcttcctt tacagcctcc caggctacat ggtcaagaag    4080
ctcctagggg cctgagcggc gcggtacca agggcgaatt ctgcagtcga ctagagctcg    4140
ctgatcagcc tcgactgtgc cttctagttg ccagccatct gttgtttgcc cctcccccgt    4200
gccttccttg acctggaag gtgccactcc cactgtcctt tcctaataaa atgaggaaat    4260
tgcatcgcat tgtctgagta ggtgtcattc tattctgggg ggtggggtgg ggcaggacag    4320
caagggggag gattgggaag acaatagcag gcatgctggg gagagatctg aggactagtc    4380
cgtcgactgt taattaagca tgctggggag agatctagga accccagtg atggagttgg    4440
ccactccctc tctgcgcgct cgctcgctca ctgaggccgc ccgggcaaag cccgggcgtc    4500
gggcgaccct tggtcgcccg gcctcagtga gcgagcgagc gcgcagagag ggagtggcca    4560
acccccccc cccccccct gcagccctgc attaatgaat cggccaacgc gcggggagag    4620
gcggtttgcg tattgggcgc tcttccgctt cctcgctcac tgactcgctg cgctcggtcg    4680
ttcggctgcg gcgagcggta tcagctcact caaaggcggt aatacggtta tccacagaat    4740
caggggataa cgcaggaaag aacatgtgag caaaaggcca gcaaaaggcc aggaaccgta    4800
aaaaggccgc gttgctggcg ttttccata ggctccgccc ccctgacgag catcacaaaa    4860
atcgacgctc aagtcagagg tggcgaaacc cgacaggact ataaagatac caggcgtttc    4920
cccctggaag ctccctcgtg cgctctcctg ttccgaccct gccgcttacc ggatacctgt    4980
ccgcctttct cccttcggga agcgtggcgc tttctcaatg ctcacgctgt aggtatctca    5040
gttcggtgta ggtcgttcgc tccaagctgg gctgtgtgca cgaaccccc gttcagcccg    5100
accgctgcgc cttatccggt aactatcgtc ttgagtccaa cccggtaaga cacgacttat    5160
cgccactggc agcagccact ggtaacagga ttagcagagc gaggtatgta ggcggtgcta    5220
cagagttctt gaagtggtgg cctaactacg gctacactag aaggacagta tttggtatct    5280
gcgctctgct gaagccagtt accttcggaa aaagagttgg tagctcttga tccggcaaac    5340
aaaccaccgc tggtagcggt ggtttttttg tttgcaagca gcagattacg cgcagaaaaa    5400
aaggatctca agaagatcct ttgatctttt ctacggggtc tgacgctcag tggaacgaaa    5460
```

```
actcacgtta agggattttg gtcatgagat tatcaaaaag gatcttcacc tagatccttt      5520
taaattaaaa atgaagtttt aaatcaatct aaagtatata tgagtaaact tggtctgaca      5580
gttaccaatg cttaatcagt gaggcaccta tctcagcgat ctgtctattt cgttcatcca      5640
tagttgcctg actcccgtc gtgtagataa ctacgtacg ggagggctta ccatctggcc       5700
ccagtgctgc aatgataccg cgagacccac gctcaccggc tccagattta tcagcaataa     5760
accagccagc cggaagggcc gagcgcagaa gtggtcctgc aactttatcc gcctccatcc     5820
agtctattaa ttgttgccgg gaagctagag taagtagttc gccagttaat agtttgcgca     5880
acgttgttgc cattgctaca ggcatcgtgg tgtcacgctc gtcgtttggt atggcttcat     5940
tcagctccgg ttcccaacga tcaaggcgag ttacatgatc ccccatgttg tgcaaaaaag    6000
cggttagctc cttcggtcct ccgatcgttg tcagaagtaa gttggccgca gtgttatcac     6060
tcatggttat ggcagcactg cataattctc ttactgtcat gccatccgta agatgctttt     6120
ctgtgactgg tgagtactca accaagtcat tctgagaata gtgtatgcgg cgaccgagtt     6180
gctcttgccc ggcgtcaata cgggataata ccgcgccaca tagcagaact ttaaaagtgc     6240
tcatcattgg aaaacgttct cggggcgaa aactctcaag gatcttaccg ctgttgagat      6300
ccagttcgat gtaacccact cgtgcaccca actgatcttc agcatctttt actttcacca     6360
gcgtttctgg gtgagcaaaa acaggaaggc aaaatgccgc aaaaaaggga ataagggcga     6420
cacggaaatg ttgaatactc atactcttcc tttttcaata ttattgaagc atttatcagg     6480
gttattgtct catgagcgga tacatatttg aatgtattta gaaaaataaa caaatagggg     6540
ttccgcgcac atttccccga aaagtgccac ctgacgtcta agaaaccatt attatcatga     6600
cattaaccta taaaaatagg cgtatcacga ggccctttcg tctcgcgcgt ttcggtgatg     6660
acggtgaaaa cctctgacac atgcagctcc cggagacggt cacagcttgt ctgtaagcgg     6720
atgccgggag cagacaagcc cgtcaggcg cgtcagcggg tgttggcggg tgtcggggct      6780
ggcttaacta tgcggcatca gagcagattg tactgagagt gcaccatatg cggtgtgaaa     6840
taccgcacag atgcgtaagg agaaaatacc gcatcaggaa attgtaaacg ttaatatttt     6900
gttaaaattc gcgttaaatt tttgttaaat cagctcattt tttaaccaat aggccgaaat     6960
cggcaaaatc ccttataaat caaaagaata gaccgagata gggttgagtg ttgttccagt     7020
ttggaacaag agtccactat taaagaacgt ggactccaac gtcaaagggc gaaaaaccgt     7080
ctatcagggc gatggcccac tacgtgaacc atcaccctaa tcaagttttt tggggtcgag     7140
gtgccgtaaa gcactaaatc ggaacccaa agggagcccc cgatttagag cttgacgggg      7200
aaagccggcg aacgtggcga gaaggaagg gaagaaagcg aaaggagcgg gcgctagggc      7260
gctggcaagt gtagcggtca cgctgcgcgt aaccaccaca cccgccgcgc ttaatgcgcc     7320
gctacagggc gcgtcgcgcc attcgccatt caggctacgc aactgttggg aagggcgatc     7380
ggtgcgggcc tcttcgctat tacgccaggc tgc                                  7413
```

<210> SEQ ID NO 3  
<211> LENGTH: 287  
<212> TYPE: DNA  
<213> ORGANISM: Artificial sequence  
<220> FEATURE:  
<223> OTHER INFORMATION: Synthetic polynucleotide

<400> SEQUENCE: 3

```
ccccgggtgc gcggcgtcgg tggtgccggc gggggcgcc aggtcgcagg cggtgtaggg      60
```

```
ctccaggcag gcggcgaagg ccatgacgtg cgctatgaag gtctgctcct gcacgccgtg    120
aaccaggtgc gcctgcgggc cgcgcgcgaa caccgccacg tcctcgcctg cgtgggtctc    180
ttcgtccagg ggcactgctg actgctgccg atactcgggg ctcccgctct cgctctcggt    240
aacatccggc cgggcgccgt ccttgagcac atagcctgga ccgtttc                  287
```

<210> SEQ ID NO 4
<211> LENGTH: 650
<212> TYPE: DNA
<213> ORGANISM: Artificial sequence
<220> FEATURE:
<223> OTHER INFORMATION: Synthetic polynucleotide

<400> SEQUENCE: 4

```
ggtaccctag ttattaatag taatcaatta cggggtcatt agttcatagc ccatatatgg     60
agttccgcgt tacataactt acggtaaatg gcccgcctgg ctgaccgccc aacgaccccc    120
gcccattgac gtcaataatg acgtatgttc ccatagtaac gccaataggg actttccatt    180
gacgtcaatg ggtggactat ttacggtaaa ctgcccactt ggcagtacat caagtgtatc    240
atatgccaag tacgccccct attgacgtca atgacggtaa atggcccgcc tggcattatg    300
cccagtacat gaccttatgg gactttccta cttggcagta catctacgta ttagtcatcg    360
ctattaccat ggtcgaggtg agccccacgt tctgcttcac tctccccatc tcccccccct    420
ccccaccccc aattttgtat ttatttattt tttaattatt ttgtgcagcg atgggggcgg    480 ggggggggg ggggcgcgcg ccaggcgggg cggggcgggg cgaggggcgg ggcggggcga    540
ggcggagagg tgcggcggca gccaatcaga gcggcgcgct ccgaaagttt cctttttatgg    600 cgaggcggcg gcggcggcgg ccctataaaa agcgaagcgc gcggcgggcg                650
```

<210> SEQ ID NO 5
<211> LENGTH: 1997
<212> TYPE: PRT
<213> ORGANISM: H. sapiens

<400> SEQUENCE: 5

```
Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
            20                  25                  30

Arg Val Leu Glu Asn Cys Glu Asp Val Ala Asp Phe Asp Glu Thr Phe
        35                  40                  45

Arg Trp Pro Val Ala Ser Ser Ile Asp Arg Asn Glu Met Leu Glu Ile
    50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                85                  90                  95

Thr Asp Thr Leu Ile Asp Asp Asn Asn Ala Ile Ile Lys Thr Ser Leu
            100                 105                 110

Cys Val Glu Val Arg Tyr Gln Ala Thr Asp Gly Thr Val Gly Ser Trp
        115                 120                 125

Asp Asp Gly Asp Phe Leu Gly Asp Glu Ser Leu Gln Glu Glu Lys
    130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
```

```
                165                 170                 175
Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
            195                 200                 205

Ala Ile Arg Leu Gly Asp Gly Leu Asp Pro Asp Ser Val Ser Leu Ala
        210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
                260                 265                 270

Pro Val Val Cys Val Glu Val Gly Asp Asp Lys Lys Tyr Thr Ser Met
                275                 280                 285

Lys Glu Ser Thr Asn Cys Pro Tyr Tyr Asn Glu Tyr Phe Val Phe Asp
            290                 295                 300

Phe His Val Ser Pro Asp Val Met Phe Asp Lys Ile Lys Ile Lys Ile
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Gly His Gln Phe
            340                 345                 350

His His Lys Trp Ala Ile Leu Ser Asp Pro Asp Asp Ile Ser Ser Gly
                355                 360                 365

Leu Lys Gly Tyr Val Lys Cys Asp Val Ala Val Val Gly Lys Gly Asp
        370                 375                 380

Asn Ile Lys Thr Pro His Lys Ala Asn Glu Thr Asp Glu Asp Asp Ile
385                 390                 395                 400

Glu Gly Asn Leu Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
        435                 440                 445

Lys Asp Leu Val Asp Pro Tyr Val Gln Val Phe Phe Ala Gly Gln Lys
        450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
                500                 505                 510

His Phe Ile Asp Leu Arg Lys Ile Ser Asn Asp Gly Asp Lys Gly Phe
            515                 520                 525

Leu Pro Thr Leu Gly Pro Ala Trp Val Asn Met Tyr Gly Ser Thr Arg
        530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
            580                 585                 590
```

```
Val Glu Gln Ala Thr Pro Ile Ser Glu Ser Cys Ala Gly Lys Met Glu
            595                 600                 605

Glu Phe Phe Leu Phe Gly Ala Phe Leu Glu Ala Ser Met Ile Asp Arg
        610                 615                 620

Arg Asn Gly Asp Lys Pro Ile Thr Phe Glu Val Thr Ile Gly Asn Tyr
625                 630                 635                 640

Gly Asn Glu Val Asp Gly Leu Ser Arg Pro Gln Arg Pro Arg Pro Arg
                645                 650                 655

Lys Glu Pro Gly Asp Glu Glu Val Asp Leu Ile Gln Asn Ala Ser
                660                 665                 670

Asp Asp Glu Ala Gly Asp Ala Gly Asp Leu Ala Ser Val Ser Ser Thr
            675                 680                 685

Pro Pro Met Arg Pro Gln Val Thr Asp Arg Asn Tyr Phe His Leu Pro
        690                 695                 700

Tyr Leu Glu Arg Lys Pro Cys Ile Tyr Ile Lys Ser Trp Trp Pro Asp
705                 710                 715                 720

Gln Arg Arg Arg Leu Tyr Asn Ala Asn Ile Met Asp His Ile Ala Asp
                725                 730                 735

Lys Leu Glu Glu Gly Leu Asn Asp Ile Gln Glu Met Ile Lys Thr Glu
            740                 745                 750

Lys Ser Tyr Pro Glu Arg Arg Leu Arg Gly Val Leu Glu Glu Leu Ser
        755                 760                 765

Cys Gly Cys Cys Arg Phe Leu Ser Leu Ala Asp Lys Asp Gln Gly His
770                 775                 780

Ser Ser Arg Thr Arg Leu Asp Arg Glu Arg Leu Lys Ser Cys Met Arg
785                 790                 795                 800

Glu Leu Glu Asn Met Gly Gln Gln Ala Arg Met Leu Arg Ala Gln Val
                805                 810                 815

Lys Arg His Thr Val Arg Asp Lys Leu Arg Leu Cys Gln Asn Phe Leu
            820                 825                 830

Gln Lys Leu Arg Phe Leu Ala Asp Glu Pro Gln His Ser Ile Pro Asp
        835                 840                 845

Ile Phe Ile Trp Met Met Ser Asn Asn Lys Arg Val Ala Tyr Ala Arg
        850                 855                 860

Val Pro Ser Lys Asp Leu Leu Phe Ser Ile Val Glu Glu Thr Gly
865                 870                 875                 880

Lys Asp Cys Ala Lys Val Lys Thr Leu Phe Leu Lys Leu Pro Gly Lys
            885                 890                 895

Arg Gly Phe Gly Ser Ala Gly Trp Thr Val Gln Ala Lys Val Glu Leu
                900                 905                 910

Tyr Leu Trp Leu Gly Leu Ser Lys Gln Arg Lys Glu Phe Leu Cys Gly
        915                 920                 925

Leu Pro Cys Gly Phe Gln Glu Val Lys Ala Ala Gln Gly Leu Gly Leu
        930                 935                 940

His Ala Phe Pro Pro Val Ser Leu Val Tyr Thr Lys Lys Gln Ala Phe
945                 950                 955                 960

Gln Leu Arg Ala His Met Tyr Gln Ala Arg Ser Leu Phe Ala Ala Asp
            965                 970                 975

Ser Ser Gly Leu Ser Asp Pro Phe Ala Arg Val Phe Phe Ile Asn Gln
                980                 985                 990

Ser Gln Cys Thr Glu Val Leu Asn  Glu Thr Leu Cys Pro  Thr Trp Asp
            995                 1000                1005
```

-continued

```
Gln Met Leu Val Phe Asp Asn Leu Glu Leu Tyr Gly Glu Ala His
1010                1015                1020

Glu Leu Arg Asp Asp Pro Pro Ile Ile Val Ile Glu Ile Tyr Asp
    1025                1030                1035

Gln Asp Ser Met Gly Lys Ala Asp Phe Met Gly Arg Thr Phe Ala
1040                1045                1050

Lys Pro Leu Val Lys Met Ala Asp Glu Ala Tyr Cys Pro Pro Arg
    1055                1060                1065

Phe Pro Pro Gln Leu Glu Tyr Tyr Gln Ile Tyr Arg Gly Asn Ala
1070                1075                1080

Thr Ala Gly Asp Leu Leu Ala Ala Phe Glu Leu Leu Gln Ile Gly
    1085                1090                1095

Pro Ala Gly Lys Ala Asp Leu Pro Pro Ile Asn Gly Pro Val Asp
1100                1105                1110

Val Asp Arg Gly Pro Ile Met Pro Val Pro Met Gly Ile Arg Pro
    1115                1120                1125

Val Leu Ser Lys Tyr Arg Val Glu Val Leu Phe Trp Gly Leu Arg
1130                1135                1140

Asp Leu Lys Arg Val Asn Leu Ala Gln Val Asp Arg Pro Arg Val
    1145                1150                1155

Asp Ile Glu Cys Ala Gly Lys Gly Val Gln Ser Ser Leu Ile His
1160                1165                1170

Asn Tyr Lys Lys Asn Pro Asn Phe Asn Thr Leu Val Lys Trp Phe
    1175                1180                1185

Glu Val Asp Leu Pro Glu Asn Glu Leu Leu His Pro Pro Leu Asn
1190                1195                1200

Ile Arg Val Val Asp Cys Arg Ala Phe Gly Arg Tyr Thr Leu Val
    1205                1210                1215

Gly Ser His Ala Val Ser Ser Leu Arg Arg Phe Ile Tyr Arg Pro
1220                1225                1230

Pro Asp Arg Ser Ala Pro Ser Trp Asn Thr Thr Val Arg Leu Leu
    1235                1240                1245

Arg Arg Cys Arg Val Leu Cys Asn Gly Gly Ser Ser Ser His Ser
1250                1255                1260

Thr Gly Glu Val Val Val Thr Met Glu Pro Glu Val Pro Ile Lys
    1265                1270                1275

Lys Leu Glu Thr Met Val Lys Leu Asp Ala Thr Ser Glu Ala Val
1280                1285                1290

Val Lys Val Asp Val Ala Glu Glu Glu Lys Glu Lys Lys Lys Lys
    1295                1300                1305

Lys Lys Gly Thr Ala Glu Glu Pro Glu Glu Glu Pro Asp Glu
1310                1315                1320

Ser Met Leu Asp Trp Trp Ser Lys Tyr Phe Ala Ser Ile Asp Thr
    1325                1330                1335

Met Lys Glu Gln Leu Arg Gln Gln Glu Pro Ser Gly Ile Asp Leu
1340                1345                1350

Glu Glu Lys Glu Glu Val Asp Asn Thr Glu Gly Leu Lys Gly Ser
    1355                1360                1365

Met Lys Gly Lys Glu Lys Ala Arg Ala Ala Lys Glu Glu Lys Lys
1370                1375                1380

Lys Lys Thr Gln Ser Ser Gly Ser Gly Gln Gly Ser Glu Ala Pro
    1385                1390                1395

Glu Lys Lys Lys Pro Lys Ile Asp Glu Leu Lys Val Tyr Pro Lys
```

-continued

```
            1400              1405              1410
Glu Leu Glu Ser Glu Phe Asp Asn Phe Glu Asp Trp Leu His Thr
    1415              1420              1425
Phe Asn Leu Leu Arg Gly Lys Thr Gly Asp Asp Glu Asp Gly Ser
    1430              1435              1440
Thr Glu Glu Arg Ile Val Gly Arg Phe Lys Gly Ser Leu Cys
    1445              1450              1455
Val Tyr Lys Val Pro Leu Pro Glu Asp Val Ser Arg Glu Ala Gly
    1460              1465              1470
Tyr Asp Ser Thr Tyr Gly Met Phe Gln Gly Ile Pro Ser Asn Asp
    1475              1480              1485
Pro Ile Asn Val Leu Val Arg Val Tyr Val Val Arg Ala Thr Asp
    1490              1495              1500
Leu His Pro Ala Asp Ile Asn Gly Lys Ala Asp Pro Tyr Ile Ala
    1505              1510              1515
Ile Arg Leu Gly Lys Thr Asp Ile Arg Asp Lys Glu Asn Tyr Ile
    1520              1525              1530
Ser Lys Gln Leu Asn Pro Val Phe Gly Lys Ser Phe Asp Ile Glu
    1535              1540              1545
Ala Ser Phe Pro Met Glu Ser Met Leu Thr Val Ala Val Tyr Asp
    1550              1555              1560
Trp Asp Leu Val Gly Thr Asp Asp Leu Ile Gly Glu Thr Lys Ile
    1565              1570              1575
Asp Leu Glu Asn Arg Phe Tyr Ser Lys His Arg Ala Thr Cys Gly
    1580              1585              1590
Ile Ala Gln Thr Tyr Ser Thr His Gly Tyr Asn Ile Trp Arg Asp
    1595              1600              1605
Pro Met Lys Pro Ser Gln Ile Leu Thr Arg Leu Cys Lys Asp Gly
    1610              1615              1620
Lys Val Asp Gly Pro His Phe Gly Pro Pro Gly Arg Val Lys Val
    1625              1630              1635
Ala Asn Arg Val Phe Thr Gly Pro Ser Glu Ile Glu Asp Glu Asn
    1640              1645              1650
Gly Gln Arg Lys Pro Thr Asp Glu His Val Ala Leu Leu Ala Leu
    1655              1660              1665
Arg His Trp Glu Asp Ile Pro Arg Ala Gly Cys Arg Leu Val Pro
    1670              1675              1680
Glu His Val Glu Thr Arg Pro Leu Leu Asn Pro Asp Lys Pro Gly
    1685              1690              1695
Ile Glu Gln Gly Arg Leu Glu Leu Trp Val Asp Met Phe Pro Met
    1700              1705              1710
Asp Met Pro Ala Pro Gly Thr Pro Leu Asp Ile Ser Pro Arg Lys
    1715              1720              1725
Pro Lys Lys Tyr Glu Leu Arg Val Ile Ile Trp Asn Thr Asp Glu
    1730              1735              1740
Val Val Leu Glu Asp Asp Asp Phe Phe Thr Gly Glu Lys Ser Ser
    1745              1750              1755
Asp Ile Phe Val Arg Gly Trp Leu Lys Gly Gln Gln Glu Asp Lys
    1760              1765              1770
Gln Asp Thr Asp Val His Tyr His Ser Leu Thr Gly Glu Gly Asn
    1775              1780              1785
Phe Asn Trp Arg Tyr Leu Phe Pro Phe Asp Tyr Leu Ala Ala Glu
    1790              1795              1800
```

```
Glu Lys Ile Val Ile Ser Lys Lys Glu Ser Met Phe Ser Trp Asp
    1805            1810                1815

Glu Thr Glu Tyr Lys Ile Pro Ala Arg Leu Thr Leu Gln Ile Trp
    1820            1825                1830

Asp Ala Asp His Phe Ser Ala Asp Asp Phe Leu Gly Ala Ile Glu
    1835            1840                1845

Leu Asp Leu Asn Arg Phe Pro Arg Gly Ala Lys Thr Ala Lys Gln
    1850            1855                1860

Cys Thr Met Glu Met Ala Thr Gly Glu Val Asp Val Pro Leu Val
    1865            1870                1875

Ser Ile Phe Lys Gln Lys Arg Val Lys Gly Trp Trp Pro Leu Leu
    1880            1885                1890

Ala Arg Asn Glu Asn Asp Glu Phe Glu Leu Thr Gly Lys Val Glu
    1895            1900                1905

Ala Glu Leu His Leu Leu Thr Ala Glu Glu Ala Glu Lys Asn Pro
    1910            1915                1920

Val Gly Leu Ala Arg Asn Glu Pro Asp Pro Leu Glu Lys Pro Asn
    1925            1930                1935

Arg Pro Asp Thr Ser Phe Ile Trp Phe Leu Asn Pro Leu Lys Ser
    1940            1945                1950

Ala Arg Tyr Phe Leu Trp His Thr Tyr Arg Trp Leu Leu Leu Lys
    1955            1960                1965

Leu Leu Leu Leu Leu Leu Leu Leu Leu Leu Ala Leu Phe Leu
    1970            1975                1980

Tyr Ser Val Pro Gly Tyr Leu Val Lys Lys Ile Leu Gly Ala
    1985            1990                1995

<210> SEQ ID NO 6
<211> LENGTH: 1997
<212> TYPE: PRT
<213> ORGANISM: H. sapiens

<400> SEQUENCE: 6

Met Ala Leu Leu Ile His Leu Lys Thr Val Ser Glu Leu Arg Gly Arg
1               5                   10                  15

Gly Asp Arg Ile Ala Lys Val Thr Phe Arg Gly Gln Ser Phe Tyr Ser
                20                  25                  30

Arg Val Leu Glu Asn Cys Glu Asp Val Ala Asp Phe Asp Glu Thr Phe
                35                  40                  45

Arg Trp Pro Val Ala Ser Ser Ile Asp Arg Asn Glu Met Leu Glu Ile
            50                  55                  60

Gln Val Phe Asn Tyr Ser Lys Val Phe Ser Asn Lys Leu Ile Gly Thr
65                  70                  75                  80

Phe Arg Met Val Leu Gln Lys Val Val Glu Glu Ser His Val Glu Val
                    85                  90                  95

Thr Asp Thr Leu Ile Asp Asp Asn Asn Ala Ile Ile Lys Thr Ser Leu
                100                 105                 110

Cys Val Glu Val Arg Tyr Gln Ala Thr Asp Gly Thr Val Gly Ser Trp
            115                 120                 125

Asp Asp Gly Asp Phe Leu Gly Asp Glu Ser Leu Gln Glu Glu Glu Lys
        130                 135                 140

Asp Ser Gln Glu Thr Asp Gly Leu Leu Pro Gly Ser Arg Pro Ser Ser
145                 150                 155                 160

Arg Pro Pro Gly Glu Lys Ser Phe Arg Arg Ala Gly Arg Ser Val Phe
```

```
              165                 170                 175
Ser Ala Met Lys Leu Gly Lys Asn Arg Ser His Lys Glu Glu Pro Gln
            180                 185                 190

Arg Pro Asp Glu Pro Ala Val Leu Glu Met Glu Asp Leu Asp His Leu
            195                 200                 205

Ala Ile Arg Leu Gly Asp Gly Leu Asp Pro Asp Ser Val Ser Leu Ala
            210                 215                 220

Ser Val Thr Ala Leu Thr Thr Asn Val Ser Asn Lys Arg Ser Lys Pro
225                 230                 235                 240

Asp Ile Lys Met Glu Pro Ser Ala Gly Arg Pro Met Asp Tyr Gln Val
                245                 250                 255

Ser Ile Thr Val Ile Glu Ala Arg Gln Leu Val Gly Leu Asn Met Asp
                260                 265                 270

Pro Val Val Cys Val Glu Val Gly Asp Asp Lys Lys Tyr Thr Ser Met
                275                 280                 285

Lys Glu Ser Thr Asn Cys Pro Tyr Tyr Asn Glu Tyr Phe Val Phe Asp
            290                 295                 300

Phe His Val Ser Pro Asp Val Met Phe Asp Lys Ile Ile Lys Ile Ser
305                 310                 315                 320

Val Ile His Ser Lys Asn Leu Leu Arg Ser Gly Thr Leu Val Gly Ser
                325                 330                 335

Phe Lys Met Asp Val Gly Thr Val Tyr Ser Gln Pro Glu His Gln Phe
            340                 345                 350

His His Lys Trp Ala Ile Leu Ser Asp Pro Asp Asp Ile Ser Ser Gly
            355                 360                 365

Leu Lys Gly Tyr Val Lys Cys Asp Val Ala Val Val Gly Lys Gly Asp
            370                 375                 380

Asn Ile Lys Thr Pro His Lys Ala Asn Glu Thr Asp Glu Asp Asp Ile
385                 390                 395                 400

Glu Gly Asn Leu Leu Leu Pro Glu Gly Val Pro Pro Glu Arg Gln Trp
                405                 410                 415

Ala Arg Phe Tyr Val Lys Ile Tyr Arg Ala Glu Gly Leu Pro Arg Met
            420                 425                 430

Asn Thr Ser Leu Met Ala Asn Val Lys Lys Ala Phe Ile Gly Glu Asn
            435                 440                 445

Lys Asp Leu Val Asp Pro Tyr Val Gln Val Phe Phe Ala Gly Gln Lys
            450                 455                 460

Gly Lys Thr Ser Val Gln Lys Ser Ser Tyr Glu Pro Leu Trp Asn Glu
465                 470                 475                 480

Gln Val Val Phe Thr Asp Leu Phe Pro Pro Leu Cys Lys Arg Met Lys
                485                 490                 495

Val Gln Ile Arg Asp Ser Asp Lys Val Asn Asp Val Ala Ile Gly Thr
                500                 505                 510

His Phe Ile Asp Leu Arg Lys Ile Ser Asn Asp Gly Asp Lys Gly Phe
            515                 520                 525

Leu Pro Thr Leu Gly Pro Ala Trp Val Asn Met Tyr Gly Ser Thr Arg
            530                 535                 540

Asn Tyr Thr Leu Leu Asp Glu His Gln Asp Leu Asn Glu Gly Leu Gly
545                 550                 555                 560

Glu Gly Val Ser Phe Arg Ala Arg Leu Leu Leu Gly Leu Ala Val Glu
                565                 570                 575

Ile Val Asp Thr Ser Asn Pro Glu Leu Thr Ser Ser Thr Glu Val Gln
            580                 585                 590
```

-continued

```
Val Glu Gln Ala Thr Pro Ile Ser Glu Ser Cys Ala Gly Lys Met Glu
    595                 600                 605
Glu Phe Phe Leu Phe Gly Ala Phe Leu Glu Ala Ser Met Ile Asp Arg
    610                 615                 620
Arg Asn Gly Asp Lys Pro Ile Thr Phe Glu Val Thr Ile Gly Asn Tyr
625                 630                 635                 640
Gly Asn Glu Val Asp Gly Leu Ser Arg Pro Gln Arg Pro Arg Pro Arg
                645                 650                 655
Lys Glu Pro Gly Asp Glu Glu Val Asp Leu Ile Gln Asn Ala Ser
                660                 665                 670
Asp Asp Glu Ala Gly Asp Ala Gly Asp Leu Ala Ser Val Ser Ser Thr
                675                 680                 685
Pro Pro Met Arg Pro Gln Val Thr Asp Arg Asn Tyr Phe His Leu Pro
    690                 695                 700
Tyr Leu Glu Arg Lys Pro Cys Ile Tyr Ile Lys Ser Trp Trp Pro Asp
705                 710                 715                 720
Gln Arg Arg Arg Leu Tyr Asn Ala Asn Ile Met Asp His Ile Ala Asp
                725                 730                 735
Lys Leu Glu Glu Gly Leu Asn Asp Ile Gln Glu Met Ile Lys Thr Glu
                740                 745                 750
Lys Ser Tyr Pro Glu Arg Arg Leu Arg Gly Val Leu Glu Glu Leu Ser
    755                 760                 765
Cys Gly Cys Cys Arg Phe Leu Ser Leu Ala Asp Lys Asp Gln Gly His
    770                 775                 780
Ser Ser Arg Thr Arg Leu Asp Arg Glu Arg Leu Lys Ser Cys Met Arg
785                 790                 795                 800
Glu Leu Glu Asn Met Gly Gln Gln Ala Arg Met Leu Arg Ala Gln Val
                805                 810                 815
Lys Arg His Thr Val Arg Asp Lys Leu Arg Leu Cys Gln Asn Phe Leu
                820                 825                 830
Gln Lys Leu Arg Phe Leu Ala Asp Glu Pro Gln His Ser Ile Pro Asp
    835                 840                 845
Ile Phe Ile Trp Met Met Ser Asn Asn Lys Arg Val Ala Tyr Ala Arg
    850                 855                 860
Val Pro Ser Lys Asp Leu Leu Phe Ser Ile Val Glu Glu Thr Gly
865                 870                 875                 880
Lys Asp Cys Ala Lys Val Lys Thr Leu Phe Leu Lys Leu Pro Gly Lys
                885                 890                 895
Arg Gly Phe Gly Ser Ala Gly Trp Thr Val Gln Ala Lys Val Glu Leu
                900                 905                 910
Tyr Leu Trp Leu Gly Leu Ser Lys Gln Arg Lys Glu Phe Leu Cys Gly
    915                 920                 925
Leu Pro Cys Gly Phe Gln Glu Val Lys Ala Ala Gln Gly Leu Gly Leu
    930                 935                 940
His Ala Phe Pro Pro Val Ser Leu Val Tyr Thr Lys Lys Gln Ala Phe
945                 950                 955                 960
Gln Leu Arg Ala His Met Tyr Gln Ala Arg Ser Leu Phe Ala Ala Asp
                965                 970                 975
Ser Ser Gly Leu Ser Asp Pro Phe Ala Arg Val Phe Phe Ile Asn Gln
                980                 985                 990
Ser Gln Cys Thr Glu Val Leu Asn  Glu Thr Leu Cys Pro  Thr Trp Asp
    995                 1000                1005
```

```
Gln Met Leu Val Phe Asp Asn Leu Glu Leu Tyr Gly Glu Ala His
1010                1015                1020

Glu Leu Arg Asp Asp Pro Pro Ile Ile Val Ile Glu Ile Tyr Asp
    1025                1030                1035

Gln Asp Ser Met Gly Lys Ala Asp Phe Met Gly Arg Thr Phe Ala
1040                1045                1050

Lys Pro Leu Val Lys Met Ala Asp Glu Ala Tyr Cys Pro Pro Arg
    1055                1060                1065

Phe Pro Pro Gln Leu Glu Tyr Tyr Gln Ile Tyr Arg Gly Asn Ala
    1070                1075                1080

Thr Ala Gly Asp Leu Leu Ala Ala Phe Glu Leu Leu Gln Ile Gly
    1085                1090                1095

Pro Ala Gly Lys Ala Asp Leu Pro Pro Ile Asn Gly Pro Val Asp
1100                1105                1110

Val Asp Arg Gly Pro Ile Met Pro Val Pro Met Gly Ile Arg Pro
    1115                1120                1125

Val Leu Ser Lys Tyr Arg Val Glu Val Leu Phe Trp Gly Leu Arg
    1130                1135                1140

Asp Leu Lys Arg Val Asn Leu Ala Gln Val Asp Arg Pro Arg Val
    1145                1150                1155

Asp Ile Glu Cys Ala Gly Lys Gly Val Gln Ser Ser Leu Ile His
1160                1165                1170

Asn Tyr Lys Lys Asn Pro Asn Phe Asn Thr Leu Val Lys Trp Phe
    1175                1180                1185

Glu Val Asp Leu Pro Glu Asn Glu Leu Leu His Pro Pro Leu Asn
    1190                1195                1200

Ile Arg Val Val Asp Cys Arg Ala Phe Gly Arg Tyr Thr Leu Val
1205                1210                1215

Gly Ser His Ala Val Ser Ser Leu Arg Arg Phe Ile Tyr Arg Pro
    1220                1225                1230

Pro Asp Arg Ser Ala Pro Ser Trp Asn Thr Thr Val Arg Leu Leu
    1235                1240                1245

Arg Arg Cys Arg Val Leu Cys Asn Gly Gly Ser Ser Ser His Ser
    1250                1255                1260

Thr Gly Glu Val Val Val Thr Met Glu Pro Glu Val Pro Ile Lys
1265                1270                1275

Lys Leu Glu Thr Met Val Lys Leu Asp Ala Thr Ser Glu Ala Val
    1280                1285                1290

Val Lys Val Asp Val Ala Glu Glu Glu Lys Glu Lys Lys Lys Lys
    1295                1300                1305

Lys Lys Gly Thr Ala Glu Glu Pro Glu Glu Glu Pro Asp Glu
    1310                1315                1320

Ser Met Leu Asp Trp Trp Ser Lys Tyr Phe Ala Ser Ile Asp Thr
1325                1330                1335

Met Lys Glu Gln Leu Arg Gln Gln Glu Pro Ser Gly Ile Asp Leu
    1340                1345                1350

Glu Glu Lys Glu Glu Val Asp Asn Thr Glu Gly Leu Lys Gly Ser
    1355                1360                1365

Met Lys Gly Lys Glu Lys Ala Arg Ala Ala Lys Glu Glu Lys Lys
    1370                1375                1380

Lys Lys Thr Gln Ser Ser Gly Ser Gly Gln Gly Ser Glu Ala Pro
    1385                1390                1395

Glu Lys Lys Lys Pro Lys Ile Asp Glu Leu Lys Val Tyr Pro Lys
```

-continued

```
            1400                1405                 1410

Glu  Leu  Glu  Ser  Glu  Phe  Asp  Asn  Phe  Glu  Asp  Trp  Leu  His  Thr
            1415                1420                 1425

Phe  Asn  Leu  Leu  Arg  Gly  Lys  Thr  Gly  Asp  Asp  Glu  Asp  Gly  Ser
            1430                1435                 1440

Thr  Glu  Glu  Glu  Arg  Ile  Val  Gly  Arg  Phe  Lys  Gly  Ser  Leu  Cys
            1445                1450                 1455

Val  Tyr  Lys  Val  Pro  Leu  Pro  Glu  Asp  Val  Ser  Arg  Glu  Ala  Gly
            1460                1465                 1470

Tyr  Asp  Ser  Thr  Tyr  Gly  Met  Phe  Gln  Gly  Ile  Pro  Ser  Asn  Asp
            1475                1480                 1485

Pro  Ile  Asn  Val  Leu  Val  Arg  Val  Tyr  Val  Val  Arg  Ala  Thr  Asp
            1490                1495                 1500

Leu  His  Pro  Ala  Asp  Ile  Asn  Gly  Lys  Ala  Asp  Pro  Tyr  Ile  Ala
            1505                1510                 1515

Ile  Arg  Leu  Gly  Lys  Thr  Asp  Ile  Arg  Asp  Lys  Glu  Asn  Tyr  Ile
            1520                1525                 1530

Ser  Lys  Gln  Leu  Asn  Pro  Val  Phe  Gly  Lys  Ser  Phe  Asp  Ile  Glu
            1535                1540                 1545

Ala  Ser  Phe  Pro  Met  Glu  Ser  Met  Leu  Thr  Val  Ala  Val  Tyr  Asp
            1550                1555                 1560

Trp  Asp  Leu  Val  Gly  Thr  Asp  Asp  Leu  Ile  Gly  Glu  Thr  Lys  Ile
            1565                1570                 1575

Asp  Leu  Glu  Asn  Arg  Phe  Tyr  Ser  Lys  His  Arg  Ala  Thr  Cys  Gly
            1580                1585                 1590

Ile  Ala  Gln  Thr  Tyr  Ser  Thr  His  Gly  Tyr  Asn  Ile  Trp  Arg  Asp
            1595                1600                 1605

Pro  Met  Lys  Pro  Ser  Gln  Ile  Leu  Thr  Arg  Leu  Cys  Lys  Asp  Gly
            1610                1615                 1620

Lys  Val  Asp  Gly  Pro  His  Phe  Gly  Pro  Pro  Gly  Arg  Val  Lys  Val
            1625                1630                 1635

Ala  Asn  Arg  Val  Phe  Thr  Gly  Pro  Ser  Glu  Ile  Glu  Asp  Glu  Asn
            1640                1645                 1650

Gly  Gln  Arg  Lys  Pro  Thr  Asp  Glu  His  Val  Ala  Leu  Leu  Ala  Leu
            1655                1660                 1665

Arg  His  Trp  Glu  Asp  Ile  Pro  Arg  Ala  Gly  Cys  Arg  Leu  Val  Pro
            1670                1675                 1680

Glu  His  Val  Glu  Thr  Arg  Pro  Leu  Leu  Asn  Pro  Asp  Lys  Pro  Gly
            1685                1690                 1695

Ile  Glu  Gln  Gly  Arg  Leu  Glu  Leu  Trp  Val  Asp  Met  Phe  Pro  Met
            1700                1705                 1710

Asp  Met  Pro  Ala  Pro  Gly  Thr  Pro  Leu  Asp  Ile  Ser  Pro  Arg  Lys
            1715                1720                 1725

Pro  Lys  Lys  Tyr  Glu  Leu  Arg  Val  Ile  Ile  Trp  Asn  Thr  Asp  Glu
            1730                1735                 1740

Val  Val  Leu  Glu  Asp  Asp  Asp  Phe  Phe  Thr  Gly  Glu  Lys  Ser  Ser
            1745                1750                 1755

Asp  Ile  Phe  Val  Arg  Gly  Trp  Leu  Lys  Gly  Gln  Gln  Glu  Asp  Lys
            1760                1765                 1770

Gln  Asp  Thr  Asp  Val  His  Tyr  His  Ser  Leu  Thr  Gly  Glu  Gly  Asn
            1775                1780                 1785

Phe  Asn  Trp  Arg  Tyr  Leu  Phe  Pro  Phe  Asp  Tyr  Leu  Ala  Ala  Glu
            1790                1795                 1800
```

```
Glu Lys Ile Val Ile Ser Lys Lys Glu Ser Met Phe Ser Trp Asp
    1805                1810                1815

Glu Thr Glu Tyr Lys Ile Pro Ala Arg Leu Thr Leu Gln Ile Trp
    1820                1825                1830

Asp Ala Asp His Phe Ser Ala Asp Asp Phe Leu Gly Ala Ile Glu
    1835                1840                1845

Leu Asp Leu Asn Arg Phe Pro Arg Gly Ala Lys Thr Ala Lys Gln
    1850                1855                1860

Cys Thr Met Glu Met Ala Thr Gly Glu Val Asp Val Pro Leu Val
    1865                1870                1875

Ser Ile Phe Lys Gln Lys Arg Val Lys Gly Trp Trp Pro Leu Leu
    1880                1885                1890

Ala Arg Asn Glu Asn Asp Glu Phe Glu Leu Thr Gly Lys Val Glu
    1895                1900                1905

Ala Glu Leu His Leu Leu Thr Ala Glu Glu Ala Glu Lys Asn Pro
    1910                1915                1920

Val Gly Leu Ala Arg Asn Glu Pro Asp Pro Leu Glu Lys Pro Asn
    1925                1930                1935

Arg Pro Asp Thr Ala Phe Val Trp Phe Leu Asn Pro Leu Lys Ser
    1940                1945                1950

Ile Lys Tyr Leu Ile Cys Thr Arg Tyr Lys Trp Leu Ile Ile Lys
    1955                1960                1965

Ile Val Leu Ala Leu Leu Gly Leu Leu Met Leu Gly Leu Phe Leu
    1970                1975                1980

Tyr Ser Leu Pro Gly Tyr Met Val Lys Lys Leu Leu Gly Ala
    1985                1990                1995

<210> SEQ ID NO 7
<211> LENGTH: 84
<212> TYPE: DNA
<213> ORGANISM: Artificial sequence
<220> FEATURE:
<223> OTHER INFORMATION: Synthetic polynucleotide

<400> SEQUENCE: 7
gtaagtatca aggttacaag acaggtttaa ggagaccaat agaaactggg cttgtcgaga      60
cagagaagac tcttgcgttt ctga                                            84

<210> SEQ ID NO 8
<211> LENGTH: 49
<212> TYPE: DNA
<213> ORGANISM: Artificial sequence
<220> FEATURE:
<223> OTHER INFORMATION: Synthetic polynucleotide

<400> SEQUENCE: 8
taggcaccta ttggtcttac tgacatccac tttgcctttc tctccacag                 49

<210> SEQ ID NO 9
<211> LENGTH: 1992
<212> TYPE: PRT
<213> ORGANISM: M. musculus

<400> SEQUENCE: 9

Met Ala Leu Ile Val His Leu Lys Thr Val Ser Glu Leu Arg Gly Lys
1               5                   10                  15

Gly Asp Arg Ile Ala Lys Val Thr Phe Arg Gly Gln Ser Phe Tyr Ser
            20                  25                  30
```

```
Arg Val Leu Glu Asn Cys Glu Gly Val Ala Asp Phe Asp Glu Thr Phe
        35                  40                  45

Arg Trp Pro Val Ala Ser Ser Ile Asp Arg Asn Glu Val Leu Glu Ile
    50                  55                  60

Gln Ile Phe Asn Tyr Ser Lys Val Phe Ser Asn Lys Leu Ile Gly Thr
65                  70                  75                  80

Phe Cys Met Val Leu Gln Lys Val Val Glu Glu Asn Arg Val Glu Val
                85                  90                  95

Thr Asp Thr Leu Met Asp Asp Ser Asn Ala Ile Ile Lys Thr Ser Leu
            100                 105                 110

Ser Met Glu Val Arg Tyr Gln Ala Thr Asp Gly Thr Val Gly Pro Trp
        115                 120                 125

Asp Asp Gly Asp Phe Leu Gly Asp Glu Ser Leu Gln Glu Glu Lys Asp
    130                 135                 140

Ser Gln Glu Thr Asp Gly Leu Leu Pro Gly Ser Arg Pro Ser Thr Arg
145                 150                 155                 160

Ile Ser Gly Glu Lys Ser Phe Arg Ser Lys Gly Arg Glu Lys Thr Lys
                165                 170                 175

Gly Gly Arg Asp Gly Glu His Lys Ala Gly Arg Ser Val Phe Ser Ala
            180                 185                 190

Met Lys Leu Gly Lys Thr Arg Ser His Lys Glu Glu Pro Gln Arg Gln
        195                 200                 205

Asp Glu Pro Ala Val Leu Glu Met Glu Asp Leu Asp His Leu Ala Ile
    210                 215                 220

Gln Leu Gly Asp Gly Leu Asp Pro Asp Ser Val Ser Leu Ala Ser Val
225                 230                 235                 240

Thr Ala Leu Thr Ser Asn Val Ser Asn Lys Arg Ser Lys Pro Asp Ile
                245                 250                 255

Lys Met Glu Pro Ser Ala Gly Arg Pro Met Asp Tyr Gln Val Ser Ile
            260                 265                 270

Thr Val Ile Glu Ala Arg Gln Leu Val Gly Leu Asn Met Asp Pro Val
        275                 280                 285

Val Cys Val Glu Val Gly Asp Asp Lys Lys Tyr Thr Ser Met Lys Glu
    290                 295                 300

Ser Thr Asn Cys Pro Tyr Tyr Asn Glu Tyr Phe Val Phe Asp Phe His
305                 310                 315                 320

Val Ser Pro Asp Val Met Phe Asp Lys Ile Ile Lys Ile Ser Val Ile
                325                 330                 335

His Ser Lys Asn Leu Leu Arg Ser Gly Thr Leu Val Gly Ser Phe Lys
            340                 345                 350

Met Asp Val Gly Thr Val Tyr Ser Gln Pro Glu His Gln Phe His His
        355                 360                 365

Lys Trp Ala Ile Leu Ser Asp Pro Asp Ile Ser Ala Gly Leu Lys
    370                 375                 380

Gly Tyr Val Lys Cys Asp Val Ala Val Gly Lys Gly Asp Asn Ile
385                 390                 395                 400

Lys Thr Pro His Lys Ala Asn Glu Thr Asp Glu Asp Ile Glu Gly
                405                 410                 415

Asn Leu Leu Pro Glu Gly Val Pro Pro Glu Arg Gln Trp Ala Arg
            420                 425                 430

Phe Tyr Val Lys Ile Tyr Arg Ala Glu Gly Leu Pro Arg Met Asn Thr
        435                 440                 445
```

-continued

Ser Leu Met Ala Asn Val Lys Lys Ala Phe Ile Gly Glu Asn Lys Asp
450                 455                 460

Leu Val Asp Pro Tyr Val Gln Val Phe Phe Ala Gly Gln Lys Gly Lys
465                 470                 475                 480

Thr Ser Val Gln Lys Ser Ser Tyr Glu Pro Leu Trp Asn Glu Gln Val
                485                 490                 495

Val Phe Thr Asp Leu Phe Pro Pro Leu Cys Lys Arg Met Lys Val Gln
            500                 505                 510

Ile Arg Asp Ser Asp Lys Val Asn Asp Val Ala Ile Gly Thr His Phe
        515                 520                 525

Ile Asp Leu Arg Lys Ile Ser Asn Asp Gly Asp Lys Gly Phe Leu Pro
    530                 535                 540

Thr Leu Gly Pro Ala Trp Val Asn Met Tyr Gly Ser Thr Arg Asn Tyr
545                 550                 555                 560

Thr Leu Leu Asp Glu His Gln Asp Leu Asn Glu Gly Leu Gly Glu Gly
                565                 570                 575

Val Ser Phe Arg Ala Arg Leu Met Leu Gly Leu Ala Val Glu Ile Leu
            580                 585                 590

Asp Thr Ser Asn Pro Glu Leu Thr Ser Ser Thr Glu Val Gln Val Glu
        595                 600                 605

Gln Ala Thr Pro Val Ser Glu Ser Cys Thr Gly Arg Met Glu Glu Phe
    610                 615                 620

Phe Leu Phe Gly Ala Phe Leu Glu Ala Ser Met Ile Asp Arg Lys Asn
625                 630                 635                 640

Gly Asp Lys Pro Ile Thr Phe Glu Val Thr Ile Gly Asn Tyr Gly Asn
                645                 650                 655

Glu Val Asp Gly Met Ser Arg Pro Leu Arg Pro Arg Pro Arg Lys Glu
            660                 665                 670

Pro Gly Asp Glu Glu Glu Val Asp Leu Ile Gln Asn Ser Ser Asp Asp
        675                 680                 685

Glu Gly Asp Glu Ala Gly Asp Leu Ala Ser Val Ser Ser Thr Pro Pro
    690                 695                 700

Met Arg Pro Gln Ile Thr Asp Arg Asn Tyr Phe His Leu Pro Tyr Leu
705                 710                 715                 720

Glu Arg Lys Pro Cys Ile Tyr Ile Lys Ser Trp Trp Pro Asp Gln Arg
                725                 730                 735

Arg Arg Leu Tyr Asn Ala Asn Ile Met Asp His Ile Ala Asp Lys Leu
            740                 745                 750

Glu Glu Gly Leu Asn Asp Val Gln Glu Met Ile Lys Thr Glu Lys Ser
        755                 760                 765

Tyr Pro Glu Arg Arg Leu Arg Gly Val Leu Glu Glu Leu Ser Cys Gly
    770                 775                 780

Cys His Arg Phe Leu Ser Leu Ser Asp Lys Asp Gln Gly Arg Ser Ser
785                 790                 795                 800

Arg Thr Arg Leu Asp Arg Glu Arg Leu Lys Ser Cys Met Arg Glu Leu
                805                 810                 815

Glu Ser Met Gly Gln Gln Ala Lys Ser Leu Arg Ala Gln Val Lys Arg
            820                 825                 830

His Thr Val Arg Asp Lys Leu Arg Ser Cys Gln Asn Phe Leu Gln Lys
        835                 840                 845

Leu Arg Phe Leu Ala Asp Glu Pro Gln His Ser Ile Pro Asp Val Phe
    850                 855                 860

Ile Trp Met Met Ser Asn Asn Lys Arg Ile Ala Tyr Ala Arg Val Pro

```
                865                 870                 875                 880
Ser Lys Asp Leu Leu Phe Ser Ile Val Glu Glu Leu Gly Lys Asp
                    885                 890                 895
Cys Ala Lys Val Lys Thr Leu Phe Leu Lys Leu Pro Gly Lys Arg Gly
                900                 905                 910
Phe Gly Ser Ala Gly Trp Thr Val Gln Ala Lys Leu Glu Leu Tyr Leu
                915                 920                 925
Trp Leu Gly Leu Ser Lys Gln Arg Lys Asp Phe Leu Cys Gly Leu Pro
                930                 935                 940
Cys Gly Phe Glu Glu Val Lys Ala Ala Gln Gly Leu Gly Leu His Ser
945                 950                 955                 960
Phe Pro Pro Ile Ser Leu Val Tyr Thr Lys Lys Gln Ala Phe Gln Leu
                965                 970                 975
Arg Ala His Met Tyr Gln Ala Arg Ser Leu Phe Ala Ala Asp Ser Ser
                980                 985                 990
Gly Leu Ser Asp Pro Phe Ala Arg Val Phe Phe Ile Asn Gln Ser Gln
                995                 1000                1005
Cys Thr Glu Val Leu Asn Glu Thr Leu Cys Pro Thr Trp Asp Gln
        1010                1015                1020
Met Leu Val Phe Asp Asn Leu Glu Leu Tyr Gly Glu Ala His Glu
        1025                1030                1035
Leu Arg Asp Asp Pro Pro Ile Ile Val Ile Glu Ile Tyr Asp Gln
        1040                1045                1050
Asp Ser Met Gly Lys Ala Asp Phe Met Gly Arg Thr Phe Ala Lys
        1055                1060                1065
Pro Leu Val Lys Met Ala Asp Glu Ala Tyr Cys Pro Pro Arg Phe
        1070                1075                1080
Pro Pro Gln Leu Glu Tyr Tyr Gln Ile Tyr Arg Gly Ser Ala Thr
        1085                1090                1095
Ala Gly Asp Leu Leu Ala Ala Phe Glu Leu Leu Gln Ile Gly Pro
        1100                1105                1110
Ser Gly Lys Ala Asp Leu Pro Pro Ile Asn Gly Pro Val Asp Met
        1115                1120                1125
Asp Arg Gly Pro Ile Met Pro Val Pro Val Gly Ile Arg Pro Val
        1130                1135                1140
Leu Ser Lys Tyr Arg Val Glu Val Leu Phe Trp Gly Leu Arg Asp
        1145                1150                1155
Leu Lys Arg Val Asn Leu Ala Gln Val Asp Arg Pro Arg Val Asp
        1160                1165                1170
Ile Glu Cys Ala Gly Lys Gly Val Gln Ser Ser Leu Ile His Asn
        1175                1180                1185
Tyr Lys Lys Asn Pro Asn Phe Asn Thr Leu Val Lys Trp Phe Glu
        1190                1195                1200
Val Asp Leu Pro Glu Asn Glu Leu Leu His Pro Leu Asn Ile
        1205                1210                1215
Arg Val Val Asp Cys Arg Ala Phe Gly Arg Tyr Thr Leu Val Gly
        1220                1225                1230
Ser His Ala Val Ser Ser Leu Arg Arg Phe Ile Tyr Arg Pro Pro
        1235                1240                1245
Asp Arg Ser Ala Pro Asn Trp Asn Thr Thr Gly Glu Val Val Val
        1250                1255                1260
Ser Met Glu Pro Glu Glu Pro Val Lys Lys Leu Glu Thr Met Val
        1265                1270                1275
```

```
Lys Leu Asp Ala Thr Ser Asp Ala Val Lys Val Asp Val Ala
1280             1285             1290

Glu Asp Glu Lys Glu Arg Lys Lys Lys Lys Lys Gly Pro Ser
1295             1300             1305

Glu Glu Pro Glu Glu Glu Pro Asp Glu Ser Met Leu Asp Trp
1310             1315             1320

Trp Ser Lys Tyr Phe Ala Ser Ile Asp Thr Met Lys Glu Gln Leu
1325             1330             1335

Arg Gln His Glu Thr Ser Gly Thr Asp Leu Glu Glu Lys Glu Glu
1340             1345             1350

Met Glu Ser Ala Glu Gly Leu Lys Gly Pro Met Lys Ser Lys Glu
1355             1360             1365

Lys Ser Arg Ala Ala Lys Glu Glu Lys Lys Lys Asn Gln Ser
1370             1375             1380

Pro Gly Pro Gly Gln Gly Ser Glu Ala Pro Glu Lys Lys Lys Ala
1385             1390             1395

Lys Ile Asp Glu Leu Lys Val Tyr Pro Lys Glu Leu Glu Ser Glu
1400             1405             1410

Phe Asp Ser Phe Glu Asp Trp Leu His Thr Phe Asn Leu Leu Arg
1415             1420             1425

Gly Lys Thr Gly Asp Asp Glu Asp Gly Ser Thr Glu Glu Glu Arg
1430             1435             1440

Ile Val Gly Arg Phe Lys Gly Ser Leu Cys Val Tyr Lys Val Pro
1445             1450             1455

Leu Pro Glu Asp Val Ser Arg Glu Ala Gly Tyr Asp Pro Thr Tyr
1460             1465             1470

Gly Met Phe Gln Gly Ile Pro Ser Asn Asp Pro Ile Asn Val Leu
1475             1480             1485

Val Arg Ile Tyr Val Val Arg Ala Thr Asp Leu His Pro Ala Asp
1490             1495             1500

Ile Asn Gly Lys Ala Asp Pro Tyr Ile Ala Ile Lys Leu Gly Lys
1505             1510             1515

Thr Asp Ile Arg Asp Lys Glu Asn Tyr Ile Ser Lys Gln Leu Asn
1520             1525             1530

Pro Val Phe Gly Lys Ser Phe Asp Ile Glu Ala Ser Phe Pro Met
1535             1540             1545

Glu Ser Met Leu Thr Val Ala Val Tyr Asp Trp Asp Leu Val Gly
1550             1555             1560

Thr Asp Asp Leu Ile Gly Glu Thr Lys Ile Asp Leu Glu Asn Arg
1565             1570             1575

Phe Tyr Ser Lys His Arg Ala Thr Cys Gly Ile Ala Gln Thr Tyr
1580             1585             1590

Ser Ile His Gly Tyr Asn Ile Trp Arg Asp Pro Met Lys Pro Ser
1595             1600             1605

Gln Ile Leu Thr Arg Leu Cys Lys Glu Gly Lys Val Asp Gly Pro
1610             1615             1620

His Phe Gly Pro His Gly Arg Val Arg Val Ala Asn Arg Val Phe
1625             1630             1635

Thr Gly Pro Ser Glu Ile Glu Asp Glu Asn Gly Gln Arg Lys Pro
1640             1645             1650

Thr Asp Glu His Val Ala Leu Ser Ala Leu Arg His Trp Glu Asp
1655             1660             1665
```

Ile Pro Arg Val Gly Cys Arg Leu Val Pro Glu His Val Glu Thr
1670                1675                1680

Arg Pro Leu Leu Asn Pro Asp Lys Pro Gly Ile Glu Gln Gly Arg
    1685                1690                1695

Leu Glu Leu Trp Val Asp Met Phe Pro Met Asp Met Pro Ala Pro
1700                1705                1710

Gly Thr Pro Leu Asp Ile Ser Pro Arg Lys Pro Lys Lys Tyr Glu
    1715                1720                1725

Leu Arg Val Ile Val Trp Asn Thr Asp Glu Val Val Leu Glu Asp
1730                1735                1740

Asp Asp Phe Phe Thr Gly Glu Lys Ser Ser Asp Ile Phe Val Arg
    1745                1750                1755

Gly Trp Leu Lys Gly Gln Gln Glu Asp Lys Gln Asp Thr Asp Val
1760                1765                1770

His Tyr His Ser Leu Thr Gly Glu Gly Asn Phe Asn Trp Arg Tyr
    1775                1780                1785

Leu Phe Pro Phe Asp Tyr Leu Ala Ala Glu Glu Lys Ile Val Met
1790                1795                1800

Ser Lys Lys Glu Ser Met Phe Ser Trp Asp Glu Thr Glu Tyr Lys
    1805                1810                1815

Ile Pro Ala Arg Leu Thr Leu Gln Ile Trp Asp Ala Asp His Phe
1820                1825                1830

Ser Ala Asp Asp Phe Leu Gly Ala Ile Glu Leu Asp Leu Asn Arg
    1835                1840                1845

Phe Pro Arg Gly Ala Lys Thr Ala Lys Gln Cys Thr Met Glu Met
1850                1855                1860

Ala Thr Gly Glu Val Asp Val Pro Leu Val Ser Ile Phe Lys Gln
    1865                1870                1875

Lys Arg Val Lys Gly Trp Trp Pro Leu Leu Ala Arg Asn Glu Asn
1880                1885                1890

Asp Glu Phe Glu Leu Thr Gly Lys Val Glu Ala Glu Leu His Leu
    1895                1900                1905

Leu Thr Ala Glu Glu Ala Glu Lys Asn Pro Val Gly Leu Ala Arg
1910                1915                1920

Asn Glu Pro Asp Pro Leu Glu Lys Pro Asn Arg Pro Asp Thr Ala
    1925                1930                1935

Phe Val Trp Phe Leu Asn Pro Leu Lys Ser Ile Lys Tyr Leu Ile
1940                1945                1950

Cys Thr Arg Tyr Lys Trp Leu Ile Ile Lys Ile Val Leu Ala Leu
    1955                1960                1965

Leu Gly Leu Leu Met Leu Ala Leu Phe Leu Tyr Ser Leu Pro Gly
1970                1975                1980

Tyr Met Val Lys Lys Leu Leu Gly Ala
    1985                1990

<210> SEQ ID NO 10
<211> LENGTH: 143
<212> TYPE: DNA
<213> ORGANISM: Artificial sequence
<220> FEATURE:
<223> OTHER INFORMATION: Synthetic polynucleotide

<400> SEQUENCE: 10
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120

```
gccaactcca tcactagggg ttc                                             143
```

<210> SEQ ID NO 11
<211> LENGTH: 143
<212> TYPE: DNA
<213> ORGANISM: Artificial sequence
<220> FEATURE:
<223> OTHER INFORMATION: Synthetic polynucleotide

<400> SEQUENCE: 11

```
acccctagtg atggagttgg ccactccctc tctgcgcgct cgctcgctca ctgaggccgc     60
ccgggcaaag cccgggcgtc gggcgacctt tggtcgcccg gcctcagtga gcgagcgagc    120
gcgcagagag ggagtggcca acc                                            143
```

<210> SEQ ID NO 12
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 12

```
cacttgcttt gtctcatctc c                                               21
```

<210> SEQ ID NO 13
<211> LENGTH: 21
<212> TYPE: DNA
<213> ORGANISM: Artificial sequence
<220> FEATURE:
<223> OTHER INFORMATION: Synthetic polynucleotide

<400> SEQUENCE: 13

```
gtcacttctt ctgggtattt c                                               21
```

<210> SEQ ID NO 14
<211> LENGTH: 6967
<212> TYPE: DNA
<213> ORGANISM: Artificial sequence
<220> FEATURE:
<223> OTHER INFORMATION: pTR22-smCBA-otoferlinNT Hs var 1 5-APSD-APhead

<400> SEQUENCE: 14

```
agggggggggg gggggggggt tggccactcc ctctctgcgc gctcgctcgc tcactgaggc     60
cgggcgacca aggtcgccc gacgcccggg ctttgcccgg cggcctcag tgagcgagcg    120
agcgcgcaga gagggagtgg ccaactccat cactaggggt cctcagatc tggcgcgccc    180
aattcggtac cctagttatt aatagtaatc aattacgggg tcattagttc atagcccata    240
tatggagttc cgcgttacat aacttacggt aaatggcccg cctggctgac cgcccaacga    300
cccccgccca ttgacgtcaa taatgacgta tgttcccata gtaacgccaa tagggacttt    360
ccattgacgt caatgggtgg actatttacg gtaaactgcc cacttggcag tacatcaagt    420
gtatcatatg ccaagtacgc ccctattga cgtcaatgac ggtaaatggc ccgcctggca    480
ttatgcccag tacatgacct tatgggactt tcctacttgg cagtacatct acgtattagt    540
catcgctatt accatggtcg aggtgagccc cacgttctgc ttcactctcc ccatctcccc    600
ccctccccca ccccaatttt gtatttattt attttttaa ttattttgtg cagcgatggg    660
ggcgggggg ggggggggc gcgcgccagg cggggcgggg cggggcgagg ggcggggcgg    720
ggcgaggcgg agaggtgcgg cggcagccaa tcagagcggc gcgctccgaa agtttccttt    780
```

```
tatggcgagg cggcggcggc ggcggcccta taaaaagcga agcgcgcggc gggcgggagt    840
cgctgcgacg ctgccttcgc cccgtgcccc gctccgccgc cgcctcgcgc cgcccgcccc    900
ggctctgact gaccgcgtta ctcccacagg tgagcgggcg ggacggccct tctcctccgg    960
gctgtaatta gcgcttggtt taatgacggc ttgtttcttt tctgtggctg cgtgaaagcc   1020
ttgaggggct ccgggagcta gagcctctgc taaccatgtt catgccttct tcttttttcct   1080
acagctcctg ggcaacgtgc tggttattgt gctgtctcat cattttggca aagaattcta   1140
gcggccgcca ccatggcctt gctcatccac ctcaagacag tctcggagct gcggggcagg   1200
ggcgaccgga tcgccaaagt gactttccga gggcaatcct tctactctcg ggtcctggag   1260
aactgtgagg atgtggctga ctttgatgag acatttcggt ggccggtggc cagcagcatc   1320
gacagaaatg agatgctgga gattcaggtt ttcaactaca gcaaagtctt cagcaacaag   1380
ctcatcggga ccttccgcat ggtgctgcag aaggtggtag aggagagcca tgtggaggtg   1440
actgacacgc tgattgatga caacaatgct atcatcaaga ccagcctgtg cgtggaggtc   1500
cggtatcagg ccactgacgg cacagtgggc tcctgggacg atgggacttt cctgggagat   1560
gagtctcttc aagaggaaga gaaggacagc caagagacgg atggactgct cccaggctcc   1620
cggcccagct cccggccccc aggagagaag agcttccgga gagccgggag gagcgtgttc   1680
tccgccatga agctcggcaa aaaccggtct cacaaggagg agccccaaag accagatgaa   1740
ccggcggtgc tggagatgga agaccttgac catctggcca ttcggctagg agatggactg   1800
gatcccgact cggtgtctct agcctcagtc acagctctca ccactaatgt ctccaacaag   1860
cgatctaagc agacattaa gatggagcca agtgctgggc ggcccatgga ttaccaggtc   1920
agcatcacgg tgatcgaggc ccggcagctg gtgggcttga acatggaccc tgtggtgtgc   1980
gtggaggtgg gtgacgacaa gaagtacaca tccatgaagg agtccactaa ctgcccctat   2040
tacaacgagt acttcgtctt cgacttccat gtctctccgg atgtcatgtt tgacaagatc   2100
atcaagattt cggtgattca ctccaagaac ctgctgcgca gtggcacccct ggtgggctcc   2160
ttcaaaatgg acgtgggaac cgtgtactcg cagccagagc accagttcca tcacaagtgg   2220
gccatcctgt ctgaccccga tgacatctcc tcggggctga agggctacgt gaagtgtgac   2280
gttgccgtgg tgggcaaagg ggacaacatc aagacgcccc acaaggccaa tgagaccgac   2340
gaagatgaca ttgaggggaa cttgctgctc cccgaggggg tgccccccga acgccagtgg   2400
gcccggttct atgtgaaaat ttaccgagca gaggggctgc cccgtatgaa cacaagcctc   2460
atggccaatg taaagaaggc tttcatcggt gaaaacaagg acctcgtgga cccctacgtg   2520
caagtcttct ttgctggcca agggcaag acttcagtgc agaagagcag ctatgagccc   2580
ctgtggaatg agcaggtcgt ctttacagac ctcttccccc cactctgcaa acgcatgaag   2640
gtgcagatcc gagactcgga caaggtcaac gacgtggcca tcggcacccca cttcattgac   2700
ctgcgcaaga tttctaatga cggagacaaa ggcttcctgc ccacactggg cccagcctgg   2760
gtgaacatgt acggctccac acgtaactac acgctgctgg atgagcatca ggacctgaac   2820
gagggcctgg gggagggtgt gtccttccgg gcccggctcc tgctgggcct ggctgtggag   2880
atcgtagaca cctccaaccc tgagctcacc agctccacag aggtgcaggt ggagcaggcc   2940
acgcccatct cggagagctg tgcaggtaaa atggaagaat tctttctctt tggagccttc   3000
ctggaggcct caatgatcga ccggagaaac ggagacaagc ccatcacctt tgaggtcacc   3060
ataggcaact atgggaacga agttgatggc ctgtcccggc cccagcggcc tcggccccgg   3120
aaggagccgg gggatgagga agaagtagac ctgattcaga acgcaagtga tgacgaggcc   3180
```

```
ggtgatgccg gggacctggc ctcagtctcc tccactccac caatgcggcc ccaggtcacc    3240
gacaggaact acttccatct gccctacctg gagcgaaagc cctgcatcta catcaagagc    3300
tggtggccgg accagcgccg ccgcctctac aatgccaaca tcatggacca cattgccgac    3360
aagctggaag aaggcctgaa cgacatacag gagatgatca aaacggagaa gtcctaccct    3420
gagcgtcgcc tgcgggggcgt cctggaggag ctgagctgtg gctgctgccg cttcctctcc    3480
ctcgctgaca aggaccaggg ccactcatcc cgcaccaggc ttgaccggga gcgcctcaag    3540
tcctgcatga gggagctggt aagtatcaag gttacaagac aggtttaagg agaccaatag    3600
aaactgggct tgtcgagaca gagaagactc ttgcgtttct gagctagccc ccgggtgcgc    3660
ggcgtcggtg gtgccggcgg ggggcgccag gtcgcaggcg gtgtagggct ccaggcaggc    3720
ggcgaaggcc atgacgtgcg ctatgaaggt ctgctcctgc acgccgtgaa ccaggtgcgc    3780
ctgcgggccg cgcgcgaaca ccgccacgtc ctcgcctgcg tgggtctctt cgtccagggg    3840
cactgctgac tgctgccgat actcggggct cccgctctcg ctctcggtaa catccggccg    3900
ggcgccgtcc ttgagcacat agcctggacc gtttcgtcga ctgttaatta agcatgctgg    3960
ggagagatct aggaacccct agtgatggag ttggccactc cctctctgcg cgctcgctcg    4020
ctcactgagg ccgcccgggc aaagcccggg cgtcgggcga cctttggtcg cccggcctca    4080
gtgagcgagc gagcgcgcag agagggagtg gccaaccccc ccccccccc cctgcagcc    4140 ctgcattaat gaatcggcca acgcgcgggg agaggcggtt tgcgtattgg gcgctcttcc    4200
gcttcctcgc tcactgactc gctgcgctcg gtcgttcggc tgcggcgagc ggtatcagct    4260
cactcaaagg cggtaatacg gttatccaca gaatcagggg ataacgcagg aaagaacatg    4320
tgagcaaaag gccagcaaaa ggccaggaac cgtaaaaagg ccgcgttgct ggcgtttttc    4380
cataggctcc gcccccctga cgagcatcac aaaaatcgac gctcaagtca gaggtggcga    4440
aacccgacag gactataaag ataccaggcg tttccccctg gaagctccct cgtgcgctct    4500
cctgttccga ccctgccgct taccggatac ctgtccgcct ttctcccttc gggaagcgtg    4560
gcgctttctc aatgctcacg ctgtaggtat ctcagttcgg tgtaggtcgt tcgctccaag    4620
ctgggctgtg tgcacgaacc ccccgttcag cccgaccgct gcgccttatc cggtaactat    4680
cgtcttgagt ccaacccggt aagacacgac ttatcgccac tggcagcagc cactggtaac    4740
aggattagca gagcgaggta tgtaggcggt gctacagagt tcttgaagtg gtggcctaac    4800
tacggctaca ctagaaggac agtatttggt atctgcgctc tgctgaagcc agttaccttc    4860
ggaaaaagag ttggtagctc ttgatccggc aaacaaacca ccgctggtag cggtggtttt    4920
tttgtttgca agcagcagat tacgcgcaga aaaaaggat ctcaagaaga tcctttgatc    4980
ttttctacgg ggtctgacgc tcagtggaac gaaaactcac gttaagggat tttggtcatg    5040
agattatcaa aaaggatctt cacctagatc cttttaaatt aaaaatgaag ttttaaatca    5100
atctaaagta tatatgagta aacttggtct gacagttacc aatgcttaat cagtgaggca    5160
cctatctcag cgatctgtct atttcgttca tccatagttg cctgactccc cgtcgtgtag    5220
ataactacga tacgggaggg cttaccatct ggccccagtg ctgcaatgat accgcgagac    5280
ccacgctcac cggctccaga tttatcagca ataaaccagc cagccggaag ggccgagcgc    5340
agaagtggtc ctgcaacttt atccgcctcc atccagtcta ttaattgttg ccgggaagct    5400
agagtaagta gttcgccagt taatagtttg cgcaacgttg ttgccattgc tacaggcatc    5460
gtggtgtcac gctcgtcgtt tggtatggct tcattcagct ccggttccca acgatcaagg    5520
```

| | |
|---|---:|
| cgagttacat gatcccccat gttgtgcaaa aaagcggtta gctccttcgg tcctccgatc | 5580 |
| gttgtcagaa gtaagttggc cgcagtgtta tcactcatgg ttatggcagc actgcataat | 5640 |
| tctcttactg tcatgccatc cgtaagatgc ttttctgtga ctggtgagta ctcaaccaag | 5700 |
| tcattctgag aatagtgtat gcggcgaccg agttgctctt gcccggcgtc aatacgggat | 5760 |
| aataccgcgc cacatagcag aactttaaaa gtgctcatca ttggaaaacg ttcttcgggg | 5820 |
| cgaaaactct caaggatctt accgctgttg agatccagtt cgatgtaacc cactcgtgca | 5880 |
| cccaactgat cttcagcatc ttttactttc accagcgttt ctgggtgagc aaaaacagga | 5940 |
| aggcaaaatg ccgcaaaaaa gggaataagg gcgacacgga aatgttgaat actcatactc | 6000 |
| ttcctttttc aatattattg aagcatttat cagggttatt gtctcatgag cggatacata | 6060 |
| tttgaatgta tttagaaaaa taaacaaata ggggttccgc gcacatttcc ccgaaaagtg | 6120 |
| ccacctgacg tctaagaaac cattattatc atgacattaa cctataaaaa taggcgtatc | 6180 |
| acgaggccct ttcgtctcgc gcgtttcggt gatgacggtg aaaacctctg acacatgcag | 6240 |
| ctcccggaga cggtcacagc ttgtctgtaa gcggatgccg ggagcagaca gcccgtcag | 6300 |
| ggcgcgtcag cgggtgttgg cgggtgtcgg gctggcttaa ctatgcggc atcagagcag | 6360 |
| attgtactga gagtgcacca tatgcggtgt gaaataccgc acagatgcgt aaggagaaaa | 6420 |
| taccgcatca ggaaattgta acgttaata ttttgttaaa attcgcgtta aattttgtt | 6480 |
| aaatcagctc attttttaac cataggccg aatcggcaa atcccttat aaatcaaaag | 6540 |
| aatagaccga gatagggttg agtgttgttc cagtttggaa caagagtcca ctattaaaga | 6600 |
| acgtggactc caacgtcaaa gggcgaaaaa ccgtctatca gggcgatggc ccactacgtg | 6660 |
| aaccatcacc ctaatcaagt tttttggggt cgaggtgccg taaagcacta atcggaacc | 6720 |
| ctaaagggag cccccgattt agagcttgac ggggaaagcc ggcgaacgtg gcgagaaagg | 6780 |
| aagggaagaa agcgaaagga gcgggcgcta gggcgctggc aagtgtagcg gtcacgctgc | 6840 |
| gcgtaaccac cacacccgcc gcgcttaatg cgccgctaca gggcgcgtcg cgccattcgc | 6900 |
| cattcaggct acgcaactgt tgggaagggc gatcggtgcg ggcctcttcg ctattacgcc | 6960 |
| aggctgc | 6967 |

<210> SEQ ID NO 15
<211> LENGTH: 7470
<212> TYPE: DNA
<213> ORGANISM: Artificial sequence
<220> FEATURE:
<223> OTHER INFORMATION: pTR22-APhead-APSA-otoferlinCT Hs var 1

<400> SEQUENCE: 15

| | |
|---|---:|
| agggggggg gggggggggt tggccactcc ctctctgcgc gctcgctcgc tcactgaggc | 60 |
| cgggcgacca aaggtcgccc gacgcccggg ctttgcccgg gcggcctcag tgagcgagcg | 120 |
| agcgcgcaga gagggagtgg ccaactccat cactagggggt tcctcagatc tggcgcgccc | 180 |
| aattggcttc gaattctagc ggccgccccc gggtgcgcgc cgtcggtggt gccgcgggg | 240 |
| ggcgccaggt cgcaggcggt gtagggctcc aggcaggcgg cgaaggccat gacgtgcgct | 300 |
| atgaaggtct gctcctgcac gccgtgaacc aggtgcgcct gcgggccgcg cgcgaacacc | 360 |
| gccacgtcct cgcctgcgtg gtctcttcg tccagggca ctgctgactg ctgccgatac | 420 |
| tcggggctcc cgctctcgct ctcggtaaca tccggccggg cgccgtcctt gagcacatag | 480 |
| cctggaccgt ttccttaagc gacgcatgct cgcgatagcc acctattggt cttactgaca | 540 |
| tccactttgc cttttctctcc acaggaaaac atggggcagc aggccaggat gctgcgggcc | 600 |

```
caggtgaagc ggcacacggt gcgggacaag ctgaggctgt gccagaactt cctgcagaag    660
ctgcgcttcc tggcggacga gccccagcac agcattcccg acatcttcat ctggatgatg    720
agcaacaaca agcgtgtcgc ctatgcccgt gtgccctcca aggacctgct cttctccatc    780
gtggaggagg agactggcaa ggactgcgcc aaggtcaaga cgctcttcct taagctgcca    840
gggaagcggg gcttcggctc ggcaggctgg acagtgcagg ccaaggtgga gctgtacctg    900
tggctgggcc tcagcaaaca gcgcaaggag ttcctgtgcg gcctgccctg tggcttccag    960
gaggtcaagg cagcccaggg cctgggcctg catgccttcc cacccgtcag cctggtctac   1020
accaagaagc aggcgttcca gctccgagcg cacatgtacc aggcccgcag cctctttgcc   1080
gccgacagca gcggactctc agaccccttt gcccgcgtct tcttcatcaa tcagagtcag   1140
tgcacagagg tgctgaatga ccctgtgt cccacctggg accagatgct ggtgttcgac   1200
aacctggagc tctatggtga agctcatgag ctgagggacg atccgcccat cattgtcatt   1260
gaaatctatg accaggattc catgggcaaa gctgacttca tgggccggac cttcgccaaa   1320
cccctggtga agatggcaga cgaggcgtac tgcccacccc gcttcccacc tcagctcgag   1380
tactaccaga tctaccgtgg caacgccaca gctggagacc tgctggcggc cttcgagctg   1440
ctgcagattg accagcagg gaaggctgac ctgccccca tcaatggccc ggtggacgtg   1500
gaccgaggtc ccatcatgcc cgtgcccatg ggcatccggc ccgtgctcag caagtaccga   1560
gtggaggtgc tgttctgggg cctacgggac ctaaagcggg tgaacctggc ccaggtggac   1620
cggccacggg tggacatcga gtgtgcaggg aagggggtgc agtcgtccct gatccacaat   1680
tataagaaga ccccaacttt caacacctc gtcaagtggt ttgaagtgga cctcccagag   1740
aacgagctgc tgcaccccgcc cttgaacatc cgtgtggtgg actgccgggc cttcggtcgc   1800
tacacactgg tgggctccca tgccgtcagc tccctgcgac gcttcatcta ccggccccca   1860
gaccgctcgg cccccagctg gaacaccacg gtcaggcttc tccggcgctg ccgtgtgctg   1920
tgcaatgggg gctcctcctc tcactccaca ggggaggttg tggtgactat ggagccagag   1980
gtacccatca agaaactgga gaccatggtg aagctggacg cgacttctga agctgttgtc   2040
aaggtggatg tggctgagga ggagaaggag aagaagaaga agaagaaggg cactgcggag   2100
gagccagagg aggaggagcc agacgagagc atgctggact ggtggtccaa gtactttgcc   2160
tccattgaca ccatgaagga gcaacttcga caacaagagc cctctggaat tgacttggag   2220
gagaaggagg aagtggacaa taccgagggc ctgaaggggt caatgaaggg caaggagaag   2280
gcaagggctg ccaaagagga gaagaagaag aaaactcaga gctctggctc tggccagggg   2340
tccgaggccc ccgagaagaa gaaacccaag attgatgagc ttaaggtata ccccaaagag   2400
ctggagtccg agtttgataa ctttgaggac tggctgcaca cttcaacttt gcttcggggc   2460
aagaccgggg atgatgagga tggctccacc gaggaggagc gcattgtggg acgcttcaag   2520
ggctccctct gcgtgtacaa agtgccactc ccagaggacg tgtcccggga agccggctac   2580
gactccacct acggcatgtt ccagggcatc ccgagcaatg accccatcaa tgtgctggtc   2640
cgagtctatg tggtccgggc cacggacctg caccctgctg acatcaacgg caaagctgac   2700
ccctacatcg ccatccggct aggcaagact gacatccgcg acaaggagaa ctacatctcc   2760
aagcagctca accctgtctt tgggaagtcc tttgacatcg aggcctcctt ccccatggaa   2820
tccatgctga cggtggctgt gtatgactgg gacctggtgg gcactgatga cctcattggg   2880
gaaaccaaga tcgacctgga gaaccgcttc tacagcaagc accgcgccac ctgcggcatc   2940
```

```
gcccagacct actccacaca tggctacaat atctggcggg accccatgaa gcccagccag    3000
atcctgaccc gcctctgcaa agacggcaaa gtggacggcc cccactttgg ccccctggg     3060
agagtgaagg tggccaaccg cgtcttcact gggccctctg agattgagga cgagaacggt    3120
cagaggaagc ccacagacga gcatgtggcg ctgttggccc tgaggcactg ggaggacatc    3180
ccccgcgcag gctgccgcct ggtgccagag catgtggaga cgaggccgct gctcaacccc    3240
gacaagccgg gcatcgagca gggccgcctg gagctgtggg tggacatgtt ccccatggac    3300
atgccagccc ctgggacgcc tctggacatc tcacctcgga gcccaagaa gtacgagctg     3360
cgggtcatca tctggaacac agatgaggtg gtcttggagg acgacgactt cttcacaggg    3420
gagaagtcca gtgacatctt cgtgaggggg tggctgaagg gccagcagga ggacaagcag    3480
gacacagacg tccactacca ctccctcact ggcgagggca acttcaactg cgcgtacctg    3540
ttcccctteg actacctggc ggcggaggag aagatcgtca tctccaagaa ggagtccatg    3600
ttctcctggg acgagaccga gtacaagatc cccgcgcggc tcaccctgca gatctgggat    3660
gcggaccact tctccgctga cgacttcctg ggggccatcg agctggacct gaaccggttc    3720
ccgcggggcg caaagacagc caagcagtgc accatggaga tggccaccgg ggaggtggac    3780
gtgccctcg tgtccatctt caagcaaaag cgcgtcaaag ctggtggcc cctcctggcc      3840
cgcaatgaga acgatgagtt tgagctcacg ggcaaggtgg aggctgagct gcatttactg    3900
acagcagagg aggcagagaa gaacccagtg ggcctggccc gcaatgaacc tgaccccta     3960
gagaaaccca accggcccga cacgagcttc atctggttcc tgaaccctct caagtcggct    4020
cgctacttct tgtggcacac gtatcgctgg ctgctcctca aactgttgct gctcctgctg    4080
ctgctcctcc tcctcgccct gttcctctac tctgtgcctg gctacctggt caagaaaatc    4140
ctcgggggcct gagcggccgc ggtaccaagg gcgaattctg cagtcgacta gagctcgctg   4200
atcagcctcg actgtgcctt ctagttgcca gccatctgtt gtttgcccct ccccgtgcc    4260
ttccttgacc ctggaaggtg ccactcccac tgtccttcc taataaaatg aggaaattgc    4320
atcgcattgt ctgagtaggt gtcattctat tctgggggt ggggtgggc aggacagcaa     4380
gggggaggat tgggaagaca atagcaggca tgctggggag agatctgagg actagtccgt    4440
cgactgttaa ttaagcatgc tggggagaga tctaggaacc cctagtgatg gagttggcca    4500
ctccctctct gcgcgctcgc tcgctcactg aggccgcccg ggcaaagccc gggcgtcggg    4560
cgacctttgg tcgcccggcc tcagtgagcg agcgagcgcg cagagaggga gtggccaacc    4620
ccccccccc ccccctgca gccctgcatt aatgaatcgg ccaacgcgcg gggagaggcg      4680
gtttgcgtat tgggcgctct ccgcttcct cgctcactga ctcgctgcgc tcggtcgttc     4740
ggctgcggcg agcggtatca gctcactcaa aggcggtaat acggttatcc acagaatcag    4800
gggataacgc aggaaagaac atgtgagcaa aaggccagca aaaggccagg aaccgtaaaa    4860
aggccgcgtt gctggcgttt ttccataggc tccgccccc tgacgagcat cacaaaaatc     4920
gacgctcaag tcagaggtgg cgaaacccga caggactata aagataccag gcgtttcccc    4980
ctggaagctc cctcgtgcgc tctcctgttc cgaccctgcc gcttaccgga tacctgtccg    5040
cctttctccc ttcgggaagc gtggcgcttt ctcaatgctc acgctgtagg tatctcagtt    5100
cggtgtaggt cgttcgctcc aagctgggct gtgtgcacga acccccgtt cagcccgacc     5160
gctgcgcctt atccggtaac tatcgtcttg agtccaaccc ggtaagacac gacttatcgc    5220
cactggcagc agccactggt aacaggatta gcagagcgag gtatgtaggc ggtgctacag    5280
agttcttgaa gtggtggcct aactacggct acactagaag gacagtattt ggtatctgcg    5340
```

```
ctctgctgaa gccagttacc ttcggaaaaa gagttggtag ctcttgatcc ggcaaacaaa    5400
ccaccgctgg tagcggtggt ttttttgttt gcaagcagca gattacgcgc agaaaaaaag    5460
gatctcaaga agatcctttg atctttcta cggggtctga cgctcagtgg aacgaaaact    5520
cacgttaagg gattttggtc atgagattat caaaaaggat cttcacctag atccttttaa    5580
attaaaaatg aagttttaaa tcaatctaaa gtatatatga gtaaacttgg tctgacagtt    5640
accaatgctt aatcagtgag gcacctatct cagcgatctg tctatttcgt tcatccatag    5700
ttgcctgact ccccgtcgtg tagataacta cgatacggga gggcttacca tctggcccca    5760
gtgctgcaat gataccgcga gacccacgct caccggctcc agatttatca gcaataaacc    5820
agccagccgg aagggccgag cgcagaagtg gtcctgcaac tttatccgcc tccatccagt    5880
ctattaattg ttgccgggaa gctagagtaa gtagttcgcc agttaatagt ttgcgcaacg    5940
ttgttgccat tgctacaggc atcgtggtgt cacgctcgtc gtttggtatg gcttcattca    6000
gctccggttc ccaacgatca aggcgagtta catgatcccc catgttgtgc aaaaaagcgg    6060
ttagctcctt cggtcctccg atcgttgtca gaagtaagtt ggccgcagtg ttatcactca    6120
tggttatggc agcactgcat aattctctta ctgtcatgcc atccgtaaga tgcttttctg    6180
tgactggtga gtactcaacc aagtcattct gagaatagtg tatgcggcga ccgagttgct    6240
cttgcccggc gtcaatacgg gataataccg cgccacatag cagaacttta aaagtgctca    6300
tcattggaaa acgttcttcg gggcgaaaac tctcaaggat cttaccgctg ttgagatcca    6360
gttcgatgta acccactcgt gcacccaact gatcttcagc atcttttact ttcaccagcg    6420
tttctgggtg agcaaaaaca ggaaggcaaa atgccgcaaa aaagggaata agggcgacac    6480
ggaaatgttg aatactcata ctcttccttt ttcaatatta ttgaagcatt tatcagggtt    6540
attgtctcat gagcggatac atatttgaat gtatttagaa aaataaacaa ataggggttc    6600
cgcgcacatt tccccgaaaa gtgccacctg acgtctaaga aaccattatt atcatgacat    6660
taacctataa aaataggcgt atcacgaggc cctttcgtct cgcgcgtttc ggtgatgacg    6720
gtgaaaacct ctgacacatg cagctcccgg agacggtcac agcttgtctg taagcggatg    6780
ccgggagcag acaagcccgt cagggcgcgt cagcgggtgt tggcgggtgt cggggctggc    6840
ttaactatgc ggcatcagag cagattgtac tgagagtgca ccatatgcgg tgtgaaatac    6900
cgcacagatg cgtaaggaga aaataccgca tcaggaaatt gtaaacgtta atattttgtt    6960
aaaattcgcg ttaaattttt gttaaatcag ctcattttt aaccaatagg ccgaaatcgg    7020
caaaatccct tataaatcaa aagaatagac cgagataggg ttgagtgttg ttccagtttg    7080
gaacaagagt ccactattaa agaacgtgga ctccaacgtc aaagggcgaa aaaccgtcta    7140
tcagggcgat ggcccactac gtgaaccatc accctaatca agttttttgg ggtcgaggtg    7200
ccgtaaagca ctaaatcgga acctaaagg gagcccccga tttagagctt gacggggaaa    7260
gccggcgaac gtggcgagaa aggaagggaa gaaagcgaaa ggagcgggcg ctagggcgct    7320
ggcaagtgta gcggtcacgc tgcgcgtaac caccacaccc gccgcgctta atgcgccgct    7380
acagggcgcg tcgcgccatt cgccattcag gctacgcaac tgttgggaag ggcgatcggt    7440
gcgggcctct tcgctattac gccaggctgc                                    7470

<210> SEQ ID NO 16
<211> LENGTH: 7470
<212> TYPE: DNA
<213> ORGANISM: Artificial sequence
<220> FEATURE:
```

<223> OTHER INFORMATION: pTR22-APhead-APSA-otoferlinCT Hs var 5

<400> SEQUENCE: 16

```
agggggggggg gggggggggt tggccactcc ctctctgcgc gctcgctcgc tcactgaggc      60
cgggcgacca aggtcgccc gacgcccggg ctttgcccgg gcggcctcag tgagcgagcg       120
agcgcgcaga gagggagtgg ccaactccat cactaggggt tcctcagatc tggcgcgccc     180
aattggcttc gaattctagc ggccgccccc gggtgcgcgg cgtcggtggt gccgcgggg      240
ggcgccaggt cgcaggcggt gtagggctcc aggcaggcgg cgaaggccat gacgtgcgct     300
atgaaggtct gctcctgcac gccgtgaacc aggtgcgcct gcgggccgcg cgcgaacacc     360
gccacgtcct cgcctgcgtg gtctcttcg tccagggca ctgctgactg ctgccgatac        420
tcggggctcc cgctctcgct tcggtaaca tccggccggg cgccgtcctt gagcacatag       480
cctggaccgt ttccttaagc gacgcatgct cgcgataggc acctattggt cttactgaca     540
tccactttgc ctttctctcc acaggaaaac atgggcagc aggccaggat gctgcgggcc       600
caggtgaagc ggcacacggt gcgggacaag ctgaggctgt gccagaactt cctgcagaag     660
ctgcgcttcc tggcggacga gccccagcac agcattcccg acatcttcat ctggatgatg     720
agcaacaaca agcgtgtcgc ctatgcccgt gtgccctcca aggacctgct cttctccatc     780
gtggaggagg agactggcaa ggactgcgcc aaggtcaaga cgctcttcct taagctgcca    840
gggaagcggg gcttcggctc ggcaggctgg acagtgcagg ccaaggtgga gctgtacctg      900
tggctgggcc tcagcaaaca gcgcaaggag ttcctgtgcg gcctgccctg tggcttccag     960
gaggtcaagg cagcccaggg cctgggcctg catgccttcc cacccgtcag cctggtctac    1020
accaagaagc aggcgttcca gctccgagcg cacatgtacc aggcccgcag cctctttgcc    1080
gccgacagca gcggactctc agaccccttt gcccgcgtct tcttcatcaa tcagagtcag   1140
tgcacagagg tgctgaatga gaccctgtgt cccacctggg accagatgct ggtgttcgac   1200
aacctggagc tctatggtga agctcatgag ctgagggacg atccgcccat cattgtcatt   1260
gaaatctatg accaggattc catgggcaaa gctgacttca tgggccggac cttcgccaaa   1320
cccctggtga agatggcaga cgaggcgtac tgcccacccc gcttcccacc tcagctcgag   1380
tactaccaga tctaccgtgg caacgccaca gctggagacc tgctggcggc cttcgagctg   1440
ctgcagattg accagcagg gaaggctgac ctgcccccca tcaatggccc ggtgacgtg    1500
gaccgaggtc ccatcatgcc cgtgcccatg gcatccggc ccgtgctcag caagtaccga      1560
gtggaggtgc tgttctgggg cctacgggac ctaaagcggg tgaacctggc ccaggtggac   1620
cggccacggg tggacatcga gtgtgcaggg aagggggtgc agtcgtccct gatccacaat   1680
tataagaaga ccccaacttt caacacctc gtcaagtgg ttgaagtgga cctcccagag     1740
aacgagctgc tgcacccgcc cttgaacatc cgtgtggtgg actgccgggc cttcggtcgc   1800
tacacactgg tgggctccca tgccgtcagc tccctgcgac gcttcatcta ccggccccca   1860
gaccgctcgg ccccccagctg gaacaccacg gtcaggcttc tccggcgctg ccgtgtgctg   1920
tgcaatgggg gctcctcctc tcactccaca ggggaggttg tggtgactat ggagccagag   1980
gtacccatca agaaactgga gaccatggtg aagctggacg cgacttctga agctgttgtc   2040
aaggtggatg tggctgagga ggagaaggag aagaagaaga agaagaaggg cactgcggag   2100
gagccagagg aggaggagcc agacgagagc atgctggact ggtggtccaa gtactttgcc   2160
tccattgaca ccatgaagga gcaacttcga caacaagagc cctctggaat tgacttggag   2220
gagaaggagg aagtggacaa taccgagggc ctgaaggggt caatgaaggg caaggagaag   2280
```

```
gcaagggctg ccaaagagga gaagaagaag aaaactcaga gctctggctc tggccagggg    2340
tccgaggccc ccgagaagaa gaaacccaag attgatgagc ttaaggtata ccccaaagag    2400
ctggagtccg agtttgataa ctttgaggac tggctgcaca ctttcaactt gcttcggggc    2460
aagaccgggg atgatgagga tggctccacc gaggaggagc gcattgtggg acgcttcaag    2520
ggctccctct gcgtgtacaa agtgccactc ccagaggacg tgtcccggga agccggctac    2580
gactccacct acggcatgtt ccagggcatc ccgagcaatg accccatcaa tgtgctggtc    2640
cgagtctatg tggtccgggc cacggacctg caccctgctg acatcaacgg caaagctgac    2700
ccctacatcg ccatccggct aggcaagact gacatccgcg acaaggagaa ctacatctcc    2760
aagcagctca accctgtctt tgggaagtcc tttgacatcg aggcctcctt ccccatggaa    2820
tccatgctga cggtggctgt gtatgactgg gacctggtgg gcactgatga cctcattggg    2880
gaaaccaaga tcgacctgga gaaccgcttc tacagcaagc accgcgccac ctgcggcatc    2940
gcccagacct actccacaca tggctacaat atctggcggg accccatgaa gcccagccag    3000
atcctgaccc gcctctgcaa agacggcaaa gtggacggcc cccactttgg gcccctggg    3060 agagtgaagg tggccaaccg cgtcttcact gggccctctg agattgagga cgagaacggt    3120
cagaggaagc ccacagacga gcatgtggcg ctgttggccc tgaggcactg ggaggacatc    3180
ccccgcgcag gctgccgcct ggtgccagag catgtggaga cgaggccgct gctcaacccc    3240
gacaagccgg gcatcgagca gggccgcctg gagctgtggg tggacatgtt ccccatggac    3300
atgccagccc ctgggacgcc tctggacatc tcacctcgga agcccaagaa gtacgagctg    3360
cgggtcatca tctggaacac agatgaggtg gtcttggagg acgacgactt cttcacaggg    3420
gagaagtcca gtgacatctt cgtgaggggg tggctgaagg ccagcagga ggacaagcag    3480 gacacagacg tccactacca ctccctcact ggcgagggca acttcaactg cgcctacctg    3540
ttccccttcg actacctggc ggcggaggag aagatcgtca tctccaagaa ggagtccatg    3600
ttctcctggg acgagaccga gtacaagatc cccgcgcggc tcaccctgca gatctgggat    3660
gcggaccact tctccgctga cgacttcctg ggggccatcg agctggacct gaaccggttc    3720
ccgcggggcg caaagacagc caagcagtgc accatgagga tggccaccgg ggaggtggac    3780
gtgcccctcg tgtccatctt caagcaaaag cgcgtcaaag ctggtggcc cctcctggcc    3840 cgcaatgaga acgatgagtt tgagctcacg ggcaaggtgg aggctgagct gcatttactg    3900
acagcagagg aggcagagaa gaacccagtg ggcctggccc gcaatgaacc tgaccccta    3960 gagaaaccca accggcccga cacggccttc gtctggttcc tcaaccctct caagtccatc    4020
aagtacctca tctgcacccg gtacaagtgg ctcatcatca agatcgtgct ggcgctgttg    4080
gggctgctca tgttggggct cttcctctac agcctccctg gctacatggt caaaaagctc    4140 cttgggcat gagcggccgc ggtaccaagg gcgaattctg cagtcgacta gagctcgctg    4200
atcagcctcg actgtgcctt ctagttgcca gccatctgtt gtttgcccct cccccgtgcc    4260
ttccttgacc ctggaaggtg ccactcccac tgtcctttcc taataaaatg aggaaattgc    4320
atcgcattgt ctgagtaggt gtcattctat tctgggggt ggggtggggc aggacagcaa    4380
gggggaggat tgggaagaca atagcaggca tgctggggag agatctgagg actagtccgt    4440
cgactgttaa ttaagcatgc tgggagaga tctaggaacc cctagtgatg gagttggcca    4500
ctccctctct gcgcgctcgc tcgctcactg aggccgcccg ggcaaagccc gggcgtcggg    4560
cgacctttgg tcgcccggcc tcagtgagcg agcgagcgcg cagagaggga gtggccaacc    4620
```

```
cccccccccc cccccctgca gccctgcatt aatgaatcgg ccaacgcgcg gggagaggcg    4680
gtttgcgtat tgggcgctct tccgcttcct cgctcactga ctcgctgcgc tcggtcgttc    4740
ggctgcggcg agcggtatca gctcactcaa aggcggtaat acggttatcc acagaatcag    4800
gggataacgc aggaaagaac atgtgagcaa aaggccagca aaaggccagg aaccgtaaaa    4860
aggccgcgtt gctggcgttt ttccataggc tccgcccccc tgacgagcat cacaaaaatc    4920
gacgctcaag tcagaggtgg cgaaacccga caggactata agataccagg cgtttcccc    4980 ctggaagctc cctcgtgcgc tctcctgttc cgaccctgcc gcttaccgga tacctgtccg    5040
cctttctccc ttcgggaagc gtggcgcttt ctcaatgctc acgctgtagg tatctcagtt    5100
cggtgtaggt cgttcgctcc aagctgggct gtgtgcacga accccccgtt cagcccgacc    5160
gctgcgcctt atccggtaac tatcgtcttg agtccaaccc ggtaagacac gacttatcgc    5220
cactggcagc agccactggt aacaggatta gcagagcgag gtatgtaggc ggtgctacag    5280
agttcttgaa gtggtggcct aactacggct acactagaag gacagtattt ggtatctgcg    5340
ctctgctgaa gccagttacc ttcggaaaaa gagttggtag ctcttgatcc ggcaaacaaa    5400
ccaccgctgg tagcggtggt ttttttgttt gcaagcagca gattacgcgc agaaaaaaag    5460
gatctcaaga agatcctttg atcttttcta cggggtctga cgctcagtgg aacgaaaact    5520
cacgttaagg gattttggtc atgagattat caaaaaggat cttcacctag atccttttaa    5580
attaaaaatg aagttttaaa tcaatctaaa gtatatatga gtaaacttgg tctgacagtt    5640
accaatgctt aatcagtgag gcacctatct cagcgatctg tctatttcgt tcatccatag    5700
ttgcctgact ccccgtcgtg tagataacta cgatacggga gggcttacca tctggcccca    5760
gtgctgcaat gataccgcga acccacgct caccggctcc agatttatca gcaataaacc    5820
agccagccgg aagggccgag cgcagaagtg gtcctgcaac tttatccgcc tccatccagt    5880
ctattaattg ttgccgggaa gctagagtaa gtagttcgcc agttaatagt ttgcgcaacg    5940
ttgttgccat tgctacaggc atcgtggtgt cacgctcgtc gtttggtatg gcttcattca    6000
gctccggttc ccaacgatca aggcgagtta catgatcccc catgttgtgc aaaaaagcgg    6060
ttagctcctt cggtcctccg atcgttgtca gaagtaagtt ggccgcagtg ttatcactca    6120
tggttatggc agcactgcat aattctctta ctgtcatgcc atccgtaaga tgcttttctg    6180
tgactggtga gtactcaacc aagtcattct gagaatagtg tatgcggcga ccgagttgct    6240
cttgcccggc gtcaatacgg gataataccg cgccacatag cagaacttta aaagtgctca    6300
tcattggaaa acgttcttcg gggcgaaaac tctcaaggat cttaccgctg ttgagatcca    6360
gttcgatgta acccactcgt gcacccaact gatcttcagc atcttttact ttcaccagcg    6420
tttctgggtg agcaaaaaca ggaaggcaaa atgccgcaaa aaagggaata agggcgacac    6480
ggaaatgttg aatactcata ctcttccttt ttcaatatta ttgaagcatt tatcagggtt    6540
attgtctcat gagcggatac atatttgaat gtatttagaa aaataaacaa ataggggttc    6600
cgcgcacatt tccccgaaaa gtgccacctg acgtctaaga aaccattatt atcatgacat    6660
taacctataa aaataggcgt atcacgaggc cctttcgtct cgcgcgtttc ggtgatgacg    6720
gtgaaaacct ctgacacatg cagctcccgg agacggtcac agcttgtctg taagcggatg    6780
ccgggagcag acaagcccgt cagggcgcgt cagcgggtgt tggcgggtgt cggggctggc    6840
ttaactatgc ggcatcagag cagattgtac tgagagtgca ccatatgcgg tgtgaaatac    6900
cgcacagatg cgtaaggaga aaataccgca tcaggaaatt gtaaacgtta atattttgtt    6960
aaaattcgcg ttaaattttt gttaaatcag ctcattttt aaccaatagg ccgaaatcgg    7020
```

```
caaaatccct tataaatcaa aagaatagac cgagataggg ttgagtgttg ttccagtttg    7080
gaacaagagt ccactattaa agaacgtgga ctccaacgtc aaagggcgaa aaaccgtcta    7140
tcagggcgat ggcccactac gtgaaccatc accctaatca agtttttgg ggtcgaggtg     7200 ccgtaaagca ctaaatcgga accctaaagg gagcccccga tttagagctt gacggggaaa    7260
gccggcgaac gtggcgagaa aggaagggaa gaaagcgaaa ggagcgggcg ctagggcgct    7320
ggcaagtgta gcggtcacgc tgcgcgtaac caccacaccc gccgcgctta atgcgccgct    7380
acagggcgcg tcgcgccatt cgccattcag gctacgcaac tgttgggaag ggcgatcggt    7440
gcgggcctct tcgctattac gccaggctgc                                    7470
```

COMPOSITIONS AND METHODS FOR EXPRESSING OTOFERLIN

CROSS-REFERENCE TO RELATED APPLICATIONS

This application is a national stage filing under 35 U.S.C. § 371 of international PCT application, PCT/US2018/031009, filed May 4, 2018, which claims priority under 35 U.S.C. § 119(e) to U.S. Provisional Application No. 62/502,462 filed on May 5, 2017, the entire contents of each of which are incorporated by reference herein.

FEDERALLY SPONSORED RESEARCH

This invention was made with government support under grants EY000331, EY021721 and DC012118 awarded by the National Institutes of Health. The government has certain rights in the invention.

BACKGROUND OF INVENTION

Nonsyndromic deafness is a form of hearing loss that is generally caused by defects or damage to the inner ear and/or middle ear. Mutations in the OTOF gene, which encodes the protein Otoferlin, are thought to cause a type of nonsyndromic deafness called Deafness, Autosomal Recessive 9 (DFNB9). Treatment of DFNB9 and other similar forms of deafness currently involves using cochlear implants for severe or profound hearing loss and hearing aids for milder forms of hearing loss. There remains a need for alternative treatment forms that do not rely on or rely less heavily on electronic devices for restoring hearing.

SUMMARY OF INVENTION

Provided herein are compositions and methods for expressing Otoferlin, e.g., in a cell or subject. As described herein, it has been found that delivery of the OTOF cDNA to otof knock-out mice via a dual adeno-associated virus (AAV) system containing different portions of the OTOF cDNA was capable of rescuing hearing in the mice to near wild-type levels.

In some aspects, the disclosure provides a method of increasing expression of Otoferlin in a cell, the method comprising contacting the cell with a first AAV particle comprising a first polynucleotide; and contacting the cell with a second AAV particle comprising a second polynucleotide, wherein the first polynucleotide comprises inverted terminal repeat sequences flanking an expression cassette containing, from 5' to 3': (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide, and the second polynucleotide comprises inverted terminal repeat sequences flanking an expression cassette containing, from 5' to 3': (a) a second region of homology containing a sequence that is homologous to a sequence in the first polynucleotide, (b) a splice acceptor site, (c) a partial coding sequence that encodes a C-terminal portion of the Otoferlin polypeptide, and (d) a polyadenylation (pA) signal sequence.

In some embodiments, the region of homology in the first and second polynucleotides is between 50 and 500 nucleotides. In some embodiments, the region of homology in the first and second polynucleotides is between 50 and 300 nucleotides. In some embodiments, the region of homology comprises the nucleotide sequence of SEQ ID NO: 3. In some embodiments, the promoter is a chimeric CMV β actin (smcBA) promoter. In some embodiments, the promoter comprises the sequence of SEQ ID NO: 4. In some embodiments, the Otoferlin polypeptide comprises the amino acid sequence of SEQ ID NO: 5 or SEQ ID NO: 6. In some embodiments, the splice donor site comprises the sequence of SEQ ID NO: 7. In some embodiments, the splice acceptor site comprises the sequence of SEQ ID NO: 8. In some embodiments, the inverted terminal repeat sequences are AAV2 inverted terminal repeat sequences. In some embodiments, the first and second AAV particle are AAV2 serotype particles. In some embodiments, the cell is ex vivo. In some embodiments, the cell is in vivo. In some embodiments, the cell is in a mammalian subject. In some embodiments, the subject has Deafness, Autosomal Recessive 9 (DFNB9).

In other aspects, the disclosure provides a composition comprising a first AAV particle comprising a first polynucleotide; and a second AAV particle comprising a second polynucleotide, wherein the first polynucleotide comprises inverted terminal repeat sequences flanking an expression cassette containing, from 5' to 3': (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide, and the second polynucleotide comprises inverted terminal repeat sequences flanking an expression cassette containing, from 5' to 3': (a) a second region of homology containing a sequence that is homologous to a sequence in the first polynucleotide. (b) a splice acceptor site, (c) a partial coding sequence that encodes a C-terminal portion of the Otoferlin polypeptide, and (d) a polyadenylation (pA) signal sequence.

In some embodiments, the region of homology in the first and second polynucleotides is between 50 and 500 nucleotides. In some embodiments, the region of homology in the first and second polynucleotides is between 50 and 300 nucleotides. In some embodiments, the region of homology comprises the nucleotide sequence of SEQ ID NO: 3. In some embodiments, the promoter is a chimeric CMV β actin (smcBA) promoter. In some embodiments, the promoter comprises the sequence of SEQ ID NO: 4. In some embodiments, the Otoferlin polypeptide comprises the amino acid sequence of SEQ ID NO: 5 or SEQ ID NO: 6. In some embodiments, the splice donor site comprises the sequence of SEQ ID NO: 7. In some embodiments, the splice acceptor site comprises the sequence of SEQ ID NO: 8. In some embodiments, the inverted terminal repeat sequences are AAV2 inverted terminal repeat sequences. In some embodiments, the first and second AAV particle are AAV2 serotype particles. In some embodiments, the composition further comprises a pharmaceutically acceptable carrier.

In yet other aspects, the disclosure provides a kit comprising a composition as described herein or comprising a first AAV particle as described herein and a second AAV particle as described herein.

These and other aspects are described in more detail herein.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 3A shows the annotated sequence of the expression cassette, including the inverted terminal repeats (TR) for the plasmid in FIG. 1A.

FIG. 3B shows the annotated sequence of the expression cassette, including the inverted terminal repeats (TR) for the plasmid in FIG. 1B.

FIG. 6A shows expression of OTOF protein in the mid-turn. FIG. 6B shows expression of OTOF protein in the apex. FIG. 6C shows the difference in OTOF expression in the base, mid-turn and apex in wild-type mice (WT, n=6) and OTOF knock-out mice treated with AAV2-OTOF-NT and AAV2-OTOF-CT (Res. KO NT+CT, n=6). The left bar in each pair of bars is WT and the right bar in each pair of bars is Res. KO NT+CT. FIG. 6D shows RT-PCR data of OTOF mRNA in wild-type (WT), OTOF knock-out mice (KO) and OTOF knock-out mice treated with AAV2-OTOF-NT and AAV2-OTOF-CT (Res. KO).

FIG. 7A is a trace of auditory brainstem response (ABR) patterns induced by auditory stimuli in wild-type mice (WT), OTOF knock-out mice either untreated (KO/KO NT) or treated (Rescued KO) with AAV2-OTOF-NT and AAV2-OTOF-CT. FIG. 7B shows the auditory brainstem response (ABR) threshold in wild-type mice (WT), untreated Otoferlin knock-out mice (KO), Otoferlin knock-out mice treated with AAV2-OTOF-NT and AAV2-OTOF-CT (Res KO NT+CT), and Otoferlin knock-out mice treated with AAV2-OTOF-NT (KO+NT). FIG. 7C shows a time course of hearing recovery in wild-type mice (WT), untreated OTOF knock-out mice (KO), Otoferlin knock-out mice treated with AAV2-OTOF-NT and AAV2-OTOF-CT (Rescued KO NT+CT), and Otoferlin knock-out mice treated with AAV2-OTOF-NT (KONT). FIG. 7D shows the click ABR threshold in wild-type mice (WT), untreated Otoferlin knock-out mice (KO), Otoferlin knock-out mice treated with AAV2-OTOF-NT and AAV2-OTOF-CT (Res. KO (NT+CT)), and Otoferlin knock-out mice treated with AAV2-OTOF-NT (KO+NT).

FIG. 8A shows OTOF protein expression in P12 and older mice treated with AAV2-OTOF-NT and AAV2-OTOF-CT.

FIG. 9A shows ABR threshold values in wild-type mice (WT), OTOF knock-out mice (KO) and OTOF knock-out mice treated with AAV2-OTOF-NT and AAV2-OTOF-CT (Rescued KO). FIG. 9B shows hearing longevity in WT, KO and Rescued KO mice.

FIG. 13 shows the annotated sequence of a human OTOF N-terminal expression cassette, including the inverted terminal repeats (TR) for the plasmid in FIG. 10.

FIG. 14 shows the annotated sequence of a human OTOF C-terminal expression cassette for isoform 1, including the inverted terminal repeats (TR) for the plasmid in FIG. 11.

FIG. 15 shows the annotated sequence of a human OTOF C-terminal expression cassette for isoform 5, including the inverted terminal repeats (TR) for the plasmid in FIG. 12.

DETAILED DESCRIPTION OF INVENTION

Figure 1A:
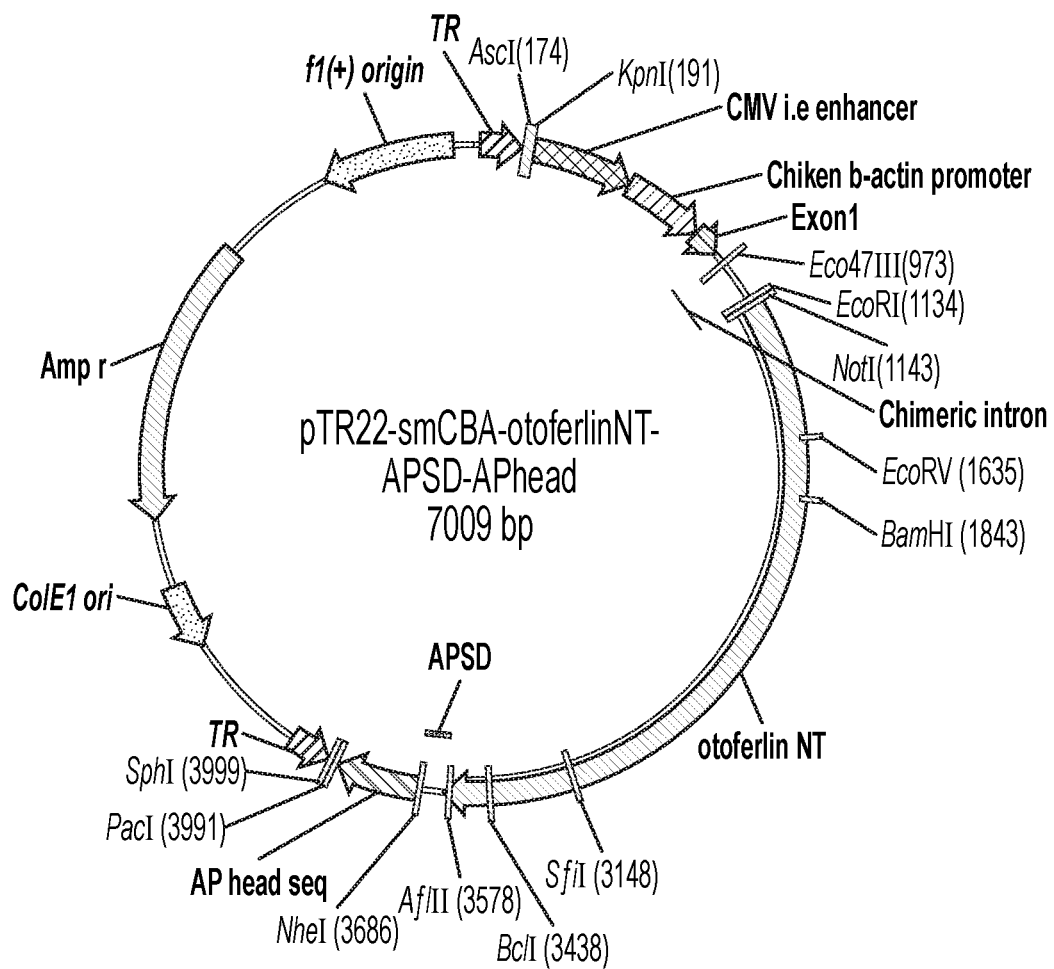
FIG. 1A is a map of a plasmid containing AAV2 inverted terminal repeats (TR) flanking a CMV enhancer, a chicken beta-actin promoter, a 5' section of the mouse Otoferlin cDNA (Otoferlin NT), a splice donor sequence (APSD), and a homologous sequence for recombination (APhead).

As described herein, it has been found that hearing can be restored in Otoferlin knock-out mice by treating the mice with two separate AAV particles, one comprising the 5' portion of the OTOF cDNA and one comprising the 3' portion of the OTOF cDNA and each comprising a region of homology for promoting homologous recombination between the 5' portion and 3' portion in vivo. This region of homology is flanked by a splice donor sequence on the 5' side within the 5' portion of the OTOF cDNA and a splice acceptor sequence on the 3' side within the 3' portion of the OTOF cDNA. Accordingly, compositions and methods are provided for increasing expression of Otoferlin.

Exemplary Definitions

Unless defined otherwise, all technical and scientific terms used herein have the same meaning as commonly understood by one of ordinary skill in the art to which this invention belongs. Although any methods and compositions similar or equivalent to those described herein can be used in the practice or testing of the present invention, the preferred methods and compositions are described herein. For purposes of the present invention, the following terms are defined below:

As used herein, the terms "nucleic acid" and "polynucleotide sequence" refer to a deoxyribonucleotide or ribonucleotide polymer in either single- or double-stranded form, and unless otherwise limited, encompass known analogs of natural nucleotides that can function in a similar manner as naturally occurring nucleotides.

The term "substantially corresponds to," "substantially homologous," or "substantial identity," as used herein, denote a characteristic of a nucleic acid or an amino acid sequence, wherein a selected nucleic acid or amino acid sequence has at least about 70 or about 75 percent sequence identity as compared to a selected reference nucleic acid or amino acid sequence. More typically, the selected sequence and the reference sequence will have at least about 76, 77, 78, 79, 80, 81, 82, 83, 84 or even 85 percent sequence identity, and more preferably, at least about 86, 87, 88, 89, 90, 91, 92, 93, 94, or 95 percent sequence identity. More preferably still, highly homologous sequences often share greater than at least about 96, 97, 98, or 99 percent sequence identity between the selected sequence and the reference sequence to which it was compared.

The percentage of sequence identity may be calculated over the entire length of the sequences to be compared, or may be calculated by excluding small deletions or additions which total less than about 25 percent or so of the chosen reference sequence. The reference sequence may be a subset of a larger sequence, such as a portion of a gene or flanking sequence, or a repetitive portion of a chromosome. However, in the case of sequence homology of two or more polynucleotide sequences, the reference sequence will typically comprise at least about 18-25 nucleotides, more typically at least about 26 to 35 nucleotides, and even more typically at least about 40, 50, 60, 70, 80, 90, or even 100 or so nucleotides.

When highly-homologous fragments are desired, the extent of percent identity between the two sequences may be at least about 80%, preferably at least about 85%, and more preferably about 90% or 95% or higher, as readily determined by one or more of the sequence comparison algorithms well-known to those of ordinary skill in the art, such as e.g., the FASTA program analysis described by Pearson and Lipman (1988).

Polynucleotides

In some aspects, polynucleotides are provided for delivering portions of coding sequences of an OTOF gene that encode the Otoferlin protein to a cell. In some embodiments, the coding sequences are derived from a human OTOF gene (see, e.g., NCBI Gene ID: 9381 and cDNA sequences NM_001287489.1, NM_004802.3, NM_194248.2, NM_194322.2, and NM_194323.2). In some embodiments, the coding sequences are derived from a mouse OTOF gene (see, e.g., NCBI Gene ID 83762 and cDNA sequences NM_001100395.1, NM_001286421.1, NM_001313767.1, and NM_031875.2). In some embodiments, a first and a second polynucleotide are provided. It is to be understood that "first," "second," "third," and the like are not meant to imply a particular order or importance unless expressly stated otherwise.

In some embodiments, the first polynucleotide comprises inverted terminal repeat sequences flanking an expression cassette containing, from 5' to 3', one or more of (a) a promoter, (b) a partial coding sequence that encodes an N-terminal portion of an Otoferlin polypeptide, (c) a splice donor site, and (d) a first region of homology containing a sequence that is homologous to a sequence in the second polynucleotide. In some embodiments, the first polynucleotide comprises at least two, at least three or all four of (a), (b), (c), and (d).

In some embodiments, the second polynucleotide comprises inverted terminal repeat sequences flanking an expression cassette containing, from 5' to 3', one or more of (a) a second region of homology containing a sequence that is homologous to a sequence in the first polynucleotide, (b) a splice acceptor site, (c) a partial coding sequence that encodes a C-terminal portion of the Otoferlin polypeptide, and (d) a polyadenylation (pA) signal sequence. In some embodiments, the second polynucleotide comprises at least two, at least three or all four of (a), (b), (c), and (d).

The partial coding sequences contained within the polynucleotides described herein may be designed so that, upon delivery of the polynucleotides, the partial coding sequences are joined together, e.g., through homologous recombination, and form a complete coding sequence that encodes an Otoferlin polypeptide.

In some embodiments, the polynucleotides are plasmids (e.g., a circular nucleic acid comprising one or more of an origin of replication, a selectable marker, and a reporter gene). In some embodiments, polynucleotides described herein, such as a plasmid, may also contain marker or reporter genes, e.g., LacZ or a fluorescent protein, and an origin of replication. In some embodiments, the plasmid is transfected into a producer cell that produces AAV particles containing the expression cassettes contained within the plasmids.

In some embodiments, the polynucleotides are nucleic acid vectors such as a recombinant adeno-associated virus (AAV) vectors. Exemplary AAV nucleic acid vectors useful according to the disclosure include single-stranded (ss) or self-complementary (sc) AAV nucleic acid vectors.

In some embodiments, recombinant AAV particles comprise the polynucleotides, such as a single-stranded (ss) or self-complementary (sc) AAV nucleic acid vectors. In some embodiments, the polynucleotides contain expression constructs as described herein and inverted terminal repeat (ITR) sequences (e.g., wild-type ITR sequences or engineered ITR sequences) flanking the expression constructs. In some embodiments, the polynucleotides are encapsidated by viral capsids.

Accordingly, in some embodiments, an AAV particle comprises a viral capsid and a polynucleotide as described herein, which is encapsidated by the viral capsid. In some embodiments, the viral capsid comprises 60 capsid protein subunits comprising VP1, VP2 and VP3. In some embodiments, the VP1, VP2, and VP3 subunits are present in the capsid at a ratio of approximately 1:1:10, respectively.

In some embodiments, polynucleotides as described herein (e.g., first and second polynucleotides) comprise regions of homology, e.g., to promote homologous recombination between the polynucleotides once delivered to a cell (see, e.g., Ghosh et al. Efficient transgene reconstitution with hybrid dual AAV vectors carrying the minimized bridging sequences. Hum Gene Ther. 2011 January; 22(1):77-83). In some embodiments, a first region of homology and a second region of homology have a threshold level of sequence identity with each other in order to promote homologous recombination. In some embodiments the first region of homology has at least 75%, at least 80%, at least 90%, at least 95%, at least 96%, at least 97%, at least 98%, at least 99% or 100% identity with the second region of homology. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, word-length=12, to obtain sequences with the desired percent sequence identity. To obtain gapped alignments for comparison purposes, Gapped BLAST can be used as described (Altschul et al., 1997). When utilizing BLAST and Gapped BLAST programs, the default parameters of the respective programs (NBLAST and XBLAST) can be used in accordance with published methods. In some embodiments, each region of homology is independently between 50 and 500, 50 and 400, 50 and 300, 100 and 500, 100 and 400, 100 and 300, 200 and 500, 200 and 400, or 200 and 300 nucleotides. In some embodiments, the regions of homology are identical and each region of homology is between 50 and 500, 50 and 400, 50 and 300, 100 and 500, 100 and 400, 100 and 300, 200 and 500, 200 and 400, or 200 and 300 nucleotides. In some embodiments, the region homology comprises a sequence that is at least 75%, at least 80%, at least 85%, at least 90%, at least 95%, at least 96%, at least 97%, at least 98%, at least 99% or 100% identical with the nucleotide sequence (SEQ ID NO: 3)
CCCCGGGTGCGCGGCGTCGGTGGTGCCGGCGGGGGGCGCCAGGTCGCAG

GCGGTGTAGGGCTCCAGGCAGGCGGCGAAGGCCATGACGTGCGCTATGA

AGGTCTGCTCCTGCACGCCGTGAACCAGGTGCGCCTGCGGGCCGCGCGC

GAACACCGCCACGTCCTCGCCTGCGTGGGTCTCTTCGTCCAGGGGCACT

GCTGACTGCTGCCGATACTCGGGGCTCCCGCTCTCGCTCTCGGTAACAT

CCGGCCGGGCGCCGTCCTTGAGCACATAGCCTGGACCGTTTC.

In some embodiments, polynucleotides described herein may comprise one or more regulatory elements. A person of ordinary skill in the art can select regulatory elements for use in appropriate host cells, for example, mammalian or human host cells. Regulatory elements include, for example, promoters, transcription termination sequences, translation termination sequences, enhancers, and polyadenylation elements. A polynucleotide described herein may comprise a promoter sequence operably linked to a nucleotide sequence encoding a desired polypeptide, such as Otoferlin. Promoters contemplated for use in the subject invention include, but are not limited to, cytomegalovirus (CMV) promoter, SV40 promoter, Rous sarcoma virus (RSV) promoter, chimeric CMV/chicken β actin promoter (CBA) and the truncated form of CBA (smCBA) (see, e.g., Haire et al. 2006 and U.S. Pat. No. 8,298,818, which is specifically incorporated herein in its entirety by express reference thereto). In some embodiments, the promoter is the truncated chimeric CMV β actin (smcBA) promoter. In some embodiments, the promoter comprises a sequence that is at least 75%, at least 80%, at least 85%, at least 90%, at least 95%, at least 96%, at least 97%, at least 98%, at least 99% or 100% identical with the nucleotide sequence (SEQ ID NO: 4)
GGTACCCTAGTTATTAATAGTAATCAATTACGGGGTCATTAGTTCATAG

CCCATATATGGAGTTCCGCGTTACATAACTTACGGTAAATGGCCCGCCT

GGCTGACCGCCCAACGACCCCCGCCCATTGACGTCAATAATGACGTATG

TTCCCATAGTAACGCCAATAGGGACTTTCCATTGACGTCAATGGGTGGA

CTATTTACGGTAAACTGCCCACTTGGCAGTACATCAAGTGTATCATATG

CCAAGTACGCCCCCTATTGACGTCAATGACGGTAAATGGCCCGCCTGGC

ATTATGCCCAGTACATGACCTTATGGGACTTTCCTACTTGGCAGTACAT

CTACGTATTAGTCATCGCTATTACCATGGTCGAGGTGAGCCCCACGTTC

TGCTTCACTCTCCCCATCTCCCCCCCCTCCCCACCCCCAATTTTGTATT

TATTTATTTTTTAATTATTTTGTGCAGCGATGGGGGCGGGGGGGGGGG

GGGGCGCGCGCCAGGCGGGGCGGGGCGGGGCGAGGGGCGGGGCGGGGCG

AGGCGGAGAGGTGCGGCGGCAGCCAATCAGAGCGGCGCGCTCCGAAAGT

TTCCTTTTATGGCGAGGCGGCGGCGGCGGCGGCCCTATAAAAAGCGAAG

CGCGCGGCGGGCG.

In some embodiments, polynucleotides as described herein comprise a partial coding sequence that encodes an N-terminal or C-terminal portion of an Otoferlin polypeptide, wherein the partial coding sequences can be spliced or otherwise combined together in vivo in order to encode an Otoferlin polypeptide. In some embodiments, the Otoferlin polypeptide is a human Otoferlin polypeptide. In some embodiments, the Otoferlin polypeptide is a long isoform of a human Otoferlin polypeptide (see, e.g., Yasunaga et al. OTOF Encodes Multiple Long and Short Isoforms: Genetic Evidence That the Long Ones Underlie Recessive Deafness DFNB9. Am. J. Hum. Genet. 67:591-600, 2000). In some embodiments, the Otoferlin polypeptide comprises a sequence that is at least 75%, at least 80%, at least 85%, at least 90%, at least 95%, at least 96%, at least 97%, at least 98%, at least 99% or 100% identical with one or both of the following amino acid sequences:

Human OTOF isoform 1-Genbank Number AF183185.1
(SEQ ID NO: 5)
MALLIHLKTVSELRGRGDRIAKVTFRGQSFYSRVLENCEDVADFDETFR

WPVASSIDRNEMLEIQVFNYSKVFSNKLIGTFRMVLQKVVEESHVEVTD

TLIDDNNAIIKTSLCVEVRYQATDGTVGSWDDGDFLGDESLQEEEKDSQ

ETDGLLPGSRPSSRPPGEKSFRRAGRSVFSAMKLGKNRSHKEEPQRPDE

PAVLEMEDLDHLAIRLGDGLDPDSVSLASVTALTTNVSNKRSKPDIKME

PSAGRPMDYQVSITVIEARQLVGLNMDPVVCVEVGDDKKYTSMKESTNC

PYYNEYFVFDFHVSPDVMFDKIIKISVIHSKNLLRSGTLVGSFKMDVGT

VYSQPEHQFHHKWAILSDPDDISSGLKGYVKCDVAVVGKGDNIKTPHKA

NETDEDDIEGNLLLPEGVPPERQWARFYVKIYRAEGLPRMNTSLMANVK

KAFIGENKDLVDPYVQVFFAGQKGKTSVQKSSYEPLWNEQVVFTDLFPP

LCKRMKVQIRDSDKVNDVAIGTHFIDLRKISNDGDKGFLPTLGPAWVNM

YGSTRNYTLLDEHQDLNEGLGEGVSFRARLLLGLAVEIVDTSNPELTSS

TEVQVEQATPISESCAGKMEEFFLFGAFLEASMIDRRNGDKPITFEVTI

GNYGNEVDGLSRPQRPRPRKEPGDEEEVDLIQNASDDEAGDAGDLASVS

STPPMRPQVTDRNYFHLPYLERKPCIYIKSWWPDQRRRLYNANIMDHIA

DKLEEGLNDIQEMIKTEKSYPERRLRGVLEELSCGCCRFLSLADKDQGH

SSRTRLDRERLKSCMRELENMGQQARMLRAQVKRHTVRDKLRLCQNFLQ

KLRFLADEPQHSIPDIFIWMMSNNKRVAYARVPSKDLLFSIVEEETGKD

CAKVKTLFLKLPGKRGFGSAGWTVQAKVELYLWLGLSKQRKEFLCGLPC

GFQEVKAAQGLGLHAFPPVSLVYTKKQAFQLRAHMYQARSLFAADSSGL

```
SDPFARVFFINQSQCTEVLNETLCPTWDQMLVFDNLELYGEAHELRDDP
PIIVIEIYDQDSMGKADFMGRTFAKPLVKMADEAYCPPRFPPQLEYYQI
YRGNATAGDLLAAFELLQIGPAGKADLPPINGPVDVDRGPIMPVPMGIR
PVLSKYRVEVLFWGLRDLKRVNLAQVDRPRVDIECAGKGVQSSLIHNYK
KNPNFNTLVKWFEVDLPENELLHPPLNIRVVDCRAFGRYTLVGSHAVSS
LRRFIYRPPDRSAPSWNTTVRLLRRCRVLCNGGSSSHSTGEVVVTMEPE
VPIKKLETMVKLDATSEAVVKVDVAEEEKEKKKKKGTAEEPEEEEPDE
SMLDWWSKYFASIDTMKEQLRQQEPSGIDLEEKEEVDNTEGLKGSMKGK
EKARAAKEEKKKKTQSSGSGQGSEAPEKKKPKIDELKVYPKELESEFDN
FEDWLHTFNLLRGKTGDDEDGSTEEERIVGRFKGSLCVYKVPLPEDVSR
EAGYDSTYGMFQGIPSNDPINVLVRVYVVRATDLHPADINGKADPYIAI
RLGKTDIRDKENYISKQLNPVFGKSFDIEASFPMESMLTVAVYDWDLVG
TDDLIGETKIDLENRFYSKHRATCGIAQTYSTHGYNIWRDPMKPSQILT
RLCKDGKVDGPHFGPPGRVKVANRVFTGPSEIEDENGQRKPTDEHVALL
ALRHWEDIPRAGCRLVPEHVETRPLLNPDKPGIEQGRLELWVDMFPMDM
PAPGTPLDISPRKPKKYELRVIIWNTDEVVLEDDDFFTGEKSSDIFVRG
WLKGQQEDKQDTDVHYHSLTGEGNFNWRYLFPFDYLAAEEKIVISKKES
MFSWDETEYKIPARLTLQIWDADHFSADDFLGAIELDLNRFPRGAKTAK
QCTMEMATGEVDVPLVSIFKQKRVKGWWPLLARNENDEFELTGKVEAEL
HLLTAEEAEKNPVGLARNEPDPLEKPNRPDTSFIWFLNPLKSARYFLWH
TYRWLLLKLLLLLLLLLLLALFLYSVPGYLVKKILGA
Human OTOF isoform 5-Genbank Number NP_001274418
                                        (SEQ ID NO: 6)
MALLIHLKTVSELRGRGDRIAKVTFRGQSFYSRVLENCEDVADFDETFR
WPVASSIDRNEMLEIQVFNYSKVFSNKLIGTFRMVLQKVVEESHVEVTD
TLIDDNNAIIKTSLCVEVRYQATDGTVGSWDDGDFLGDESLQEEEKDSQ
ETDGLLPGSRPSSRPPGEKSFRRAGRSVFSAMKLGKNRSHKEEPQRPDE
PAVLEMEDLDHLAIRLGDGLDPDSVSLASVTALTTNVSNKRSKPDIKME
PSAGRPMDYQVSITVIEARQLVGLNMDPVVCVEVGDDKKYTSMKESTNC
PYYNEYFVFDFHVSPDVMFDKIIKISVIHSKNLLRSGTLVGSFKMDVGT
VYSQPEHQFHHKWAILSDPDDISSGLKGYVKCDVAVVGKGDNIKTPHKA
NETDEDDIEGNLLLPEGVPPERQWARFYVKIYRAEGLPRMNTSLMANVK
KAFIGENKDLVDPYVQVFFAGQKGKTSVQKSSYEPLWNEQVVFTDLFPP
LCKRMKVQIRDSDKVNDVAIGTHFIDLRKISNDGDKGFLPTLGPAWVNM
YGSTRNYTLLDEHQDLNEGLGEGVSFRARLLLGLAVEIVDTSNPELTSS
TEVQVEQATPISESCAGKMEEFFLFGAFLEASMIDRRNGDKPITFEVTI
GNYGNEVDGLSRPQRPRPRKEPGDEEEVDLIQNASDDEAGDAGDLASVS
STPPMRPQVTDRNYFHLPYLERKPCIYIKSWWPDQRRRLYNANIMDHIA
DKLEEGLNDIQEMIKTEKSYPERRLRGVLEELSCGCCRFLSLADKDQGH
SSRTRLDRERLKSCMRELENMGQQARMLRAQVKRHTVRDKLRLCQNFLQ
KLRFLADEPQHSIPDIFIWMMSNNKRVAYARVPSKDLLFSIVEEETGKD
CAKVKTLFLKLPGKRGFGSAGWTVQAKVELYLWLGLSKQRKEFLCGLPC
```

```
GFQEVKAAQGLGLHAFPPVSLVYTKKQAFQLRAHMYQARSLFAADSSGL
SDPFARVFFINQSQCTEVLNETLCPTWDQMLVFDNLELYGEAHELRDDP
PIIVIEIYDQDSMGKADFMGRTFAKPLVKMADEAYCPPRFPPQLEYYQI
YRGNATAGDLLAAFELLQIGPAGKADLPPINGPVDVDRGPIMPVPMGIR
PVLSKYRVEVLFWGLRDLKRVNLAQVDRPRVDIECAGKGVQSSLIHNYK
KNPNFNTLVKWFEVDLPENELLHPPLNIRVVDCRAFGRYTLVGSHAVSS
LRRFIYRPPDRSAPSWNTTVRLLRRCRVLCNGGSSSHSTGEVVVTMEPE
VPIKKLETMVKLDATSEAVVKVDVAEEEKEKKKKKGTAEEPEEEEPDE
SMLDWWSKYFASIDTMKEQLRQQEPSGIDLEEKEEVDNTEGLKGSMKGK
EKARAAKEEKKKKTQSSGSGQGSEAPEKKKPKIDELKVYPKELESEFDN
FEDWLHTFNLLRGKTGDDEDGSTEEERIVGRFKGSLCVYKVPLPEDVSR
EAGYDSTYGMFQGIPSNDPINVLVRVYVVRATDLHPADINGKADPYIAI
RLGKTDIRDKENYISKQLNPVFGKSFDIEASFPMESMLTVAVYDWDLVG
TDDLIGETKIDLENRFYSKHRATCGIAQTYSTHGYNIWRDPMKPSQILT
RLCKDGKVDGPHFGPPGRVKVANRVFTGPSEIEDENGQRKPTDEHVALL
ALRHWEDIPRAGCRLVPEHVETRPLLNPDKPGIEQGRLELWVDMFPMDM
PAPGTPLDISPRKPKKYELRVIIWNTDEVVLEDDDFFTGEKSSDIFVRG
WLKGQQEDKQDTDVHYHSLTGEGNFNWRYLFPFDYLAAEEKIVISKKES
MFSWDETEYKIPARLTLQIWDADHFSADDFLGAIELDLNRFPRGAKTAK
QCTMEMATGEVDVPLVSIFKQKRVKGWWPLLARNENDEFELTGKVEAEL
HLLTAEEAEKNPVGLARNEPDPLEKPNRPDTAFVWFLNPLKSIKYLICT
RYKWLIIKIVLALLGLLMLGLFLYSLPGYMVKKLLGA
```

In some embodiments, the Otoferlin polypeptide is a mouse Otoferlin polypeptide. In some embodiments, the Otoferlin polypeptide comprises a sequence that is at least 75%, at least 80%, at least 85%, at least 90%, at least 95%, at least 96%, at least 97%, at least 98%, at least 99% or 100% identical with the following amino acid sequence:

```
Mouse OTOF Isoform 1-Genbank Number NP_001093865.1
                                      (SEQ ID NO: 9)
MALIVHLKTVSELRGKGDRIAKVTFRGQSFYSRVLENCEGVADFDETFR
WPVASSIDRNEVLEIQIFNYSKVFSNKLIGTFCMVLQKVVEENRVEVTD
TLMDDSNAIIKTSLSMEVRYQATDGTVGPWDDGDFLGDESLQEEKDSQE
TDGLLPGSRPSTRISGEKSFRSKGREKTKGGRDGEHKAGRSVFSAMKLG
KTRSHKEEPQRQDEPAVLEMEDLDHLAIQLGDGLDPDSVSLASVTALTS
NVSNKRSKPDIKMEPSAGRPMDYQVSITVIEARQLVGLNMDPVVCVEVG
DDKKYTSMKESTNCPYYNEYFVFDFHVSPDVMFDKIIKISVIHSKNLLR
SGTLVGSFKMDVGTVYSQPEHQFHHKWAILSDPDDISAGLKGYVKCDVA
VVGKGDNIKTPHKANETDEDDIEGNLLLPEGVPPERQWARFYVKIYRAE
GLPRMNTSLMANVKKAFIGENKDLVDPYVQVFFAGQKGKTSVQKSSYEP
LWNEQVVFTDLFPPLCKRMKVQIRDSDKVNDVAIGTHFIDLRKISNDGD
KGFLPTLGPAWVNMYGSTRNYTLLDEHQDLNEGLGEGVSFRARLMLGLA
```

```
-continued
VEILDTSNPELTSSTEVQVEQATPVSESCTGRMEEFFLFGAFLEASMID

RKNGDKPITFEVTIGNYGNEVDGMSRPLRPRPRKEPGDEEEVDLIQNSS

DDEGDEAGDLASVSSTPPMRPQITDRNYFHLPYLERKPCIYIKSWWPDQ

RRRLYNANIMDHIADKLEEGLNDVQEMIKTEKSYPERRLRGVLEELSCG

CHRFLSLSDKDQGRSSRTRLDRERLKSCMRELESMGQQAKSLRAQVKRH

TVRDKLRSCQNFLQKLRFLADEPQHSIPDVFIWMMSNNKRIAYARVPSK

DLLFSIVEEELGKDCAKVKTLFLKLPGKRGFGSAGWTVQAKLELYLWLG

LSKQRKDFLCGLPCGFEEVKAAQGLGLHSFPPISLVYTKKQAFQLRAHM

YQARSLFAADSSGLSDPFARVFFINQSQCTEVLNETLCPTWDQMLVFDN

LELYGEAHELRDDPPIIVIEIYDQDSMGKADFMGRTFAKPLVKMADEAY

CPPRFPPQLEYYQIYRGSATAGDLLAAFELLQIGPSGKADLPPINGPVD

MDRGPIMPVPVGIRPVLSKYRVEVLFWGLRDLKRVNLAQVDRPRVDIEC

AGKGVQSSLIHNYKKNPNFNTLVKWFEVDLPENELLHPPLNIRVVDCRA

FGRYTLVGSHAVSSLRRFIYRPPDRSAPNWNTTGEVVVSMEPEEPVKKL

ETMVKLDATSDAVVKVDVAEDEKERKKKKKKGPSEEPEEEEPDESMLDW

WSKYFASIDTMKEQLRQHETSGTDLEEKEEMESAEGLKGPMKSKEKSRA

AKEEKKKKNQSPGPGQGSEAPEKKKAKIDELKVYPKELESEFDSFEDWL

HTFNLLRGKTGDDEDGSTEEERIVGRFKGSLCVYKVPLPEDVSREAGYD

PTYGMFQGIPSNDPINVLVRIYVVRATDLHPADINGKADPYIAIKLGKT

DIRDKENYISKQLNPVFGKSFDIEASFPMESMLTVAVYDWDLVGTDDLI

GETKIDLENRFYSKHRATCGIAQTYSIHGYNIWRDPMKPSQILTRLCKE

GKVDGPHFGPHGRVRVANRVFTGPSEIEDENGQRKPTDEHVALSALRHW

EDIPRVGCRLVPEHVETRPLLNPDKPGIEQGRLELWVDMFPMDMPAPGT

PLDISPRKPKKYELRVIVWNTDEVVLEDDDFFTGEKSSDIFVRGWLKGQ

QEDKQDTDVHYHSLTGEGNFNWRYLFPFDYLAAEEKIVMSKKESMFSWD

ETEYKIPARLTLQIWDADHFSADDFLGAIELDLNRFPRGAKTAKQCTME

MATGEVDVPLVSIFKQKRVKGWWPLLARNENDEFELTGKVEAELHLLTA

EEAEKNPVGLARNEPDPLEKPNRPDTAFVWFLNPLKSIKYLICTRYKWL

IIKIVLALLGLLMLALFLYSLPGYMVKKLLGA
```

In some embodiments, polynucleotides described herein comprise a splice donor or splice acceptor site. In some embodiments, the splice donor and/or splice acceptor sites contain splice consensus sequences. In some embodiments, the splice donor and/or splice acceptor sites contain sequences splice consensus sequences derived from alkaline phosphatase. In some embodiments, the splice donor site comprises a sequence that is at least 75%, at least 80%, at least 85%, at least 90%, at least 95%, at least 96%, at least 97%, at least 98%, at least 99% or 100% identical with the nucleotide sequence GTAAGTATCAAGGTTACAA-GACAGGTTTAAGGAGACCAATAGAAACTGGGC-TTGTC GAGACAGAGAAGACTCTTGCGTTTCTGA (SEQ ID NO: 7). In some embodiments, the splice acceptor site comprises a sequence that is at least 75%, at least 80%, at least 85%, at least 90%, at least 95%, at least 96%, at least 97%, at least 98%, at least 99% or 100% identical with the nucleotide sequence

```
                                              (SEQ ID NO: 8)
TAGGCACCTATTGGTCTTACTGACATCCACTTTGCCTTTCTCTCCACAG.
```

In some embodiments, polynucleotides described herein comprise ITR sequences. The ITR sequences of a polynucleotide described herein can be derived from any AAV serotype (e.g., 1, 2, 3, 4, 5, 6, 7, 8, 9, or 10) or can be derived from more than one serotype. In some embodiments of the polynucleotide provided herein, the ITR sequences are derived from AAV2. ITR sequences and plasmids containing ITR sequences are known in the art and commercially available (see, e.g., products and services available from Vector Biolabs, Philadelphia, PA; Cellbiolabs, San Diego, CA; Agilent Technologies, Santa Clara, Ca; and Addgene, Cambridge, MA; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference). An exemplary AAV2 ITR sequence for flanking the 5' end of an expression construct comprises the sequence: TTGGCCACTCCCTC-TCTGCGCGCTCGCTCGCTCACTGAGGCCGGGC-GACCAAAGGTC GCCCGACGCCCGGGCTTTGCCC-GGGCGGCCTCAGTGAGCGAGCGAGCGCGCAGAGA GGGAGTGGCCAACTCCATCACTAGGGGTTC (SEQ ID NO: 10). An exemplary AAV2 ITR sequence for flanking the 3' end of an expression construct comprises the sequence

```
                                             (SEQ ID NO: 11)
ACCCCTAGTGATGGAGTTGGCCACTCCCTCTCTGCGCGCTCGCTCGCT

CACTGAGGCCGCCCGGGCAAAGCCCGGGCGTCGGGCGACCTTTGGTCG

CCCGGCCTCAGTGAGCGAGCGAGCGCGCAGAGAGGGAGTGGCCAACC.
```

In some embodiments, polynucleotides described herein may further optionally include one or more transcription termination sequences, one or more translation termination sequences, one or more signal peptide sequences, one or more internal ribosome entry sites (IRES), and/or one or more enhancer elements, or any combination thereof. Transcription termination regions can typically be obtained from the 3' untranslated region of a eukaryotic or viral gene sequence. Transcription termination sequences can be positioned downstream of a coding sequence to provide for efficient termination. Signal peptide sequences are amino-terminal peptidic sequences that encode information responsible for the location of an operably-linked polypeptide to one or more post-translational cellular destinations, including, for example, specific organelle compartments, or to the sites of protein synthesis and/or activity, and even to the extracellular environment. In some embodiments, a polynucleotide as described herein comprises a bovine growth hormone polyadenylation signal.

In some embodiments, the expression constructs contained within the polynucleotides described herein are no more than 5 kilobases, no more than 4 kilobases, or no more than 3 kilobases in size. In some embodiments, the expression construct is between 4 and 5 kilobases in size.

In some embodiments, polynucleotides described herein are contained within one or more recombinant AAV particles (e.g., first and second AAV particles). The AAV particles may be of any AAV serotype (e.g., 1, 2, 3, 4, 5, 6, 7, 8, 9, or 10), including any derivative (including non-naturally occurring variants of a serotype) or pseudotype. Non-limiting examples of derivatives and pseudotypes include AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6(Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan Al, Schaffer D V, Samulski R J.). In some embodiments, the first and second AAV particle are AAV2 serotype particles.

Methods of producing AAV particles and polynucleotides are known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the polynucleotides (e.g., as plasmids) may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the AAV particle can be packaged and subsequently purified.

In some embodiments, the one or more helper plasmids includes a first helper plasmid comprising a rep gene and a cap gene and a second helper plasmid comprising other genes that assist in AAV production, such as a E1a gene, a E1b gene, a E4 gene, a E2a gene, and a VA gene. In some embodiments, the rep gene is a rep gene derived from AAV2. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, PA; Cellbiolabs, San Diego, CA; Agilent Technologies, Santa Clara, Ca; and Addgene, Cambridge, MA; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adenoassociated viral vector reference standards, Molecular Therapy, Vol. 16, 1185-1188).

An exemplary, non-limiting, AAV particle production method is described next. One or more helper plasmids are produced or obtained, which comprise rep and cap ORFs for the desired AAV serotype and the adenoviral VA, E2A (DBP), and E4 genes under the transcriptional control of their native promoters. HEK293 cells (available from ATCC®) are transfected via $CaPO_4$-mediated transfection, lipids or polymeric molecules such as Polyethylenimine (PEI) with the helper plasmid(s) and a plasmid containing a polynucleotide described herein. Alternatively, in another non-limiting example, Sf9-based producer stable cell lines are infected with a single recombinant baculovirus containing the polynucleotide. As a further non-limiting alternative, in another example HEK293 or BHK cell lines are infected with a HSV containing the polynucleotide and optionally one or more helper HSVs containing rep and cap ORFs as described herein and the adenoviral VA, E2A (DBP), and E4 genes under the transcriptional control of their native promoters. The HEK293, BHK, or Sf9 cells are then incubated for at least 60 hours to allow for AAV particle production. The AAV particles can then be purified using any method known in the art or described herein, e.g., by iodixanol step gradient, CsCl gradient, chromatography, or polyethylene glycol (PEG) precipitation.

The disclosure also contemplates host cells that comprise at least one of the disclosed AAV particles or polynucleotides. Such host cells include mammalian host cells, with human host cells being preferred, and may be either isolated, in cell or tissue culture. In the case of genetically modified animal models (e.g., a mouse), the transformed host cells may be comprised within the body of a non-human animal itself.

Methods and Subjects

In some aspects, methods of increasing expression of Otoferlin in a cell are provided. In some embodiments, the method comprises contacting the cell with a first AAV particle as described herein comprising a first polynucleotide as described herein; and contacting the cell with a second AAV particle as described herein comprising a second polynucleotide as described herein. In some embodiments, the cell is a mammalian cell such as a mouse or human cell. In some embodiments, the cell is ex vivo. In some embodiments, the cell is in vivo. In some embodiments, the cell is a cell of the ear (e.g., the cell of a human ear). In some embodiments, the cell is a cell of the inner ear (e.g., the cell of a human inner ear). In some embodiments, the cell is in a subject (e.g., a mammalian subject such as a human subject).

Other aspects of the disclosure relate to treatment of a disease or condition caused by decreased or absent expression or activity of Otoferlin. In some embodiments, the method comprises administering to a subject a therapeutically effective amount of a first AAV particle as described herein comprising a first polynucleotide as described herein and a therapeutically effective amount of a second AAV particle as described herein comprising a second polynucleotide as described herein. In some embodiments, the subject is a human subject and the subject has Deafness, Autosomal Recessive 9 (DFNB9). In some embodiments, the subject is a human subject having impaired vestibular function or a vestibular disorder (see, e.g., Dulon et al. Otoferlin is Critical for a Highly Sensitive and Linear Calcium Dependent Exocytosis at Vestibular Hair Cell Ribbon Synapses. J Neurosci. 2009; 29(34): 10474-10487).

To "treat" a disease as the term is used herein, means to reduce the frequency or severity of at least one sign or symptom of a disease or disorder experienced by a subject.

The compositions described above or elsewhere herein are typically administered to a subject in an effective amount, that is, an amount capable of producing a desirable result. The desirable result will depend upon the active agent being administered. For example, an effective amount of AAV particles may be an amount of the particles that are capable of transferring an expression construct to a host organ, tissue, or cell. A therapeutically acceptable amount may be an amount that is capable of treating a disease, e.g., DFNB9. As is well known in the medical and veterinary arts, dosage for any one subject depends on many factors, including the subject's size, body surface area, age, the particular composition to be administered, the active ingredient(s) in the composition, time and route of administration, general health, and other drugs being administered concurrently.

The AAV particles or polynucleotides may be delivered in the form of a composition, such as a composition comprising the active ingredient, such as AAV particles described herein, and a pharmaceutically acceptable carrier as described herein. The AAV particles or polynucleotides may be prepared in a variety of compositions, and may also be formulated in appropriate pharmaceutical vehicles for administration to human or animal subjects. In some embodiments, where first and second AAV particles are utilized, the first and second AAV particles may be contained within the same composition or within different compositions and may be administered together or separately.

In some embodiments, the AAV particles administered to a subject may be provided in a composition having a concentration on the order ranging from $10^6$ to $10^{14}$ particles/ml or $10^3$ to $10^{15}$ particles/ml, or any values there between for either range, such as for example, about $10^6$, $10^7$, $10^8$, $10^9$, $10^{10}$, $10^{11}$, $10^{12}$, $10^{13}$, or $10^{14}$ particles/ml. In one embodiment, AAV particles of higher than $10^{13}$ particles/ml are be administered. In some embodiments, the number of AAV particles administered to a subject may be on the order ranging from $10^6$ to $10^{14}$ vector genomes(vgs)/ml or $10^3$ to $10^{15}$ vgs/ml, or any values therebetween for either range, such as for example, about $10^6$, $10^7$, $10^8$, $10^9$, $10^{10}$, $10^{11}$, $10^{12}$, $10^{13}$, or $10^{14}$ vgs/ml. In one embodiment, AAV particles of higher than $10^{13}$ vgs/ml are be administered. The AAV particles can be administered as a single dose, or divided into two or more administrations as may be required to achieve therapy of the particular disease or disorder being treated. In some embodiments, 0.0001 ml to 10 mls are delivered to a subject. In some embodiments, the number of AAV particles administered to a subject may be on the order ranging from $10^6$-$10^{14}$ vg/kg, or any values therebetween, such as for example, about $10^6$, $10^7$, $10^8$, $10^9$, $10^{10}$, $10^{11}$, $10^{12}$, $10^{13}$, or $10^{14}$ vgs/kg. In some embodiments, when a first AAV particle comprising a first polynucleotide as described herein and second AAV particle comprising a second polynucleotide as described herein are administered, the amount administered is the same for both particles. In some embodiments, when a first AAV particle comprising a first polynucleotide as described herein and second AAV particle comprising a second polynucleotide as described herein are administered, the amount administered is different for each particle.

If desired, AAV particles may be administered in combination with other agents or treatments as well, such as, e.g., proteins or polypeptides or various pharmaceutically-active agents, including one or more systemic or topical administrations of therapeutic polypeptides, biologically active fragments, or variants thereof. In fact, there is virtually no limit to other components that may also be included, given that the additional agents do not cause a significant adverse effect upon contact with the target cells or host tissues. The AAV particles may thus be delivered along with various other agents or treatments as required in the particular instance. In some embodiments, AAV particle treatment may be accompanied by use of a hearing aid.

In certain circumstances it will be desirable to deliver the AAV particles in suitably formulated pharmaceutical compositions disclosed herein either subcutaneously, parenterally, intravenously, intramuscularly, intraperitoneally, by oral or nasal inhalation, or by direct injection to one or more cells, tissues, or organs. In some embodiments, the administration is a route suitable for systemic delivery, such as by intravenous injection or infusion. In some embodiments, the administration is to the ear, e.g., via intra-cochlear administration. The pharmaceutical forms of the AAV particle compositions suitable for injectable use include sterile aqueous solutions or dispersions. In some embodiments, the form is sterile and fluid to the extent that easy syringability exists. In some embodiments, the form is stable under the conditions of manufacture and storage and is preserved against the contaminating action of microorganisms, such as bacteria and fungi. The carrier can be a solvent or dispersion medium containing, for example, water, saline, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, intravitreal, subretinal, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by, e.g., FDA Office of Biologics standards.

Sterile injectable solutions are prepared by incorporating the AAV particles in the required amount in the appropriate solvent with several of the other ingredients enumerated above, as required, followed by filtered sterilization or another sterilization technique. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The amount of AAV particle or polynucleotide compositions and time of administration of such compositions will be within the purview of the skilled artisan having benefit of the present teachings. It is likely, however, that the administration of therapeutically effective amounts of the disclosed compositions may be achieved by a single administration, such as for example, a single injection of sufficient numbers of infectious particles to provide therapeutic benefit to the patient undergoing such treatment. Alternatively, in some circumstances, it may be desirable to provide multiple, or successive administrations of the AAV particle compositions, either over a relatively short, or a relatively prolonged period of time, as may be determined by the medical practitioner overseeing the administration of such compositions.

The composition may include AAV particles, either alone, or in combination with one or more additional active ingredients, which may be obtained from natural or recombinant sources or chemically synthesized.

Toxicity and efficacy of the compositions utilized in methods of the disclosure can be determined by standard pharmaceutical procedures, using either cells in culture or experimental animals to determine the LD50 (the dose lethal to 50% of the population). The dose ratio between toxicity and efficacy is the therapeutic index and it can be expressed as the ratio LD50/ED50. Those compositions that exhibit large therapeutic indices are preferred. While those that exhibit toxic side effects may be used, care should be taken to design a delivery system that minimizes the potential damage of such side effects. The dosage of compositions as described herein lies generally within a range that includes an ED50 with little or no toxicity. The dosage may vary within this range depending upon the dosage form employed and the route of administration utilized.

Aspects of the disclosure relate to methods for use with a subject, such as human or non-human primate subjects. Non-limiting examples of non-human primate subjects include macaques (e.g., cynomolgus or rhesus macaques), marmosets, tamarins, spider monkeys, owl monkeys, vervet monkeys, squirrel monkeys, baboons, gorillas, chimpanzees, and orangutans. In some embodiments, the subject is a human subject. Other exemplary subjects include domesticated animals such as dogs and cats; livestock such as horses, cattle, pigs, sheep, goats, and chickens; and other animals such as mice, rats, guinea pigs, and hamsters.

In some embodiments, the subject has or is suspected of having a disease that may be treated with gene therapy. In some embodiments, the subject has or is suspected of having Deafness, Autosomal Recessive 9 (DFNB9). DFNB9 is an autosomal recessive form of deafness though to be caused by mutations in the OTOF gene that result in a decrease in expression, functionality, or both, of the Otoferlin protein. Otoferlin protein has been shown to be important for exocytosis at the auditory ribbon synapse (see, e.g., Roux et al. Otoferlin, defective in a human deafness form, is essential for exocytosis at the auditory ribbon synapse. (2006) Cell 127(2):277-89). Subjects having DFNB9 can be identified by the skilled physician, e.g., using a combination of electrophysiologic testing of auditory brain stem responses (ABRs) and genetic testing to identify mutations in the OTOF gene (see, e.g., OMIM entries 603681 and 601071). In some embodiments, the subject is a human subject that has one or more of the following nonsense or missense mutations in the OTOF gene: TYR730TER, GLN829TER, PRO1825ALA, PRO50ARG, LEU1011PRO, ILE515THR, ARG1939GLN, or GLY541SER. In some embodiments, the subject is a human subject that has an A-to-G transition at the intron 8/exon 9 junction (IVS8-2A-G) or an G-to-A transition at position+1, the first intronic nucleotide in the splice donor site of exon 5 or a G-C transversion in the donor splice site of intron 39. In some embodiments, the subject is a human subject that has a one base pair deletion (1778G) in exon 16, leading to a stop codon, and a 6141G-A change, resulting in an ARG-to-GLN substitution in exon 48.

Compositions

Other aspects of the disclosure relate to compositions comprising AAV particles or polynucleotides described herein. In some embodiments, AAV particles described herein are added to a composition, e.g., a pharmaceutical composition.

In some embodiments, the composition comprises a pharmaceutically acceptable carrier. The term "carrier" refers to a diluent, adjuvant, excipient, or vehicle with which the AAV particles are administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of AAV particles to human subjects. Such compositions may further optionally comprise a liposome, a lipid, a lipid complex, a microsphere, a microparticle, a nanosphere, or a nanoparticle, or may be otherwise formulated for administration to the cells, tissues, organs, or body of a subject in need thereof. Methods for making such compositions are well known and can be found in, for example, Remington: The Science and Practice of Pharmacy, $22^{nd}$ edition, Pharmaceutical Press, 2012.

Typically, such compositions may contain at least about 0.1% of the therapeutic agent (e.g., AAV particles) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., AAV particles) in each therapeutically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In some embodiments, a composition described herein may be administered to a subject in need thereof, such as a subject having DFNB9. In some embodiments, a method described herein may comprise administering a composition or multiple compositions comprising AAV particles as described herein to a subject in need thereof. In some embodiments, the subject is a human subject. In some embodiments, the subject has or is suspected of having a disease that may be treated with gene therapy, such as DFNB9. In some embodiments, the subject has been diagnosed with DFNB9.

Kits

Other aspects of the disclosure relate to kits comprising AAV particles or polynucleotides as described herein in one or more containers. Kits can optionally include pharmaceutically acceptable carriers and/or diluents. In some embodiments, the kit includes instructions or packaging materials that describe how to administer AAV particles or polynucleotides contained within the kit to a selected cell or recipient. Containers of the kit can be of any suitable material, e.g., glass, plastic, metal, etc., and of any suitable size, shape, or configuration. In some embodiments, the kits may include one or more ampoules or syringes that contain AAV particles or polynucleotides in a suitable liquid or solution form.

EXAMPLES

Rescue of Hearing in OTOF Knock-Out Mice Using Adeno-Associated Virus Gene Therapy Approach Introduction Otoferlin is the key calcium sensor for neurotransmitter release in the ear (see, e.g., Roux 2006). Otoferlin is mainly expressed in the inner hair cells of the cochlea and only few other cells of the central nervous system (see, e.g., Yasunaga et al. 1999& 2000). It is a member of the ferlin family of transmembrane proteins which share a common C2 domain also found in synaptotagmin, PKC and PLC.

Mutations in the human OTOF gene, which encodes human Otoferlin, cause a type of nonsyndromic deafness called Deafness, Autosomal Recessive 9 (DFNB9). OTOF knock-out mice have also been shown to have severe hearing loss despite normal inner hair cell development and auditory ribbon synapse formation (see, e.g., Roux et al. (2006) Otoferlin, defective in a human deafness form, is essential for exocytosis at the auditory ribbon synapse. Cell. 127:277-289). However, Otof$^{-/-}$ mice lose the auditory brain stem response across all sound frequencies due to complete abolishment of synaptic exocytosis and, as a consequence, abolishment of neurotransmitter release from synaptic vesicles.

DFNB9 manifests in humans as two phenotypes, as a nonsyndromic bilateral loss of hearing before the acquiring of language and less frequently as a temperature-sensitive nonsyndromic auditory neuropathy. It was first discovered in an affected Lebanese family (Chaib et al. 1996) and has since been found in many parts of the world (see, e.g., Adato et al. 2000, Rodriguez-Ballesteros et al. 2003, Choi et al. 2009, Matsunaga et al. 2012).

Current treatment in humans with DFNB9 utilizes cochlear implants and hearing aids. In addition, for the temperature-sensitive form of DFNB9, prevention of fevers and other conditions that would cause the body temperature to rise are important. Applicants sought to use adeno-associated virus (AAV) as a means to restore expression of OTOF in the knock-out mice as a proof-of-concept for using AAV to delivery OTOF as a treatment for DFNB9. The mouse OTOF cDNA is 5979 base pairs in length whereas most AAVs cannot package more than approximately 4.8 kilobases of genome. As a result, a dual vector system was used to separately deliver the 5' portion of the cDNA and the 3' portion of the cDNA as separate AAV constructs such that the full-length cDNA could be reassembled in vivo once delivered.

Methods

Dual AAV Vector Constructs

Figure 1B:
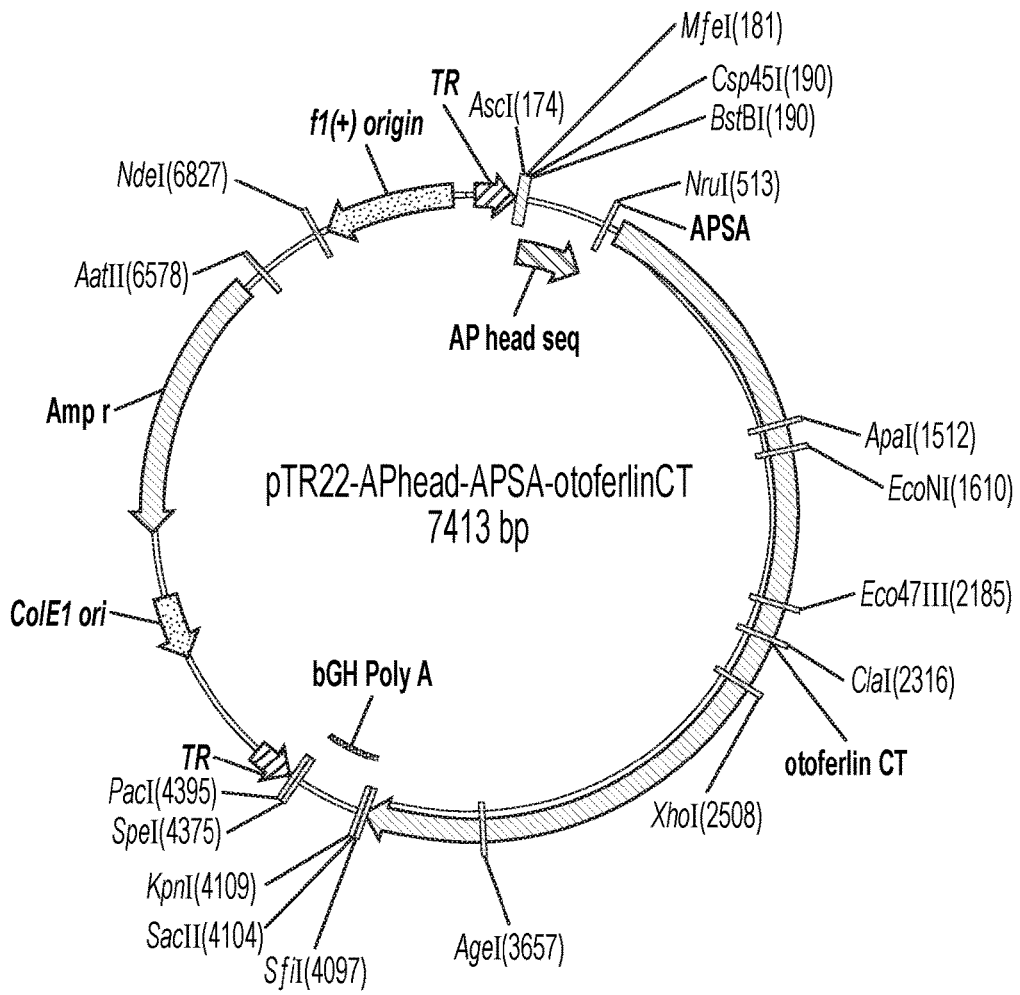
FIG. 1B is a map of a plasmid containing AAV2 inverted terminal repeats (TR) flanking a homologous sequence for recombination (APhead), a splice acceptor sequence (APSA), a 3' section of the mouse Otoferlin cDNA (Otoferlin CT), a bovine growth hormone polyadenylation signal (bGH PolyA).
Figure 2:
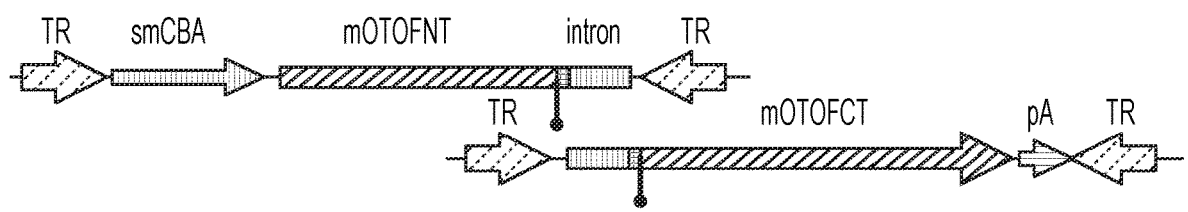
FIG. 2 is a schematic of the two expression cassettes in the plasmids in FIGS. 1A and 1B.

A mouse OTOF cDNA was split into two sections, a 5' and 3' section and inserted into two AAV ITR-containing plasmids. The sequence of each of the two cassettes in the plasmids is shown below and the maps of each construct are shown in FIGS. 1 and 2. Annotated versions of the cassettes are shown in FIGS. 3A and 3B. Each cassette contains a region of homology to promote homologous recombination between the 5' and 3' ends of the cDNA in vivo (see Ghosh et al., 2011). Once recombined in vivo, the full-length cDNA contains a splice donor/splice acceptor pair that causes splicing out of the region of homology. The vectors were packaged into AAV2 serotype particles using standard plasmid transfection methods as previously described (see Zolotukhin et al. Production and purification of serotype 1, 2, and 5 recombinant adeno-associated viral vectors. Methods 28 (2002) 158-167). The viral particles were purified by standard methods as previously described (see Zolotukhin et al. Production and purification of serotype 1, 2, and 5 recombinant adeno-associated viral vectors. Methods 28 (2002) 158-167). The viral particles carrying the 5' portion of the OTOF cDNA are also referred to herein as "AAV2-OTOF-NT." The viral particles carrying the 3' portion of the OTOF cDNA are also referred to herein as "AAV2-OTOF-CT."

pTR22-smCBA-otoferlinNT-APSD-APhead (SEQ ID NO: 1)

AGGGGGGGGGGGGGGGGGTTGGCCACTCCCTCTCTGCGCGCTCGCTC

GCTCACTGAGGCCGGGCGACCAAAGGTCGCCCGACGCCCGGGCTTTGC

CCGGGCGGCCTCAGTGAGCGAGCGAGCGCGCAGAGAGGGAGTGGCCAA

CTCCATCACTAGGGGTTCCTCAGATCTGGCGCGCCCAATTCGGTACCC

TAGTTATTAATAGTAATCAATTACGGGGTCATTAGTTCATAGCCCATA

TATGGAGTTCCGCGTTACATAACTTACGGTAAATGGCCCGCCTGGCTG

ACCGCCCAACGACCCCCGCCCATTGACGTCAATAATGACGTATGTTCC

CATAGTAACGCCAATAGGGACTTTCCATTGACGTCAATGGGTGGACTA

TTTACGGTAAACTGCCCACTTGGCAGTACATCAAGTGTATCATATGCC

AAGTACGCCCCCTATTGACGTCAATGACGGTAAATGGCCCGCCTGGCA

TTATGCCCAGTACATGACCTTATGGGACTTTCCTACTTGGCAGTACAT

CTACGTATTAGTCATCGCTATTACCATGGTCGAGGTGAGCCCCACGTT

CTGCTTCACTCTCCCCATCTCCCCCCCCTCCCCACCCCCAATTTTGTA

TTTATTTATTTTTTAATTATTTTGTGCAGCGATGGGGCGGGGGGGG

GGGGGGCGCGCGCCAGGCGGGCGGGCGGGCGAGGGCGGGCGG

GGCGAGGCGGAGAGGTGCGGCGGCAGCCAATCAGAGCGGCGCGCTCCG

AAAGTTTCCTTTTATGGCGAGGCGGCGGCGGCGGCGGCCCTATAAAAA

GCGAAGCGCGCGGCGGGCGGGAGTCGCTGCGACGCTGCCTTCGCCCCG

TGCCCCGCTCCGCCGCCGCCTCGCGCCGCCCGCCCCGGCTCTGACTGA

```
CCGCGTTACTCCCACAGGTGAGCGGGCGGGACGGCCCTTCTCCTCCGG
GCTGTAATTAGCGCTTGGTTTAATGACGGCTTGTTTCTTTTCTGTGGC
TGCGTGAAAGCCTTGAGGGGCTCCGGGAGCTAGAGCCTCTGCTAACCA
TGTTCATGCCTTCTTCTTTTTCCTACAGCTCCTGGGCAACGTGCTGGT
TATTGTGCTGTCTCATCATTTTGGCAAAGAATTCTAGCGGCCGCCACC
ATGGCCCTGATTGTTCACCTCAAGACTGTCTCAGAGCTCCGAGGCAAA
GGTGACCGGATTGCCAAAGTCACTTTCCGAGGGCAGTCTTTCTACTCC
CGGGTCCTGGAGAACTGCGAGGGTGTGGCTGACTTTGATGAGACGTTC
CGGTGGCCAGTGGCCAGCAGCATCGACCGGAATGAAGTGTTGGAGATT
CAGATTTTCAACTACAGCAAAGTCTTCAGCAACAAGCTGATAGGGACC
TTCTGCATGGTGCTGCAGAAAGTGGTGGAGGAGAATCGGGTAGAGGTG
ACCGACACGCTGATGGATGACAGCAATGCTATCATCAAGACCAGCCTG
AGCATGGAGGTCCGGTATCAGGCCACAGATGGCACTGTGGGCCCCTGG
GATGATGGAGACTTCCTGGGAGATGAATCCCTCCAGGAGGAGAAGGAC
AGCCAGGAGACAGATGGGCTGCTACCTGGTTCCCGACCCAGCACCCGG
ATATCTGGCGAGAAGAGCTTTCGCAGCAAAGGCAGAGAGAAGACCAAG
GGAGGCAGAGATGGCGAGCACAAAGCGGGAAGGAGTGTGTTCTCGGCC
ATGAAACTCGGCAAAACTCGGTCCCACAAAGAGGAGCCCCAAAGACAA
GATGAGCCAGCAGTGCTGGAGATGAGGACCTGGACCACCTAGCCATT
CAGCTGGGGATGGGCTGGATCCTGACTCCGTGTCTCTAGCCTCGGTC
ACCGCTCTCACCAGCAATGTCTCCAACAAACGGTCTAAGCCAGATATT
AAGATGGAGCCCAGTGCTGGAAGGCCCATGGATTACCAGGTCAGCATC
ACAGTGATTGAGGCTCGGCAGCTGGTGGGCTTGAACATGGACCCTGTG
GTGTGTGTGGAGGTGGGTGATGACAAGAAATACACGTCAATGAAGGAG
TCCACAAACTGCCCTTACTACAACGAGTACTTTGTCTTCGACTTCCAT
GTCTCTCCTGATGTCATGTTTGACAAGATCATCAAGATCTCGGTTATC
CATTCTAAGAACCTGCTTCGGAGCGGCACCCTGGTGGGTTCCTTCAAA
ATGGATGTGGGGACTGTGTATTCCCAGCCTGAACACCAGTTCCATCAC
AAATGGGCCATCCTGTCAGACCCCGATGACATCTCTGCTGGGTTGAAG
GGTTATGTAAAGTGTGATGTCGCTGTGGTGGGCAAGGGAGACAACATC
AAGACACCCCACAAGGCCAACGAGACGGATGAGGACGACATTGAAGGG
AACTTGCTGCTCCCCGAGGGCGTGCCCCCCGAACGGCAGTGGGCACGG
TTCTATGTGAAAATTTACCGAGCAGAGGGACTGCCCCGGATGAACACA
AGCCTCATGGCCAACGTGAAGAAGGCGTTCATCGGTGAGAACAAGGAC
CTCGTCGACCCCTATGTGCAAGTCTTCTTTGCTGGACAAAAGGGCAAA
ACATCAGTGCAGAAGAGCAGCTATGAGCCGCTATGGAATGAGCAGGTC
GTCTTCACAGACTTGTTCCCCCCACTCTGCAAACGCATGAAGGTGCAG
ATCCGGGACTCTGACAAGGTCAATGATGTGGCCATCGGCACCCACTTC
ATCGACCTGCGCAAGATTTCCAACGATGGAGACAAAGGCTTCCTGCCT
ACCCTCGGTCCAGCCTGGGTGAACATGTACGGCTCCACGCGCAACTAC
ACACTGCTGGACGAGCACCAGGACTTGAATGAAGGCCTGGGGGAGGGT
GTGTCCTTCCGGGCCCGCCTCATGTTGGGACTAGCTGTGGAGATCCTG
GACACCTCCAACCCAGAGCTCACCAGCTCCACGGAGGTGCAGGTGGAG
CAGGCCACGCCTGTCTCGGAGAGCTGCACAGGGAGAATGGAAGAATTT
TTTCTATTTGGAGCCTTCTTGGAAGCCTCAATGATTGACCGGAAAAAT
GGGGACAAGCCAATTACCTTTGAGGTGACCATAGGAAACTACGGCAAT
GAAGTCGATGGTATGTCCCGGCCCCTGAGGCCTCGGCCCCGGAAAGAG
CCTGGGGATGAAGAAGAGGTAGACCTGATTCAGAACTCCAGTGACGAT
GAAGGTGACGAAGCCGGGGACCTGGCCTCGGTGTCCTCCACCCCACCT
ATGCGGCCCCAGATCACGGACAGGAACTATTTCCACCTGCCCTACCTG
GAGCGCAAGCCCTGCATCTATATCAAGAGCTGGTGGCCTGACCAGAGG
CGGCGCCTCTACAATGCCAACATCATGGATCACATTGCTGACAAGCTG
GAAGAAGGCCTGAATGATGTACAGGAGATGATCAAAACGGAGAAGTCC
TACCCGGAGCGCCGCCTGCGGGGTGTGCTAGAGGAACTCAGCTGTGGC
TGCCACCGCTTCCTCTCCCTCTCGGACAAGGACCAGGGCCGCTCGTCC
CGCACCAGGCTGGATCGAGAGCGTCTTAAGTCCTGTATGAGGGAGTTG
GTAAGTATCAAGGTTACAAGACAGGTTTAAGGAGACCAATAGAAACTG
GGCTTGTCGAGACAGAGAAGACTCTTGCGTTTCTGAGCTAGCCCCCGG
GTGCGCGGCGTCGGTGGTGCCGGCGGGGGCGCCAGGTCGCAGGCGGT
GTAGGGCTCCAGGCAGGCGGCGAAGGCCATGACGTGCGCTATGAAGGT
CTGCTCCTGCACGCCGTGAACCAGGTGCGCCTGCGGGCCGCGCGCGAA
CACCGCCACGTCCTCGCCTGCGTGGGTCTCTTCGTCCAGGGGCACTGC
TGACTGCTGCCGATACTCGGGGCTCCCGCTCTCGCTCTCGGTAACATC
CGGCCGGGCGCCGTCCTTGAGCACATAGCCTGGACCGTTTCGTCGACT
GTTAATTAAGCATGCTGGGGAGAGATCTAGGAACCCCTAGTGATGGAG
TTGGCCACTCCCTCTCTGCGCGCTCGCTCGCTCACTGAGGCCGCCCGG
GCAAAGCCCGGGCGTCGGGCGACCTTTGGTCGCCCGGCCTCAGTGAGC
GAGCGAGCGCGCAGAGAGGGAGTGGCCAACCCCCCCCCCCCCCCCCCT
GCAGCCCTGCATTAATGAATCGGCCAACGCGCGGGGAGAGGCGGTTTG
CGTATTGGGCGCTCTTCCGCTTCCTCGCTCACTGACTCGCTGCGCTCG
GTCGTTCGGCTGCGGCGAGCGGTATCAGCTCACTCAAAGGCGGTAATA
CGGTTATCCACAGAATCAGGGGATAACGCAGGAAAGAACATGTGAGCA
AAAGGCCAGCAAAAGGCCAGGAACCGTAAAAAGGCCGCGTTGCTGGCG
TTTTTCCATAGGCTCCGCCCCCCTGACGAGCATCACAAAAATCGACGC
TCAAGTCAGAGGTGGCGAAACCCGACAGGACTATAAAGATACCAGGCG
TTTCCCCCTGGAAGCTCCCTCGTGCGCTCTCCTGTTCCGACCCTGCCG
CTTACCGGATACCTGTCCGCCTTTCTCCCTTCGGGAAGCGTGGCGCTT
TCTCAATGCTCACGCTGTAGGTATCTCAGTTCGGTGTAGGTCGTTCGC
TCCAAGCTGGGCTGTGTGCACGAACCCCCCGTTCAGCCCGACCGCTGC
GCCTTATCCGGTAACTATCGTCTTGAGTCCAACCCGGTAAGACACGAC
TTATCGCCACTGGCAGCAGCCACTGGTAACAGGATTAGCAGAGCGAGG
```

TATGTAGGCGGTGCTACAGAGTTCTTGAAGTGGTGGCCTAACTACGGC
TACACTAGAAGGACAGTATTTGGTATCTGCGCTCTGCTGAAGCCAGTT
ACCTTCGGAAAAAGAGTTGGTAGCTCTTGATCCGGCAAACAAACCACC
GCTGGTAGCGGTGGTTTTTTTGTTTGCAAGCAGCAGATTACGCGCAGA
AAAAAAGGATCTCAAGAAGATCCTTTGATCTTTTCTACGGGGTCTGAC
GCTCAGTGGAACGAAAACTCACGTTAAGGGATTTTGGTCATGAGATTA
TCAAAAAGGATCTTCACCTAGATCCTTTTAAATTAAAAATGAAGTTTT
AAATCAATCTAAAGTATATATGAGTAAACTTGGTCTGACAGTTACCAA
TGCTTAATCAGTGAGGCACCTATCTCAGCGATCTGTCTATTTCGTTCA
TCCATAGTTGCCTGACTCCCCGTCGTGTAGATAACTACGATACGGGAG
GGCTTACCATCTGGCCCCAGTGCTGCAATGATACCGCGAGACCCACGC
TCACCGGCTCCAGATTTATCAGCAATAAACCAGCCAGCCGGAAGGGCC
GAGCGCAGAAGTGGTCCTGCAACTTTATCCGCCTCCATCCAGTCTATT
AATTGTTGCCGGGAAGCTAGAGTAAGTAGTTCGCCAGTTAATAGTTTG
CGCAACGTTGTTGCCATTGCTACAGGCATCGTGGTGTCACGCTCGTCG
TTTGGTATGGCTTCATTCAGCTCCGGTTCCCAACGATCAAGGCGAGTT
ACATGATCCCCCATGTTGTGCAAAAAAGCGGTTAGCTCCTTCGGTCCT
CCGATCGTTGTCAGAAGTAAGTTGGCCGCAGTGTTATCACTCATGGTT
ATGGCAGCACTGCATAATTCTCTTACTGTCATGCCATCCGTAAGATGC
TTTTCTGTGACTGGTGAGTACTCAACCAAGTCATTCTGAGAATAGTGT
ATGCGGCGACCGAGTTGCTCTTGCCCGGCGTCAATACGGGATAATACC
GCGCCACATAGCAGAACTTTAAAAGTGCTCATCATTGGAAAACGTTCT
TCGGGGCGAAAACTCTCAAGGATCTTACCGCTGTTGAGATCCAGTTCG
ATGTAACCCACTCGTGCACCCAACTGATCTTCAGCATCTTTTACTTTC
ACCAGCGTTTCTGGGTGAGCAAAAACAGGAAGGCAAAATGCCGCAAAA
AAGGGAATAAGGGCGACACGGAAATGTTGAATACTCATACTCTTCCTT
TTTCAATATTATTGAAGCATTTATCAGGGTTATTGTCTCATGAGCGGA
TACATATTTGAATGTATTTAGAAAAATAAACAAATAGGGGTTCCGCGC
ACATTTCCCCGAAAAGTGCCACCTGACGTCTAAGAAACCATTATTATC
ATGACATTAACCTATAAAAATAGGCGTATCACGAGGCCCTTTCGTCTC
GCGCGTTTCGGTGATGACGGTGAAAACCTCTGACACATGCAGCTCCCG
GAGACGGTCACAGCTTGTCTGTAAGCGGATGCCGGGAGCAGACAAGCC
CGTCAGGGCGCGTCAGCGGGTGTTGGCGGGTGTCGGGGCTGGCTTAAC
TATGCGGCATCAGAGCAGATTGTACTGAGAGTGCACCATATGCGGTGT
GAAATACCGCACAGATGCGTAAGGAGAAAATACCGCATCAGGAAATTG
TAAACGTTAATATTTTGTTAAAATTCGCGTTAAATTTTTGTTAAATCA
GCTCATTTTTTAACCAATAGGCCGAAATCGGCAAAATCCCTTATAAAT
CAAAAGAATAGACCGAGATAGGGTTGAGTGTTGTTCCAGTTTGGAACA
AGAGTCCACTATTAAAGAACGTGGACTCCAACGTCAAAGGGCGAAAAA
CCGTCTATCAGGGCGATGGCCCACTACGTGAACCATCACCCTAATCAA
GTTTTTTGGGGTCGAGGTGCCGTAAAGCACTAAATCGGAACCCTAAAG

GGAGCCCCCGATTTAGAGCTTGACGGGGAAAGCCGGCGAACGTGGCGA
GAAAGGAAGGGAAGAAAGCGAAAGGAGCGGGCGCTAGGGCGCTGGCAA
GTGTAGCGGTCACGCTGCGCGTAACCACCACACCCGCCGCGCTTAATG
CGCCGCTACAGGGCGCGTCGCGCCATTCGCCATTCAGGCTACGCAACT
GTTGGGAAGGGCGATCGGTGCGGGCCTCTTCGCTATTACGCCAGGCTG
C pTR22-APhead-APSA-otoferlinCT
               (SEQ ID NO: 2)
AGGGGGGGGGGGGGGGGGTTGGCCACTCCCTCTCTGCGCGCTCGCTC
GCTCACTGAGGCCGGGCGACCAAAGGTCGCCCGACGCCCGGGCTTTGC
CCGGGCGGCCTCAGTGAGCGAGCGAGCGCGCAGAGAGGGAGTGGCCAA
CTCCATCACTAGGGGTTCCTCAGATCTGGCGCGCCCAATTGGCTTCGA
ATTCTAGCGGCCGCCCCCGGGTGCGCGGCGTCGGTGGTGCCGGCGGGG
GGCGCCAGGTCGCAGGCGGTGTAGGGCTCCAGGCAGGCGGCGAAGGCC
ATGACGTGCGCTATGAAGGTCTGCTCCTGCACGCCGTGAACCAGGTGC
GCCTGCGGGCCGCGCGCGAACACCGCCACGTCCTCGCCTGCGTGGGTC
TCTTCGTCCAGGGGCACTGCTGACTGCTGCCGATACTCGGGGCTCCCG
CTCTCGCTCTCGGTAACATCCGGCCGGGCGCCGTCCTTGAGCACATAG
CCTGGACCGTTTCCTTAAGCGACGCATGCTCGCGATAGGCACCTATTG
GTCTTACTGACATCCACTTTGCCTTTCTCTCCACAGGAGAGCATGGGA
CAGCAGGCCAAGAGCCTGAGGGCTCAGGTGAAGCGGCACACTGTTCGG
GACAAGCTGAGGTCATGCCAGAACTTTCTGCAGAAGCTACGCTTCCTG
GCGGATGAGCCCCAGCACAGCATTCCTGATGTGTTCATTTGGATGATG
AGCAACAACAAACGTATCGCCTATGCCCGCGTGCCTTCCAAAGACCTG
CTCTTCTCCATCGTGGAGGAGGAACTGGGCAAGGACTGCGCCAAAGTC
AAGACCCTCTTCCTGAAGCTGCCAGGGAAGAGGGGCTTCGGCTCGGCA
GGCTGGACAGTACAGGCCAAGCTGGAGCTCTACCTGTGGCTGGGCCTC
AGCAAGCAGCGAAAGGACTTCCTGTGTGGTCTGCCCTGTGGCTTCGAG
GAGGTCAAGGCAGCCCAAGGCCTGGGCCTGCATTCCTTTCCGCCCATC
AGCCTAGTCTACACCAAGAAGCAAGCCTTCCAGCTCCGAGCACACATG
TATCAGGCCCGAAGCCTCTTTGCTGCTGACAGCAGTGGGCTCTCTGAT
CCCTTTGCCCGTGTCTTCTTCATCAACCAGAGCCAATGCACTGAGGTT
CTAAACGAGACACTGTGTCCCACCTGGGACCAGATGCTGGTATTTGAC
AACCTGGAGCTGTACGGTGAAGCTCACGAGTTACGAGATGATCCCCCC
ATCATTGTCATTGAAATCTACGACCAGGACAGCATGGGCAAAGCCGAC
TTCATGGGCCGGACCTTCGCCAAGCCCCTGGTGAAGATGGCAGATGAA
GCATACTGCCCACCTCGCTTCCCGCCGCAGCTTGAGTACTACCAGATC
TACCGAGGCAGTGCCACTGCCGGAGACCTACTGGCTGCCTTCGAGCTG
CTGCAGATTGGGCCATCAGGGAAGGCTGACCTGCCACCCATCAATGGC
CCAGTGGACATGGACAGAGGGCCCATCATGCCTGTGCCCGTGGGAATC
CGGCCAGTGCTCAGCAAGTACCGAGTGGAGGTGCTGTTCTGGGGCCTG -continued

```
AGGGACCTAAAGAGGGTGAACCTGGCCCAGGTGGACCGACCACGGGTG

GACATCGAGTGTGCAGGAAAGGGGGTACAATCCTCCCTGATTCACAAT

TATAAGAAGAACCCCAACTTCAACACGCTGGTCAAGTGGTTTGAAGTG

GACCTCCCGGAGAATGAGCTCCTGCACCCACCCTTGAACATCCGAGTG

GTAGATTGCCGGGCCTTTGGACGATACACCCTGGTGGGTTCCCACGCA

GTCAGCTCACTGAGGCGCTTCATCTACCGACCTCCAGACCGCTCAGCC

CCCAACTGGAACACCACAGGGGAGGTTGTAGTAAGCATGGAGCCTGAG

GAGCCAGTTAAGAAGCTGGAGACCATGGTGAAACTGGATGCGACTTCT

GATGCTGTGGTCAAGGTGGATGTGGCTGAAGATGAGAAGGAAAGGAAG

AAGAAGAAAAGAAAGGCCCGTCAGAGGAGCCAGAGGAGGAAGAGCCC

GATGAGAGCATGCTGGATTGGTGGTCCAAGTACTTCGCCTCCATCGAC

ACAATGAAGGAGCAACTTCGACAACATGAGACCTCTGGAACTGACTTG

GAAGAGAAGGAAGAGATGGAAAGCGCTGAGGGCCTGAAGGGACCAATG

AAGAGCAAGGAGAAGTCCAGAGCTGCAAAGGAGGAGAAAAAGAAGAAA

AACCAGAGCCCTGGCCCTGGCCAGGGATCGGAGGCTCCTGAGAAGAAG

AAAGCCAAGATCGATGAGCTTAAGGTGTACCCCAAGGAGCTGGAATCG

GAGTTTGACAGCTTTGAGGACTGGCTGCACACCTTCAACCTGTTGAGG

GGCAAGACGGGAGATGATGAGGATGGCTCCACAGAGGAGGAGCGCATA

GTAGGCCGATTCAAGGGCTCCCTCTGTGTGTACAAAGTGCCACTCCCA

GAAGATGTATCTCGAGAAGCTGGCTATGATCCCACCTATGGAATGTTC

CAGGGCATCCCAAGCAATGACCCCATCAATGTGCTGGTCCGAATCTAT

GTGGTCCGGGCCACAGACCTGCACCCGGCCGACATCAATGGCAAAGCT

GACCCCTATATTGCCATCAAGTTAGGCAAGACCGACATCCGAGACAAG

GAGAACTACATCTCCAAGCAGCTCAACCCTGTGTTTGGGAAGTCCTTT

GACATTGAGGCCTCCTTCCCCATGGAGTCCATGTTGACAGTGGCCGTG

TACGACTGGGATCTGGTGGGCACTGATGACCTCATCGGAGAAACCAAG

ATTGACCTGGAAAACCGCTTCTACAGCAAGCATCGCGCCACCTGCGGC

ATCGCACAGACCTATTCCATACATGGCTACAATATCTGGAGGGACCCC

ATGAAGCCCAGCCAGATCCTGACACGCCTCTGTAAAGAGGGCAAAGTG

GACGGCCCCCACTTTGGTCCCCATGGGAGAGTGAGGGTTGCCAACCGT

GTCTTCACGGGGCCTTCAGAAATAGAGGATGAGAATGGTCAGAGGAAG

CCCACAGATGAGCACGTGGCACTGTCTGCTCTGAGACACTGGGAGGAC

ATCCCCCGGGTGGGCTGCCGCCTTGTGCCGGAACACGTGGAGACCAGG

CCGCTGCTCAACCCTGACAAGCCAGGCATTGAGCAGGGCCGCCTGGAG

CTGTGGGTGGACATGTTCCCCATGGACATGCCAGCCCCTGGGACACCT

CTGGATATATCCCCCAGGAAACCCAAGAAGTACGAGCTGCGGGTCATC

GTGTGGAACACAGACGAGGTGGTCCTGGAAGACGATGATTTCTTCACG

GGAGAGAAGTCCAGTGACATTTTTGTGAGGGGTGGCTGAAGGGCCAG

CAGGAGGACAAACAGGACACAGATGTCCACTATCACTCCCTCACGGGG

GAGGGCAACTTCAACTGGAGATACCTCTTCCCCTTCGACTACCTAGCG

GCCGAAGAGAAGATCGTTATGTCCAAAAAGGAGTCTATGTTCTCCTGG
```

-continued

```
GATGAGACGGAGTACAAGATCCCTGCGCGGCTCACCCTGCAGATCTGG

GACGCTGACCACTTCTCGGCTGACGACTTCCTGGGGGCTATCGAGCTG

GACCTGAACCGGTTCCCGAGGGGCGCTAAGACAGCCAAGCAGTGCACC

ATGGAGATGGCCACCGGGGAGGTGGACGTACCCCTGGTTTCCATCTTT

AAACAGAAACGTGTCAAAGGCTGGTGGCCCCTCCTGGCCCGCAATGAG

AATGATGAGTTTGAGCTCACAGGCAAAGTGGAGGCGGAGCTACACCTA

CTCACGGCAGAGGAGGCAGAGAAGAACCCTGTGGGCCTGGCTCGCAAT

GAACCTGATCCCCTAGAAAAACCCAACCGGCCTGACACGGCATTCGTC

TGGTTCCTGAACCCACTCAAATCTATCAAGTACCTCATCTGCACCCGG

TACAAGTGGCTGATCATCAAGATCGTGCTGGCGCTGCTGGGGCTGCTC

ATGCTGGCCCTCTTCCTTTACAGCCTCCCAGGCTACATGGTCAAGAAG

CTCCTAGGGGCCTGAGCGGCCGCGGTACCAAGGGCGAATTCTGCAGTC

GACTAGAGCTCGCTGATCAGCCTCGACTGTGCCTTCTAGTTGCCAGCC

ATCTGTTGTTTGCCCCTCCCCCGTGCCTTCCTTGACCCTGGAAGGTGC

CACTCCCACTGTCCTTTCCTAATAAAATGAGGAAATTGCATCGCATTG

TCTGAGTAGGTGTCATTCTATTCTGGGGGGTGGGGTGGGCAGGACAG

CAAGGGGGAGGATTGGGAAGACAATAGCAGGCATGCTGGGGAGAGATC

TGAGGACTAGTCCGTCGACTGTTAATTAAGCATGCTGGGGAGAGATCT

AGGAACCCCTAGTGATGGAGTTGGCCACTCCCTCTCTGCGCGCTCGCT

CGCTCACTGAGGCCGCCCGGGCAAAGCCCGGGCGTCGGGCGACCTTTG

GTCGCCCGGCCTCAGTGAGCGAGCGAGCGCGCAGAGAGGGAGTGGCCA

ACCCCCCCCCCCCCCCCCTGCAGCCCTGCATTAATGAATCGGCCAAC

GCGCGGGGAGAGGCGGTTTGCGTATTGGGCGCTCTTCCGCTTCCTCGC

TCACTGACTCGCTGCGCTCGGTCGTTCGGCTGCGGCGAGCGGTATCAG

CTCACTCAAAGGCGGTAATACGGTTATCCACAGAATCAGGGGATAACG

CAGGAAAGAACATGTGAGCAAAAGGCCAGCAAAAGGCCAGGAACCGTA

AAAAGGCCGCGTTGCTGGCGTTTTTCCATAGGCTCCGCCCCCCTGACG

AGCATCACAAAAATCGACGCTCAAGTCAGAGGTGGCGAAACCCGACAG

GACTATAAAGATACCAGGCGTTTCCCCCTGGAAGCTCCCTCGTGCGCT

CTCCTGTTCCGACCCTGCCGCTTACCGGATACCTGTCCGCCTTTCTCC

CTTCGGGAAGCGTGGCGCTTTCTCAATGCTCACGCTGTAGGTATCTCA

GTTCGGTGTAGGTCGTTCGCTCCAAGCTGGGCTGTGTGCACGAACCCC

CCGTTCAGCCCGACCGCTGCGCCTTATCCGGTAACTATCGTCTTGAGT

CCAACCCGGTAAGACACGACTTATCGCCACTGGCAGCAGCCACTGGTA

ACAGGATTAGCAGAGCGAGGTATGTAGGCGGTGCTACAGAGTTCTTGA

AGTGGTGGCCTAACTACGGCTACACTAGAAGGACAGTATTTGGTATCT

GCGCTCTGCTGAAGCCAGTTACCTTCGGAAAAAGAGTTGGTAGCTCTT

GATCCGGCAAACAAACCACCGCTGGTAGCGGTGGTTTTTTTGTTTGCA

AGCAGCAGATTACGCGCAGAAAAAAAGGATCTCAAGAAGATCCTTTGA

TCTTTTCTACGGGGTCTGACGCTCAGTGGAACGAAAACTCACGTTAAG
```

-continued
```
GGATTTTGGTCATGAGATTATCAAAAAGGATCTTCACCTAGATCCTTT

TAAATTAAAAATGAAGTTTTAAATCAATCTAAAGTATATATGAGTAAA

CTTGGTCTGACAGTTACCAATGCTTAATCAGTGAGGCACCTATCTCAG

CGATCTGTCTATTTCGTTCATCCATAGTTGCCTGACTCCCCGTCGTGT

AGATAACTACGATACGGGAGGGCTTACCATCTGGCCCCAGTGCTGCAA

TGATACCGCGAGACCCACGCTCACCGGCTCCAGATTTATCAGCAATAA

ACCAGCCAGCCGGAAGGGCCGAGCGCAGAAGTGGTCCTGCAACTTTAT

CCGCCTCCATCCAGTCTATTAATTGTTGCCGGGAAGCTAGAGTAAGTA

GTTCGCCAGTTAATAGTTTGCGCAACGTTGTTGCCATTGCTACAGGCA

TCGTGGTGTCACGCTCGTCGTTTGGTATGGCTTCATTCAGCTCCGGTT

CCCAACGATCAAGGCGAGTTACATGATCCCCCATGTTGTGCAAAAAAG

CGGTTAGCTCCTTCGGTCCTCCGATCGTTGTCAGAAGTAAGTTGGCCG

CAGTGTTATCACTCATGGTTATGGCAGCACTGCATAATTCTCTTACTG

TCATGCCATCCGTAAGATGCTTTTCTGTGACTGGTGAGTACTCAACCA

AGTCATTCTGAGAATAGTGTATGCGGCGACCGAGTTGCTCTTGCCCGG

CGTCAATACGGGATAATACCGCGCCACATAGCAGAACTTTAAAAGTGC

TCATCATTGGAAAACGTTCTTCGGGGCGAAAACTCTCAAGGATCTTAC

CGCTGTTGAGATCCAGTTCGATGTAACCCACTCGTGCACCCAACTGAT

CTTCAGCATCTTTTACTTTCACCAGCGTTTCTGGGTGAGCAAAAACAG

GAAGGCAAAATGCCGCAAAAAAGGGAATAAGGGCGACACGGAAATGTT

GAATACTCATACTCTTCCTTTTTCAATATTATTGAAGCATTTATCAGG

GTTATTGTCTCATGAGCGGATACATATTTGAATGTATTTAGAAAAATA

AACAAATAGGGGTTCCGCGCACATTTCCCCGAAAAGTGCCACCTGACG

TCTAAGAAACCATTATTATCATGACATTAACCTATAAAAATAGGCGTA

TCACGAGGCCCTTTCGTCTCGCGCGTTTCGGTGATGACGGTGAAAACC

TCTGACACATGCAGCTCCCGGAGACGGTCACAGCTTGTCTGTAAGCGG

ATGCCGGGAGCAGACAAGCCCGTCAGGGCGCGTCAGCGGGTGTTGGCG

GGTGTCGGGGCTGGCTTAACTATGCGGCATCAGAGCAGATTGTACTGA

GAGTGCACCATATGCGGTGTGAAATACCGCACAGATGCGTAAGGAGAA

AATACCGCATCAGGAAATTGTAAACGTTAATATTTTGTTAAAATTCGC

GTTAAATTTTGTTAAATCAGCTCATTTTTTAACCAATAGGCCGAAAT

CGGCAAAATCCCTTATAAATCAAAAGAATAGACCGAGATAGGGTTGAG

TGTTGTTCCAGTTTGGAACAAGAGTCCACTATTAAAGAACGTGGACTC

CAACGTCAAAGGGCGAAAAACCGTCTATCAGGGCGATGGCCCACTACG

TGAACCATCACCCTAATCAAGTTTTTTGGGGTCGAGGTGCCGTAAAGC

ACTAAATCGGAACCCTAAAGGGAGCCCCCGATTTAGAGCTTGACGGGG

AAAGCCGGCGAACGTGGCGAGAAAGGAAGGGAAGAAAGCGAAAGGAGC

GGGCGCTAGGGCGCTGGCAAGTGTAGCGGTCACGCTGCGCGTAACCAC

CACACCCGCCGCGCTTAATGCGCCGCTACAGGGCGCGTCGCGCCATTC

GCCATTCAGGCTACGCAACTGTTGGGAAGGGCGATCGGTGCGGGCCTC

TTCGCTATTACGCCAGGCTGC
```

Transfection of HEK 293 Cells

HEK 293 cells were grown on poly-lysine-coated coverslips in growth medium. 1 μl of each virus was used for each well as follows: Control cells without virus, cells with AAV2-OTOF n-terminal portion (AAV2-OTOF-NT), cells with AAV2-OTOF c-terminal portion (AAV2-OTOF-CT) and cells with both viruses (AAV2-OTOF-NT and AAV2-OTOF-CT). The cells were stained with anti-OTOF antibody and mounted on glass slides.

OTOF Knock-Out Mice

The OTOF knock-out mice used were generated in a previous study (see Roux et al. (2006) Otoferlin, defective in a human deafness form, is essential for exocytosis at the auditory ribbon synapse. Cell. 127:277-289). Briefly, two fragments containing the genomic sequences 5' and 3' to exons 14 and 15 of Otof were amplified by PCR. The 5 kb BamHI-XhoI-BssHII and 6 kb BssHII-SfiI-BamHI-NaeI 129/SvPas fragments were inserted into pUC19 (New England BioLabs) previously modified by inserting a BamHI-XhoI-BssHII-SfiI-NaeI-HindIII polylinker. A loxP-hygro-loxP (the gene conferring resistance to hygromycin under control of the phosphoglycerate kinase gene [Pgk-1] promoter) cassette was inserted into the BssHII site. All constructs were sequenced, and the sequences obtained were compared with the 129/SvPas genomic sequence 282 CK35 ES cells resistant to hygromycin were screened for homologous recombination and monoinsertion events by Southern blot analysis. Two clones were injected into C57BL/6N blastocysts to create chimeric animals. Transmission of the mutant Otof allele was detected by PCR in agouti pups. Positive pups in the F1 progeny were crossed with Pgk-1-cre mice in a mixed C57BL/6-129/SvPas background. F2 animals carrying an allele in which the hygromycin selection cassette was deleted (Otoftm1Ugds allele) were selected by PCR, using primers 5'-CACTTGCTTTGTCT CATCTCC-3' (SEQ ID NO: 12) and 5'-GTCACTTCTTCTGGGTATTTC-3' (SEQ ID NO: 13), generating a 507 base pair PCR product. The heterozygous animals were interbred to generate $Otof^{-/-}$, $Otof^{+/-}$, and $Otof^{+/+}$ mice. The knockout mice were generated in C57BL/6-129/SvPas background as described above. Because this background strain is known to have some age-related hearing loss, the mice were back-crossed with FVB mice strain to the $10^{th}$ generation to obtain an FVB homogeneous genetic background with no known age-related hearing loss.

Delivery of AAV to Mice

OTOF knock-out mice (newborn and older than P10) were injected with 1 microliter of viral particles of each of the two AAV constructs using a round window membrane (RWM) injection as previously described (see Akil et al. (2012) Restoration of Hearing in the VGLUT3 Knockout Mouse Using Virally-Mediated Gene Therapy. Neuron. 75(2): 283-293 and Akil et al. (2015) Surgical Method for Virally Mediated Gene Delivery to the Mouse Inner Ear through the Round Window Membrane. J. Vis. Exp. (97), e52187). AAV2-OTOF-NT ($6.32 \times 10^{12}$ vg/ml) and AAV2-OTOE-CT ($4.5 \times 10^{12}$ vg/ml) were delivered through the RWM to P1-3 mice. AAV2-OTOF-NT ($1.43 \times 10^{13}$ vg/ml) and AAV2-OTOF-CT ($3.12 \times 10^{13}$ vg/ml) were delivered through the RWM to P≥12 mice. ABR tests were conducted 7 days after injection. Expression of OTOF protein in the mice was measured using anti-OTOF antibody to label cells in cochlear whole mounts. Reverse-transcriptase (RT)-PCR was used to screen for the presence of OTOF mRNA within the cochlear tissue of the mice. Wild-type mice were also injected using the same technique with AAV2-GFP to assess viral delivery to cochlea with AAV2 serotype. Cochlea were whole mounted and stained with anti-GFP antibody.

Auditory Brainstem Response (ABR) Testing

Hearing tests were performed as previously described (Akil et al. (2006) Progressive deafness and altered cochlear innervation in knockout mice lacking prosaposin. J. Neurosci. 26:13076-13088 and Akil et al. (2016) Mouse Auditory Brainstem Response Testing. Bio Protoc. 6(6)) with the otoferlin knockout (OTOF KO) mice, rescued OTOF KO mice and wild-type (WT) littermates. Briefly, all auditory testing was performed in a sound-proof chamber. Before acoustic testing, mice were anesthetized by intraperitoneal injection of a mixture of ketamine hydrochloride (Ketaset, 100 mg/ml) and xylazine hydrochloride (xyla-ject, 10 mg/ml) and boosted with one-fifth the original dose as required. Body temperature was maintained with a heating pad and monitored with a rectal probe throughout recording.

The evoked acoustic brainstem response (ABR) thresholds were differentially recorded from the scalp of the mice. Responses were recorded using subdermal needle electrodes at the vertex, below the pinna of the left ear (reference), and below the contralateral ear (ground). The sound stimuli used included clicks (5 ms duration, 31 Hz) and tone pips at 8, 16, and 32 kHz (10 ms duration, cos 2 shaping, 21 Hz). Measurements were recorded using the TDT BioSig III system (Tucker Davis Technologies). For each stimulus, electroencephalographic (EEG) activity was recorded for 20 ms (at a sampling rate of 25 kHz) and filtered (0.3-3 kHz). Waveforms from 512 stimuli were averaged for click responses. Waveforms from 1000 stimuli were examined to identify frequency-specific tone-burst stimuli (8, 16, and 32 kHz). ABR waveforms were recorded in 5 dB sound pressure level (SPL) intervals down from the maximum amplitude. The threshold was defined as the lowest stimulus level at which response peaks for waves I-V were clearly and repetitively present upon visual inspection. These threshold judgments were confirmed by analysis of stored waveforms. The comparison of each group of animals was performed using one way ANOVA with Bonferroni's post hoc testing.

Results

Two different AAV plasmid constructs were generated to deliver the 5' half and the 3' half of the mouse OTOF cDNA to the inner ear of OTOF knock-out mice (OTOF N-terminal virus and OTOF C-terminal virus). The two constructs were packaged separately into AAV2 particles. The AAV2 particles were then pooled together and used to treat HEK 293 cells or were injected into the inner ear of OTOF knock-out mice.

Figure 4:
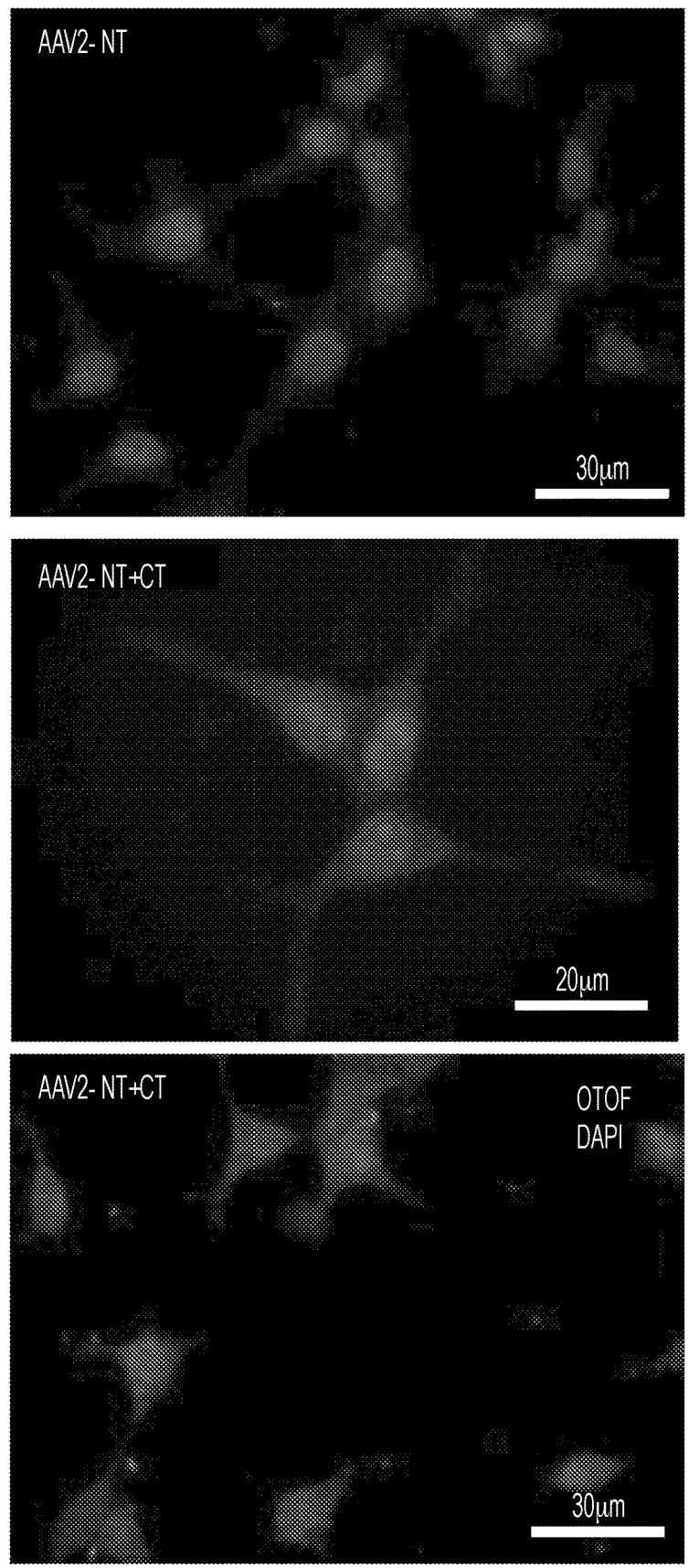
FIG. 4 is a series of photographs showing expression of OTOF protein in HEK 293 cells treated with AAV2-OTOF-NT (AAV-NT) or AAV2-OTOF-NT and AAV2-OTOF-CT (AAV2-NT+CT).

It was shown that HEK 293 cells only expressed Otoferlin protein when transfected with both viruses (FIG. 4). No expression of Otoferlin protein was observed in untreated cells, or in cells transfected with only the OTOF N-terminal (FIG. 4) or OTOF C-terminal virus.

Figure 5:
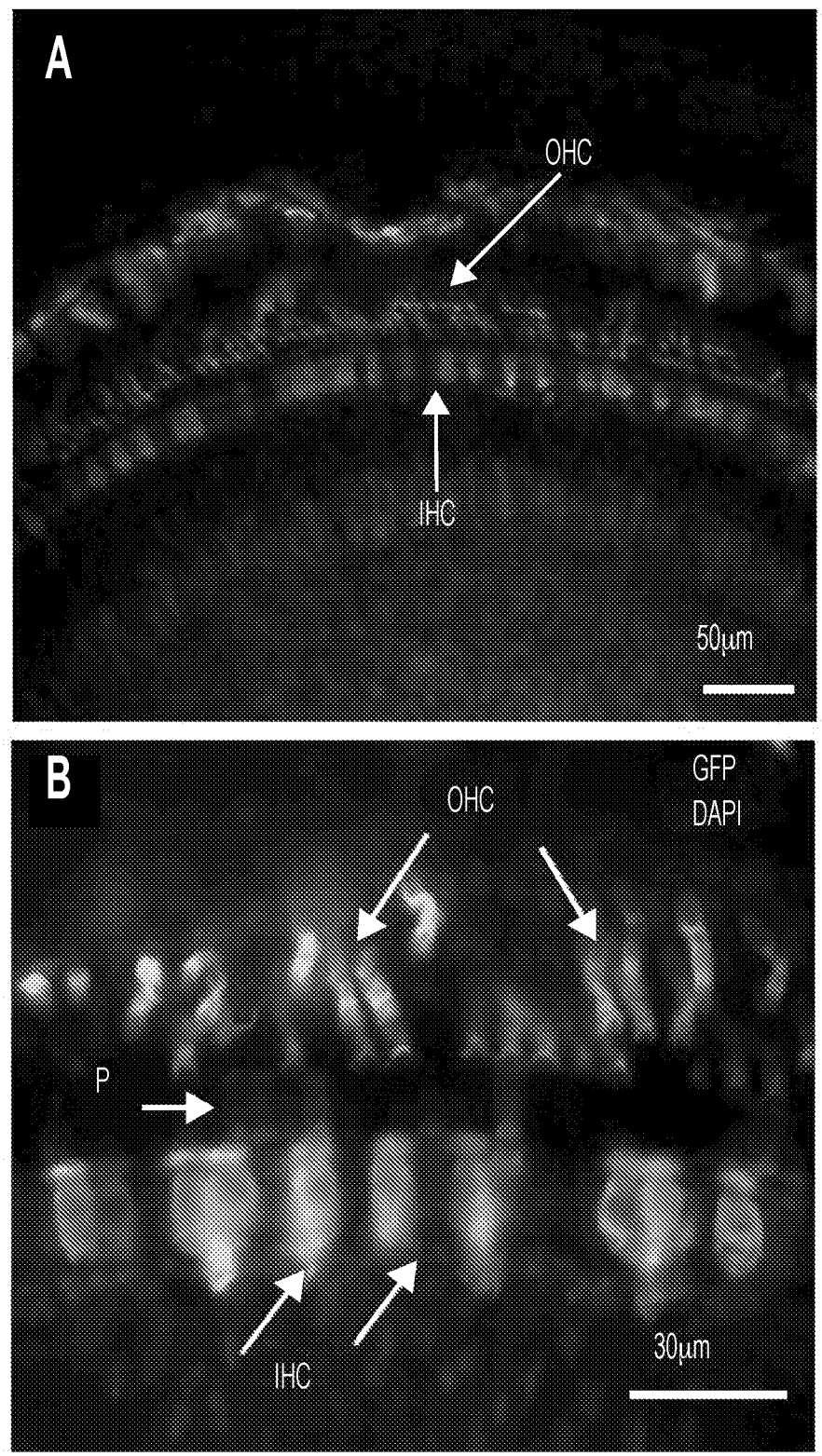
FIG. 5 is a series of photographs showing expression of GFP in the cochlea organ of Corti surface preparations from wild-type mice treated with AAV2-GFP.
Figure 6A:
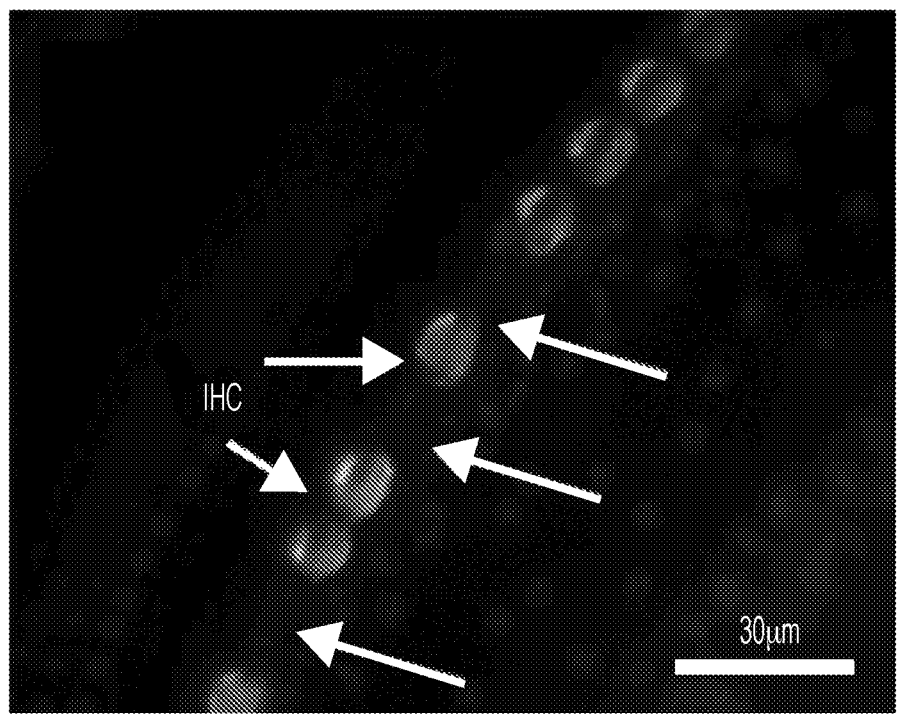
FIGS. 6A-D are a series of photographs and a graph showing OTOF expression in the cochlea of P1-P3 mice.
Figure 6B:
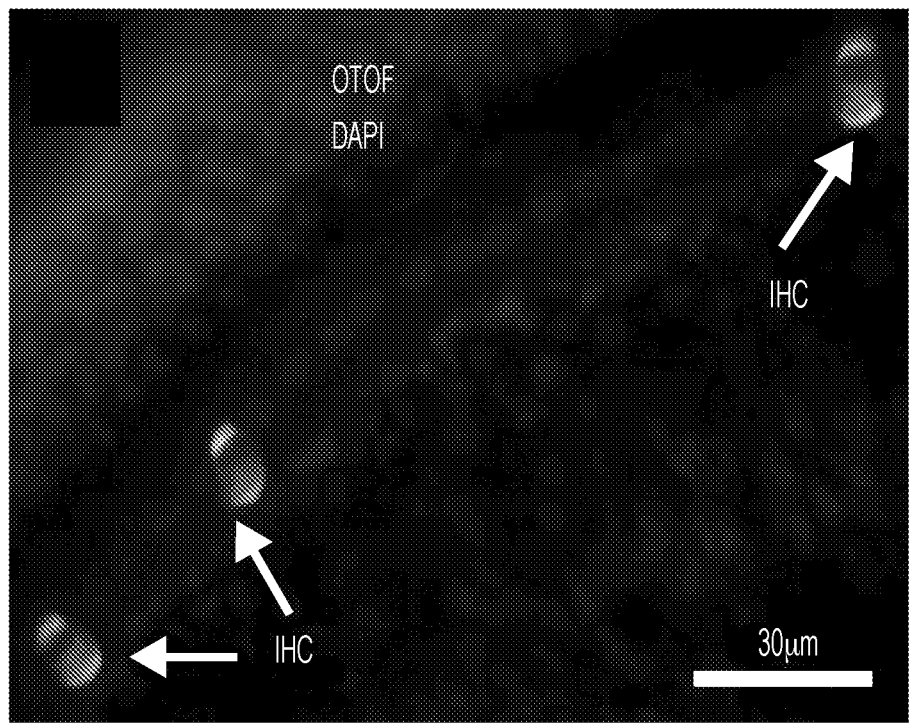
Figure 6C:
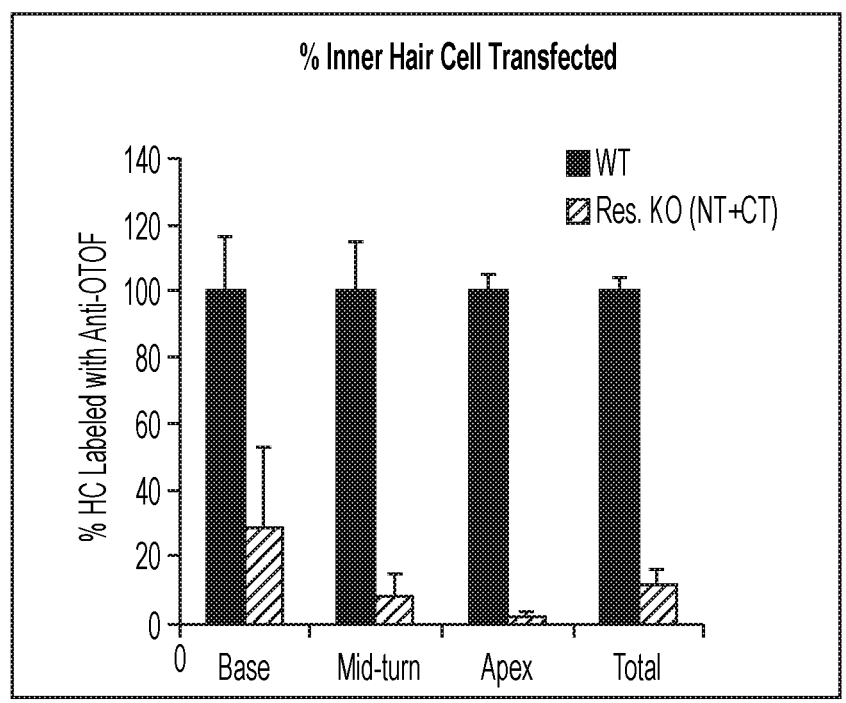
Figure 6D:
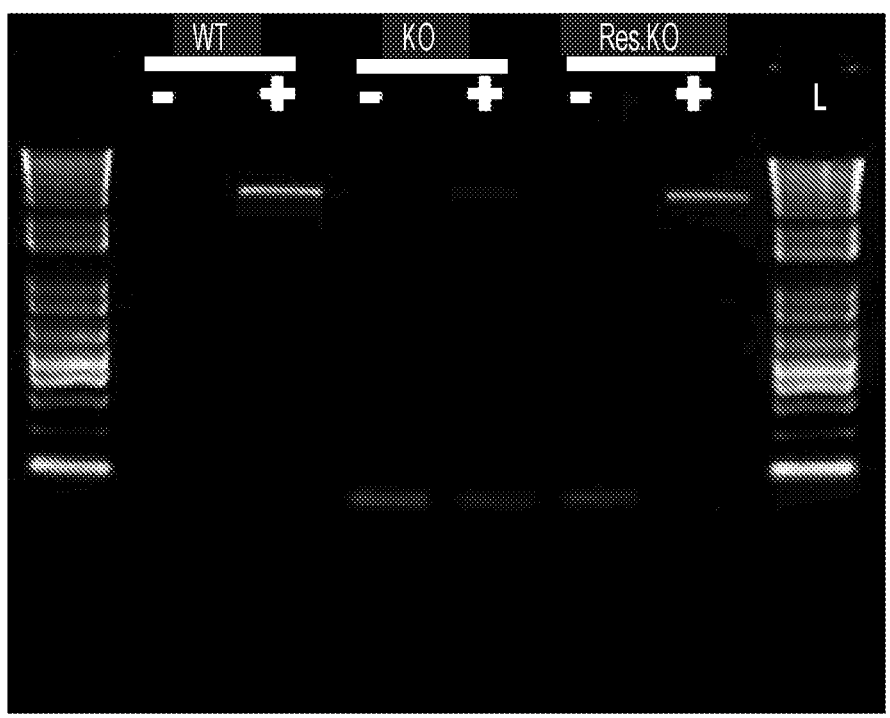
Figure 7A:
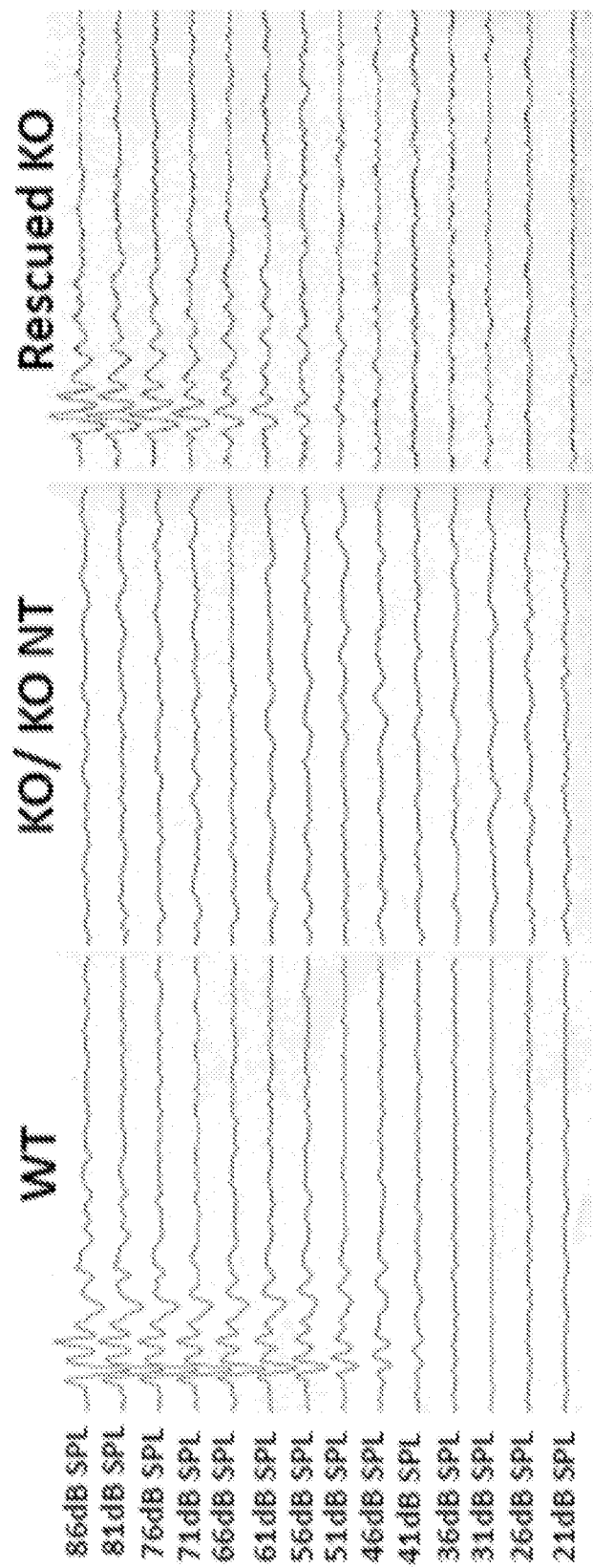
FIGS. 7A-D show a hearing assessment in mice.
Figure 7B:
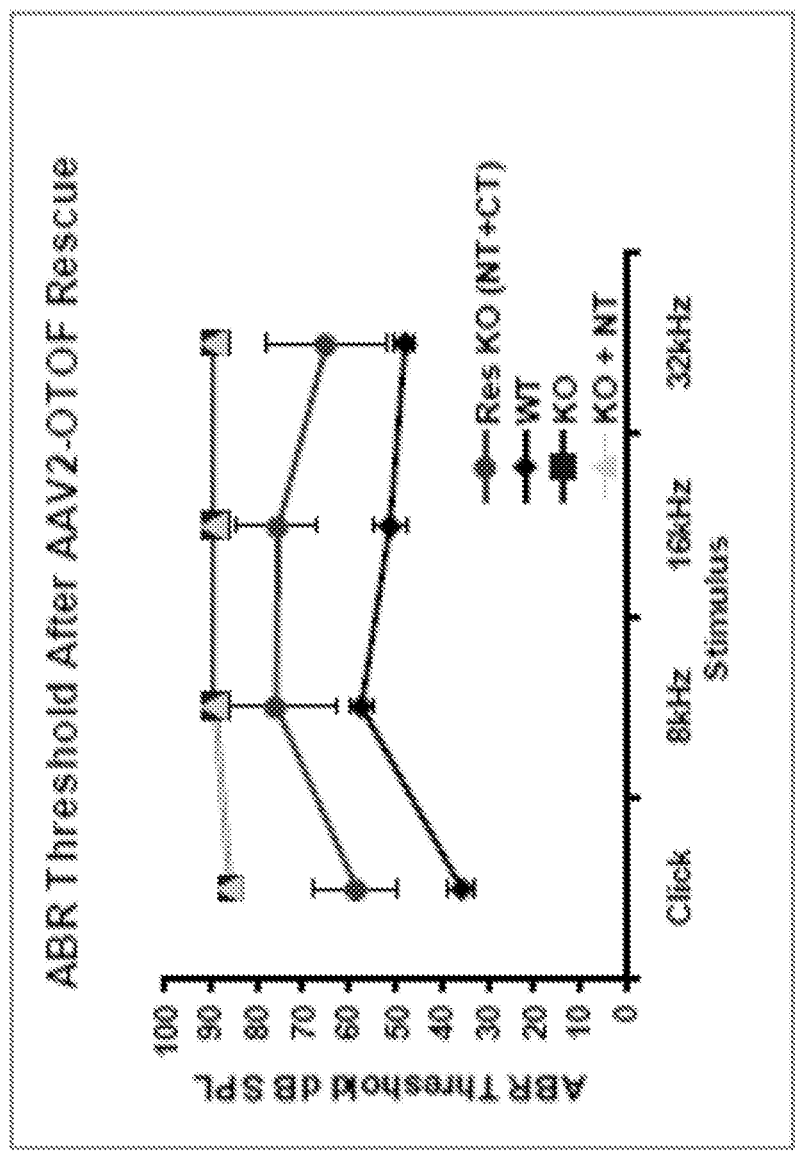
Figure 7C:
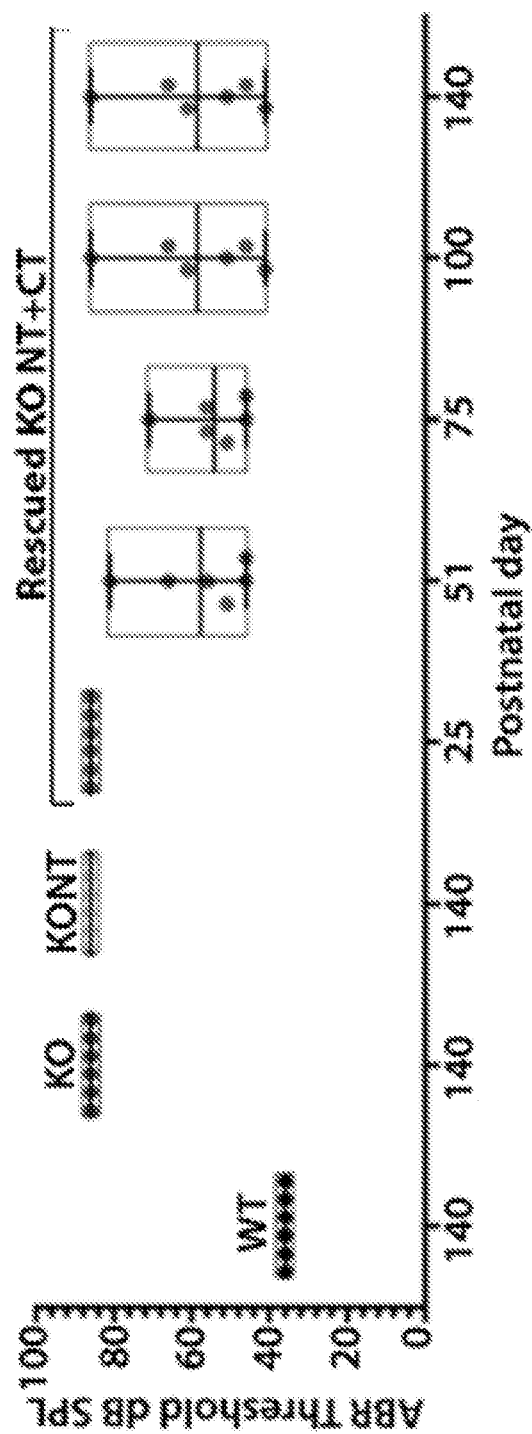
Figure 7D:
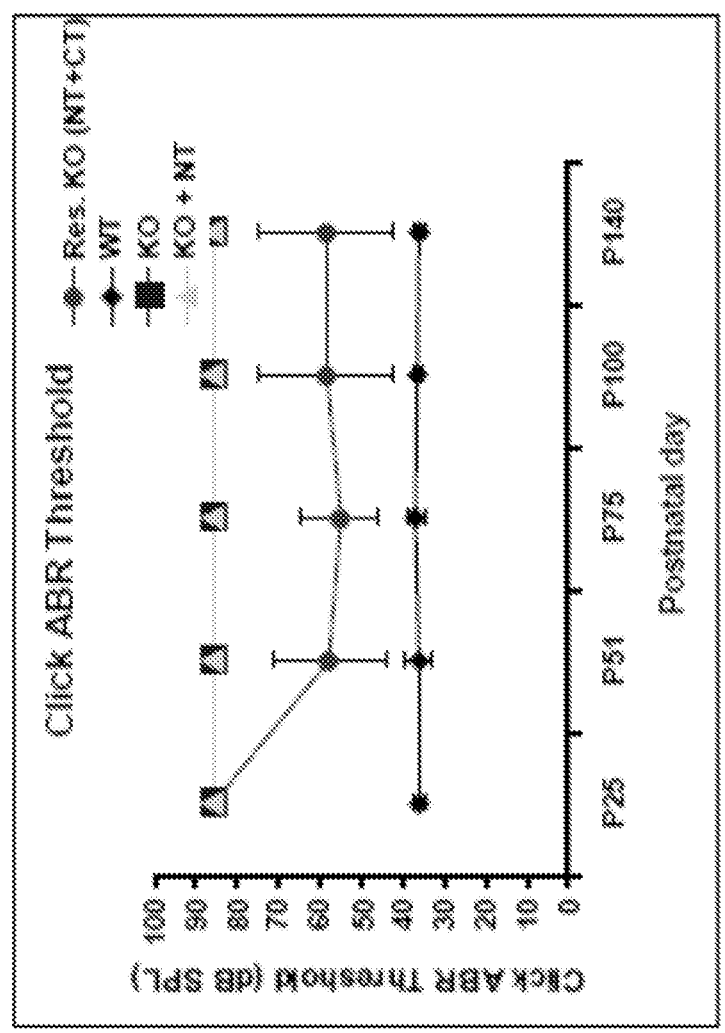

Next, the ability of AAV2 to transduce the mouse cochlea was assess using an AAV2-GFP reporter virus. It was shown that AAV2 transfects a number of cell types including inner hair cells (IHC), outer hair cells (OHC), pillar cells (P) and other supporting cells (SC) in the organ of Corti (FIG. 5). Thus, AAV2 can transduce mouse cochlea effectively.

Mice were then treated with the pooled OTOF N-terminal and C-terminal viruses and compared to various controls. Otoferlin protein was found to be expressed upon treatment with both viruses (FIG. 6). The largest number of transfected inner hair cells (IHCs) were observed in the base and fewer in the mid-turn and apex (FIG. 6). IHCs counts demonstrated that ~11% of IHCs were labeled overall, with significant differences seen between the base (~29%), mid-turn (~8%), and apex (~2%). (FIG. 6). RT-PCR was used to show that OTOF mRNA was in whole cochlear extract and was the same size in both wild-type and OTOF knock-out mice treated with both viruses (FIG. 6). In contrast, the untreated OTOF knock-out mouse cochleae did not demonstrate OTOF mRNA expression. No products were detected when RT-PCR was performed in the absence of reverse transcriptase.

Next, hearing tests were performed to determine whether the Otoferlin expressed by the delivery of both the N- and C-terminal viruses was capable of rescuing hearing function. ABR waveforms from the wild-type and the OTOF knock-out mice treated with both viruses were similar, documenting hearing recovery in the rescued KO mice whereas untreated OTOF knock-out mice controls and the OTOF knock-out mice transfected with just OTOF N-terminal virus show no hearing recovery (FIG. 7). At P70, partial hearing recovery (improved ABR thresholds) was seen to clicks and at specific frequencies 8, 16 and 32 kHz in the OTOF knock-out mice treated with both viruses, while at 8 and 16 kHz the ABR thresholds appear to be slightly elevated, though still significantly better than untreated OTOF knock-out mice (FIG. 7). Remarkably, hearing was maintained in the OTOF knock-out mice treated with both viruses (KO NT+CT) for more than 4 months (FIG. 7), although ABR thresholds were somewhat variable. Non-transfected KO controls and the KO transfected with OTOF NT remained deaf (FIG. 7).

Figure 8A:
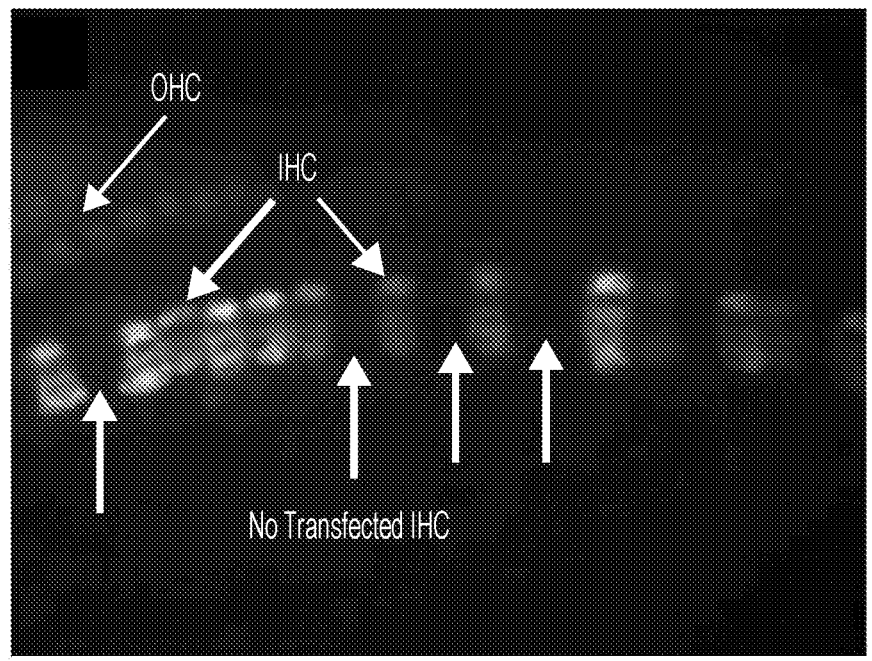
FIGS. 8A and B show Otoferlin protein expression in the OTOF rescued KO mice inner hair cells.
Figure 8B:
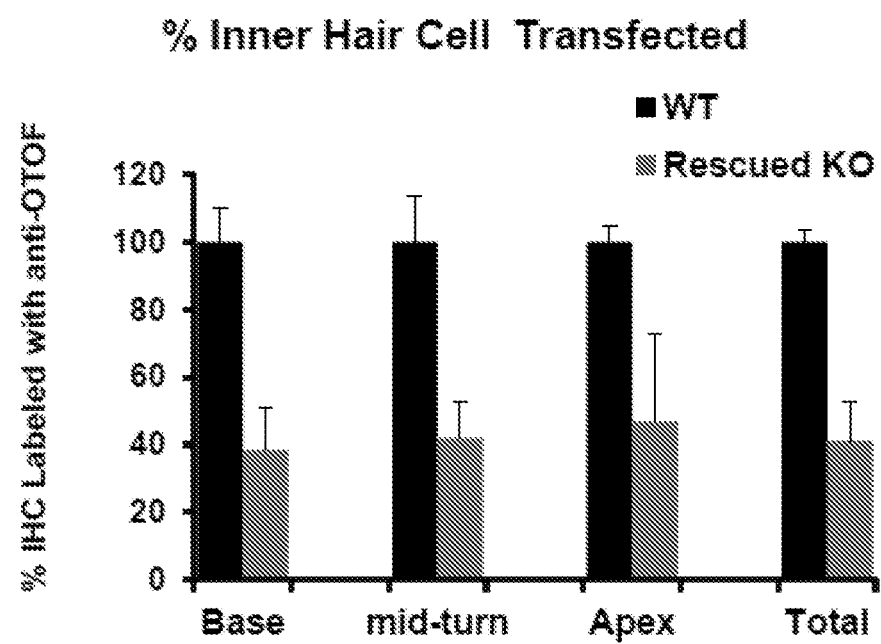
FIG. 8B shows the percent of inner hair cells expressing OTOF in wild-type mice (WT, n=5) and OTOF knock-out mice treated with AAV2-OTOF-NT and AAV2-OTOF-CT (Rescued KO, n=5). The left bar in each pair of bars is WT and the right bar in each pair of bars is Rescued KO.

Next, OTOF knock-out mice older than P12 treated with both viruses. The dually transfected IHCs expressed OTOF, with homogenous transfection rates seen in the base (not shown) and the apex (FIG. 8). IHCs counts demonstrated that ~41% of IHCs were labeled overall, with slight differences seen between the base (~38%), mid-turn (~42%), and apex (~47%) (FIG. 8).

Figure 9A:
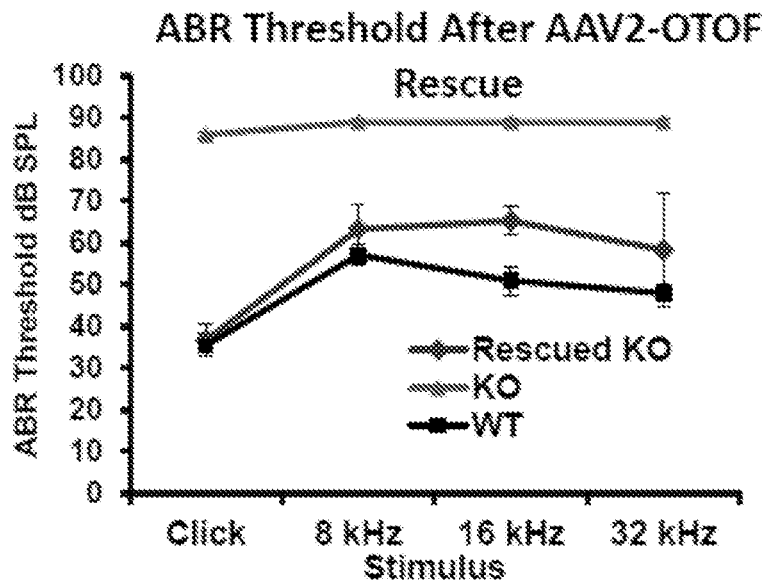
FIGS. 9A and 9B are a series of graphs showing hearing assessment.
Figure 9B:
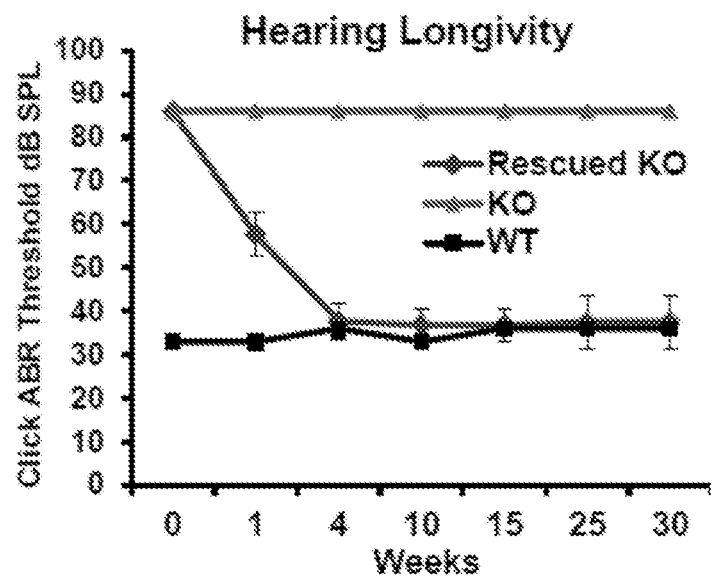
Figure 10:
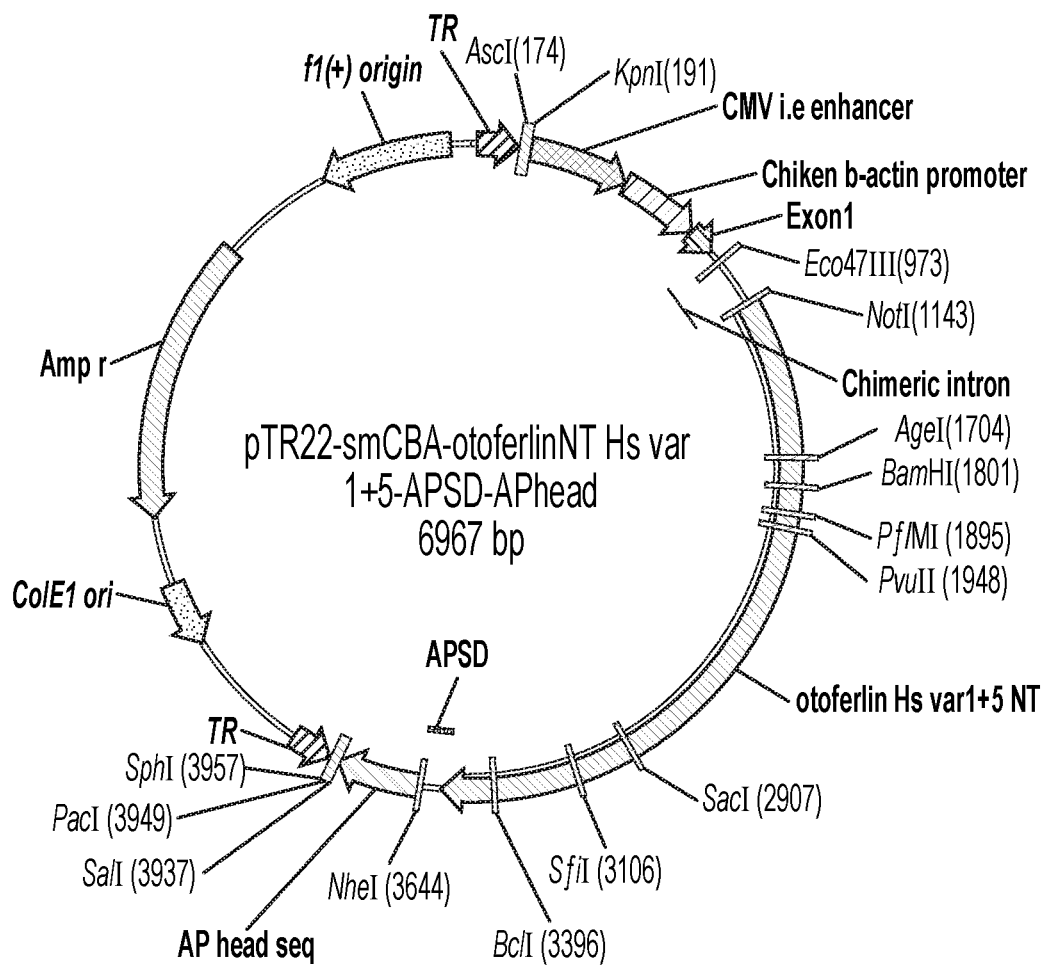
FIG. 10 is a map of a plasmid containing AAV2 inverted terminal repeats (TR) flanking a CMV enhancer, a chicken beta-actin promoter, a 5' section of a human Otoferlin cDNA (Otoferlin NT), a splice donor sequence (APSD), and a homologous sequence for recombination (APhead).
Figure 11:
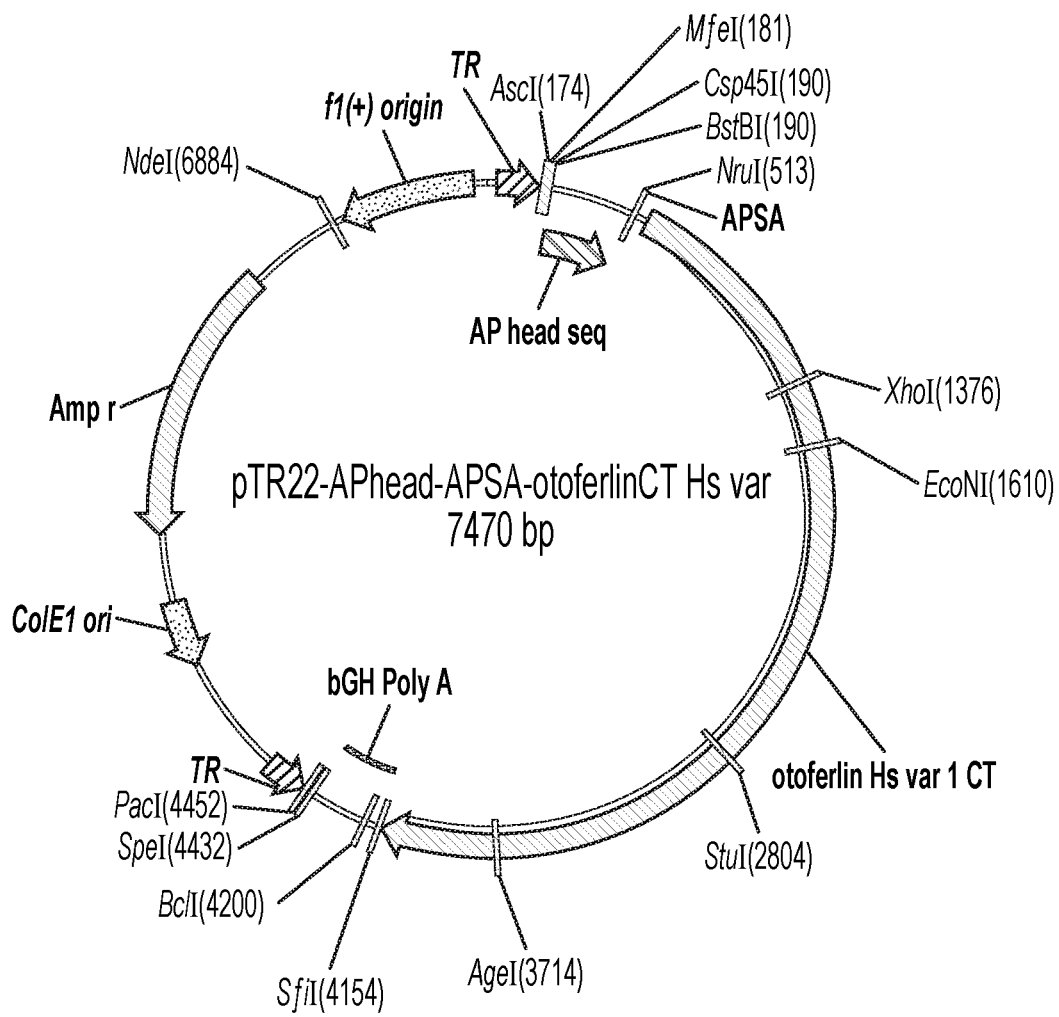
FIG. 11 is a map of a plasmid containing AAV2 inverted terminal repeats (TR) flanking a homologous sequence for recombination (APhead), a splice acceptor sequence (APSA), a 3' section of a human Otoferlin cDNA (Otoferlin CT) encoding isoform 1 of Otoferlin, a bovine growth hormone polyadenylation signal (bGH PolyA).
Figure 12:
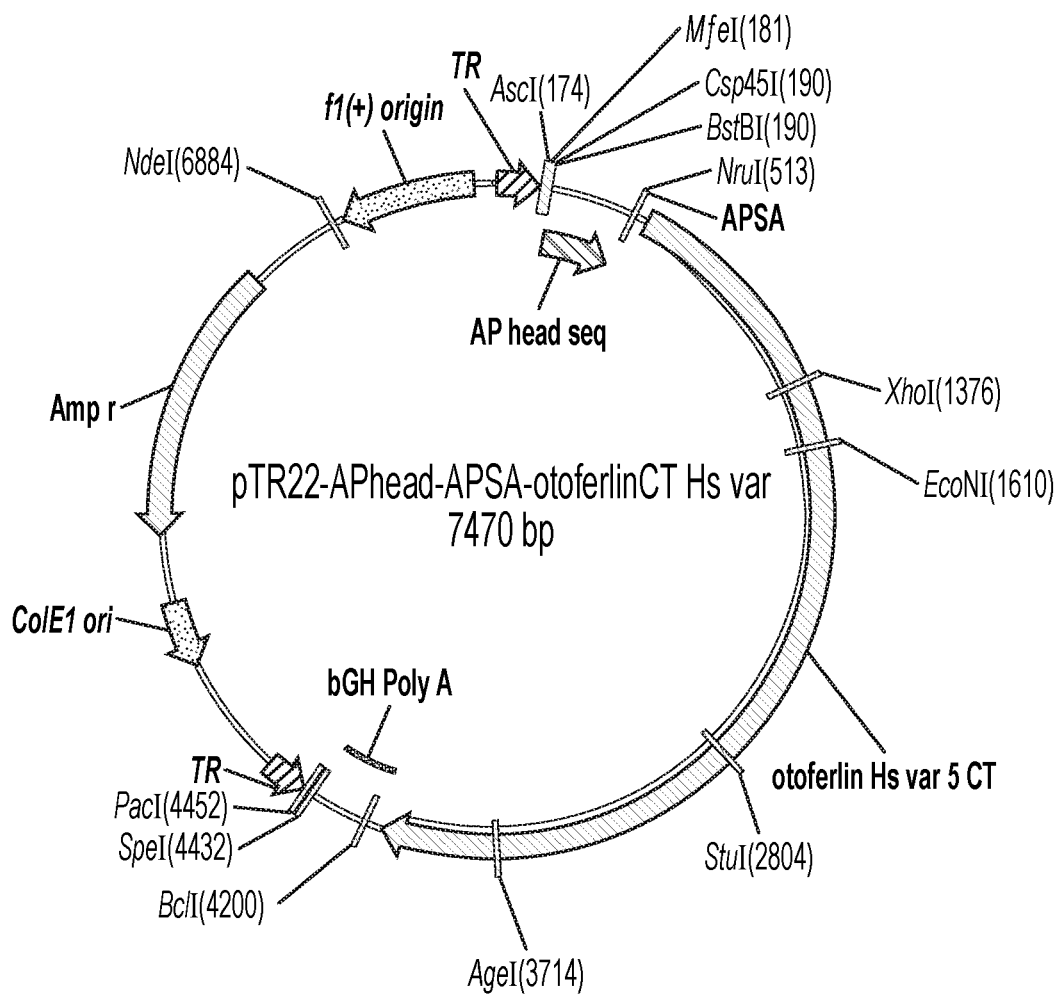
FIG. 12 is a map of a plasmid containing AAV2 inverted terminal repeats (TR) flanking a homologous sequence for recombination (APhead), a splice acceptor sequence (APSA), a 3' section of the mouse Otoferlin cDNA (Otoferlin CT) encoding isoform 5 of Otoferlin, a bovine growth hormone polyadenylation signal (bGH PolyA).

At P60 all OTOF knock-out mice treated with both viruses demonstrated normal ABR threshold to clicks stimulus while at specific frequencies 8, 16 and 32 kHz the ABR thresholds appeared to be slightly elevated, though still significantly better than untreated OTOF knock-out mice (FIG. 9). A time course of hearing recovery following injection of both viruses into OTOF knock-out mice at an age older than P12 showed that hearing was maintained in the treated mice for more than 30 weeks, and the ABR thresholds were restored to the WT levels (FIG. 9).

These results demonstrate that a use of more than one AAV construct to deliver different parts of an OTOF cDNA can result in a functional cDNA in vivo. These results also demonstrate that hearing loss can be treated by delivery of OTOF cDNA using an AAV delivery system.

Example 2: Human OTOF Dual Vector Constructs

Provided below are example dual vector sequences for expressing Human Otoferlin protein isoforms 1 and 5. The cDNAs encoding both isoforms 1 and 5 contain the same N-terminal sequence such that the same N-terminal vector can be used for expressing both isoforms. Vector maps and annotated sequences corresponding to the below sequences are shown in FIGS. 10-15.

```
pTR22-smCBA-otoferlinNT Hs var 1 + 5-APSD-APhead
                                        (SEQ ID NO: 14)
AGGGGGGGGGGGGGGGGGGTTGGCCACTCCCTCTCTGCGCGCTCGCTC

GCTCACTGAGGCCGGGCGACCAAAGGTCGCCCGACGCCCGGGCTTTGC
```

-continued

```
CCGGGCGGCCTCAGTGAGCGAGCGAGCGCGCAGAGAGGGAGTGGCCAA
CTCCATCACTAGGGGTTCCTCAGATCTGGCGCGCCCAATTCGGTACCC
TAGTTATTAATAGTAATCAATTACGGGGTCATTAGTTCATAGCCCATA
TATGGAGTTCCGCGTTACATAACTTACGGTAAATGGCCCGCCTGGCTG
ACCGCCCAACGACCCCGCCCATTGACGTCAATAATGACGTATGTTCC
CATAGTAACGCCAATAGGGACTTTCCATTGACGTCAATGGGTGGACTA
TTTACGGTAAACTGCCCACTTGGCAGTACATCAAGTGTATCATATGCC
AAGTACGCCCCCTATTGACGTCAATGACGGTAAATGGCCCGCCTGGCA
TTATGCCCAGTACATGACCTTATGGGACTTTCCTACTTGGCAGTACAT
CTACGTATTAGTCATCGCTATTACCATGGTCGAGGTGAGCCCCACGTT
CTGCTTCACTCTCCCCATCTCCCCCCCCTCCCCACCCCCAATTTTGTA
TTTATTTATTTTTTAATTATTTTGTGCAGCGATGGGGGCGGGGGGGGG
GGGGGGCGCGCGCCAGGCGGGGCGGGGCGGGGCGAGGGCGGGGCGG
GGCGAGGCGGAGAGGTGCGGCGGCAGCCAATCAGAGCGGCGCGCTCCG
AAAGTTTCCTTTTATGGCGAGGCGGCGGCGGCGGCGGCCCTATAAAAA
GCGAAGCGCGCGGCGGGCGGGAGTCGCTGCGACGCTGCCTTCGCCCCG
TGCCCCGCTCCGCCGCCGCCTCGCGCCGCCCGCCCCGGCTCTGACTGA
CCGCGTTACTCCCACAGGTGAGCGGGCGGGACGGCCCTTCTCCTCCGG
GCTGTAATTAGCGCTTGGTTTAATGACGGCTTGTTTCTTTTCTGTGGC
TGCGTGAAAGCCTTGAGGGGCTCCGGGAGCTAGAGCCTCTGCTAACCA
TGTTCATGCCTTCTTCTTTTTCCTACAGCTCCTGGGCAACGTGCTGGT
TATTGTGCTGTCTCATCATTTTGGCAAAGAATTCTAGCGGCCGCCACC
ATGGCCTTGCTCATCCACCTCAAGACAGTCTCGGAGCTGCGGGGCAGG
GGCGACCGGATCGCCAAAGTGACTTTCCGAGGGCAATCCTTCTACTCT
CGGGTCCTGGAGAACTGTGAGGATGTGGCTGACTTTGATGAGACATTT
CGGTGGCCGGTGGCCAGCAGCATCGACAGAAATGAGATGCTGGAGATT
CAGGTTTTCAACTACAGCAAAGTCTTCAGCAACAAGCTCATCGGGACC
TTCCGCATGGTGCTGCAGAAGGTGGTAGAGGAGAGCCATGTGGAGGTG
ACTGACACGCTGATTGATGACAACAATGCTATCATCAAGACCAGCCTG
TGCGTGGAGGTCCGGTATCAGGCCACTGACGGCACAGTGGGCTCCTGG
GACGATGGGACTTCCTGGGAGATGAGTCTCTTCAAGAGGAAGAGAAG
GACAGCCAAGAGACGGATGGACTGCTCCCAGGCTCCCGGCCCAGCTCC
CGGCCCCCAGGAGAAGAGCTTCCGGAGAGCCGGGAGGAGCGTGTTC
TCCGCCATGAAGCTCGGCAAAAACCGGTCTCACAAGGAGGAGCCCCAA
AGACCAGATGAACCGGCGGTGCTGGAGATGGAAGACCTTGACCATCTG
GCCATTCGGCTAGGAGATGGACTGGATCCCGACTCGGTGTCTCTAGCC
TCAGTCACAGCTCTCACCACTAATGTCTCCAACAAGCGATCTAAGCCA
GACATTAAGATGGAGCCAAGTGCTGGGCGGCCCATGGATTACCAGGTC
AGCATCACGGTGATCGAGGCCCGGCAGCTGGTGGGCTTGAACATGGAC
CCTGTGGTGTGCGTGGAGGTGGGTGACGACAAGAAGTACACATCCATG
```

```
AAGGAGTCCACTAACTGCCCCTATTACAACGAGTACTTCGTCTTCGAC
TTCCATGTCTCTCCGGATGTCATGTTTGACAAGATCATCAAGATTTCG
GTGATTCACTCCAAGAACCTGCTGCGCAGTGGCACCCTGGTGGGCTCC
TTCAAAATGGACGTGGGAACCGTGTACTCGCAGCCAGAGCACCAGTTC
CATCACAAGTGGGCCATCCTGTCTGACCCCGATGACATCTCCTCGGGG
CTGAAGGGCTACGTGAAGTGTGACGTTGCCGTGGTGGGCAAAGGGGAC
AACATCAAGACGCCCCACAAGGCCAATGAGACCGACGAAGATGACATT
GAGGGGAACTTGCTGCTCCCCAGGGGGTGCCCCCCGAACGCCAGTGG
GCCCGGTTCTATGTGAAAATTTACCGAGCAGAGGGGCTGCCCCGTATG
AACACAAGCCTCATGGCCAATGTAAAGAAGGCTTTCATCGGTGAAAAC
AAGGACCTCGTGGACCCCTACGTGCAAGTCTTCTTTGCTGGCCAGAAG
GGCAAGACTTCAGTGCAGAAGAGCAGCTATGAGCCCCTGTGGAATGAG
CAGGTCGTCTTTACAGACCTCTTCCCCCCACTCTGCAAACGCATGAAG
GTGCAGATCCGAGACTCGGACAAGGTCAACGACGTGGCCATCGGCACC
CACTTCATTGACCTGCGCAAGATTTCTAATGACGGAGACAAAGGCTTC
CTGCCCACACTGGGCCCAGCCTGGGTGAACATGTACGGCTCCACACGT
AACTACACGCTGCTGGATGAGCATCAGGACCTGAACGAGGGCCTGGGG
GAGGGTGTGTCCTTCCGGGCCCGGCTCCTGCTGGGCCTGGCTGTGGAG
ATCGTAGACACCTCCAACCCTGAGCTCACCAGCTCCACAGAGGTGCAG
GTGGAGCAGGCCACGCCCATCTCGGAGAGCTGTGCAGGTAAAATGGAA
GAATTCTTTCTCTTTGGAGCCTTCCTGGAGGCCTCAATGATCGACCGG
AGAAACGGAGACAAGCCCATCACCTTTGAGGTCACCATAGGCAACTAT
GGGAACGAAGTTGATGGCCTGTCCCGGCCCCAGCGGCCTCGGCCCCGG
AAGGAGCCGGGGATGAGGAAGAAGTAGACCTGATTCAGAACGCAAGT
GATGACGAGGCCGGTGATGCCGGGGACCTGGCCTCAGTCTCCTCCACT
CCACCAATGCGGCCCCAGGTCACCGACAGGAACTACTTCCATCTGCCC
TACCTGGAGCGAAAGCCCTGCATCTACATCAAGAGCTGGTGGCCGGAC
CAGCGCCGCCGCCTCTACAATGCCAACATCATGGACCACATTGCCGAC
AAGCTGGAAGAAGGCCTGAACGACATACAGGAGATGATCAAAACGGAG
AAGTCCTACCCTGAGCGTCGCCTGCGGGGCGTCCTGGAGGAGCTGAGC
TGTGGCTGCTGCCGCTTCCTCTCCCTCGCTGACAAGGACCAGGGCCAC
TCATCCCGCACCAGGCTTGACCGGGAGCGCCTCAAGTCCTGCATGAGG
GAGCTGGTAAGTATCAAGGTTACAAGACAGGTTTAAGGAGACCAATAG
AAACTGGGCTTGTCGAGACAGAGAAGACTCTTGCGTTTCTGAGCTAGC
CCCCGGGTGCGCGGCGTCGGTGGTGCCGGCGGGGGGCGCCAGGTCGCA
GGCGGTGTAGGGCTCCAGGCAGGCGGCGAAGGCCATGACGTGCGCTAT
GAAGGTCTGCTCCTGCACGCCGTGAACCAGGTGCGCCTGCGGGCCGCG
CGCGAACACCGCCACGTCCTCGCCTGCGTGGGTCTCTTCGTCCAGGGG
CACTGCTGACTGCTGCCGATACTCGGGGCTCCCGCTCTCGCTCTCGGT
AACATCCGCCGGGCGCCGTCCTTGAGCACATAGCCTGGACCGTTTCG
TCGACTGTTAATTAAGCATGCTGGGGAGAGATCTAGGAACCCCTAGTG
```

```
ATGGAGTTGGCCACTCCCTCTCTGCGCGCTCGCTCGCTCACTGAGGCC
GCCCGGGCAAAGCCCGGGCGTCGGGCGACCTTTGGTCGCCCGGCCTCA
GTGAGCGAGCGAGCGCGCAGAGAGGGAGTGGCCAACCCCCCCCCCCCC
CCCCCTGCAGCCCTGCATTAATGAATCGGCCAACGCGCGGGGAGAGGC
GGTTTGCGTATTGGGCGCTCTTCCGCTTCCTCGCTCACTGACTCGCTG
CGCTCGGTCGTTCGGCTGCGGCAGCGGTATCAGCTCACTCAAAGGCG
GTAATACGGTTATCCACAGAATCAGGGGATAACGCAGGAAAGAACATG
TGAGCAAAAGGCCAGCAAAAGGCCAGGAACCGTAAAAAGGCCGCGTTG
CTGGCGTTTTTCCATAGGCTCCGCCCCCTGACGAGCATCACAAAAAT
CGACGCTCAAGTCAGAGGTGGCGAAACCCGACAGGACTATAAAGATAC
CAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTG
GCGCTTTCTCAATGCTCACGCTGTAGGTATCTCAGTTCGGTGTAGGTC
GTTCGCTCCAAGCTGGGCTGTGTGCACGAACCCCCCGTTCAGCCCGAC
CGCTGCGCCTTATCCGGTAACTATCGTCTTGAGTCCAACCCGGTAAGA
CACGACTTATCGCCACTGGCAGCAGCCACTGGTAACAGGATTAGCAGA
GCGAGGTATGTAGGCGGTGCTACAGAGTTCTTGAAGTGGTGGCCTAAC
TACGGCTACACTAGAAGGACAGTATTTGGTATCTGCGCTCTGCTGAAG
CCAGTTACCTTCGGAAAAAGAGTTGGTAGCTCTTGATCCGGCAAACAA
ACCACCGCTGGTAGCGGTGGTTTTTTTGTTTGCAAGCAGCAGATTACG
CGCAGAAAAAAAGGATCTCAAGAAGATCCTTTGATCTTTTCTACGGGG
TCTGACGCTCAGTGGAACGAAAACTCACGTTAAGGGATTTTGGTCATG
AGATTATCAAAAGGATCTTCACCTAGATCCTTTTAAATTAAAAATGA
AGTTTTAAATCAATCTAAAGTATATATGAGTAAACTTGGTCTGACAGT
TACCAATGCTTAATCAGTGAGGCACCTATCTCAGCGATCTGTCTATTT
CGTTCATCCATAGTTGCCTGACTCCCCGTCGTGTAGATAACTACGATA
CGGGAGGGCTTACCATCTGGCCCCAGTGCTGCAATGATACCGCGAGAC
CCACGCTCACCGGCTCCAGATTTATCAGCAATAAACCAGCCAGCCGGA
AGGGCCGAGCGCAGAAGTGGTCCTGCAACTTTATCCGCCTCCATCCAG
TCTATTAATTGTTGCCGGGAAGCTAGAGTAAGTAGTTCGCCAGTTAAT
AGTTTGCGCAACGTTGTTGCCATTGCTACAGGCATCGTGGTGTCACGC
TCGTCGTTTGGTATGGCTTCATTCAGCTCCGGTTCCCAACGATCAAGG
CGAGTTACATGATCCCCATGTTGTGCAAAAAAGCGGTTAGCTCCTTC
GGTCCTCCGATCGTTGTCAGAAGTAAGTTGGCCGCAGTGTTATCACTC
ATGGTTATGGCAGCACTGCATAATTCTCTTACTGTCATGCCATCCGTA
AGATGCTTTTCTGTGACTGGTGAGTACTCAACCAAGTCATTCTGAGAA
TAGTGTATGCGGCGACCGAGTTGCTCTTGCCCGGCGTCAATACGGGAT
AATACCGCGCCACATAGCAGAACTTTAAAAGTGCTCATCATTGGAAAA
CGTTCTTCGGGGCGAAAACTCTCAAGGATCTTACCGCTGTTGAGATCC
AGTTCGATGTAACCCACTCGTGCACCCAACTGATCTTCAGCATCTTTT
```

```
ACTTTCACCAGCGTTTCTGGGTGAGCAAAAACAGGAAGGCAAAATGCC
GCAAAAAAGGGAATAAGGGCGACACGGAAATGTTGAATACTCATACTC
TTCCTTTTTCAATATTATTGAAGCATTTATCAGGGTTATTGTCTCATG
AGCGGATACATATTTGAATGTATTTAGAAAAATAAACAAATAGGGGTT
CCGCGCACATTTCCCCGAAAAGTGCCACCTGACGTCTAAGAAACCATT
ATTATCATGACATTAACCTATAAAAATAGGCGTATCACGAGGCCCTTT
CGTCTCGCGCGTTTCGGTGATGACGGTGAAAACCTCTGACACATGCAG
CTCCCGGAGACGGTCACAGCTTGTCTGTAAGCGGATGCCGGGAGCAGA
CAAGCCCGTCAGGGCGCGTCAGCGGGTGTTGGCGGGTGTCGGGGCTGG
CTTAACTATGCGGCATCAGAGCAGATTGTACTGAGAGTGCACCATATG
CGGTGTGAAATACCGCACAGATGCGTAAGGAGAAAATACCGCATCAGG
AAATTGTAAACGTTAATATTTTGTTAAAATTCGCGTTAAATTTTTGTT
AAATCAGCTCATTTTTTAACCAATAGGCCGAAATCGGCAAAATCCCTT
ATAAATCAAAAGAATAGACCGAGATAGGGTTGAGTGTTGTTCCAGTTT
GGAACAAGAGTCCACTATTAAAGAACGTGGACTCCAACGTCAAAGGGC
GAAAAACCGTCTATCAGGGCGATGGCCCACTACGTGAACCATCACCCT
AATCAAGTTTTTTGGGGTCGAGGTGCCGTAAAGCACTAAATCGGAACC
CTAAAGGGAGCCCCCGATTTAGAGCTTGACGGGGAAAGCCGGCGAACG
TGGCGAGAAAGGAAGGGAAGAAAGCGAAAGGAGCGGGCGCTAGGGCGC
TGGCAAGTGTAGCGGTCACGCTGCGCGTAACCACCACACCCGCCGCGC
TTAATGCGCCGCTACAGGGCGCGTCGCGCCATTCGCCATTCAGGCTAC
GCAACTGTTGGGAAGGGCGATCGGTGCGGGCCTCTTCGCTATTACGCC
AGGCTGC pTR22-APhead-APSA-otoferlinCT Hs var 1
                                    (SEQ ID NO: 15)
AGGGGGGGGGGGGGGGGGGTTGGCCACTCCCTCTCTGCGCGCTCGCTC
GCTCACTGAGGCCGGGCGACCAAAGGTCGCCCGACGCCCGGGCTTTGC
CCGGGCGGCCTCAGTGAGCGAGCGAGCGCGCAGAGAGGGAGTGGCCAA
CTCCATCACTAGGGGTTCCTCAGATCTGGCGCGCCCAATTGGCTTCGA
ATTCTAGCGGCCGCCCCGGGTGCGCGGCGTCGGTGGTGCCGGCGGGG
GGCGCCAGGTCGCAGGCGGTGTAGGGCTCCAGGCAGGCGGCGAAGGCC
ATGACGTGCGCTATGAAGGTCTGCTCCTGCACGCCGTGAACCAGGTGC
GCCTGCGGGCCGCGCGCGAACACCGCCACGTCCTCGCCTGCGTGGGTC
TCTTCGTCCAGGGGCACTGCTGACTGCTGCCGATACTCGGGGCTCCCG
CTCTCGCTCTCGGTAACATCCGGCCGGGCGCCGTCCTTGAGCACATAG
CCTGGACCGTTTCCTTAAGCGACGCATGCTCGCGATAGGCACCTATTG
GTCTTACTGACATCCACTTTGCCTTTCTCTCCACAGGAAAACATGGGG
CAGCAGGCCAGGATGCTGCGGGCCCAGGTGAAGCGGCACACGGTGCGG
GACAAGCTGAGGCTGTGCCAGAACTTCCTGCAGAAGCTGCGCTTCCTG
GCGGACGAGCCCCAGCACAGCATTCCCGACATCTTCATCTGGATGATG
AGCAACAACAAGCGTGTCGCCTATGCCCGTGTGCCCTCCAAGGACCTG
CTCTTCTCCATCGTGGAGGAGGAGACTGGCAAGGACTGCGCCAAGGTC
```

-continued

AAGACGCTCTTCCTTAAGCTGCCAGGGAAGCGGGGCTTCGGCTCGGCA
GGCTGGACAGTGCAGGCCAAGGTGGAGCTGTACCTGTGGCTGGGCCTC
AGCAAACAGCGCAAGGAGTTCCTGTGCGGCCTGCCCTGTGGCTTCCAG
GAGGTCAAGGCAGCCCAGGGCCTGGGCCTGCATGCCTTCCCACCCGTC
AGCCTGGTCTACACCAAGAAGCAGGCGTTCCAGCTCCGAGCGCACATG
TACCAGGCCCGCAGCCTCTTTGCCGCCGACAGCAGCGGACTCTCAGAC
CCCTTTGCCCGCGTCTTCTTCATCAATCAGAGTCAGTGCACAGAGGTG
CTGAATGAGACCCTGTGTCCCACCTGGGACCAGATGCTGGTGTTCGAC
AACCTGGAGCTCTATGGTGAAGCTCATGAGCTGAGGGACGATCCGCCC
ATCATTGTCATTGAAATCTATGACCAGGATTCCATGGGCAAAGCTGAC
TTCATGGGCCGGACCTTCGCCAAACCCTGGTGAAGATGGCAGACGAG
GCGTACTGCCCACCCCGCTTCCCACCTCAGCTCGAGTACTACCAGATC
TACCGTGGCAACGCCACAGCTGGAGACCTGCTGGCGGCCTTCGAGCTG
CTGCAGATTGGACCAGCAGGGAAGGCTGACCTGCCCCCCATCAATGGC
CCGGTGGACGTGGACCGAGGTCCCATCATGCCCGTGCCCATGGGCATC
CGGCCCGTGCTCAGCAAGTACCGAGTGGAGGTGCTGTTCTGGGGCCTA
CGGGACCTAAAGCGGGTGAACCTGGCCCAGGTGGACCGGCCACGGGTG
GACATCGAGTGTGCAGGGAAGGGGGTGCAGTCGTCCCTGATCCACAAT
TATAAGAAGAACCCCAACTTCAACACCCTCGTCAAGTGGTTTGAAGTG
GACCTCCCAGAGAACGAGCTGCTGCACCCGCCCTTGAACATCCGTGTG
GTGGACTGCCGGGCCTTCGGTCGCTACACACTGGTGGGCTCCCATGCC
GTCAGCTCCCTGCGACGCTTCATCTACCGGCCCCAGACCGCTCGGCC
CCCAGCTGGAACACCACGGTCAGGCTTCTCCGGCGCTGCCGTGTGCTG
TGCAATGGGGGCTCCTCCTCTCACTCCACAGGGGAGGTTGTGGTGACT
ATGGAGCCAGAGGTACCCATCAAGAAACTGGAGACCATGGTGAAGCTG
GACGCGACTTCTGAAGCTGTTGTCAAGGTGGATGTGGCTGAGGAGGAG
AAGGAGAAGAAGAAGAAGAAGGGCACTGCGGAGGAGCCAGAGGAG
GAGGAGCCAGACGAGAGCATGCTGGACTGGTGGTCCAAGTACTTTGCC
TCCATTGACACCATGAAGGAGCAACTTCGACAACAAGAGCCCTCTGGA
ATTGACTTGGAGGAGAAGGAGGAAGTGGACAATACCGAGGGCCTGAAG
GGGTCAATGAAGGGCAAGGAGAAGGCAAGGGCTGCCAAAGAGGAGAAG
AAGAAGAAAACTCAGAGCTCTGGCTCTGGCCAGGGGTCCGAGGCCCCC
GAGAAGAAGAAACCCAAGATTGATGAGCTTAAGGTATACCCCAAAGAG
CTGGAGTCCGAGTTTGATAACTTTGAGGACTGGCTGCACACTTTCAAC
TTGCTTCGGGGCAAGACCGGGGATGATGAGGATGGCTCCACCGAGGAG
GAGCGCATTGTGGGACGCTTCAAGGGCTCCCTCTGCGTGTACAAAGTG
CCACTCCCAGAGGACGTGTCCCGGGAAGCCGGCTACGACTCCACCTAC
GGCATGTTCCAGGGCATCCCGAGCAATGACCCCATCAATGTGCTGGTC
CGAGTCTATGTGGTCCGGGCCACGGACCTGCACCCTGCTGACATCAAC
GGCAAAGCTGACCCCTACATCGCCATCCGGCTAGGCAAGACTGACATC

-continued

CGCGACAAGGAGAACTACATCTCCAAGCAGCTCAACCCTGTCTTTGGG
AAGTCCTTTGACATCGAGGCCTCCTTCCCCATGGAATCCATGCTGACG
GTGGCTGTGTATGACTGGGACCTGGTGGGCACTGATGACCTCATTGGG
GAAACCAAGATCGACCTGGAGAACCGCTTCTACAGCAAGCACCGCGCC
ACCTGCGGCATCGCCCAGACCTACTCCACACATGGCTACAATATCTGG
CGGGACCCCATGAAGCCCAGCCAGATCCTGACCCGCCTCTGCAAAGAC
GGCAAAGTGGACGGCCCCCACTTTGGGCCCCCTGGGAGAGTGAAGGTG
GCCAACCGCGTCTTCACTGGGCCCTCTGAGATTGAGGACGAGAACGGT
CAGAGGAAGCCCACAGACGAGCATGTGGCGCTGTTGGCCCTGAGGCAC
TGGGAGGACATCCCCCGCGCAGGCTGCCGCCTGGTGCCAGAGCATGTG
GAGACGAGGCCGCTGCTCAACCCCGACAAGCCGGGCATCGAGCAGGGC
CGCCTGGAGCTGTGGGTGGACATGTTCCCCATGGACATGCCAGCCCCT
GGGACGCCTCTGGACATCTCACCTCGGAAGCCCAAGAAGTACGAGCTG
CGGGTCATCATCTGGAACACAGATGAGGTGGTCTTGGAGGACGACGAC
TTCTTCACAGGGGAGAAGTCCAGTGACATCTTCGTGAGGGGGTGGCTG
AAGGGCCAGCAGGAGGACAAGCAGGACACAGACGTCCACTACCACTCC
CTCACTGGCGAGGGCAACTTCAACTGGCGCTACCTGTTCCCCTTCGAC
TACCTGGCGGCGGAGGAGAAGATCGTCATCTCCAAGAAGGAGTCCATG
TTCTCCTGGGACGAGACCGAGTACAAGATCCCCGCGCGGCTCACCCTG
CAGATCTGGGATGCGGACCACTTCTCCGCTGACGACTTCCTGGGGGCC
ATCGAGCTGGACCTGAACCGGTTCCCGCGGGGCGCAAAGACAGCCAAG
CAGTGCACCATGGAGATGGCCACCGGGGAGGTGGACGTGCCCCTCGTG
TCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAG
CTGCATTTACTGACAGCAGAGGAGGCAGAGAAGAACCCAGTGGGCCTG
GCCCGCAATGAACCTGACCCCCTAGAGAAACCCAACCGGCCCGACACG
AGCTTCATCTGGTTCCTGAACCCTCTCAAGTCGGCTCGCTACTTCTTG
TGGCACACGTATCGCTGGCTGCTCCTCAAACTGTTGCTGCTCCTGCTG
CTGCTCCTCCTCCTCGCCCTGTTCCTCTACTCTGTGCCTGGCTACCTG
GTCAAGAAAATCCTCGGGGCCTGAGCGGCCGCGGTACCAAGGGCGAAT
TCTGCAGTCGACTAGAGCTCGCTGATCAGCCTCGACTGTGCCTTCTAG
TTGCCAGCCATCTGTTGTTTGCCCCTCCCCCGTGCCTTCCTTGACCCT
GGAAGGTGCCACTCCCACTGTCCTTTCCTAATAAAATGAGGAAATTGC
ATCGCATTGTCTGAGTAGGTGTCATTCTATTCTGGGGGGTGGGGTGGG
GCAGGACAGCAAGGGGGAGGATTGGGAAGACAATAGCAGGCATGCTGG
GGAGAGATCTGAGGACTAGTCCGTCGACTGTTAATTAAGCATGCTGGG
GAGAGATCTAGGAACCCCTAGTGATGGAGTTGGCCACTCCCTCTCTGC
GCGCTCGCTCGCTCACTGAGGCCGCCCGGGCAAAGCCCGGGCGTCGGG
CGACCTTTGGTCGCCCGGCCTCAGTGAGCGAGCGAGCGCGCAGAGAGG
GAGTGGCCAACCCCCCCCCCCCCCCCCCTGCAGCCCTGCATTAATGAA
TCGGCCAACGCGCGGGGAGAGGCGGTTTGCGTATTGGGCGCTCTTCCG

CTTCCTCGCTCACTGACTCGCTGCGCTCGGTCGTTCGGCTGCGGCGAG
CGGTATCAGCTCACTCAAAGGCGGTAATACGGTTATCCACAGAATCAG
GGGATAACGCAGGAAAGAACATGTGAGCAAAAGGCCAGCAAAAGGCCA
GGAACCGTAAAAAGGCCGCGTTGCTGGCGTTTTTCCATAGGCTCCGCC
CCCCTGACGAGCATCACAAAAATCGACGCTCAAGTCAGAGGTGGCGAA
ACCCGACAGGACTATAAAGATACCAGGCGTTTCCCCCTGGAAGCTCCC
TCGTGCGCTCTCCTGTTCCGACCCTGCCGCTTACCGGATACCTGTCCG
CCTTTCTCCCTTCGGGAAGCGTGGCGCTTTCTCAATGCTCACGCTGTA
GGTATCTCAGTTCGGTGTAGGTCGTTCGCTCCAAGCTGGGCTGTGTGC
ACGAACCCCCCGTTCAGCCCGACCGCTGCGCCTTATCCGGTAACTATC
GTCTTGAGTCCAACCCGGTAAGACACGACTTATCGCCACTGGCAGCAG
CCACTGGTAACAGGATTAGCAGAGCGAGGTATGTAGGCGGTGCTACAG
AGTTCTTGAAGTGGTGGCCTAACTACGGCTACACTAGAAGGACAGTAT
TTGGTATCTGCGCTCTGCTGAAGCCAGTTACCTTCGGAAAAAGAGTTG
GTAGCTCTTGATCCGGCAAACAAACCACCGCTGGTAGCGGTGGTTTTT
TTGTTTGCAAGCAGCAGATTACGCGCAGAAAAAAAGGATCTCAAGAAG
ATCCTTTGATCTTTTCTACGGGGTCTGACGCTCAGTGGAACGAAAACT
CACGTTAAGGGATTTTGGTCATGAGATTATCAAAAAGGATCTTCACCT
AGATCCTTTTAAATTAAAAATGAAGTTTTAAATCAATCTAAAGTATAT
ATGAGTAAACTTGGTCTGACAGTTACCAATGCTTAATCAGTGAGGCAC
CTATCTCAGCGATCTGTCTATTTCGTTCATCCATAGTTGCCTGACTCC
CCGTCGTGTAGATAACTACGATACGGGAGGGCTTACCATCTGGCCCCA
GTGCTGCAATGATACCGCGAGACCCACGCTCACCGGCTCCAGATTTAT
CAGCAATAAACCAGCCAGCCGGAAGGGCCGAGCGCAGAAGTGGTCCTG
CAACTTTATCCGCCTCCATCCAGTCTATTAATTGTTGCCGGGAAGCTA
GAGTAAGTAGTTCGCCAGTTAATAGTTTGCGCAACGTTGTTGCCATTG
CTACAGGCATCGTGGTGTCACGCTCGTCGTTTGGTATGGCTTCATTCA
GCTCCGGTTCCCAACGATCAAGGCGAGTTACATGATCCCCCATGTTGT
GCAAAAAAGCGGTTAGCTCCTTCGGTCCTCCGATCGTTGTCAGAAGTA
AGTTGGCCGCAGTGTTATCACTCATGGTTATGGCAGCACTGCATAATT
CTCTTACTGTCATGCCATCCGTAAGATGCTTTTCTGTGACTGGTGAGT
ACTCAACCAAGTCATTCTGAGAATAGTGTATGCGGCGACCGAGTTGCT
CTTGCCCGGCGTCAATACGGGATAATACCGCGCCACATAGCAGAACTT
TAAAAGTGCTCATCATTGGAAAACGTTCTTCGGGGCGAAAACTCTCAA
GGATCTTACCGCTGTTGAGATCCAGTTCGATGTAACCCACTCGTGCAC
CCAACTGATCTTCAGCATCTTTTACTTTCACCAGCGTTTCTGGGTGAG
CAAAAACAGGAAGGCAAAATGCCGCAAAAAAGGGAATAAGGGCGACAC
GGAAATGTTGAATACTCATACTCTTCCTTTTTCAATATTATTGAAGCA
TTTATCAGGGTTATTGTCTCATGAGCGGATACATATTTGAATGTATTT
AGAAAAATAAACAAATAGGGGTTCCGCGCACATTTCCCCGAAAAGTGC

CACCTGACGTCTAAGAAACCATTATTATCATGACATTAACCTATAAAA
ATAGGCGTATCACGAGGCCCTTTCGTCTCGCGCGTTTCGGTGATGACG
GTGAAAACCTCTGACACATGCAGCTCCCGGAGACGGTCACAGCTTGTC
TGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGA
TTGTACTGAGAGTGCACCATATGCGGTGTGAAATACCGCACAGATGCG
TAAGGAGAAAATACCGCATCAGGAAATTGTAAACGTTAATATTTTGTT
AAAATTCGCGTTAAATTTTTGTTAAATCAGCTCATTTTTTAACCAATA
GGCCGAAATCGGCAAAATCCCTTATAAATCAAAAGAATAGACCGAGAT
AGGGTTGAGTGTTGTTCCAGTTTGGAACAAGAGTCCACTATTAAAGAA
CGTGGACTCCAACGTCAAAGGGCGAAAAACCGTCTATCAGGGCGATGG
CCCACTACGTGAACCATCACCCTAATCAAGTTTTTTGGGGTCGAGGTG
CCGTAAAGCACTAAATCGGAACCCTAAAGGGAGCCCCCGATTTAGAGC
TTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCG
CGTAACCACCACACCCGCCGCGCTTAATGCGCCGCTACAGGGCGCGTC
GCGCCATTCGCCATTCAGGCTACGCAACTGTTGGGAAGGGCGATCGGT
GCGGGCCTCTTCGCTATTACGCCAGGCTGC pTR22-APhead-APSA-otoferlinCT Hs var 5
(SEQ ID NO: 16)
AGGGGGGGGGGGGGGGGGTTGGCCACTCCCTCTCTGCGCGCTCGCTC
GCTCACTGAGGCCGGGCGACCAAAGGTCGCCCGACGCCCGGGCTTTGC
CCGGGCGGCCTCAGTGAGCGAGCGAGCGCGCAGAGAGGGAGTGGCCAA
CTCCATCACTAGGGGTTCCTCAGATCTGGCGCGCCCAATTGGCTTCGA
ATTCTAGCGGCCGCCCCCGGGTGCGCGGCGTCGGTGGTGCCGGCGGGG
GGCGCCAGGTCGCAGGCGGTGTAGGGCTCCAGGCAGGCGGCGAAGGCC
ATGACGTGCGCTATGAAGGTCTGCTCCTGCACGCCGTGAACCAGGTGC
GCCTGCGGGCCGCGCGCGAACACCGCCACGTCCTCGCCTGCGTGGGTC
TCTTCGTCCAGGGGCACTGCTGACTGCTGCCGATACTCGGGGCTCCCG
CTCTCGCTCTCGGTAACATCCGGCCGGGCGCCGTCCTTGAGCACATAG
CCTGGACCGTTTCCTTAAGCGACGCATGCTCGCGATAGGCACCTATTG
GTCTTACTGACATCCACTTTGCCTTTCTCTCCACAGGAAAACATGGGG
CAGCAGGCCAGGATGCTGCGGGCCCAGGTGAAGCGGCACACGGTGCGG
GACAAGCTGAGGCTGTGCCAGAACTTCCTGCAGAAGCTGCGCTTCCTG
GCGGACGAGCCCCAGCACAGCATTCCCGACATCTTCATCTGGATGATG
AGCAACAACAAGCGTGTCGCCTATGCCCGTGTGCCCTCCAAGGACCTG
CTCTTCTCCATCGTGGAGGAGGAGACTGGCAAGGACTGCGCCAAGGTC
AAGACGCTCTTCCTTAAGCTGCCAGGGAAGCGGGGCTTCGGCTCGGCA
GGCTGGACAGTGCAGGCCAAGGTGGAGCTGTACCTGTGGCTGGGCCTC
AGCAAACAGCGCAAGGAGTTCCTGTGCGGCCTGCCCCTGTGGCTTCCAG
GAGGTCAAGGCAGCCCAGGGCCTGGGCCTGCATGCCTTCCCACCCGTC
AGCCTGGTCTACACCAAGAAGCAGGCGTTCCAGCTCCGAGCGCACATG -continued

```
TACCAGGCCCGCAGCCTCTTTGCCGCCGACAGCAGCGGACTCTCAGAC
CCCTTTGCCCGCGTCTTCTTCATCAATCAGAGTCAGTGCACAGAGGTG
CTGAATGAGACCCTGTGTCCCACCTGGGACCAGATGCTGGTGTTCGAC
AACCTGGAGCTCTATGGTGAAGCTCATGAGCTGAGGGACGATCCGCCC
ATCATTGTCATTGAAATCTATGACCAGGATTCCATGGGCAAAGCTGAC
TTCATGGGCCGGACCTTCGCCAAACCCCTGGTGAAGATGGCAGACGAG
GCGTACTGCCCACCCCGCTTCCCACCTCAGCTCGAGTACTACCAGATC
TACCGTGGCAACGCCACAGCTGGAGACCTGCTGGCGGCCTTCGAGCTG
CTGCAGATTGGACCAGCAGGGAAGGCTGACCTGCCCCCCATCAATGGC
CCGGTGGACGTGGACCGAGGTCCCATCATGCCCGTGCCCATGGGCATC
CGGCCCGTGCTCAGCAAGTACCGAGTGGAGGTGCTGTTCTGGGGCCTA
CGGGACCTAAAGCGGGTGAACCTGGCCCAGGTGGACCGGCCACGGGTG
GACATCGAGTGTGCAGGGAAGGGGGTGCAGTCGTCCCTGATCCACAAT
TATAAGAAGAACCCCAACTTCAACACCCTCGTCAAGTGGTTTGAAGTG
GACCTCCCAGAGAACGAGCTGCTGCACCCGCCCTTGAACATCCGTGTG
GTGGACTGCCGGGCCTTCGGTCGCTACACACTGGTGGGCTCCCATGCC
GTCAGCTCCCTGCGACGCTTCATCTACCGGCCCCCAGACCGCTCGGCC
CCCAGCTGGAACACCACGGTCAGGCTTCTCCGGCGCTGCCGTGTGCTG
TGCAATGGGGGCTCCTCCTCTCACTCCACAGGGGAGGTTGTGGTGACT
ATGGAGCCAGAGGTACCCATCAAGAAACTGGAGACCATGGTGAAGCTG
GACGCGACTTCTGAAGCTGTTGTCAAGGTGGATGTGGCTGAGGAGGAG
AAGGAGAAGAAGAAGAAGAAGAAGGGCACTGCGGAGGAGCCAGAGGAG
GAGGAGCCAGACGAGAGCATGCTGGACTGGTGGTCCAAGTACTTTGCC
TCCATTGACACCATGAAGGAGCAACTTCGACAACAAGAGCCCTCTGGA
ATTGACTTGGAGGAGAAGGAGGAAGTGGACAATACCGAGGGCCTGAAG
GGGTCAATGAAGGGCAAGGAGAAGGCAAGGGCTGCCAAAGAGGAGAAG
AAGAAGAAACTCAGAGCTCTGGCTCTGGCCAGGGGTCCGAGGCCCCC
GAGAAGAAGAAACCCAAGATTGATGAGCTTAAGGTATACCCCAAAGAG
CTGGAGTCCGAGTTTGATAACTTTGAGGACTGGCTGCACACTTTCAAC
TTGCTTCGGGGCAAGACCGGGGATGATGAGGATGGCTCCACCGAGGAG
GAGCGCATTGTGGGACGCTTCAAGGGCTCCCTCTGCGTGTACAAAGTG
CCACTCCCAGAGGACGTGTCCCGGGAAGCCGGCTACGACTCCACCTAC
GGCATGTTCCAGGGCATCCCGAGCAATGACCCCATCAATGTGCTGGTC
CGAGTCTATGTGGTCCGGGCCACGGACCTGCACCCTGCTGACATCAAC
GGCAAAGCTGACCCCTACATCGCCATCCGGCTAGGCAAGACTGACATC
CGCGACAAGGAGAACTACATCTCCAAGCAGCTCAACCCTGTCTTTGGG
AAGTCCTTTGACATCGAGGCCTCCTTCCCCATGGAATCCATGCTGACG
GTGGCTGTGTATGACTGGGACCTGGTGGGCACTGATGACCTCATTGGG
GAAACCAAGATCGACCTGGAGAACGCTTCTACAGCAAGCACCGCGCC
ACCTGCGGCATCGCCCAGACCTACTCCACACATGGCTACAATATCTGG
```

```
CGGGACCCCATGAAGCCCAGCCAGATCCTGACCCGCCTCTGCAAAGAC
GGCAAAGTGGACGGCCCCCACTTTGGGCCCCCTGGGAGAGTGAAGGTG
GCCAACCGCGTCTTCACTGGGCCCTCTGAGATTGAGGACGAGAACGGT
CAGAGGAAGCCCACAGACGAGCATGTGGCGCTGTTGGCCCTGAGGCAC
TGGGAGGACATCCCCCGCGCAGGCTGCCGCCTGGTGCCAGAGCATGTG
GAGACGAGGCCGCTGCTCAACCCCGACAAGCCGGGCATCGAGCAGGGC
CGCCTGGAGCTGTGGGTGGACATGTTCCCCATGGACATGCCAGCCCCT
GGGACGCCTCTGGACATCTCACCTCGGAAGCCCAAGAAGTACGAGCTG
CGGGTCATCATCTGGAACACAGATGAGGTGGTCTTGGAGGACGACGAC
TTCTTCACAGGGGAGAAGTCCAGTGACATCTTCGTGAGGGGTGGCTG
AAGGGCCAGCAGGAGGACAAGCAGGACACAGACGTCCACTACCACTCC
CTCACTGGCGAGGGCAACTTCAACTGGCGCTACCTGTTCCCCTTCGAC
TACCTGGCGGCGGAGGAGAAGATCGTCATCTCCAAGAAGGAGTCCATG
TTCTCCTGGGACGAGACCGAGTACAAGATCCCCGCGCGGCTCACCCTG
CAGATCTGGGATGCGGACCACTTCTCCGCTGACGACTTCCTGGGGGCC
ATCGAGCTGGACCTGAACCGGTTCCCGCGGGGCGCAAAGACAGCCAAG
CAGTGCACCATGGAGATGGCCACCGGGGAGGTGGACGTGCCCCTCGTG
TCCATCTTCAAGCAAAAGCGCGTCAAAGGCTGGTGGCCCCTCCTGGCC
CGCAATGAGAACGATGAGTTTGAGCTCACGGGCAAGGTGGAGGCTGAG
CTGCATTTACTGACAGCAGAGGAGGCAGAGAAGAACCCAGTGGGCCTG
GCCCGCAATGAACCTGACCCCCTAGAGAAACCCAACCGGCCCGACACG
GCCTTCGTCTGGTTCCTCAACCCTCTCAAGTCCATCAAGTACCTCATC
TGCACCCGGTACAAGTGGCTCATCATCAAGATCGTGCTGGCGCTGTTG
GGGCTGCTCATGTTGGGGCTCTTCCTCTACAGCCTCCCTGGCTACATG
GTCAAAAAGCTCCTTGGGGCATGAGCGGCCGCGGTACCAAGGGCGAAT
TCTGCAGTCGACTAGAGCTCGCTGATCAGCCTCGACTGTGCCTTCTAG
TTGCCAGCCATCTGTTGTTTGCCCCTCCCCCGTGCCTTCCTTGACCCT
GGAAGGTGCCACTCCCACTGTCCTTTCCTAATAAAATGAGGAAATTGC
ATCGCATTGTCTGAGTAGGTGTCATTCTATTCTGGGGGGTGGGGTGGG
GCAGGACAGCAAGGGGGAGGATTGGGAAGACAATAGCAGGCATGCTGG
GGAGAGATCTGAGGACTAGTCCGTCGACTGTTAATTAAGCATGCTGGG
GAGAGATCTAGGAACCCCTAGTGATGGAGTTGGCCACTCCCTCTCTGC
GCGCTCGCTCGCTCACTGAGGCCGCCCGGGCAAAGCCCGGGCGTCGGG
CGACCTTTGGTCGCCCGGCCTCAGTGAGCGAGCGAGCGCGCAGAGAGG
GAGTGGCCAACCCCCCCCCCCCCCCCCTGCAGCCCTGCATTAATGAA
TCGGCCAACGCGCGGGGAGAGGCGGTTTGCGTATTGGGCGCTCTTCCG
CTTCCTCGCTCACTGACTCGCTGCGCTCGGTCGTTCGGCTGCGGCGAG
CGGTATCAGCTCACTCAAAGGCGGTAATACGGTTATCCACAGAATCAG
GGGATAACGCAGGAAAGAACATGTGAGCAAAAGGCCAGCAAAAGGCCA
GGAACCGTAAAAAGGCCGCGTTGCTGGCGTTTTTCCATAGGCTCCGCC
CCCCTGACGAGCATCACAAAAATCGACGCTCAAGTCAGAGGTGGCGAA
```

-continued

```
ACCCGACAGGACTATAAAGATACCAGGCGTTTCCCCCTGGAAGCTCCC
TCGTGCGCTCTCCTGTTCCGACCCTGCCGCTTACCGGATACCTGTCCG
CCTTTCTCCCTTCGGGAAGCGTGGCGCTTTCTCAATGCTCACGCTGTA
GGTATCTCAGTTCGGTGTAGGTCGTTCGCTCCAAGCTGGGCTGTGTGC
ACGAACCCCCGTTCAGCCCGACCGCTGCGCCTTATCCGGTAACTATC
GTCTTGAGTCCAACCCGGTAAGACACGACTTATCGCCACTGGCAGCAG
CCACTGGTAACAGGATTAGCAGAGCGAGGTATGTAGGCGGTGCTACAG
AGTTCTTGAAGTGGTGGCCTAACTACGGCTACACTAGAAGGACAGTAT
TTGGTATCTGCGCTCTGCTGAAGCCAGTTACCTTCGGAAAAAGAGTTG
GTAGCTCTTGATCCGGCAAACAAACCACCGCTGGTAGCGGTGGTTTTT
TTGTTTGCAAGCAGCAGATTACGCGCAGAAAAAAAGGATCTCAAGAAG
ATCCTTTGATCTTTTCTACGGGGTCTGACGCTCAGTGGAACGAAAACT
CACGTTAAGGGATTTTGGTCATGAGATTATCAAAAAGGATCTTCACCT
AGATCCTTTTAAATTAAAAATGAAGTTTTAAATCAATCTAAAGTATAT
ATGAGTAAACTTGGTCTGACAGTTACCAATGCTTAATCAGTGAGGCAC
CTATCTCAGCGATCTGTCTATTTCGTTCATCCATAGTTGCCTGACTCC
CCGTCGTGTAGATAACTACGATACGGGAGGGCTTACCATCTGGCCCCA
GTGCTGCAATGATACCGCGAGACCCACGCTCACCGGCTCCAGATTTAT
CAGCAATAAACCAGCCAGCCGGAAGGGCCGAGCGCAGAAGTGGTCCTG
CAACTTTATCCGCCTCCATCCAGTCTATTAATTGTTGCCGGGAAGCTA
GAGTAAGTAGTTCGCCAGTTAATAGTTTGCGCAACGTTGTTGCCATTG
CTACAGGCATCGTGGTGTCACGCTCGTCGTTTGGTATGGCTTCATTCA
GCTCCGGTTCCCAACGATCAAGGCGAGTTACATGATCCCCCATGTTGT
GCAAAAAAGCGGTTAGCTCCTTCGGTCCTCCGATCGTTGTCAGAAGTA
AGTTGGCCGCAGTGTTATCACTCATGGTTATGGCAGCACTGCATAATT
CTCTTACTGTCATGCCATCCGTAAGATGCTTTTCTGTGACTGGTGAGT
ACTCAACCAAGTCATTCTGAGAATAGTGTATGCGGCGACCGAGTTGCT
CTTGCCCGGCGTCAATACGGGATAATACCGCGCCACATAGCAGAACTT
TAAAAGTGCTCATCATTGGAAAACGTTCTTCGGGGCGAAAACTCTCAA
GGATCTTACCGCTGTTGAGATCCAGTTCGATGTAACCCACTCGTGCAC
CCAACTGATCTTCAGCATCTTTTACTTTCACCAGCGTTTCTGGGTGAG
CAAAAACAGGAAGGCAAAATGCCGCAAAAAAGGGAATAAGGGCGACAC
GGAAATGTTGAATACTCATACTCTTCCTTTTTCAATATTATTGAAGCA
TTTATCAGGGTTATTGTCTCATGAGCGGATACATATTTGAATGTATTT
AGAAAAATAAACAAATAGGGGTTCCGCGCACATTTCCCCGAAAAGTGC
CACCTGACGTCTAAGAAACCATTATTATCATGACATTAACCTATAAAA
ATAGGCGTATCACGAGGCCCTTTCGTCTCGCGCGTTTCGGTGATGACG
GTGAAAACCTCTGACACATGCAGCTCCCGGAGACGGTCACAGCTTGTC
TGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGA
TTGTACTGAGAGTGCACCATATGCGGTGTGAAATACCGCACAGATGCG
TAAGGAGAAAATACCGCATCAGGAAATTGTAAACGTTAATATTTTGTT
AAAATTCGCGTTAAATTTTTGTTAAATCAGCTCATTTTTTAACCAATA
GGCCGAAATCGGCAAAATCCCTTATAAATCAAAAGAATAGACCGAGAT
AGGGTTGAGTGTTGTTCCAGTTTGGAACAAGAGTCCACTATTAAAGAA
CGTGGACTCCAACGTCAAAGGGCGAAAAACCGTCTATCAGGGCGATGG
CCCACTACGTGAACCATCACCCTAATCAAGTTTTTTGGGGTCGAGGTG
CCGTAAAGCACTAAATCGGAACCCTAAAGGGAGCCCCCGATTTAGAGC
TTGACGGGGAAAGCCGGCGAACGTGGCGAGAAAGGAAGGGAAGAAAGC
GAAAGGAGCGGGCGCTAGGGCGCTGGCAAGTGTAGCGGTCACGCTGCG
CGTAACCACCACACCCGCCGCGCTTAATGCGCCGCTACAGGGCGCGTC
GCGCCATTCGCCATTCAGGCTACGCAACTGTTGGGAAGGGCGATCGGT
GCGGGCCTCTTCGCTATTACGCCAGGCTGC
```

REFERENCES

1) Adato Al, Raskin L, Petit C, Bonne-Tamir B Deafness heterogeneity in a Druze isolate from the Middle East: novel OTOF and PDS mutations, low prevalence of GJB2 35delG mutation and indication for a new DFNB locus.Eur J Hum Genet. 2000 June; 8(6):437-42.
2) Allocca M, Doria M, Petrillo M, Colella P, Garcia-Hoyos M, Gibbs D, Kim S R, Maguire A, Rex T S, Di Vicino U, Cutillo L, Sparrow J R, Williams D S, Bennett J, Auricchio A. Serotype-dependent packaging of large genes in adeno-associated viral vectors results in effective gene delivery in mice. J Clin Invest. 2008 May; 118(5):1955-64.
3) Chaib, H., Place, C., Salem, N., Chardenoux, S., Vincent, C., Weissenbach, J., El-Zir, E., Loiselet, J., Petit, C. A gene responsible for a sensorineural nonsyndromic recessive deafness maps to chromosome 2p22-23. Hum. Molec. Genet. 1996 5: 155-158.
4) Choi, B. Y., Ahmed, Z. M., Riazuddin, S., Bhinder, M. A., Shahzad, M., Husnain, T., Riazuddin, S., Griffith, A. J., Friedman, T. B. Identities and frequencies of mutations of the otoferlin gene (OTOF) causing DFNB9 deafness in Pakistan. Clin. Genet. 2009 75: 237-243.
5) Dong B, Nakai H, Xiao W. Characterization of genome integrity for oversized recombinant AAV vector. Mol Ther. 2010 January; 18(1):87-92.
6) Ghosh A, Yue Y, Duan D. Efficient transgene reconstitution with hybrid dual AAV vectors carrying the minimized bridging sequences. Hum Gene Ther. 2011 January; 22(1):77-83.
7) Hirsch M L, Agbandje-McKenna M, Samulski R J. Little vector, big gene transduction: fragmented genome reassembly of adeno-associated virus. Mol Ther. 2010 January; 18(1):6-8.
8) Lai Y, Yue Y, Duan D. Evidence for the failure of adeno-associated virus serotype 5 to package a viral genome > or =8.2 kb. Mol Ther. 2010 January; 18(1):75-9.
9) Matsunaga Ti, Mutai H, Kunishima S, Namba K, Morimoto N, Shinjo Y, Arimoto Y, Kataoka Y, Shintani T, Morita N, Sugiuchi T, Masuda S, Nakano A, Taiji H, Kaga K. A prevalent founder mutation and genotype-phenotype correlations of OTOF in Japanese patients with auditory neuropathy. Clin Genet. 2012 November; 82(5):425-32. doi: 10.1111/j.1399-0004.2012.01897.x. Epub 2012 Jun. 1.

10) Rodriguez-Ballesteros M, del Castillo F J, Martin Y, Moreno-Pelayo M A, Morera C, Prieto F, Marco J, Morant A, Gallo-Terán J, Morales-Angulo C, Navas C, Trinidad G, Tapia M C, Moreno F, del Castillo I. Auditory neuropathy in patients carrying mutations in the otoferlin gene (OTOF). Hum Mutat. 2003 December; 22(6):451-6.

11) Roux I, Safieddine S, Nouvian R, Grati M, Simmler M C, Bahloul A, Perfettini I, Le Gall M, Rostaing P, Hamard G, Triller A, Avan P, Moser T, Petit C. Otoferlin, defective in a human deafness form, is essential for exocytosis at the auditory ribbon synapse. Cell. 2006 Oct. 20; 127(2): 277-89.

12) Wu Z, Yang H, Colosi P. Effect of genome size on AAV vector packaging. Mol Ther. 2010 January; 18(1):80-6.

13) Yasunaga S, Grati M, Chardenoux S, Smith T N, Friedman T B, Lalwani A K, Wilcox E R, Petit C. Am J Hum Genet. OTOF encodes multiple long and short isoforms: genetic evidence that the long ones underlie recessive deafness DFNB9. 2000 September; 67(3):591-600. Epub 2000 Jul. 19.

14) Yasunaga S, Grati M, Cohen-Salmon M, El-Amraoui A, Mustapha M, Salem N, El-Zir E, Loiselet J, Petit C. A mutation in OTOF, encoding otoferlin, a FER-1-like protein, causes DFNB9, a nonsyndromic form of deafness. Nat Genet. 1999 April; 21(4):363-9.

15) Didier Dulon, Saaid Safieddine, Sherri M. Jones, Christine Petit. Otoferlin is Critical for a Highly Sensitive and Linear Calcium Dependent Exocytosis at Vestibular Hair Cell Ribbon Synapses. J Neurosci. 2009 August.

16) Zippora Brownstein, Yoni Bhonker and Karen B Avraham. High-throughput sequencing to decipher the genetic heterogeneity of deafness. Brownstein et al. Genome Biology 2012, 13:245

17) Rodriguez-Ballesteros et al. (2003) "Auditory neuropathy in patients carrying mutations in the otoferlin gene (OTOF)" Hum Mutat.; 22 (6):451-456.

18) Petersen M B, Willems P J: Non-syndromic, autosomal-recessive deafness. Clin Genet. 2006; 69 (5): 371-92.

19) Smith R, Gurrola J, Kelley P. OTOF-Related Deafness. In: Pagon R, Bird T, Dolan C, Stephens K, eds. Gene Reviews. Seattle: Internet; 2008

20) Roux I, Safieddine S, Nouvian R et al. Otoferlin, defective in a human deafness form, is essential for exocytosis at the auditory ribbon synapse. Cell 2006; 127:277-89

21) Kral A, O'Donoghue G M: Profound deafness in childhood. N Engl J Med. 2010; 363(15):1438-50. doi: 10.1056/NEJMra0911225.

22) Dyka F M, Boye S L, Chiodo V A, Hauswirth W W, Boye S E., Dual Adeno-Associated Virus Vectors Result in Efficient In Vitro and In Vivo Expression of an Oversized Gene MY07A, Hum Gene Ther Methods. 2014; 25 (2):166-77. doi: 10.1089/hgtb.2013.212.

23) Akil O, Seal R P, Burke K, Wang C, Alemi A, During M, Edwards R H, Lustig L R: Restoration of hearing in the VGLUT3 knockout mouse using virally mediated gene therapy. Neuron. 2012; 75 (2):283-93. doi: 10.1016/j.neuron.2012.05.019.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of treating hearing loss in a human subject having a mutation in an OTOF gene associated with Deafness, Autosomal Recessive 9 (DFNB9), the method comprising:
 administering to inner hair cells in an inner ear of the subject a first adeno-associated virus (AAV) particle comprising a first polynucleotide and
 a second AAV particle comprising a second polynucleotide, wherein
 (i) the first polynucleotide comprises inverted terminal repeat sequences flanking an expression cassette containing, from 5' to 3':
  (a) a promoter,
  (b) a partial coding sequence that encodes an N-terminal portion of an Otoferlin polypeptide,
  (c) a splice donor site, and
  (d) a first region of homology containing a sequence that is homologous to a sequence in the second polynucleotide, and
 (ii) the second polynucleotide comprises inverted terminal repeat sequences flanking an expression cassette containing, from 5' to 3':
  (a) a second region of homology containing a sequence that is homologous to a sequence in the first polynucleotide,
  (b) a splice acceptor site,
  (c) a partial coding sequence that encodes a C-terminal portion of the Otoferlin polypeptide, and
  (d) a polyadenylation (pA) signal sequence,
 wherein the first region of homology and the second region of homology are between 50 and 500 nucleotides, wherein the Otoferlin polypeptide comprises the amino acid sequence of SEQ ID NO: 6, and wherein, when introduced into a human cell, the first polynucleotide and the second polynucleotide combine to form a polynucleotide that encodes a full-length Otoferlin polypeptide.

2. The method of claim 1, wherein the first region of homology and the second region of homology are between 50 and 300 nucleotides.

3. The method of claim 2, wherein each of the first and second regions of homology comprises the nucleotide sequence of SEQ ID NO: 3.

4. The method of claim 1, wherein the promoter is a chimeric cytomegalovirus (CMV) chicken β actin promoter or a truncated chimeric CMV/chicken β actin promoter.

5. The method of claim 4, wherein the promoter comprises the sequence of SEQ ID NO: 4.

6. The method of claim 1, wherein the splice donor site comprises the sequence of SEQ ID NO: 7.

7. The method of claim 1, wherein the splice acceptor site comprises the sequence of SEQ ID NO: 8.

8. The method of claim 1, wherein the inverted terminal repeat sequences are AAV2 inverted terminal repeat sequences.

9. The method of claim 1, wherein the first and second AAV particle are AAV2 serotype particles.

* * * * *